US006762188B1

(12) United States Patent
Pendergast et al.

(10) Patent No.: US 6,762,188 B1
(45) Date of Patent: Jul. 13, 2004

(54) PHARMACEUTICALLY ACTIVE BENZOQUINAZOLINE COMPOUNDS

(75) Inventors: William Pendergast, Durham, NC (US); Scott Howard Dickerson, Chapel Hill, NC (US); Julius Vass Johnson, Chapel Hill, NC (US); Robert Ferone, Raleigh, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/952,394

(22) Filed: Sep. 12, 2001

Related U.S. Application Data

(63) Continuation of application No. 09/588,790, filed on Jun. 6, 2000, now Pat. No. 6,306,865.

(30) Foreign Application Priority Data

Jun. 19, 1990 (GB) .............................................. 9013615

(51) Int. Cl.[7] .......................................... A61K 31/502
(52) U.S. Cl. ...................................... 514/267; 544/257
(58) Field of Search ................................ 514/257, 267

(56) References Cited

U.S. PATENT DOCUMENTS

| | | | |
|---|---|---|---|
| 4,564,616 A | 1/1986 | Jones et al. | |
| 4,814,335 A | 3/1989 | Kim | |
| 5,405,851 A | 4/1995 | Pendergast et al. | |
| 5,661,155 A | 8/1997 | Pendergast et al. | |
| 5,663,337 A | 9/1997 | Pendergast et al. | |
| 6,090,941 A | 7/2000 | Pendergast et al. | |
| 6,306,865 B1 | 10/2001 | Pendergast et al. | |
| 6,579,877 B2 | 6/2003 | Smith et al. | |

FOREIGN PATENT DOCUMENTS

| | | |
|---|---|---|
| DE | 2188319 | 9/1987 |
| DE | 2202847 | 10/1988 |
| EP | 0 204 529 | 12/1986 |
| EP | 0 265 126 | 4/1988 |
| EP | 0 296 848 | 12/1988 |
| EP | 0 316 657 | 5/1989 |
| EP | 0 318 225 | 5/1989 |
| FR | 2 029 439 | 10/1970 |
| GB | 2175 903 A | 12/1986 |
| WO | 91/19700 | 12/1991 |

OTHER PUBLICATIONS

Draetta et al, Annual Reports in Medicinal Chemistry, vol. 31, pp 241–246 (1996).*
J. Vebrel and R. Carrie, Bull. Soc. Chim. Fr., 1982m p. 161.
Rosowski, et al., J. Heterocyclic Chem., 1972, 9(6), p. 1449–51.
J. H. Burkhalter and J.R. Campbell, J. Org. Chem., 1961, 26, p. 4232.
W. Rode, K.J. Scanlon, J.B. Hynes, J.R. Bertino, J. Biol. Chem., 1979, 254, p 11538.
Roberts, Biochemistry, 1966, 5, p. 3546.
Dev et al., J. Biol. Chem., 1989, 264, p. 19132.
S.D. Patil et al., J. Med. Chem., 1989, 32, p. 1284.
Marsham et al., "Quinazoline Antifolate Synthase Inhibitors Bridge Modifications and Conformationally Restricted Analogues in the C2–Methyl Series", J. Med. Chem. 34, 1991, pp. 2209–2218.
Hughes et al., "Replacement of the para–Aminobenzoyl Portion of a Series od C2–Desamino C2–Methyl–Dideazafolic Acid Derivatives: Effect on Thymidylate Synthase (TS) Inhibition and Cytotoxicity", Poster at the 1989 AACR Meeting.
Marsham et al., "Quinazoline Antifolate Synthase Inhibitors: Nitrogen, Oxygen, Sulfur and Chlorine Substituents in the C2 Position", J. Med. Chem. 32, 1989, pp. 569–575.
"Thymidylate Synthase (TS) Inhibitory and Cytotoxic Activity of a Series of C2 Substituted 5,8–deazafolates", Poster at the 1988 AACR Meeting.
Jones et al., "Quinazoline Antifolates Inhibiting Thymidylate Synthase: Variation of the Amino Acid", J. Med. Chem., 29, 1986, pp. 1114–1118.
Jones et al., "Quinazoline Antifolates Inhibiting Thymidylate Synthase: Benzoyl Ring Modifications", J. Med. Chem., 29, 1986, pp. 468–472.
Jones et al., "Quinazoline Antifolates Inhibiting Thymidylate Synthase: Variation of the $N^{10}$ Substituent", J. Med. Chem., 28, 1985, pp. 1468–1476.
"Analogues in the C2–Methyl Series", J. Med. Chem., 1991, 34, pp. 2209–2219.
D.J. Brown, "The Pyrmidines", 1962, pp. 31–32 and 44–50.
Clinton et al., J. Am. Chem. Soc., 1949, vol. 71, pp. 3366–3370.

(List continued on next page.)

Primary Examiner—John M. Ford
(74) Attorney, Agent, or Firm—John L. Lemanowicz

(57) ABSTRACT

Compounds of formula (I) or salts thereof, wherein the dotted Line represents a single or double bond, $R^1$ is alkyl or amino optionally substituted by alkyl, alkanoyl or benzyl group; $R^2$, $R^3$, $R^4$ and $R^5$ are the same or different and each is selected from hydrogen, phenyl, halo, nitro, a group $S(O)_n R^8$ wherein n is the integer 0, 1 or 2 and $R^8$ is halo or alkyl or a group $NR^9R^{10}$ wherein $R^9$ and $R^{10}$ are both hydrogen, a group $NR^{11}R^{12}$ wherein $R^{11}$ and $R^{12}$ are the same or different and each is hydrogen or alkyl, a group $OR^{13}$ wherein $R^{13}$ is hydrogen or $C_{1-4}$ of alkyl optionally substituted by halo; a $C_{1-4}$ aliphatic group optionally substituted by a group $OR^{14}$ or $NR^{14}R^{15}$ wherein $R^{14}$ and $R^{15}$ are the same or different and each is hydrogen or alkyl; or two of $R^2$ to $R^5$ are linked together to form a benzo group, or one of $R^2$ to $R^5$ is a group X—Y—$R^{16}$ wherein X is $CH_2$, $NR^{17}$, CO or $S(O)_m$ and Y is $CH_2$, $NR^{17}$, O or $S(O)_m$, or X—Y is O, $NR^{17}$, —CH=CH— or N=N—, are disclosed as pharmacological agents useful in the treatment of tumours. Pharmaceutical compositions and methods for the preparation of compounds of formula (I) are also described.

14 Claims, No Drawings

OTHER PUBLICATIONS

Mehta et al., Indian J. Chem., 1967, vol. 5(6), p. 231–33.
Mehta et al., Indian J. Chem., 1968, vol. 6(6), p. 294–96.
Taylor et al., J. Org. Chem., 1968, vol. 33(5), pp. 1719–1727.
Parrot–Lopez et al., J. Heterocycl. Chem., 1986, vol. 23(4), pp. 1039–1043.
Sengupta et al., J. Hetercycl. Chem., 1973, vol. 10(1), pp. 59–63.
Robev, Dok. Bolg. Akad, Nauk., 1986, vol. 39(4), pp. 47–50 (No Translation).
Robev, Dok. Bolg. Akad. Nauk., 1986, vol. 40(12), pp. 41–44 (No Translation).
Dean et al., J. Heterocycl. Chem., 1982, vol. 19(1), pp. 171–176.
Sengupta et al., J. Org. Chem., 1972, vol. 37(9), pp. 1323–1328.
Kelenda et al., Chem Abstr., 1971, vol. 75, No. 28253, pp. 539.
Taylor et al., Tetrahedron, 1967, vol. 23, p. 2081–93.

* cited by examiner

PHARMACEUTICALLY ACTIVE BENZOQUINAZOLINE COMPOUNDS

This is a continuation of Ser. No. 09/588,790 filed Jun. 6, 2000 now U.S. Pat. No. 6,306,865.

The present invention relates to novel benzoquinazoline thymidylate synthase inhibitors, to processes for preparing them and pharmaceutical formulations containing them. U.S. Pat. No. 4,814,335 discloses inter alia that compounds of the formula (0):

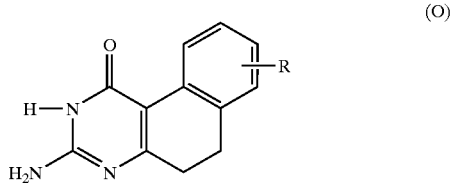

wherein R is hydrogen, fluoro, nitro, optionally substituted amino, carboxy, azido, alkoxy, trimethylsulphonyl, trifluoromethylsulphonyl or alkoxycarbonyl have biological response-modifying activity, i.e. antiviral, antibacterial and anticancer activity. However, no specific examples of compounds of the formula (0) are provided.

Thymidylate synthase is an enzyme catalysing the terminal step in the de novo synthesis of thymidylate required for DNA synthesis. It has been postulated that inhibitors of this enzyme may be expected to have anti-tumour activity and it has been reported (Jones et al, J. Med. Chem. 1986, 29, 468) that the in-vivo antitumour activity of $N^{10}$-propargyl-5,8-dideazafolic acid arises solely from its inhibitory effect on this enzyme.

It has now been found that a group of benzoquinazoline compounds are inhibitors of the enzyme thymidylate synthase and have antitumour activity.

Accordingly, the present invention provides compounds of the formula (I)

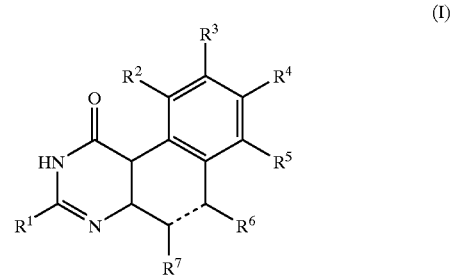

or a salt thereof, wherein the dotted line represents a single or double bond, $R^1$ is $C_{1-4}$ alkyl or amino optionally substituted by a $C_{1-4}$ alkyl, $C_{1-5}$ alkanoyl or benzyl group;

$R^2$, $R^3$, $R^4$ and $R^5$ are the same or different and each is selected from hydrogen, phenyl, halo, nitro, a group $S(O)_n R^8$ wherein n is the integer 0, 1 or 2 and $R^8$ is halo or is $C_{1-4}$ alkyl or a group $NR^9 R^{10}$ wherein $R^9$ and $R^{10}$ are both hydrogen,
a group $NR^{11}R^{12}$ wherein $R^{11}$ and $R^{12}$ are the same or different and each is hydrogen or $C_{1-4}$ alkyl,
a group $OR^{13}$ wherein $R^{13}$ is hydrogen or $C_{1-4}$ alkyl optionally substituted by halo;
a $C_{1-4}$ aliphatic group optionally substituted by a group $OR^{14}$ or $NR^{14}R^{15}$ wherein $R^{14}$ and $R^{15}$ are the same or different and each is hydrogen or $C_{1-4}$ alkyl;

or two of $R^2$ to $R^5$ are linked together to form a benzo group, or one of $R^2$ to $R^5$ is a group —X—Y—$R^{16}$ wherein X is $CH_2$, $NR^{17}$, CO or $S(O)_m$ and m is 0, 1 or 2 and $R^{17}$ is hydrogen or a $C_{1-4}$ aliphatic group and Y is $CH_2$, $NR^{17'}$, O, or $S(O)_{m'}$, wherein m' is 0, 1 or 2 and $R^{17'}$ is hydrogen or a $C_{1-4}$ aliphatic group provided that X and Y are only the same when each is $CH_2$, or —X—Y— is a group —O—, —$NR^{17}$—, —CH=CH— or —N=N— wherein $R^{17}$ is as hereinbefore defined, $R^{16}$ is a $C_{1-4}$ aliphatic group or a 5- or 6-membered aromatic ring optionally substituted by a group $R^{18}$ at a position at least one carbon atom removed from that linked to Y, the 5- or 6-membered ring being optionally further substituted by a halo atom; and $R^{18}$ is halo, $C_{1-4}$ alkoxy, nitro, nitrile, $C_{1-4}$ alkyl optionally substituted by halo, halo or a group $COR^{19}$ wherein $R^{19}$ is hydroxy, $C_{1-4}$ alkoxy or $C_{1-6}$ alkyl optionally substituted by one or two carboxyl groups or $C_{1-12}$ esters thereof or $R^{19}$ is a group $NR^{20}R^{21}$ wherein $R^{20}$ and $R^{21}$ are the same or different and each is hydrogen or $C_{1-4}$ alkyl optionally substituted by hydroxy or $R^{19}$ is an amino acid group or an ester thereof in which the first nitrogen atom of the amino acid group may be linked to the 5- or 6-membered aromatic ring to form a further 5- or 6-membered heterocyclic ring or $R^{19}$ is an $C_{2-3}$ alkylene group linked to the 5- or 6-membered aromatic ring to form a further 5- or 6-membered ring;

$R^6$ and $R^7$ are the same or different and each is $C_{1-4}$ alkyl optionally substituted by hydroxy or $C_{1-4}$ alkoxy or together form a benzo group;

provided that at least one of $R^2$ to $R^7$ is other than hydrogen and that $R^4$ is not methoxy when $R^1$ is hydroxy or methyl.

By the term halo is meant fluoro, bromo, chloro and iodo.

By the term $C_{1-4}$ aliphatic group is meant a $C_{1-4}$ alkyl, alkenyl, or alkynyl group.

By the term amino acid group is meant naturally occurring amino acids.

Preferred amino acid groups include glycine, glutamic acid and polyglutamic and groups.

When the amino acid group is linked to the 5- or 6-membered aromatic ring, this is via a carbon atom of the aromatic ring adjacent to carbon to which $COR^{19}$ is attached.

Preferably the dotted line is a double bond.

Suitable substituents for the aromatic ring $R^{16}$ include halo, $C_{1-4}$ alkyl and $C_{1-4}$ alkoxy each optionally substituted by one to five halo atoms. Most suitably there are one or two substituents selected from fluoro, chloro, methyl, trifluoromethyl and methoxy, and preferably fluoro, or no substituents on the aromatic ring. In one preferred embodiment, —X—Y—$R^{16}$ is a group

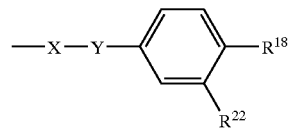

wherein $R^{18}$ is as hereinbefore defined and preferably a group $COR^{19}$ as hereinbefore defined and $R^{22}$ is hydrogen or fluoro.

In a further preferred embodiment X—Y—R$^{16}$ is a group

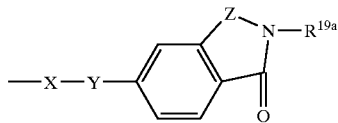

wherein H$_2$NR$^{19a}$ is a glutamic or polyglutamic acid group and Z is CH$_2$, S or O.

Suitably, R$^1$ is an amino group optionally substituted by one or two methyl or ethyl groups or R$^1$ is a methyl or ethyl group. Preferably R$^1$ is an amino or methyl group.

Suitably, at most only three, and preferably at most only two, of R$^2$ to R$^5$ are other than hydrogen and each is independently selected from hydrogen, halo, hydroxy, nitro, C$_{1-3}$ alkyl optionally substituted by hydroxy or C$_{1-2}$ alkoxy, C$_{1-3}$ alkoxy, amino optionally substituted by one or two methyl or ethyl groups, or a group S(O)nR$^{23}$ wherein n is 0, 1 or 2 and R$^{23}$ is a C$_{1-4}$ alkyl group or an amino group optionally substituted by one or two methyl or ethyl groups, or one of R$^2$ to R$^5$ is a group —X—Y—R$^{24}$ where R$^{24}$ is a group

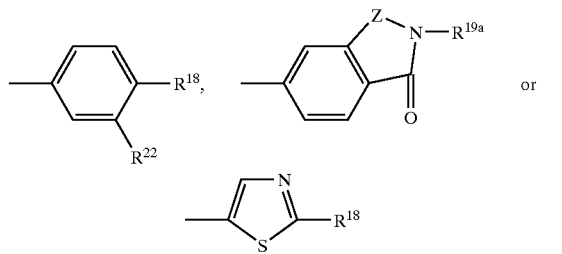

wherein R$^{18}$, R$^{19a}$, R$^{22}$ and Z are as hereinbefore defined. In one preferred embodiment R$^{18}$ is nitro or a group

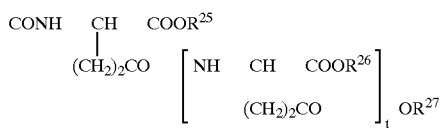

wherein R$^{25}$, R$^{26}$ and R$^{27}$ are the same or different and each is hydrogen or a C$_{1-4}$ alkyl group and t is an integer from 0 to 6. Preferably R$^{25}$, R$^{26}$ and R$^{27}$ are hydrogen and t is 0. Preferably Z is CH$_2$ or S.

Preferably one of R$^2$ to R$^5$ is a group —X—Y—R$^{24}$ as hereinbefore defined. Preferably R$^3$ is a group —X—Y—R$^{24}$.

Suitably R$^6$ and R$^7$ are the same or different and each is hydrogen, methyl, ethyl or methyl substituted by bromo, hydroxy or methoxy. Preferably R$^7$ is hydrogen and R$^6$ is methyl.

Preferably —X—Y— is a group —SO$_2$NR$^{17}$— or CH$_2$NR$^{17}$ wherein R$^{17}$ is as hereinbefore defined.

Suitably R$^{17}$ is hydrogen or a C$_{1-4}$ alkyl or alkenyl group and preferably R$^{17}$ is hydrogen or methyl.

One group of compounds of the present invention is that of the formula (Ia)

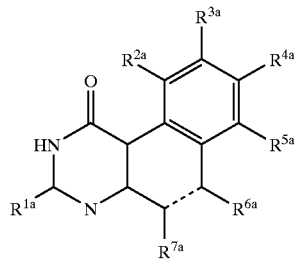

(Ia)

or a salt thereof, wherein the dotted line represents a single or double bond, R$^{1a}$ is C$_{1-4}$ alkyl or amino optionally substituted by a C$_{1-4}$ alkyl, C$_{1-5}$ alkanoyl or benzyl group; R$^{2a}$, R$^{3a}$, R$^{4a}$ and R$^{5a}$ are the same or different and each is selected from hydrogen, halo, nitro, a group S(O)$_n$R$^{8a}$ wherein n is the integer 0, 1 or 2 and R$^{8a}$ is halo or is a C$_{1-4}$ alkyl or amino group; a group NR$^{11a}$R$^{12a}$ wherein R$^{1a}$ and R$^{12a}$ are the same or different and each is hydrogen or C$_{1-4}$ alkyl, a group OR$^{13a}$ wherein R$^{13a}$ is hydrogen or C$_{1-4}$ alkyl optionally substituted by halo, a C$_{1-4}$ aliphatic group optionally substituted by a group OR$^{14a}$ or NR$^{14a}$R$^{15a}$ wherein R$^{14a}$ and R$^{15a}$ are the same or different and each is hydrogen or C$_{1-4}$ alkyl, or one of R$^{2a}$ to R$^{5a}$ is a group —X—Y—R wherein X is CH$_2$, NR$^{17a}$, CO or S(O)$_m$ and m is 0, 1 or 2 and R$^{17a}$ is hydrogen or a C$_{1-4}$ aliphatic group and Y is CH$_2$, NR$^{17'a}$, O, or S(O)$_{m'}$ wherein m' is 0, 1 or 2 and R$^{17'a}$ is hydrogen or a C$_{1-4}$ aliphatic group provided that X and Y are only the same when each is CH$_2$, or —X—Y— is a group —NR$^{17a}$, —CH=CH— or —N=N— wherein R$^{17a}$ is as hereinbefore defined, R$^{16a}$ is a C$_{1-4}$ aliphatic group or an optionally substituted 5- or 6-membered aromatic ring substituted by a group R$^{18a}$ at a position at least one carbon atom removed from that linked to Y and R$^{18a}$ is nitro, nitrile, C$_{1-4}$ alkyl optionally substituted by halo, halo or a group COR$^{19a}$ wherein R$^{19a}$ is C$_{1-6}$ alkyl optionally substituted by one or two carboxyl groups or C$_{1-4}$ alkoxy, a group CONR$^{20a}$R$^{21a}$ wherein R$^{20a}$ and R$^{21a}$ are the same or different and each is hydrogen or C$_{1-4}$ alkyl or R$^{19a}$ is a glutamic or polyglutamic acid group or an ester thereof in which the first nitrogen atom of the glutamic or polyglutamic acid group may be linked to the 5- or 6-membered aromatic ring to form a further 5- or 6-membered heterocyclic ring; R$^{6a}$ and R$^{7a}$ are the same or different and each is C$_{1-4}$ alkyl optionally substituted by hydroxy or C$_{1-4}$ alkoxy or together form a benzo group, provided that at least one of R$^{2a}$ to R$^{7a}$ is other than hydrogen and that R$^{4a}$ is not methoxy when R$^{1a}$ is hydroxy or methyl.

A further group of compounds of the present invention is that of the formula (II)

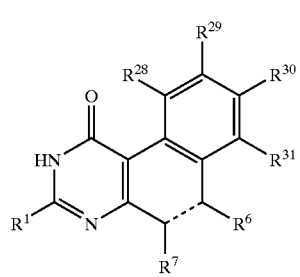

(II)

or a salt thereof, wherein R$^1$, R$^6$, R$^7$ and the dotted line are as hereinbefore defined and R$^{28}$ to R$^{31}$ are the same or different and each is selected from hydrogen, halo, nitro, a group $S(O)_nR^8$, a group $NR^{11}R^{12}$, a group $OR^{13}$, or a $C_{1-4}$ aliphatic group optionally substituted by a group $OR^{14}$ or $NR^{14}R^{15}$ wherein $R^8$, $R^{11}$, $R^{12}$, $R^{13}$, $R^{14}$ and $R^{15}$ are as hereinbefore defined, provided that $R^{28}$ to $R^{31}$ are not all hydrogen and that $R^{30}$ is not methoxy wherein $R^1$ is hydroxy or methyl.

A preferred group of compounds of the present invention is that of the formula (III):

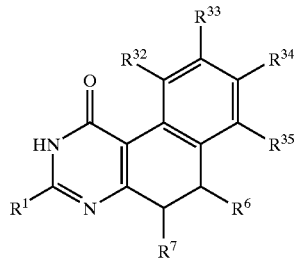

(III)

or a salt thereof, wherein $R^1$, $R^6$ and $R^7$ are as hereinbefore defined and $R^{32}$ to $R^{35}$ are the same or different and one is a group X—Y—$R^{16}$ and the others are the same or different and each is selected from hydrogen, halo, nitro, a group $S(O)_nR^8$, a group $NR^{11}R^{12}$, a group $OR^{13}$ or a $C_{1-4}$ aliphatic group optionally substituted by a group $OR^{14}$ or $NR^{14}R^{15}$, wherein X, Y, $R^8$, $R^{11}$, $R^{12}$, $R^{13}$, $R^{14}$, $R^{15}$ and $R^{16}$ are as hereinbefore defined.

A further preferred group of compounds of the present invention is that of the formula (IV):

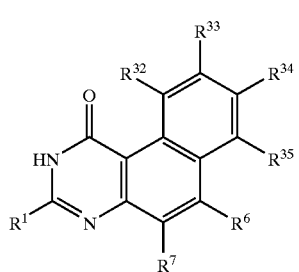

(IV)

wherein $R^1$, $R^6$, $R^7$ and $R^{32}$ to $R^{32}$ are as hereinbefore defined.

Preferably $R^{33}$ is a group X—Y—$R^{16}$ as hereinbefore defined.

Preferred compounds of the formula (I) include:

3-Amino-9-bromobenzo[f]quinazolin-1(2H)-one

3-Amino-9-ethynylbenzo[f]quinazolin-1(2H)-one

N-(4-((3-Amino-1,2,5,6-tetrahydro-1-oxobenzo[f]quinazolin-9-yl)sulfonamido)benzoyl)-L-glutamic acid N-(4-((1,2,5,6-tetrahydro-3-methyl-1-oxobenzo[f]quinazolin-9-yl)-sulfonamido)benzoyl)-L-glutamic acid N-(4-((1,2-Dihydro-3-methyl-1-oxobenzo[f]quinazolin-9-yl)sulfonamido)-benzoyl)-L-glutamic acid N-(4-(((1,2-Dihydro-3-methyl-1-oxobenzo[f]quinazolin-9-yl)methyl)amino)-2-fluorobenzoyl)-L-glutamic acid N-(4(((1,2-Dihydro-3-methyl-1-oxobenzo[f]quinazolin-9-yl)methyl)amino)benzoyl)-L-glumatic acid (S)-2-(5-(((1,2-Dihydro-3-methyl-1-oxobenzo[f]quinazolin-9-yl)methyl)-amino-1-oxo-2-isoindolinyl) glutamic acid 9-((4-Acetylanilino)methyl)-3-methylbenzo[f]quinazolin-1(2H)-one 3-Methyl-9-((4-nitroanilino)methyl)benzo[f]quinazolin-1(2H)-one N-(4-(((3-Amino-1,2-dihydro-1-oxobenzo[f]quinazolin-9-yl)methyl)amino)benzoyl)-L-glutamic acid 3-Amino-9-((4-nitroanilino)methyl)benzo[f]quinazolin-1(2H)-one 9-((4-Acetylanilino)methyl)-3-aminobenzo[f]quinazolin-1(2H)-one (RS)-2-(2-(4-(((1,2-Dihydro-3-methyl-1-oxobenzo[f]quinazolin-9-yl)methyl)amino)phenyl)-2-oxoethyl) glutaric acid Ethyl-4-(4-(((1,2-dihydro-3-methyl-1-oxobenzo[f]quinazolin-9-yl)methyl)amino)phenyl)-4-oxobutyrate 4-(4-(((1,2-Dihydro-3-methyl-1-oxobenzo[f]quinazolin-9-yl)methyl)amino)phenyl)-4-oxobutyric acid N-(4-(((1,2-Dihydro-3-methyl-1-oxobenzo[f]quinazolin-9-yl)methyl)amino)-2-fluorobenzoyl)glycine Ethyl N-(4-(((1,2-Dihydro-3-methyl-1-oxobenzo[f]quinazolin-9-yl)methyl)amino)-2-fluorobenzoyl) glycinate Certain compounds of the formula (I) contain asymmetric carbon atoms and are, therefore, capable of existing as optical isomers. The individual isomers and mixtures of these are included within the scope of the present invention.

Salts of the compounds of the present invention may comprise acid addition salts derived from an amino group or anionic species derived from a compound of formula (I), for example when this is substituted by a carboxy group, and a cation. In both types of salts, the therapeutic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycollic, gluconic, succinic and methanesulphonic and arylsulphonic, for example p-toluenesulphonic, acids. Examples of salts comprising an anionic species derived from a compound of formula (I) and a cation include ammonium salts, alkali metal salts, such as sodium and potassium salts, alkaline earth salts, such as magnesium and calcium salts, and salts formed with organic bases, for example, amino salts derived from mono-, di- or tri-(lower alkyl) or (lower alkanol)amines, such as triethanolamine and diethylamino-ethylamine, and salts with heterocyclic amines such as piperidine, pyridine, piperazine and morpholine. The pharmaceutically acceptable salts together with the salts which are not thus acceptable have utility in the isolation and/or the purification of the compounds of the invention, and the pharmaceutically unacceptable salts are also useful in being convertible to the pharmaceutically acceptable salts by techniques well known in the art.

Esters of compounds of the formula (I), formed from compounds of the formula (I) which contain a carboxy group are often useful intermediates in the preparation of the parent acid.

The present invention also provides a process for the preparation of compounds of the formula (I) which comprises a method well known to those skilled in the art, for example:

(i) when it is required to prepare a compound of the formula (I) wherein the dotted line represents a single bond, the reaction of a compound of the formula (V)

(V)

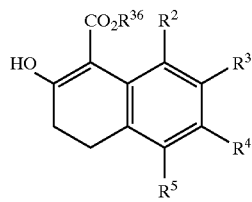

wherein $R^2$ to $R^5$ are as hereinbefore defined and $R^{36}$ is a $C_{1-4}$ alkyl group, with a compound

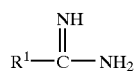

wherein $R^1$ is as hereinbefore defined. This reaction is suitably carried out in a polar solvent, for example a $C_{1-4}$ alkanol or glycol, conveniently methanol or ethanol, normally in the presence of a base, for example a metal alkoxide conveniently formed from the metal and the solvent, i.e. sodium methoxide or ethoxide, at an elevated temperature, for example 50° to 150° C. and conveniently 60° to 90° C. The compound of the formula

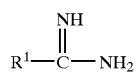

is conveniently liberated in situ from a salt form, for example the hydrochloride or carbonate salt, by the base which is preferably present in the reaction mixture. This reaction is a preferred method for preparing those compounds of the formula (I) wherein one of $R^2$ to $R^5$ is not a group $XYR^{16}$.

(ii) the direct insertion of a substituent $R^2$, $R^3$, $R^4$ or $R^5$ into the aromatic ring system. This is particularly suitable for the insertion of halo or nitro substituents or a group $SO_2$hal. This is carried out by methods conventionally employed to insert these substituents on aromatic ring systems, for example in the case of a bromo substituent: reaction of the corresponding compound where $R^2$ to $R^7$ are all hydrogen with bromine in a suitable solvent such as glacial acetic acid at a temperature between 20° and 100° C., conveniently between 50° and 70° C.; in the case of a substituent $SO_2$hal: reaction of the corresponding compound where $R^2$ to $R^7$ are all hydrogen with a halosulphonic acid at a temperature between −5° and 100° C., conveniently between 20° and 30° C.; in the case of a nitro substituent: reaction of the corresponding compound where $R^2$ to $R^7$ are hydrogen with nitric acid or potassium nitrate in sulphuric acid at −30° to 50° C. and conveniently at −5° to 5° C. The position of attachment of the substituent to the aromatic ring system may be effected by, inter alia, the nature of the substituent $R^1$. Thus, when $R^1$ is an amino group an $SO_2$ group will be attached to the 8-position but when $R^1$ is a methyl group an $SO_2$ group will be attached to the 9-position.

(iii) the hydrolysis of a compound of the formula (VI)

(VI)

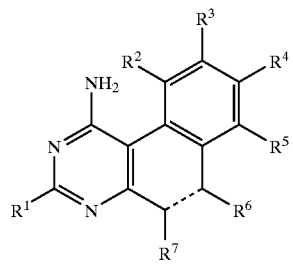

wherein $R^1$ to $R^7$ are as hereinbefore defined. This hydrolysis is conveniently carried out by acid, for example a mineral acid such as hydrochloric acid, at a temperature of between 20° and 120° C. and conveniently at between 60° and 100° C.

(iv) the conversion of one compound of the formula (I) to a further compound of the formula (I), for example:
  (a) the dehydrogenation of a compound of the formula (VII):

(VII)

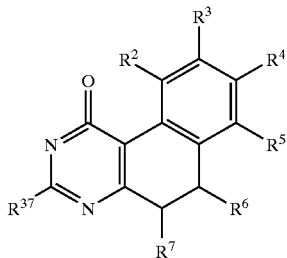

wherein $R^1$ to $R^7$ are as hereinbefore defined and $R^{37}$ is $C_{1-4}$ alkyl or a primary, secondary or tertiary amino group within the definition of $R^1$ or when it is desired to prepare a compound of the formula (I) wherein $R^1$ is a primary amino or a hydroxy group $R^{37}$ is a protected amino or hydroxy group; and thereafter removing the protecting group where appropriate. This dehydrogenation is conveniently carried out by (i) bromination of the 5- or 6-position of the compound of the formula (VII) by a reagent such as N-bromosuccinimide followed by dehydrobromination (ii) catalytic dehydrogenation in inert solvent (e.g. diglyme), (iii) dehydrogenation with DDQ. Reaction (i) is conveniently carried out in the presence of a base, such as pyridine, in a inert solvent, for example benzene, at a non-extreme temperature, for example between 0 and 80° C. The pivaloyl group is a suitable protecting group when $R^1$ is $NH_2$.

The compounds of the formula (VII) are conveniently prepared from the corresponding compounds of the formula (V) as described in method (i) above.

(b) when it is desired to prepare a compound of the formula (I) wherein one of $R^2$ to $R^5$ is a group $S(O)_mYR^{16}$ wherein Y and $R^{16}$ are as hereinbefore defined, the reaction of the analogous precursor substituted by the group $SO_2$hal with a compound $HYR^{16}$ wherein hal is halo and $R^{16}$ is as hereinbefore defined. Suitably this reaction is carried out in a basic medium, for example pyridine, at an elevated temperature, i.e. 25 to 175° C. The precursor is prepared by analogy to method (ii) above whereby a compound of formula (I) or (II), wherein at least one of $R^2$–$R^5$ is H in the position desired for substitution, is reacted with chlorosulfonic acid at −5 to 100° C.

(c) when it is desired to prepare a compound of the formula (I) substituted by an amino group the reduction of the corresponding compound substituted by a nitro group. Reduction is suitably carried out by hydrogenation in the presence of a transition metal catalyst for example palladium on charcoal in an inert solvent, for example an alkanol, such as ethanol, at a non-extreme temperature, for example (25 to 35° C.).

(d) when it is desired to prepare a compound of the formula (I) substituted by a hydroxy group, the removal of an alkyl group from the corresponding alkoxy compound. This reaction is conveniently carried out in the presence of a strong acid, such as hydrobromic acid at a non-extreme temperature.

(e) when there is more than one substituent $R^2$ to $R^5$, removal of one of the substituents, for example removal of bromine by catalytic debromination, such as hydrogenation in the presence of a transition metal catalyst, conveniently palladium on charcoal, in a polar solvent such as a $C_{1-4}$ alkanol at between 0° and 50° C. conveniently 20° to 30° C.

(f) when one of $R^2$ to $R^5$ is an alkyl group, the halogenation of this alkyl group, for example bromination by N-bromo-succinimide in an inert solvent, such as benzene, at a temperature between 20° and 120° C., conveniently 70° to 90° C.

(g) the displacement of a leaving group from a substituent $R^2$ to $R^5$ by another group, for example conversion of a haloalkyl group to an hydroxyalkyl or alkoxyalkyl group by reaction with an alkali metal hydroxide or alkoxide respectively in alkanol, at a temperature between 20° and 120° C.; or conversion of a group $CH_2hal$ wherein hal is halo to a group $CH_2YR^{16}$ by reaction with a compound $HYR^{16}$ wherein Y and $R^{16}$ are as hereinbefore defined, for example N-(4-aminobenzoyl)-L-glutamic acid diethyl ester, ethyl N-(4-amino-2-fluorobenzoyl)glycinate or 4-fluoroanilino, in a dipolar aprotic solvent, such as dimethylformamide, at a non-extreme temperature, for example 25° to 160° C. and conveniently 95° to 105° C. optionally followed by the addition of a weak base such as sodium or patassium carbonate or bicarbonate.

(h) the replacement of one substituent $R^2$ to $R^5$ by another substituent $R^2$ to $R^5$, for example displacement of bromo by an alkynyl moiety which is preferably protected by a trialkylsilyl group in the presence of a suitable catalyst, such as palladium acetate. The trialkylsilyl group may then be removed by base catalysed hydrolysis, for example with potassium carbonate. The alkynyl group can be reduced, by catalytic hydrogenation, to an alkenyl or alkyl group.

When $R^1$ is an amino group, it is often convenient to carry out these conversions with the amino group protected, for example with a pivaloyl group.

The compounds of the formula (V) may be prepared by the reaction of a dialkyl carbonate with a compound of the formula (VIII)

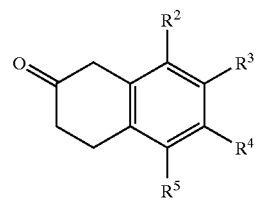

(VIII)

wherein $R^2$ to $R^5$ are as hereinbefore defined in the presence of a base, conveniently sodium hydride. This reaction is analogous to that described by J. Vebrel and R. Carrie (Bull. Soc. Chim. Fr., 1982, 161).

The compounds of the formula (VI) wherein $R^1=NH_2$ may be prepared by the reaction of dicyandiamide with a compound of the formula (VIII). This reaction is described by Rosowsky et al (J. Heterocyclic Chem. 9, 263 (1972).

The compounds of the formula (VIII) may be prepared by methods well known to those skilled in the art, for example by methods analogous to those described by J. Vebrel and R. Carrie (Bull. Soc. Chim. Fr., 1982, 161) and J. H. Burkhalter and J. R. Campbell (J. Org. Chem., 26, 4332 (1961) and those outlined in Schemes 1, 2 and 3 appended hereto.

The present invention also relates to novel chemical intermediates of the formula (VI). Compounds of the formula (VI) possess pharmocological properties and may therefore be useful in their own right as well as being useful intermediates in the preparation of compounds of the formula (I).

Whilst it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as hereinbefore defined, and a pharmaceutically acceptable carrier therefor.

The pharmaceutical formulation may optionally contain other therapeutic agents that may usefully be employed in conjunction with the compound or salt of the present invention, for example a pyrimidine nucleoside transport inhibitor that is capable of enhancing the antineoplastic activity of the compounds and salts of the present invention. The expression "pharmaceutically acceptable" as used herein in relation to the carrier is used in the sense of being compatible with the compound or salt of the invention employed in the formulation and with any other therapeutic agent that may be present, and not being detrimental to the recipient thereof. The carrier itself may constitute one or more excipients conventionally used in the art of pharmacy that enable the compound or salt of the present invention and any other therapeutic agent that may be present, to be formulated as a pharmaceutical formulation.

The pharmaceutical formulations of the present invention include those suitable for oral, parenteral (including subcutaneous, intradermal, intramuscular and intravenous) and rectal administration although the most suitable route will probably depend upon, for example, the condition and identity of the recipient. The formulations may conveniently be presented in unit dosage form and may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or a non-aqueous liquid such as a syrup, elixir or a draught, or as an oil-in-water liquid emulsion or a water-in-oil liquid emulsion. The formulation may also be a bolus, electuary or paste.

Generally, a tablet is the most convenient pharmaceutical formulation suitable for oral administration. A tablet may be made by compressing or moulding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating agent and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqueous sterile injection solutions which may contain, for example, an anti-oxidant, a buffer, a bacteriostat and a solution which renders the composition isotonic with the blood of the recipient, and aqueous and non-aqueous sterile suspensions which may contain, for example, a suspending agent and a thickening agent. The formulations may be presented in uni-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

The pharmaceutical formulations of the present invention suitable for rectal administration may be presented as a suppository containing, for example, cocoa butter and polyethylene glycol.

As mentioned hereinbefore, compounds and salts of formula (I) have anti-neoplastic activity as demonstrated hereinafter in the human colon SW480 adenocarcinoma cell culture cytotoxicity tests in which representative compounds of the present invention have been shown to be active. Compounds and salts of formula (I) also have anti-neoplastic activity as determined hereinafter in the human breast MCF7 adenocarcinoma cell culture cytotoxicity tests. It has thus been established that compounds of the present invention are able to inhibit neoplastic growth. Therefore, compounds and salts of the present invention are of use in medicine and in particular in the treatment of neoplastic growth, including solid tumours such as melanoma, breast and colon tumours in mammals. Accordingly, the present invention yet further provides a method for the treatment of susceptible malignant tumours and leukemia in an animal, e.g., a mammal, which comprises administering to the animal a therapeutically effective amount of a compound or salt of the present invention. In the alternative, there is also provided a compound or salt of the present invention for use in medicine and in particular for use in the treatment of a neoplastic growth, e.g., malignant tumours.

The present invention also provides the use of a compound of formula (I) or a salt thereof for the manufacture of a medicament for the treatment of neoplastic growth.

The animal requiring treatment with a compound or salt of the present invention is usually a mammal, such as a human being.

Particular examples of a neoplastic growth requiring treatment include malignant tumours.

Compounds and salts of the formula (I) also inhibit the enzyme Thymidylate Synthase from *E. coli* and *Candida Albicans*. Therefore, compounds and salts of the present invention may be of use in the treatment of bacterial and fungal infections in mammals.

The route by which the compound or salt of the present invention is administered to the animal may be oral, topical, parenteral (including subcutaneous, intradermal, intramuscular, intravenous or rectal). If the compound or salt is presented in the form of a pharmaceutical formulation, which, as mentioned hereinbefore, is preferred, then the actual formulation employed will of course depend on the route of administration elected by the physician or veterinarian. For example, if oral administration is preferred, then the pharmaceutical formulation employed is, preferably, one which is suitable for such a route.

A therapeutically effective amount of a compound or salt of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of the present invention for the treatment of neoplastic growth, for example colon or breast carcinoma will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt of the present invention may be determined as a proportion of the effective amount of the compound par se.

An effective amount of a compound of the present invention for the treatment of disorders of the immune system (e.g. rheumatoid arthritis and tissue rejection) and related diseases such as psoriasis, will generally be in the range of 0.07–10 mg/kg body weight of recipient (mammal) per day. Thus for a 70 kg adult human, the actual amount per day would usually be from about 5–700 mg per day and this amount may be given in a single dose per day, or more usually dosing would be intermittent e.g. at 12 hourly intervals or weekly. An effective amount of a salt of the present invention may be determined as a proportion of the effective amount of the compound per se.

The treatment of neoplastic growth with a compound of the present invention may at times require the administration to the animal of an antidote or rescue agent, e.g. thymidine.

The following examples illustrate the preparation of compounds of the present invention, their pharmacological properties and formulations containing them.

EXAMPLE A

Alkyl 3,4-dihydro-2-hydroxy-1-naphthoates were prepared by reaction of sodium enolates of the starting 2-tetralones with dimethyl or diethyl carbonate in the presence or absence or a co-solvent such as toluene. For example,

Methyl 7-bromo-3,4-dihydro-2-hydroxy-1-naphthoate

To a refluxing stirred suspension of sodium hydride (5.6 g of 80% in oil, 187 mmoles) in dry dimethyl carbonate (120 ml) under a nitrogen atmosphere was added a solution of 7-bromo-2-tetralone (14 g, 61 mmoles) in dry dimethyl carbonate (60 ml) dropwise over 40 minutes. Refluxing was continued for an additional 45 minutes and then cooled to room temperature. The reaction was carefully quenched with glacial acetic acid, diluted with one volume of water and extracted with ethyl acetate (150 ml). The organic phase was dried over magnesium sulfate, filtered and evaporated under reduced pressure to leave a residue which was purified using silica gel column chromatography eluting with ethyl acetate:hexane (39:7) to give methyl 7-bromo-3,4-dihydro-2-hydroxy-1-naphthoate as a white solid. (15.2 g, 86%).

The following 3,4-dihydro-2-hydroxy-1-naphthoates were prepared using the procedure described above without significant modification: methyl, ethyl 4-methyl, methyl 5-fluoro, ethyl 5-chloro, methyl 5-bromo, ethyl 5-iodo, ethyl-5-methyl-, ethyl 5-phenyl-, ethyl 6-fluoro-, ethyl 6-chloro-, ethyl 6-bromo-, ethyl 7-fluoro, ethyl 7-chloro, ethyl 7-bromo-, ethyl 7-iodo-, ethyl-7-methyl-, ethyl 7-phenyl-, methyl 7-ethoxy-, methyl 7-methylthio-, methyl 7-ethylthio-, ethyl 8-chloro-, ethyl-4,4-dimethyl-, ethyl-5,7-dimethyl-, ethyl 6,7-dichloro-, ethyl 6,7-dimethoxy-, ethyl 6-chloro-4-methyl-, and ethyl 7-chloro-3,4-dihydro-2-hydroxy-4-methyl-1-naphthoate.

The following 2-tetralones were obtained from commercial suppliers 2-tetralone; 5-methoxy-2-tetralone; 6-methoxy-2-tetralone; 7-methoxy-2-tetralone; and 6,7-dimethoxy-2-tetralone.

Other 2-tetralones were obtained by one or two methods A) from the corresponding 1-tetralones by a four-step carbonyl transposition sequence[1], or B) from appropriately substituted phenylacetic acids by cyclization of the corresponding acid chlorides with ethylene or propylene under Friedel-Crafts conditions[2]. For example:

Method A

4,4-Dimethyl-2-tetralone

To a stirred suspension of sodium borohydride (3.5 g, 93 mmoles) in dry methanol (50 ml) at 0° C. under a nitrogen atmosphere was added a solution of 4,4-dimethyl-1-tetralone (10 g, 57.4 mmoles) in dry methanol:toluene (1:3) dropwise over a 45 minute period. After this time the mixture was allowed to warm to room temperature, and then two volumes of water were added. After stirring for 1 hour, the organic layer was separated, dried over magnesium sulfate, filtered, and evaporated under reduced pressure to leave a light yellow oil. This was purified by silica gel column chromatrography eluting with ethyl acetate:hexane (1:9) to give 1,2,3,4-tetrahydro-4,4-dimethyl-1-naphthol as a colorless oil. (9.89 g, 98%).

A mixture of 1,2,3,4-tetrahydro-4,4-dimethyl-1-naphthol (9.6 g, 54.5 mmoles) in 20% aqueous oxalic acid was stirred and heated to reflux for 5 hours. After cooling, the reaction mixture was diluted with one volume of water and then extracted with one volume of ether. The aqueous layer was extracted again with one volume of ethyl acetate and the combined organic phases were dried over magnesium sulfate, filtered, and evaporated under reduced pressure to leave an oil which was purified using silica gel column chromatography, eluting with ethyl acetate:hexane (0.1:49.9) to give 1,2-dihydro-1,1-dimethylnaphthalene as a colorless oil. (4.76 g, 55%).

To a stirred mixture of 30% hydrogen peroxide (5 ml) and 97% formic acid (20 ml) in a round bottom flask equipped with an additional funnel, thermometer, and an ice water bath was added 1,2-dihydro-1,1-dimethylnaphthalene (4.5 g, 28 mmoles) dropwise at 5° C. under a nitrogen atmosphere. When the addition was complete, the reaction vessel was raised above the cooling bath to allow the reaction temperature to rise to just between 35° C. at which point the flask was immersed again. In this manner the temperature of the reaction was maintained between 30 and 35° C. for 45 minutes. After this time the exothermic phase of the reaction ended and the mixture was allowed to cool to room temperature. A solution of 10% aqueous ferric sulfate was added in portions of a few milliliters each until cloudiness persisted in the stirred mixture and then all solvent was removed under reduced pressure. The viscous brown residue was refluxed with 20% $H_2SO_4$ (20 ml) for 4 hours and then cooled, extracted three times with ether (75 ml each), dried over magnesium sulfate, filtered and evaporated to leave a brown oil. This was purified using silica gel column chromatography eluting with ethyl acetate:hexane (7:93) to give 4,4-dimethyl-2-tetralone. (3.4 g, 74%). Overall yield=40%.

Using method A, 4-methyl-2-tetralone and 5,7-dimethyl-2-tetralone were also prepared.

Method B

6-Bromo-2-tetralone

A mixture of oxalyl chloride (10 g) and 4-bromophenylacetic acid[3] (25 g, 11.6 mmoles) was stirred under a nitrogen atmosphere at room temperature for 2 hours and then refluxed for 4 hours more. After cooling, the excess oxalyl chloride was removed by evaporation under reduced pressure to give crude 4-bromophenylacetyl chloride as a light yellow oil which was not purified further.

To a two-liter round bottom flask equipped with a gas inlet tube connected to an external tank of ethylene, an addition funnel containing a solution of the crude 4-bromophenylacetyl chloride described above in methylene chloride (75 ml), a thermometer, a gas inlet adapter connected to a bubbler and a positive nitrogen flow, and a heavy-duty magnetic stirrer was added dry methylene chloride (1000 ml) and aluminum chloride (56 g, 0.42 mole). The stirred suspension was cooled to –10° C. using an ice/salt bath, and ethylene was introduced through the gas inlet tube, which was positioned just above the vortex. Dropwise addition of the phenylacetyl chloride solution was started at a moderate rate, and adjusted periodically so that the reaction temperature stayed below 0° C. Ethylene flow was continued for 30 minutes after addition of the acid chloride solution was complete, and then reaction mixture was poured over 2000 ml of ice, stirred vigorously for a few minutes, and left to sit until the ice melted. The methylene chloride layer was separated and the aqueous layer was extracted three times with methylene chloride (100 ml each). Combined methylene chloride layers were filtered through a short silica gel plug and then evaporated under reduced pressure to leave an amber-colored oil, which was purified using silica gel column chromatrography, eluting with ethyl acetate:hexane (35:65) to give 6-bromo-2-tetralone as an amber crystalline solid. (25 g, 95%).

The following 2-tetralones were also prepared using method B 5-fluoro-, 5-chloro-, 5-bromo-, 5-iodo-, 5-methyl-, 5-phenyl-, 6-fluoro-, 6-chloro-, 7-fluoro-, 7-chloro-, 7-bromo-, 7-iodo-, 7-methyl-, 7-phenyl-, 7-ethoxy-, 7-methylthio-, 7-ethylthio-, 8-chloro-, 6,7-dichloro-, 6-chloro-4-methyl-, and 7-chloro-4-methyl-2-tetralone.

1. J. Vebrel and R. Carrie, *Bull. Soc. Chim. Fr.,*
2. J. H. Burkhalter and J. R. Campbell, *J. Org. Chem.*, 26, 4932, 1961.
3. 3-substituted phenylacetic acids led to mixtures of 5- and 7-substituted 2-tetralones which were separable by silica gel column chromatography or recrystallization from ether:hexane or ethyl acetate:hexane solvent mixtures.

The phenylacetic acids required for the syntheses of the 2-tetralones were generally commercially available. The following exceptions (3-ethoxy-, 3-ethylthio-, 3-methylthio- and 3-phenylphenylacetic acids) were synthesized as indicated below.

3-Ethoxyphenylacetic acid

A. Methyl 3-ethoxyphenylacetate

Methyl 3-hydroxyphenylacetate (132.5 g, 0.80 mole) was added dropwise to a suspension of 50% NaH (43.2 g, 0.90 mole) in DMF (ie) at 0° C. under $N_2$. The solution was stirred 1 hour at room temperature, cooled in an ice bath, and ethyl bromide (120 ml, 1.6 mole) added. The reaction mixture was stirred overnight at room temperature, filtered, and concentrated in vacuo. A solution of the residue in diethyl ether was washed with dilute NaOH solution and saturated NaCl, dried ($Na_2SO_4$) and concentrated in vacuo. The residue was purified by chromatography on silica gel eluting with ethyl acetate:hexane (1:39→1:9) to give methyl 3-ethoxyphenylacetate (94.9 g). $^1$H NMR (DMSO-$d_6$, 200 MHz) δ: 1.30 (t, J=7 Hz, 3H, ethyl$CH_3$), 3.59 (s, 3H, ester$CH_3$), 3.61 (s, 2H, Ar$CH_2$), 3.98 (q, J=7 Hz, 2H, ethyl$CH_2$), 6.78–6.81 (m, 3H), 7.16–7.24 (m, 1H).

B. 3-Ethoxyohenylacetic acid

A solution of methyl 3-ethoxyphenylacetate (92.6 g, 0.4 mole) in methanol (600 ml) and 6.25 N NaOH (400 ml) was stirred overnight at room temperature and then filtered and concentrated in vacuo to remove the methanol. The solution was adjusted to pH 1 with concentrated HCl, the resulting precipitate filtered, washed with ice water, and dried under high vacuum to give 3-ethoxyphenyl acetic acid (74.5 g). M.p=89–90° C. $^1$H NMR (DMSO-$d_6$, 200 MHz) δ: 1.30 (6, J=7 Hz, 3H, $CH_3$), 3.50 (s, 2H, Ar$CH_2$), 3.98 (q, J=7 Hz, 2H, ethyl$CH_2$), 6.75–6.80 (m, 3H, Ar), 7.14–7.23 (m, 1H, Ar). (Lit. ref.: J. Med. Chem, 1980, 23(4) 437–444.

2-(3-Biphenylyl)acetic acid

A. 2-(3-Biphenylyl)ethanol

To a solution of 3-bromobiphenyl (18 g, 77 mmol) in diethyl ether (150 ml) under $N_2$ cooled to −78° C. was added 1.6 M t-butyl lithium in pentane (100 ml, 0.16 mole) via cannula over a 15 minute period. The solution was stirred 30 minutes at −78° C., ethylene oxide (9 g, 0.2 mole added and the reaction mixture allowed to warm to room temperature over a 1 hour period. The solution was boiled briefly to drive off excess ethylene oxide, transferred to a separatory funnel, a small volume of water added, and neutralized with concentrated HCl. The organic solution was dried (MgSO$_4$), concentrated in vacuo and the residue purified by chromatography on silica gel eluting with ethyl acetate:hexane (1:4) to give 2-(3-biphenylyl)ethanol (10.5 g). $^1$H NMR (CDCl$_3$, 60 MHz) δ: 2.81 (t, J=7 Hz, 2H, $CH_2$), 3.76 (t, J=7 Hz, 2H, $CH_2$), 6.95–7.70 (m, 9H, Ar).

B. 2-(3-Biphenylyl)acetic acid

To a stirred solution of 2-(3'-biphenyl)ethanol (10.5 g, 53.0 mmol) in acetone (100 ml) at 0° C. was added 3N chromium trioxide in dilute sulphuric acid (~20 ml) portion wise over a 30 minute period until the orange color persisted. The mixture was stirred for 20 minutes, ethanol added to destroy the excess of oxidant and the solution concentrated in vacuo. The residue was taken up in ethyl acetate-diethyl ether (250 ml), washed with water and saturated brine, dried (MgSO$_4$) and concentrated in vacuo. The residue was purified by chromatography on silica gel eluting with ethyl acetate:hexane (2:3) to give 2-(3-biphenylyl) acetic acid (3.35 g). $^1$H NMR (CDCl$_3$, 60 MHz) δ: 3.61 (s, 2H, CH$_2$), 7.00–7.65 (m, 9H, Ar).

3-Ethylthiophenylacetic acid

To a solution of methyl 3-aminophenylacetate (102 g, 0.62 mole) in 1N HCl (1600 ml) cooled in an ice bath was added NaNO$_2$ (42.7 g, 0.62 mole) portionwise and the solution stirred for 20 minutes. A solution of potassium ethanethiolate was prepared by adding ethanethiol (202 ml, 2.73 mole) dropwise over 10 minutes to a solution of 87.5% KOH (159 g, 2.48 mole) in water (1.2 l) at 0° C. The diazonium salt solution was then added via cannula to the solution of potassium ethanethiolate and the reaction mixture was stirred 30 minutes in an ice bath. Diethyl ether (~1.5 l) was added and the mixture was stirred 1.5 hours at room temperature. The ether layer was separated, the aqueous phase further extracted with diethyl ether (3×700 ml), and the combined ether solutions concentrated. The residue was eluted from silica gel with ethyl acetate:hexane (1:19) to give a mixture of methyl 3-ethylthiophenylacetate $^1$H NMR (DMSO-$d_6$, 200 MHz) δ: 1.21 (t, J=7 Hz, 3H, ethyl$CH_3$), 2.95 $CH_2$), 3.60 (s, 3H, O$CH_3$), 3.65 (s, 2H, Ar$CH_2$), 7.02–7.44 (m, Ar), and methyl phenylacetate (85.9 g). The esters (84 g) were hydrolyzed in a solution of methanol (500 ml) and 6.25 N NaOH (100 ml) stirred overnight at room temperature. The solution was concentrated in vacuo to remove the methanol, the remaining solution acidified with concentrated HCl and the resulting solid was extracted into diethyl ether. The ether solution was washed with brine (3×100 ml), dried (Na$_2$SO$_4$) and concentrated. Vacuum distillation (0.5 mm Hg) gave a distillate (100–115° C.) of phenylacetic acid and a residue of 3-ethylthiophenylacetic acid. The residue in the flask solidified upon cooling to give 3-ethylthiophenylacetic acid (49.8 g). Mp=49–51° C. $^1$H NMR (DMSO-$d_6$, 200 MHz) δ: 1.21 (t, J=7 Hz, 3H, CH$_3$), 2.95 (q, J=7 Hz, 2H, SCH$_2$), 3.54 (s, 2H, ArCH), 7.01–7.28 (m, 4H, Ar), 12.33 (br s, 1H, CO$_2$H). Mass spectrum (CI-CH$_4$): 197 (M+1, 100%).

3-Methylthiophenylacetic acid

Prepared in an essentially similar fashion from methyl 3-aminophenyl-acetate (11 g, 0.67 mole) and potassium methanethiolate (2.68 mole) to give 3-methylthiophenylacetic acid (21.0 g). Mp=76–77° C., $^1$H NMR (DMSO-$d_6$, 200 MHz) δ: 2.44 (s, 3H, SCH$_3$), 3.53 (s, 2H, ArCH$_2$), 7.02–7.28 (m, 4H, Ar), 12.30 (br s, 1H, CO$_2$H). Mass spectrum (CI-CH$_4$): 183 (M+1, 100%). (Lit. ref.: Plant Physiol 42(11) 2596–1600 (1967).

The intermediate 7-ethynyl-2-tetralone for the synthesis of 3-amino-5,6-dihydro-9-ethynylbenzo[f]quinazolin-1 (2H)-one was synthesized as described below.

7-Ethynyl-2-tetralone

A. 7'-Bromo-3',4'-dihydrospiro[1,3-dioxolane-2,2'(1'H)-naphthalene]

A solution of 7-bromo-2-tetralone (1.1 g, 4.9 mmol), ethylene glycol (0.62 g, 10 mmol), and p-toluensulfonic acid (80 mg, 0.42 mmol) in benzene (20 ml) was stirred under $N_2$ at reflux utilizing a Dean-Stark trap for 45 minutes. The cooled solution was diluted with diethyl ether (60 ml), washed with saturated NaHCO$_3$ solution (2×10 ml), dried (MgSO$_4$) and concentrated in vacuo to give 7'-bromo-3',4'- dihydrospiro[1,3-dioxolane-2,2'(1'H)-naphthalene] as an oil (1.2 g). $^1$H NMR (CDCl$_3$, 200 MHz) δ: 1.95 (t, J=7 Hz, 2H, CH$_2$), 2.91 (t, J=7 Hz, 2H, CH$_2$), 2.95 (s, 2H, CH$_2$), 4.01 (s, 4H, OCH$_2$CH$_2$O), 6.97 (d, J=8 Hz, 1H, Ar), 7.15–7.27 (m, 2H, Ar).

B. 3'4'-Dihydro-7'-[2-trimethylsilyl)ethynyl]spiro[1,3-dioxolane-2,2'(1'H)-naphthalene]

A solution of 7'-bromo-3',4'-dihydrospiro[1,3-dioxolane-2,2'(1H)-naphthalene] (3.40 g, 12.6 mmol), trimethylsilylacetylene (7.0 ml, 50 mmol) (Aldrich), triphenylphosphine (0.66 g, 2.50 mmol), and palladium acetate (0.28 g, 1.25 mmol) in triethylamine (18 ml) was stirred at 70° C. for 18 hours and then concentrated in vacuo. The residue was absorbed onto silica gel from a diethyl ether solution and partially purified by elution through silica gel (15 g) with diethyl ether:hexane (1:9). Further purification by chromatography on silica gel eluting with ethyl acetate:hexane (1:19) gave 3',4'-dihydro-7'[2-(trimethylsilyl)-ethynyl]spiro[1,3-dioxolane-2,2'(1'H)-naphthalene] (1.45 g). $^1$H NMR (CDCl$_3$ 200 MHz) δ: 0.23 (s, 9H, SiMe$_3$), 1.93 (t, J=7 Hz, 2CH$_2$), 2.95 (t, J=7 Hz, 2H, CH$_2$), 4.02 (s, 4H, OCH$_2$CH$_2$O), 7.03 (d, J=8 Hz, 1H, Ar), 7.17 (s, 1H, Ar), 7.21 (d, J=8 Hz, 1H, Ar).

C. 7'-Ethynyl-3',4'-dihydrospiro[1,3-dioxolane-2,2'(1'H)-naphthalene]

A solution of 3',4'dihydro-7'[2-(trimethylsilyl)ethynyl]spiro[1,3-dioxolane-2,2'(1'H)-naphthalene] (1.45 g, 5.02 mmol) and suspended K$_2$CO$_3$ (0.50 g) in methanol (20 ml) was stirred at room temperature for 30 minutes. The solution was then filtered and concentrated in vacuo. The residue was absorbed onto silica gel (2 g) and purified by chromatography on silica gel (11 g) eluting with diethyl ether:hexane (1:9) to give 7'-ethynyl-3',4'-dihydrospiro[1,3-dioxolane-2,2'(1'H)-naphthalene] as a solid (0.85 g). $^1$H NMR (CDCl$_3$, 200 MHz) δ: 1.94 (t, J=7 Hz, 2H, CH$_2$), 2.95 (s, 2H, CH$_2$), 2.98 (t, J=7 Hz, 2H, CH$_2$), 3.01 (s, 1H, ethynylH), 4.02 (s, 4H, OCH$_2$CH$_2$O), 7.07 (d, J=8 Hz, 1H, Ar), 7.19 (s, 1H, Ar), 7.24 (d, J=8 Hz, 1H, Ar).

D. 7-Ethynyl-2-tetralone

A solution of 7'-ethynyl-3',4'-dihydrospiro[1,3-dioxolane-2,2'(1'H)naphthalene] (0.85 g, 3.9 mmol) in THF (15 ml) and 1N HCl (5 ml) was stirred overnight at room temperature. Concentrated HCl (2×0.5 ml) was then added in two aliquots 2 hours apart. After stirring a further 2 hours the solution was diluted with diethyl ether, the aqueous phase was separated, and the solution dried (MgSO$_4$) and concentrated in vacuo. The residue was purified by chromatography on silica gel (15 g) eluting with diethyl ether:hexane (1:9→1:4) to give 7-ethynyl-2-tetralone as a solid (0.31 g). $^1$H NMR (CDCl$_3$, 200 MHz) δ: 2.54 (t, J=7 Hz, 2H, CH$_2$), 3.05 (s, 1H, ethynylH), 3.06 (t, J=7 Hz, 2H, CH$_2$), 3.56 (s, 2H, CH$_2$), 7.18 (d, J=8 Hz, 1H, Ar), 7.26 (s, 1H, Ar), 7.34 (d, J=8 Hz, 1H, Ar).

EXAMPLE 1

3-Amino-9-bromo-5,6-dihydrobenzo[f]quinazolin-1(2H)-one

A solution of sodium ethoxide was prepared by adding freshly cut sodium (2.72 g, 118 mmoles) to absolute ethanol (350 ml). Guanidine hydrochloride (11.3 g, 118 mmoles) was added and the mixture was stirred and heated to reflux under a nitrogen atmosphere. A solution of ethyl 7-bromo-3,4-dihydro-2-hydroxy-1-naphthoate (11.72 g, 39.4 mmoles) in absolute ethanol (75 ml) was added dropwise over 2.5 hours. Refluxing was continued for an additional 21.5 hours, after which time the mixture was cooled to room temperature and filtered. Ethanol was evaporated under reduced pressure to give a yellow-colored foam which was dissolved in 0.1 N NaOH (100 ml). The basic solution was extracted with ether and neutralized with acetic acid: water (1:9) to cause precipitation of the product. The precipitate was collected, washed with water and ether, and dried to give 3-amino-9-bromo-5,6-dihydrobenzo[f]quinazolin-1(2H)-one as an off-white powdery solid. (6.45 g, 53%) $^1$H NMR (DMSO-d$_6$, 80 MHz) δ: 2.45–2.90 (m, 4H, CH$_2$CH$_2$); 6.80 (br s, 2H, NH$_2$); 7.03–7.29 (m, 2H, ArH); 8.60–8.75 (m, 1H, Ar); 11.0 (br s, 1H, NH). Anal. Calculated for C$_{12}$H$_{10}$BrN$_3$O.H$_2$O C, 46.47; H, 3.90; Br, 25.76; N, 13.55. Found: C, 46.58; H, 3.85; N, 13.60; Br, 25.87.

The following compounds were prepared from appropriately substituted methyl or ethyl 3,4-dihydro-2-hydroxy-1-naphthoates, using the procedure described in the above example without significant modification:

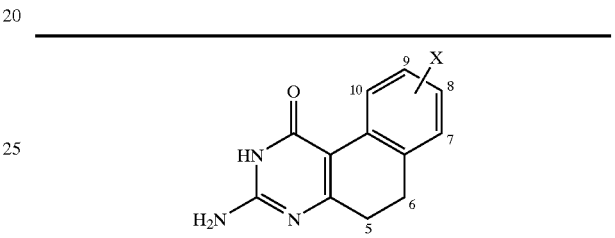

| X | $^1$HNMR (200 MHz)$^a$ in DMSO-d$_6{}^a$, (δ) |
|---|---|
| 6-CH$_3$ | $^b$1.26(d, J=6.8Hz, 3H, CH$_3$); 2.62(dd, J=16.9, 6.4Hz, 1H, H$^5$); 3.01(dd, J=16.5, 6.1Hz, H$^5$); 3.11(m, 1H, H$^6$); 7.21–7.29(m, 3H, Ar); 8.25–8.28(m, 1H, Ar). |
| 7-F | 2.48–2.63(m, 2H, CH$_2$); 2.70–2.84(m, 2H, CH$_2$); 6.72(br s, 2H, NH$_2$); 6.88(ddd, J=8, 8, 2Hz, 1H, Ar); 7.14(ddd, J=8, 8, 6Hz, 1H, Ar); 8.30(d, J=8Hz, 1H, Ar); 10.93(br s, 1H, NH). |
| 7-Cl | 2.56(m, 2H, CH$_2$); 2.88(m, 2H, CH2); 6.71(s, 2H, NH2); 7.14(d, J=4Hz, 2H, Ar); 8.45(t, J=4Hz, 1H, Ar); 10.92(s, 1H, NH). |
| 7-Br | $^c$2.5–3.0(m, 4H[partially obscured by DMSO], CH$_2$CH$_2$); 6.78(br s, 2H, NH$_2$); 6.99–7.40(m, 2H, Ar); 8.46–8.57(m, 1H, Ar); 11.1(br s, 1H, NH). |
| 7-I | 2.50–2.58(m, 2H, CH$_2$); 2.79–2.88(m, 2H, CH$_2$); 6.73(br s, 2H, NH$_2$); 6.89(t, J=8Hz, 1H, Ar); 7.55(dd, 8, 1Hz, 1H, Ar); 8.49(dd, J=8, 1Hz, 1H, Ar); 10.96(br s, 1H, NH). |
| 7-CH$_3$ | 2.22(s, 3H, CH$_3$); 2.46–2.55(m, 2H, CH$_2$); 2.65–2.73(m, 2H, CH$_2$); 6.60(s, 2H, NH$_2$); 6.90(m, 1H, Ar); 7.00(t, J=7.6Hz, 1H, Ar); 8.29(d, J=7.5Hz, 1H, Ar); 10.85(br s, 1H, NH). |
| 7-phenyl | 2.39–2.72(m, 4H, CH$_2$CH$_2$); 6.68(br s, 2H, NH$_2$); 7.00(dd, J=7.8, 1Hz, 1H, Ar); 7.20(t, J=7.8Hz, 1H, Ar); 7.30–7.47(m, 5H, Ar); 8.45(d, J=7.7Hz, 1H, Ar). |
| 8-F | 2.53(m, 2H, CH$_2$); 2.77(m, 2H, CH$_2$); 6.65(br s, 2H, NH$_2$); 6.87–7.01(m, 2H, Ar); 8.45(dd, J=8.5, 6.3Hz, 1H, Ar); 10.93(br s, 1H, NH). |
| 8-Cl | 2.54(m, 2H, CH$_2$); 2.77(m, 2H, CH$_2$); 6.72(br s, 2H, NH$_2$); 7.17(d, J=8.2Hz, 1H, Ar); 7.19(s, 1H, Ar); 8.45(d, J=8.2Hz, 1H, Ar); 10.98(br s, 1H, NH). |
| 8-Br | 2.55(t, J=7.5Hz, 2H, CH$_2$); 2.79(t, J=7.4Hz, 2H, CH$_2$); 6.75(br s, 2H, NH$_2$); 7.32(dd, J=8.4, 2.3Hz, 1H, Ar); 7.34(s, 1H, Ar); 8.40(d, J=8.4Hz, 1H, Ar); 11.00(br s, 1H, NH). |
| 9-F | 2.54–2.77(m, 4H, CH$_2$CH$_2$); 6.70–6.86(m, 3H, NH$_2$ + Ar); 7.10–7.16(m, 1H, Ar); 8.21–8.27(m, 1H, Ar). |
| 9-I | 2.47–2.75(m, 4H[partially obscured by DMSO], CH$_2$CH$_2$); 6.74(br s, 2H, NH$_2$); 6.93(d, J=8.0Hz, 1H, Ar); 7.36(dd, J=8.0, 1.9Hz, 1H, Ar); 8.81(d, J=1.9Hz, 1H, Ar); 11.00(br s, 1H, NH). |
| 9-CH$_3$ | 2.23(s, 3H, CH$_3$); 2.47–2.56(m, 2H, CH$_2$); 2.65–2.73(m, 2H, CH$_2$); 6.61(br s, 2H, NH$_2$); 6.82(dd, J=7.5, 1.2Hz, 1H, Ar); 6.99(d, J=7.4Hz, 1H, Ar); 8.23(d, J=1.2Hz, 1H, Ar); 10.85(br s, 1H, NH). |

-continued

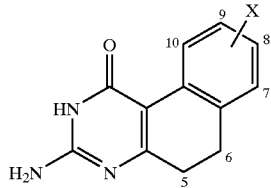

| X | ¹HNMR (200 MHz)[a] in DMSO-d₆[a], (δ) |
|---|---|
| 9-ethynyl | 2.45–2.63(m, 2H, CH₂); 2.68–2.85(m, 2H, CH₂); 4.01(s, 1H, CH); 6.71(br s, 2H, NH₂); 7.13(s, 2H, Ar); 8.57(s, 1H, Ar); 10.99(br s, 1H, NH). |
| 9-phenyl | 2.57–2.84(m, 4H, CH₂CH₂); 6.70(br s, 2H, NH₂); 7.23(d, J=7.8Hz, 1H, Ar); 7.31–7.36(m, 2H, Ar); 7.46(t, J=7.8Hz, 2H, Ar); 7.59(d, J=7.1Hz, 2H, Ar); 8.79(d, J=2Hz, 1H, Ar); 10.95(br s, 1H, NH). |
| 9-OC₂H₅ | 1.29(t, J=7Hz, 3H, CH₃); 2.43–2.60(m, 2H, ArCH₂); 2.60–2.75(m, 2H, ArCH₂); 3.93(q, J=7Hz, 2H, OCH₂); 6.60(dd, J=8, 3Hz, 1H, Ar); 6.64(br s, 2H, NH₂); 6.99(d, J=8Hz, 1H, Ar); 8.09(d, J=3Hz, 1H, Ar). |
| 9-SCH₃ | 2.42(s, 3H, CH₃); 2.46–2.59(m, 2H, CH₂); 2.64–2.78(m, 2H, CH₂); 6.68(br s, 2H, NH₂); 6.93(dd, J=8, 2Hz, 1H, Ar); 7.07(d, J=8Hz, 1H, Ar); 8.43(d, J=2Hz, 1H, Ar); 10.91(br s, 1H, NH). |
| 9-SC₂H₅ | 1.21(t, J=7Hz, 3H, CH₃); 2.48–2.60(m, 2H, ArCH₂); 2.55–2.69(m, 2H, ArCH₂); 2.88(q, J=7Hz, 2H, SCH₂); 6.65(br s, 2H, NH₂); 7.00(dd, J=8, 2Hz, 1H, Ar); 7.07(d, J=8Hz, 1H, Ar); 8.47(d, J=2Hz, 1H, Ar). |
| 10-Cl[c] | 2.50–2.94(m, 4H[partially obscured by DMSO], CH₂CH₂); 6.75(br s, 2H, NH₂); 7.16(m, 2H, Ar); 8.47(m, 1H, Ar); 10.97(br s, 1H, NH). |
| 6,6-(CH₃)₂ | 1.18(s, 6H, (CH₃)₂); 2.45(s, 2H, CH₂); 6.63(br s, 2H, NH₂); 7.03–7.16(m, 2H, Ar); 7.23–7.31(m, 1H, Ar); 8.47–8.54(m, 1H, Ar); 10.89(br s, 1H, NH). |
| 6-CH₃-8-Cl | 1.12(d, J=7Hz, 3H, CH₃); 2.35(dd, J=16.2, 6.6Hz, 1H, C⁵H); 2.72(dd, J=16.1, 5.9Hz, 1H, C⁵H); 2.95(m, 1H, C⁶H); 6.69(br s, 2H, NH₂); 7.17(dd, J=9, 2Hz, 1H, Ar); 7.19(s, 1H, Ar); 8.49(d, J=9Hz, 1H, Ar); 10.96(br s, 1H, NH). |
| 6-CH₃-9-Cl | 1.10(d, J=7Hz, 3H, CH₃); 2.35(dd, J=16, 7Hz, 1H, C⁵H); 2.72(dd, J=16, 6Hz, 1H, C⁵H); 2.94(m, 1H, C⁶H); 6.75(br s, 2H, NH₂); 7.08(dd, J=8, 2Hz, 1H, Ar); 7.16(d, J=8Hz, 1H, Ar); 8.54(d, J=2Hz, 1H, Ar); 11.01(br s, 1H, NH). |
| 7,8-benzo | 2.65(m, 2H, CH₂); 3.19(m, 2H, CH₂); 6.72(br s, 2H, NH₂); 7.37–7.48(m, 2H, Ar); 7.69(d, J=8.8Hz, 1H, Ar); 7.81(d, J=8.0Hz, 1H, Ar); 8.06(d, J=8.4Hz, 1H, Ar); 8.68(d, J=8.8Hz, 1H, Ar); 10.96(br s, 1H, NH). |
| 7,9-(CH₃)₂ | [b]2.23(s, 3H, CH₃); 2.25(s, 3H, CH₃); 2.77–2.91(m, 4H, CH₂CH₂); 6.99(s, 1H, Ar); 7.89(s, 1H, Ar). |
| 8,9-Cl₂ | 2.47–2.82(m, 4H[partially obscured by DMSO], CH₂CH₂); 6.82(br s, 2H, NH₂); 7.40(s, 1H, Ar); 8.67(s, 1H, Ar); 11.09(br s, 1H, NH). |
| 8,9-(OCH₃)₂ | [d]2.53(m, 2H, CH₂); 2.71(m, 2H, CH₂); 3.71(s, 3H, CH₃); 3.74(s, 3H, CH₃); 6.58(br s, 2H, NH₂); 6.78(s, 1H, Ar); 8.21(s, 1H, Ar); 10.82(br s, 1H, NH). |

All compounds gave elemental analyses consistent with the indicated structures.
[a]Except where indicated.
[b]TFA-d, 300 MHz
[c]80 MHz
[d]300 MHz

EXAMPLE 2

3-Amino-9-bromobenzo[f]quinazolin-1(2H)-one

A. N-(9-Bromo-1,2,5,6-tetrahydro-1-oxobenzo[f]quinazolin-3-yl)pivalamide

3-Amino-9-bromo-5,6-dihydrobenzo[f]quinazolin-1(2H)-one (5.83 g, 20 mmoles) and pivalic anhydride (200 ml) were stirred and heated to 185° C. under a nitrogen atmosphere for 1 hour. After cooling, excess pivalic anhydride was evaporated under reduced pressure. The residue was triturated with ether:hexanes (1:1) (200 ml), filtered and dried to give N-(9-bromo-1,2,5,6-tetrahydro-1-oxo-benzo[f]quinazolin-3-yl)pivalamide as an off-white solid. (6.1 g, 81%). ¹H NMR (DMSO-d₆, 300 MHz) δ: 1.23 (s, 9H, t-butyl); 2.73–2.85 (m, 4H, CH₂CH₂); 7.18 (d, J=8.1 Hz, 1H, Ar); 7.34 (dd, J=7.8, 2.1 Hz, 1H, Ar); 8.70 (d, J=2.0 Hz, 1H, Ar); 11.35 (br s, 1H, NH).

B. N-(9-Bromo-1,2-dihydro-1-oxobenzo[f]quinazolin-3-yl) pivalamide

A mixture of N-(9-bromo-1,2,5,6-tetrahydro-1-oxobenzo [f]quinazolin-3-yl)pivalamide (1.09 g, 2.9 mmoles) and pyridine (0.28 ml, 3.5 mmoles) in dry benzene (100 ml) was stirred and heated to reflux under a nitrogen atmosphere. N-Bromosuccinimide (0.57 g, 3.2 mmoles) was added in a single portion, and the mixture was vigorously stirred and refluxed for 1.5 hours. After cooling, benzene and excess pyridine were removed under reduced pressure, leaving a light yellow residue which was then triturated with methanol:methylene chloride (1:1), filtered and dried to give N-(9-bromo-1,2-dihydro-1-oxobenzo[f]quinazolin-3-yl) pivalamide. (0.4 g, 37%) ¹H NMR (DMSO-d₆, 200 MHz) δ: 1.26 (s, 9H, t-butyl); 7.58 (d, J=9.0 Hz, 1H, Ar); 7.74 (dd, J=8.7, 2.1 Hz, 1H, Ar); 7.98 (d, J=8.8 Hz, 1H, Ar); 8.25 (d, J=9.0 Hz, 1H, Ar); 9.92 (d, J=2.0 Hz, 1H, Ar); 11.35 (br s, 1H, NH); 12.35 (br s, 1H, NH).

C. 3-Amino-9-bromobenzo[f]quinazolin-1(2H)-one

A solution of N-(9-bromo-1,2-dihydro-1-oxobenzo[f]quinazolin-3-yl)pivalamide (0.15 g, 0.4 mmole) in 0.75 N NaOH (7 ml) was stirred and heated to 75° C. under a nitrogen atmosphere for 10.5 hours. The solution was cooled and made slightly acidic with acetic acid to cause precipitation of the product. The precipitate was collected, washed successively with water, methanol and ether, and dried to give 3-amino-9-bromobenzo[f]quinazolin 1(2H)-one as an off-white solid. (0.115 g, 99%) ¹H NMR (DMSO-d₆, 200 MHz) δ: 6.64 (br s, 2H, NH₂); 7.31 (d, J=8.8 Hz, 1H, Ar); 7.57 (dd, J=8.5, 1.9 Hz, 1H, Ar); 7.83 (d, J=8.6 Hz, 1H, Ar); 8.02 (d, J=9.0 Hz, 1H, Ar); 9.83 (s, 1H, Ar); 11.28 (br 5, 1H, NH).

The following compounds were prepared from appropriately substituted 5,6-dihydrobenzo[f]quinazolin-1(2H)-ones, using the same route described in the above example

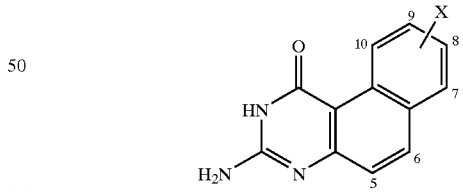

| X | ¹H NMR (200 MHz) in DMSO-d6 (δ) |
|---|---|
| 7-F | 6.64(br s, 2H, NH₂); 7.24(ddd, J=11, 8, 1Hz, 1H, Ar); 7.37(d, J=9Hz, 1H, Ar); 7.57(ddd, J=8, 8, 6Hz, 1H, Ar); 8.16(d, J=9Hz, 1H, Ar); 9.42(d, J=9Hz, 1H, Ar); 11.21(br s, 1H, NH). |
| 7-Cl | 6.64(br s, 2H, NH₂); 7.44(d, J=9.4Hz, 1H, Ar); 7.51–7.61(m, 2H, Ar); 8.31(d, J=9.4Hz, 1H, Ar); 9.67(dd, J=6.9, 2.7Hz, 1H, Ar); 11.22(br s, 2H, NH). |
| 7-Br | 6.65(s, 2H, NH₂); 7.44(d, J=9.2Hz, 1H, Ar); 7.49(t, J=7.6Hz, 1H, Ar); 7.77(dd, J=7.6, 1.1Hz, 1H, Ar); 8.29(d, J=9.3Hz, 1H, Ar); 9.73(dd, J=8.6, 0.8Hz, 1H, Ar); 11.25(br s, 1H, NH). |

-continued

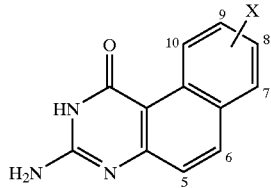

| X | $^1$H NMR (200 MHz) in DMSO-d6 (δ) |
|---|---|
| 7-I | 6.65(br s, 2H, NH$_2$); 7.31(t, J=8.0Hz, 1H, Ar); 7.41(d, J=9.2Hz, 1H, Ar); 8.04(dd, J=7.4, 1.0Hz, 1H, Ar); 8.16(d, J=9.2Hz, 1H, Ar); 9.76(d, J=8.6Hz, 1H, Ar); 11.25(br s, 1H, NH). |
| 8-F | 6.54(br s, 2H, NH$_2$); 7.35(d, J=8.8Hz, 1H, Ar); 7.47(dt, J=9.1, 2.9Hz, 1H, Ar); 7.68(dd, J=10.0, 2.9Hz, 1H, Ar); 8.01(d, J=8.8Hz, 1H, Ar); 9.68(dd, J=9.1, 6.1Hz, 1H, Ar); 11.18(br s, 1H, NH). |
| 8-Cl | 6.61(br s, 2H, NH$_2$); 7.34(d, J=8.8Hz, 1H, Ar); 7.59(dd, J=9.2, 2.2Hz, 1H, Ar); 7.98(d, J=2.2Hz, 1H, Ar); 8.00(d, J=8.8Hz, 1H, Ar); 9.62(d, J=9.2Hz, 1H, Ar); 11.23(br s, 1H, NH). |
| 9-F | 6.63(br s, 2H, NH$_2$); 7.23–7.37(m, 2H, Ar); 7.91–8.06(m, 2H, Ar); 9.34(dd, J=13.3, 2.5Hz, 1H, Ar); 11.21 (br s, 1H, NH). |
| 9-Cl | 6.62(br s, 2H, NH$_2$); 7.30(d, J=9.0Hz, 1H, Ar); 7.45(dd, J=8.5, 2.2Hz, 1H, Ar); 7.90(d, J=8.6Hz, 1H, Ar); 8.04(d, J=8.9Hz, 1H, Ar); 9.68(d, J=1.8Hz, 1H, Ar); 11.25(br s, 1H, NH). |
| 9-I | 6.61(br s, 2H, NH$_2$); 7.30(d, J=8.9Hz, 1H, Ar); 7.63–7.75(m, 2H, Ar,); 8.00(d, J=8.9Hz, 1H, Ar); 10.05(s, 1H, Ar); 11.25(br s, 1H, NH). |
| 6-CH$_3$-8-Cl | 2.62(s, 3H, CH$_3$); 6.57(br s, 2H, NH$_2$); 7.23(s, 1H, Ar); 7.60(dd, J=9.2, 2.3Hz, 1H, Ar); 7.96(d, J=2.3Hz, 1H, Ar); 9.71(d, J=9.2Hz, 1H, Ar). |
| 6-CH$_3$-9-Cl | 2.62(s, 3H, CH$_3$); 6.62(br s, 2H, NH$_2$); 7.19(s, 1H, Ar); 7.48(dd, J=8.8, 2.2Hz, 1H, Ar); 7.98(d, J=8.8Hz, 1H, Ar); 9.76(d, J=2.2Hz, 1H, Ar); 11.21(br s, 1H, NH). |
| 8,9-Cl$_2$ | 6.72(br s, 2H, NH$_2$); 7.35(d, J=9Hz, 1H, Ar); 8.02(d, J=9Hz, 1H, Ar); 8.20(s, 1H, Ar); 9.84(s, 1H, Ar); 11.38(br s, 1H, NH). |
| 8-Br-9-OC$_2$H$_5$* | 1.44(t, J=6.9Hz, 3H, CH$_3$); 4.20(q, J=7.0Hz, 2H, CH$_2$); 6.63(s, 2H, NH$_2$); 7.17(d, J=8.9Hz, 1H, Ar); 7.93(d, J=8.9Hz, 1H, Ar); 8.16(s, 1H, Ar); 9.30(s, 1H, Ar); 11.19(br s, 1H, NH). |
| 8-NO$_2$-9-Br | 6.92(br s, 2H, NH$_2$); 7.44(d, J=9Hz, 1H, Ar); 8.20(d, J=9Hz, 1H, Ar); 8.72(s, 1H, Ar); 10.05(s, 1H, Ar); 11.5(br s, 1H, NH). |

*Prepared by bromination in situ of the corresponding 9-ethoxy-substituted intermediate during the NBS-aromatization step.

All compounds gave elemental analyses consistent with the indicated structures.

EXAMPLE 3

9-Bromo-5,6-dihydro-3-methylbenzo[f]quinazolin-1(2H)-one

A solution of sodium ethoxide was prepared by adding freshly cut sodium (0.73 g, 32 mmoles) to absolute ethanol (40 ml). Acetamidine hydrochloride (3.2 g, 34 mmoles) was added and the mixture was stirred and heated to reflux under a nitrogen atmosphere. A solution of methyl 7-bromo-3,4-dihydro-2-hydroxy-1-naphthoate (2.98 g, 10.5 mmoles) in a small volume of absolute ethanol was added rapidly.

After 20 hours of refluxing, the mixture was cooled and neutralized with glacial acetic acid to cause precipitation of the product. The precipitate was collected, washed with water and ethanol, and dried to give 9-bromo-5,6-dihydro-3-methylbenzo[f]quinazolin-1(2H)-one as a white solid. (2.21 g, 72%) $^1$H NMR (DMSO-d$_6$, 200 MHz) δ 2.30 (s, 3H, CH$_3$); 2.65–2.85 (m, 4H, CH$_2$CH$_2$); 7.17 (d, J=8.0 Hz, 1H, Ar); 7.35 (dd, J=8.0, 2.2 Hz, 1H, Ar); 8.76 (d, J=2.2 Hz, 1H, Ar); 12.67 (br s, 1H, NH).

The following compounds were prepared from appropriately substituted methyl or ethyl 3,4-dihydro-2-hydroxy-1-naphthoates, using the procedure described in the above example without significant modification:

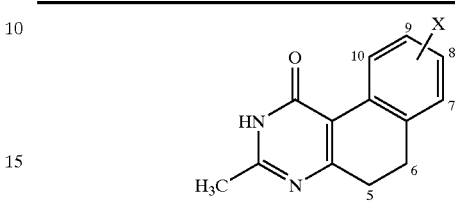

| X | 1HNMR (200 MHz)$^a$ in DMSO-d6 (δ) |
|---|---|
| 7-Cl | 2.30(s, 3H, CH$_3$); 2.71(t, J=8.2Hz, 2H, CH$_2$); 2.94(t, J=8.2Hz, 2H, CH$_2$); 7.23(t, J=8Hz, 1H, Ar); 7.31(dd, J=8, 2Hz, 1H, Ar); 8.57(d, J=8, 2Hz, 1H, Ar); 12.61(br s, 1H, NH). |
| 7-Br | 2.30(s, 3H, CH$_3$); 2.71(m, 2H, CH$_2$); 2.94(m, 2H, CH$_2$); 7.16(t, J=8Hz, 1H, Ar); 7.45(dd, J=8, 1Hz, 1H, Ar); 8.60(dd, J=8, 1Hz, 1H, Ar); 12.62(br s, 1H, NH). |
| 7-I | 2.30(s, 3H, CH$_3$); 2.65–2.75(m, 2H, CH$_2$); 2.85–2.95(m, 2H, CH$_2$); 6.98(t, J=8Hz, 1H, Ar); 7.70(dd, J=8, 1Hz, 1H, Ar); 8.61(d, J=8, 1Hz, 1H, Ar); 12.58(s, 1H, NH). |
| 8-F | 2.28(s, 3H, CH$_3$); 2.61–2.91(m, 4H, CH$_2$CH$_2$); 6.96–7.12(m, 2H, Ar), 8.60(dd, J=8.6, 6.2Hz, 1H, Ar); 12.56(br s, 1H, NH). |
| 8-Br | $^b$2.31(s, 3H, CH$_3$); 2.70(t, 2H, CH$_2$); 2.86(t, 2H, CH$_2$); 7.41(dd, J=8.5, 2Hz, 1H, Ar); 7.45(d, J=2Hz, 1H, Ar); 8.53(d, J=8.4Hz, 1H, Ar); 12.60(br s, 1H, NH). |
| 9-F | 2.30(s, 3H, CH$_3$); 2.63–2.85(m, 4H, CH$_2$CH$_2$); 6.98(ddd, J=11, 8.5, 3Hz, 1H, Ar); 7.22(dd, J=8.2, 6.3Hz, 1H, Ar); 8.37(dd, J=11.8, 3Hz, 1H, Ar). |
| 9-Cl | 2.30(s, 3H, CH$_3$); 2.64–2.87(m, 4H, CH$_2$CH$_2$); 7.23(s, 2H, Ar); 8.63(s, 1H, Ar); 12.66(br s, 1H, NH). |
| 9-I | 2.30(s, 3H, CH$_3$); 2.62–2.85(m, 4H, CH$_2$CH$_2$); 7.02(d, J=8Hz, 1H, Ar); 7.51(dd, J=8, 2Hz, 1H, Ar); 8.93(d, J=2Hz, 1H, Ar); 12.62(br s, 1H, NH). |
| 9-CH$_3$ | $^b$2.31(s, 3H, CH3); 2.30(s, 3H, ArCH$_3$); 2.63–2.72(m, 2H, CH$_2$); 2.72–2.82(m, 2H, CH$_2$); 6.99(dd, J=8, 1Hz, 1H, Ar); 7.10(d, J=8Hz, 1H, Ar); 8.41(d, J=1Hz, 1H, Ar); 12.55(br s, 1H, NH). |

$^a$Except where indicated.
$^b$300 MHz

All compounds gave correct elemental analyses for the indicated structure.

EXAMPLE 4

9-Bromo-3-methylbenzo[f]quinazolin-1(2H)-one

A mixture of 9-Bromo-5,6-dihydro-3-methylbenzo[f]quinazolin-1(2H)-one (1.0 g, 3.4 mmoles), N-bromosuccinimide (0.63 g, 3.5 mmoles) and pyridine (0.3 ml, 3.7 mmoles) in dry benzene (350 ml) was reacted in the same manner as for the corresponding 3-pivalamide (Example 2). After cooling, benzene and excess pyridine were removed under reduced pressure. The residue was triturated with methanol:water (1:1) and filtered to leave a crude product which was recrystallized from methanol to give 9-bromo-3-methylbenzo[f]quinazolin-1(2H)-one as an off-white solid. (0.47 g, 37%) $^1$H NMR (DMSO-d$_6$, 200 MHz) δ: 2.57 (s, 3H, CH$_3$); 7.73 (d, J=9.0 Hz, 1H, Ar); 7.86 (dd, J=8.6, 2.0 Hz, 1H, Ar); 8.09 (d, J=8.7 Hz, 1H, Ar); 8.41 (d, J=8.8 Hz, 1H, Ar); 9.92 (d, J=2.0 Hz, 1H, Ar).

The following compounds were prepared from appropriately substituted 5,6-dihydro-3-methylbenzo[f]quinazolin-1

(2H)-ones, using the same procedure described in the above example

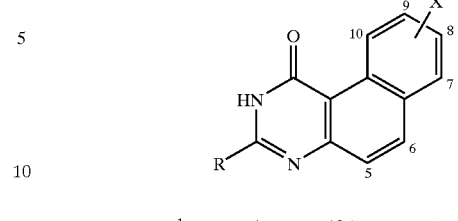

| X | $^1$H NMR (200 MHz)$^a$ in DMSO-$d_6$ ($\delta$) |
|---|---|
| 7-Cl | 2.43(s, 3H, CH$_3$); 7.70(t, J=7.7Hz, 1H, Ar); 7.78(d, J=9.2Hz, 1H, Ar); 7.80(dd, J=7.7, 1.3Hz, 1H, Ar); 8.52(d, J=9.2Hz, 1H, Ar); 9.87(d, J=7.7Hz, 1H, Ar); 12.67(br s, 1H, NH). |
| 7-Br | $^b$2.49(s, 3H, CH$_3$); 7.67(t, J=8.1Hz, 1H, Ar); 7.82(d, J=9.2Hz, 1H, Ar); 8.02(dd, J=7.6, 1.0Hz, 1H, Ar); 8.54(d, J=9.1Hz, 1H, Ar); 9.93(d, J=8.6Hz, 1H, Ar). |
| 7-I | 2.43(s, 3H, CH$_3$); 7.41(t, J=8.1Hz, 1H, Ar); 7.73(d, J=9.2Hz, 1H, Ar); 8.23(dd, J=7.4, 1.1Hz, 1H, Ar); 8.35(d, J=9.2Hz, 1H, Ar); 9.94(d, J=8.6Hz, 1H, Ar); 12.64(br s, 1H, NH). |
| 8-F | 2.41(s, 3H, CH$_3$); 7.54–7.72(m, 2H, ArH$^9$); 7.85(dd, J=9.8, 2.8Hz, 1H, Ar); 8.22(d, J=9.0Hz, 1H, Ar); 9.88(dd, J=8.5, 6.0Hz, 1H, Ar); 12.60(br s, 1H, NH). |
| 8-Br | $^b$2.43(s, 3H, CH$_3$); 7.68(d, J=8.9Hz, 1H, Ar); 7.86(dd, J=9.2, 2.3Hz, 1H, Ar); 8.24(d, J=9.0Hz, 1H, Ar); 8.33(d, J=2.2Hz, 1H, Ar); 9.76(d, J=9.1Hz, 1H, Ar); 12.66(br s, 1H, NH). |
| 9-F | 2.47(s, 3H, CH$_3$); 7.63(dt, J=8.6, 2.8Hz, 1H, Ar); 7.68(d, J=9.0Hz, 1H, Ar); 8.22(dd, J=9.0, 6.2Hz, 1H, Ar); 8.42(d, J=9.0Hz, 1H, Ar); 9.42(dd, J=8.8, 2.8Hz, 1H, Ar). |
| 9-Cl | 2.53(s, 3H, CH$_3$); 7.69(d, J=8.9Hz, 1H, Ar); 7.72(dd, J=8.6, 2.3Hz, 1H, Ar); 8.14(d, J=8.9Hz, 1H, Ar); 8.37(d, J=8.6Hz, 1H, Ar); 9.78(d, J=2.3Hz, 1H, Ar). |
| 9-I | 2.42(s, 3H, CH$_3$); 7.63(d, J=8.7Hz, 1H, Ar); 7.81(d, J=8.7Hz, 1H, Ar); 7.92(dd, J=8.7, 1.6Hz, 1H, Ar); 8.22(d, J=8.7Hz, 1H, Ar); 10.24(d, J=8.7Hz, 1H, Ar); 12.64(br s, 1H, NH). |

$^a$Except where indicated.
$^b$300 MHz.

All compounds gave elemental analyses consistent with the indicated structures.

EXAMPLE 5

3-Amino-7,9-dimethylbenzo[f]quinazolin-1(2H)-one

A mixture of 3-amino-5,6-dihydro-7,9-dimethylbenzo[f]quinazolin-1(2H)one (0.25 g, 1.04 mmole) and 10% palladium on carbon (0.5 g) in diglyme (25 ml) was vigorously stirred and refluxed under a nitrogen atmosphere for 2.5 hours, and then filtered while still hot through a bed of celite. Diglyme was removed from the filtrate under reduced pressure, and the residue was triturated with hot methanol, filtered, washed with methanol and ether, and dried to give 3-amino-7,9-di-methylbenzo[f]quinazolin-1(2H)-one as an off-white solid. (0.14 g, 55%) $^1$H NMR (DMSO-$d_6$, 200 MHz) $\delta$: 2.43 (s, 3H, CH$_3$); 2.60 (s, 3H, CH$_3$); 6.48 (s, 2H, NH$_2$); 7.14 (s, 1H, Ar); 7.25 (d, J=9.2 Hz, 1H, Ar); 8.11 (d, J=9.1 Hz, 1H, Ar); 9.38 (s, 1H, Ar); 11.07 (s, 1H, NH).

The following compounds were prepared from the corresponding 5,6-dihydro compounds in the same manner as described in the above example:

| R | X | $^1$H NMR (200 MHz)$^a$ in DMSO-$d_6$ ($\delta$) |
|---|---|---|
| NH$_2$ | 6-CH$_3$ | 2.63(s, 3H, CH$_3$); 6.52(s, 2H, NH$_2$); 7.18(s, 1H, Ar); 7.46(dt, J=8.1, 1.4Hz, 1H, Ar); 7.59(dt, J=8.3, 1.4Hz, 1H, Ar); 7.97(dd, J=8.0, 1.2Hz, 1H, Ar); 9.69(d, J=8.2Hz, 1H, Ar); 11.06(s, 1H, NH). |
| NH$_2$ | 7-CH$_3$ | 2.64(s, 3H, CH$_3$); 6.50(br s, 2H, NH$_2$); 7.26–7.49(m, 3H, Ar); 8.17(d, J=8.5Hz, 1H, Ar); 9.55(d, J=8.5Hz, 1H, Ar); 11.09(br s, 1H, NH). |
| NH$_2$ | 9-CH$_3$ | $^b$2.47(s, 3H, CH3); 6.48(br s, 2H, NH$_2$); 7.16–7.29(m, 2H, Ar); 7.75(d, J=8.2Hz, 1H, Ar); 7.95(d, J=8.2Hz, 1H, Ar); 9.44(s, 1H, Ar); 11.09(br s, 1H, NH). |
| CH$_3$ | 9-CH$_3$ | $^c$2.42(s, 3H, pyr-CH$_3$); 2.56(s, 3H, ArCH$_3$); 7.48(dd, J=8, 2Hz, 1H, Ar); 7.55(d, J=9Hz, 1H Ar); 7.93(d, J=8Hz, 1H, Ar); 8.19(d, J=9Hz, 1H, Ar); 9.65(d, J=1Hz, 1H, Ar); 12.52(br s, 1H, NH). |

$^a$Except where indicated.
$^b$The N-(5,6-dihydro)pivalamide derivative was dehydrogenated, followed by removal of the pivaloyl group as described in example 2.
$^c$300 MHz The compounds gave elemental analyses consistent with the indicated structure.

EXAMPLE 6

3-Amino-9-methoxybenzo[f]quinazolin-1(2H)-one

A mixture of N-(1,2,5,6-tetrahydro-9-methoxy-1-oxobenzo[f]quinazolin-3-yl)pivalamide (0.93 g, 2.84 mmoles) and 2,3-dichloro-5,6-dicyano-1,4-benzoquinone (0.8 g, 3.5 mmoles) in dry benzene (60 ml) was refluxed under a nitrogen atmosphere for 3 hours. After cooling, benzene was removed under reduced pressure and the residue was purified on a silica gel column eluting with chloroform to give N-(1,2-dihydro-9-methoxy-1-oxobenzo[f]quinazolin-3-yl)pivalamide (0.9 g).

The N-pivaloyl protecting group was removed with aqueous NaOH in the same manner as in example 2 to give 3-amino-9-methoxybenzo[f]quinazolin-1(2H)-one as a white solid. (0.58 g, 85%) $^1$H NMR (DMSO-$d_6$, 200 MHz) $\delta$: 3.86 (s, 3H, CH$_3$); 6.51 (s, 2H, NH$_2$); 7.08 (dd, J=8.8, 2.5 Hz, 1H, Ar); 7.12 (d, J=8.9 Hz, 1H, Ar); 7.77 (d, J=8.8 Hz, 1H, Ar); 7.93 (d, J=8.8 Hz, 1H, Ar); 9.18 (d, J=2.5 Hz, 1H, Ar); 11.03 (s, 1H, NH).

The following compounds were prepared from the corresponding N-(5,6-dihydro)pivalamides using the procedure described in the above example

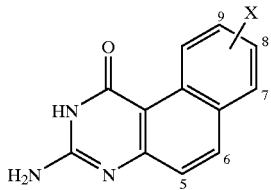

| X | 1H NMR (200 MHz) in DMSO-d6 (δ) |
|---|---|
| 9-OC$_2$H$_5$ | 1.39(t, J=6.9Hz, 3H, CH$_3$); 4.26(q, J=7.0Hz, 2H, CH$_2$); 6.51(br s, 2H, NH$_2$); 7.06(dd, J=8.8, 2Hz, 1H, Ar); 7.11(d, J=8.8Hz, 1H, Ar); 7.76(d, J=8.8Hz, 1H, Ar); 7.92(d, J=8.8Hz, 1H, Ar); 9.18(d, J=2Hz, 1H, Ar); 11.03(br s, 1H, NH). |
| 9-SCH$_3$ | 2.55(s, 3H, SCH$_3$); 6.50(br s, 2H, NH$_2$); 7.19(d, J=9Hz, 1H, Ar); 7.32(dd, J=8.5, 2Hz, 1H, Ar); 7.78(d, J=8.5Hz, 1H, Ar); 7.95(d, J=9Hz, 1H, Ar); 9.51(d, J=2Hz, 1H, Ar); 11.04(br s, 1H, NH). |
| 9-SC$_2$H$_5$ | 1.31(t, J=7Hz, 3H, CH$_3$); 3.07(q, J=7Hz, 2H, CH$_2$); 6.64(br s, 2H, NH$_2$); 7.21(d, J=9Hz, 1H, Ar); 7.35(dd, J=8.4, 2Hz, 1H, Ar); 7.79(d, J=8.4Hz, 1H, Ar); 7.95(d, J=9Hz, 1H, Ar); 9.59(s, 1H, Ar); 11.05(br s, 1H, NH). |

All compounds gave elemental analyses consistent with the indicated structure.

EXAMPLE 7

3-Amino-9-hydroxybenzo[f]quinazolin-1(2H)-one

A solution of 3-amino-9-methoxybenzo[f]quinazolin-1(2H)-one (0.33 g, 1.37 mmoles) in 48% HBr (8 ml) was stirred and heated at 110° C. for 50 hours. After cooling, the mixture was neutralized by careful addition of solid NaOH to cause precipitation of the product. The precipitate was collected, washed with water and dried.

The crude product was converted to the N-pivalamide derivative by reaction with pivalic anhydride in the same manner as in example 2, and purified on a silica gel column eluting with 0 to 0.8% methanol:chloroform.

The pivaloyl group was removed with base in the same manner as in example 2 to give 3-amino-9-hydroxybenzo[f]quinazolin-1(2H)-one as a tan solid. (0.22 g, 65%) $^1$H NMR (DMSO-d$_6$, 200 MHz) δ: 6.45 (br s, 2H, NH$_2$); 6.93 (dd, J=8.6, 2.2 Hz, 1H, Ar); 7.03 (d, J=8.8 Hz, 1H, Ar); 7.67 (d, J=8.6 Hz, 1H, Ar); 7.86 (d, J=8.8 Hz, 1H, Ar); 9.01 (d, J=2.2 Hz, 1H, Ar); 9.77 (s, 1H, OH); 11.02 (br s, 1H, NH).

In a similar manner, 3-amino-9-hydroxy-5,6-dihydrobenzo[f]quinazolin-1(2H)-one was prepared from 3-amino-9-methoxy-5,6-dihydrobenzo-[f]quinazolin-1(2H)-one. (53%) $^1$H NMR (DMSO-d$_6$, 200 MHz) δ: 2.40–2.70 (m, 4H, CH$_2$CH$_2$); 6.41 (dd, J=8.2, 2.5 Hz, 1H, Ar); 6.59 (br s, 2H, H$_2$); 6.88 (d, J=8.2 Hz, 1H, Ar); 7.96 (d, J=2.5 Hz, 1H, Ar); 8.91 (s, 1H, ArOH); 10.87 (br s, 1H, NH). Anal. Calculated for C$_{12}$H$_{11}$N$_3$O$_2$.3/10H$_2$O.5/4CH$_3$OH: C, 57.94; H, 6.09; N, 15.30. Found: C, 57.97; H, 5.95; N, 15.34.

EXAMPLE 8

3-Amino-6-(methoxymethyl)benzo[f]quinazolin-1(2H)-one

A. N-(6-(Bromomethyl)-1,2-dihydro-1-oxobenzo[f]quinazolin-3-yl))pivalamide

To a solution of N-(6-methyl-1,2-dihydro-1-oxobenzo[f]quinazolin-3-yl)pivalamide (1.76 g, 5.7 mmoles) in dry benzene (150 ml) was added N-bromosuccinimide (1.01 g, 5.7 mmoles) and dibenzoyl peroxide (15 mg). The mixture was heated to reflux under a nitrogen atmosphere for 2.5 hours. After cooling, benzene was removed under reduced pressure, and the residue was purified on a silica gel column eluting with chloroform to give N-(6-(bromomethyl)-1,2-dihydro-1-oxobenzo[f]quinazolin-3-yl)pivalamide as an off-white solid. (1.4 g, 57%) $^1$H NMR (DMSO-d$_6$, 200 MHz) δ: 1.27 (s, 9H, t-butyl); 5.26 (s, 2H, CH$_2$Br); 7.63–7.81 (m, 3H, Ar); 8.26 (dd, J=7.6, 2.0 Hz, 1H, Ar); 9.81 (dd, J=7.8, 2.0 Hz, 1H, Ar); 11.27 (s, 1H, NH); 12.33 (s, 1H, NH). Anal. Calculated for C$_{18}$H$_{18}$BrN$_3$O$_2$: C, 55.68; H, 4.67; N, 10.82. Found C, 55.48; H, 4.84; N, 10.57.

B. 3-Amino-6-(methoxymethyl)benzo[f]quinazolin-1(2H)-one

A solution of N-(6-(bromomethyl)-1,2-dihydro-1-oxobenzo[f]quinazolin-3-yl)pivalamide (0.28 g, 0.72 mmole) in 0.3 M sodium methoxide (25 ml) was stirred and heated at 650° C. under a nitrogen atmosphere for 4 hours. After cooling, the mixture was acidified to pH 6 with glacial acetic acid, and then all solvent was removed under reduced pressure. The residue was triturated with water (20 ml), then filtered, washed with water and acetone, and dried to give 3-amino-6-(methoxymethyl)benzo[f]quinazolin-1(2H)-one as an off-white solid. (0.12 g, 58%) $^1$H NMR (DMSO-d$_6$, 200 MHz) d 3.39 (s, 3H, OCH$_3$); 4.85 (s, 2H, CH$_2$); 6.54 (br s, 2H, NH$_2$); 7.33 (s, 1H, Ar); 7.44 (dt, J=6.9, 1.4 Hz, 1H, Ar); 7.59 (dt, J=6.9, 1.4 Hz, 1H, Ar); 7.96 (dd, J=8.2, 1.0 Hz, 1H, Ar); 9.69 (d, J=8 Hz, 1H, Ar); 11.11 (br s, 1H, NH); 11.91 (br s, <1H, pyr-NH$^+$). Anal. Calculated for C$_{14}$H$_{13}$N$_3$O$_2$.1/2HOAc.1/10H$_2$O: C, 62.75; H, 5.34; N, 14.64. Found C, 62.74; H, 5.31; N, 14.64.

In a similar manner, 3-amino-6-(hydroxymethyl)benzo[f]quinazolin-1(2H)-one was prepared by substituting 0.6 N aqueous NaOH in place of sodium methoxide. (32%) $^1$H NMR (DMSO-d$_6$, 200 MHz) δ: 4.95 (d, J=4.2 Hz, 2H, CH$_2$); 5.44 (t, J=4.2 Hz, 1H, OH); 6.52 (br s, 2H, NH$_2$); 7.40 (s, 1H, Ar); 7.43 (dt, J=7.9, 1.5 Hz, 1H, Ar); 7.57 (dt, J=7.9, 1.5 Hz, 1H, Ar); 7.94 (dd, J=7.9, 1.5 Hz, 1H, Ar); 9.70 (d, J=7.9 Hz, 1H, Ar); 11.10 (br s, 1H, NH). Anal. Calculated for C$_{13}$H$_{11}$N$_3$O$_2$.CH$_3$COOH: C, 59.80; H, 5.02; N, 13.95. Found: C, 59.80; H, 5.04; N, 13.91.

EXAMPLE 9

3-Amino-9-bromo-10-nitrobenzo[f]quinazolin-1(2H)-one

To a stirred solution of 3-amino-9-bromobenzo[f]quinazolin-1(2H)-one (3.0 g, 10.3 mmoles) in 98% sulphuric acid (125 ml) at 0–50° C. was added finely divided potassium nitrate (1.05 g, 10.3 mmoles) in several portions over a 20 minute period. After stirring at 0° C. for 2 hours more, the mixture was poured onto 1000 ml of crushed ice and allowed to stand until all the ice melted. A fine, light yellow precipitate was then filtered, washed with water, and resuspended in 2 N NaOH with stirring for 3 hours. After this time, the suspension was filtered, and the solid was resuspended in dilute aqueous acetic acid with vigorous stirring and sonication. The bright yellow solid was filtered, washed with water, dried and triturated with boiling ethanol (500 ml) to give, after drying, 3-amino-9-bromo-10-nitrobenzo[f]quinazolin-1(2H)-one. (2.74 g, 72%) $^1$H NMR (DMSO-d$_6$, 200 MHz) δ: 6.91 (br s, 2H, NH$_2$); 7.42 (d, J=9 Hz, 1H, Ar); 7.86 (d, J=7 Hz, 1H, Ar); 8.06 (d, J=9 Hz, 1H, Ar); 8.13 (d, J=7 Hz, 1H, Ar); 11.25 (br s, 1H, NH).

The following compounds were prepared from the corresponding benzo[f]quinazolin-1(2H)-ones in the same manner as described in the above example:

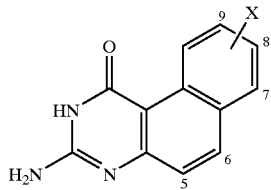

| X | 1H NMR (200 MHz)[a] in DMSO-d6 (δ) |
|---|---|
| 7-NO$_2$[b] | 7.16(br s, 2H, NH$_2$); 7.51(d, J=9.5Hz, 1H, Ar); 7.72(t, J=7.8Hz, 1H, Ar); 8.03(dd, J=7.8, 1.2Hz, 1H, Ar); 8.23(d, J=9.5Hz, 1H, Ar); 10.18(d, J=7.3Hz, 1H, Ar). |
| 8-NO$_2$[b] | 6.85(br s, 2H, NH$_2$); 7.43(d, J=8.9Hz, 1H, Ar); 8.30(d, J=8.9Hz, 1H, Ar); 8.32(dd, J=9.4, 2.6Hz, Ar); 8.88(d, J=2.6Hz, 1H, Ar); 9.76(d, J=9.4Hz, 1H, Ar); 11.38(br s, 1H, NH). |
| 5,6-dihydro-8-NO$_2$[c] | [d]2.75–2.99(br m, 4H, CH$_2$CH$_2$); 8.02–8.05(d, J=3Hz, 1H, Ar); 8.05–8.08(m, 1H, Ar); 8.40(br s, 3H, NH3$^+$); 8.55–8.61(d, J=5Hz, 1H, Ar). |
| 10-NO$_2$[b] | 6.82(s, 2H, NH$_2$); 7.40(d, J=9Hz, 1H, Ar); 7.54(t, J=7.8Hz, 1H, Ar); 8.04(d, J=7.8Hz, 1H, Ar); 8.13(d, J=9Hz, 1H, Ar); 8.17(d, J=7.8Hz, 1H, Ar); 11.20(br s, 1H, NH). |
| 7-NO$_2$-8-F | 6.77(br s, 2H, NH$_2$); 7.56(d, J=9.3Hz, 1H, Ar); 7.82(t, J=9.8Hz, 1H, Ar); 7.92(d, J=9.3Hz, 1H, Ar); 9.98(dd, J=9.7, 5.6Hz, 1H, Ar); 11.42(br s, 1H, NH). |
| 7-NO$_2$-8-Br | 6.93(br s, 2H, NH$_2$); 7.52(d, J=9.4Hz, 1H, Ar); 7.73(d, J=9.3Hz, 1H, Ar); 7.99(d, J=9.4Hz, 1H, Ar); 9.76(d, J=9.3Hz, 1H, Ar); 11.6(br s, 1H, NH). |
| 9-Br-5,6-dihydro-8-NO$_2$ | 2.61(t, J=8Hz, 2H, CH$_2$); 2.86(t, J=8Hz, 2H, CH$_2$); 7.06(br s, 2H, NH$_2$); 7.89(s, 1H, Ar); 8.93(s, 1H, Ar); 11.23(br s, 1H, NH). |
| 8,10-(NO$_2$)$_2$[e] | 7.15(br s, 2H, NH$_2$); 7.54(d, J=9.0Hz, 1H, Ar); 8.41(d, J=9.2Hz, 1H, Ar); 8.65(d, J=2.4Hz, 1H, Ar); 9.18(d, J=2.3Hz, 1H, Ar); 11.47(br s, 1H, NH). |
| 8-F-10-NO$_2$[f] | 6.85(br s, 2H, NH$_2$); 7.44(d, J=8.9Hz, 1H, Ar); 8.05–8.20(m, 3H, Ar); 11.26(s, 1H, NH). |

[a]Except where noted.
[b]Separated from a mixture of 7-, 8-, and 10-isomers by fractional crystallizations (diethyl ether: pivalic anhydride (2:1) and/or ethyl acetate: diethyl ether (1:1)) of the N-pivalamide derivatives, followed by removal of the pivaloyl group as described in example 2.
[c]Recrystallized from 9M H$_2$SO$_4$.
[d]80 MHz
[e]Two moles of potassium nitrate per mole of starting material was used.
[f]Isolated from the NaOH filtrate by neutralization, filtration of the resulting solid, conversion of the water-washed and dried material to the N-pivalamide derivative as described in example 2, purification by silica gel chromatography using chloroform as eluent, and removal of the pivaloyl group as described in example 2.

In a similar manner, 5,6-dihydro-3-methyl-8-nitrobenzo[f]quinazolin-1(2H)-one was prepared from 5,6-dihydro-3-methylbenzo[f]quinazolin-1(2H)-one with the following modification. A solution of the reaction mixture in water was neutralized (pH 7) with NaOH pellets to cause precipitation of the crude product which was filtered, redissolved in 1 N NaOH, precipitated with acetic acid, filtered, washed with water and dried. The solid was then triturated with hot methanol, filtered and dried to give the pure product. $^1$H NMR (DMSO-d$_6$, 200 MHz) δ: 2.32 (s, 3H, CH$_3$); 2.76 (t, J=8.0 Hz, 2H, CH$_2$); 2.99 (t, J=8.0 Hz, 2H, CH$_2$); 8.05–8.15 (m, 2H, Ar); 8.82 (d, J=9.4 Hz, 1H, Ar); 12.8 (br s, 1H, NH).

All compounds gave elemental analyses consistent with the assigned structures.

EXAMPLE 10
3-Amino-8-bromo-9-nitrobenzo[f]quinazolin-1(2H)-one 1,3-Diamino-5,6-dihydrobenzo[f]quinazoline (1.0 g, 4.7 mmol) was suspended in glacial acetic acid (1 ml), and bromine (1.0 ml) was added dropwise with stirring. The first few drops were rapidly decolorized, but on completion of the addition the solid had completely dissolved and the solution remained a deep red. Stirring was continued at room temperature for a further two hours, the reaction mixture poured into water (50 ml), and the yellow solid removed by filtration. The crude bromo-compound was dried overnight in vacuo at room temperature, suspended in M—HCl, and the suspension heated briefly to boiling. The cooled suspension was filtered, the solid washed with water and dried in vacuo overnight to yield the title compound (1.10 g, 66%) as a cream solid, mp.>250° C. $^1$H NMR (DMSO-d$_6$, 80 MHz) δ: 2.65–2.90 (m, 4H, ArCH$_2$), 7.33–7.68 (m, 3H, Ar), 7.15–7.85 (br s, 2H, NH$_2$), 7.90–8.35 (br s, 2H, NH$_2$), 12.30–13.70 (br s, 1H, NH). Mass spectrum (EI): 290 (M$^+$, 100%); 211 ((M−79)$^+$, 12.7%). Anal. Calculated for C$_{12}$H$_{11}$BrN$_4$.HCl.7/5H$_2$O: C, 40.85; H, 4.23; N, 15.88. Found: C, 40.82; H, 3.52; N, 15.88.

To a mixture of fuming nitric acid (7 ml) and sulphuric acid (6 ml) at 0° C. was added 1,3-diamino-8-bromo-5,6-dihydrobenzo[f]quinazoline (1.0 g, 3.4 mmoles) in a single portion. The reaction mixture was stirred at 0–5° C. for 45 minutes, and then slowly poured onto ice (15 g). The resulting precipitate was filtered, washed with water (10 ml) and ether (10 ml), and resuspended in boiling 1N HCl (100 ml) for 1 hour. After cooling, the solid was filtered, triturated with hot ethanol, filtered again, washed with ethanol and ether, and dried to give 3-amino-8-bromo-9-nitrobenzo[f]quinazolin-1(2H)-one as a pale yellow solid. (0.59 g, 45%) $^1$H NMR (DMSO-d$_6$, 80 MHz) δ: 7.62–7.71 (d, J=7 Hz, 1H, Ar); 7.77 (s, 3H, NH$_3$$^+$); 8.23–8.34 (d, J=9 Hz, 1H, Ar); 8.59 (s, 1H, Ar); 10.08 (s, 1H, Ar). Anal. Calculated for C$_{12}$H$_7$BrN$_4$O$_3$.1/2HNO$_3$.H$_2$O C, 37.47; H, 2.49; N, 16.39. Found C, 37.20; H, 2.24; N, 16.00.

EXAMPLE 11
3,10-Diamino-9-bromobenzo[f]quinazolin-1(2H)-one

A. N-(9-Bromo-1,2-dihydro-10-nitro-1-oxobenzo[f]quinazolin-3-yl)pivalamide

Pivalic anhydride (20 ml) was reacted with 3-amino-9-bromo-10-nitro-benzo[f]quinazolin-1(2H)-one (2.44 g, 7.28 mmoles) in the same manner as in example 2. The product was purified by trituration with hot ethyl acetate to give N-(9-bromo-1,2-dihydro-10-nitro-1-oxobenzo[f]quinazolin-3-yl)pivalamide as a light yellow solid. (1.67 g, 55%) $^1$H NMR (DMSO-d$_6$, 200 MHz) δ: 1.25 (s, 9H, t-butyl); 7.69 (d, J=8.8 Hz, 1H, Ar); 8.02 (d, J=8.7 Hz, 1H, Ar); 8.20 (d, J=8.8 Hz, 1H, Ar); 8.34 (d, J=9.0 Hz, 1H, Ar); 11.45 (br s, 1H, NH); 12.18 (br s, 1H, NH).

B. N-(10-Amino-9-bromo-1,2-dihydro-1-oxobenzo[f]quinazolin-3-yl)pivalamide

A mixture of N-(9-bromo-1,2-dihydro-10-nitro-1-oxobenzo[f]quinazolin-3-yl)pivalamide (0.8 g, 1.9 mmoles) and iron powder (0.44 g, 7.8 mmoles) in ethanol:glacial acetic acid/1:1 (25 ml) was stirred and heated to reflux under a nitrogen atmosphere for 3 hours. The reaction mixture was poured into chloroform:water/2:1 (150 ml) and neutralized by addition of solid sodium bicarbonate. The chloroform layer was separated, and the aqueous phase was washed twice with chloroform (50 ml each). Combined chloroform layers were dried over sodium sulfate, filtered and evaporated under reduced pressure. The crude product was purified on a silica gel column eluting with chloroform to give N-(10-amino-9-bromo-1,2-dihydro-1-oxobenzo[f]quinazolin-3-yl)pivalamide as a bright yellow solid. (0.66 g, 89%) ¹H NMR (DMSO-d₆, 200 MHz) δ: 1.27 (s, 9H, t-butyl); 6.51 (s, 2H, NH₂); 7.22 (d, J=8.4 Hz, 1H, Ar); 7.51 (br d, J=9 Hz, 1H, Ar); 7.72 (d, J=8.4 Hz, 1H, Ar); 8.12 (d, J=9.0 Hz, 1H, Ar); 11.40 (br s, 1H, NH); 12.45 (br s, 1H, NH).

C. 3,10-Diamino-9-bromobenzo[f]quinazolin-1(2H)-one

N-(10-Amino-9-bromo-1,2-dihydro-1-oxobenzo[f]quinazolin-3-yl)pivalamide (0.58 g, 1.5 mmoles) was reacted with aqueous sodium hydroxide as described for the analogous 9-bromo compound (example 2). The product was precipitated from the reaction mixture with acetic acid, filtered and washed with water to give 3,10-diamino-9-bromobenzo[f]quinazolin-1(2H)-one as a yellow solid. (0.36 g, 80%) ¹H NMR (DMSO-d₆, 200 MHz) δ: 6.49 (br s, 2H, NH₂); 6.69 (br s, 2H, NH₂); 7.09 (d, J=8.4 Hz, 1H, Ar); 7.22 (d, J=8.9 Hz, 1H, Ar); 7.56 (d, J=8.4 Hz, 1H, Ar); 7.90 (d, J=8.9 Hz, 1H, Ar); 11.47 (br s, 1H, NH).

The following compounds were prepared from the corresponding bromo-nitro compounds as described in the above example:

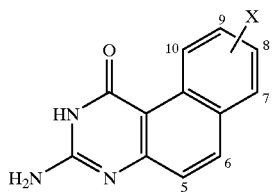

| X | ¹H NMR (200 MHz) in DMSO-d₆ (δ) |
|---|---|
| 7-NH₂-8-Br | 7.42(d, J=9.2Hz, 1H, Ar); 7.68(d, J=9.2Hz, 1H, Ar); 8.19(br s, 2H, NH₂); 8.62(d, J=9.2Hz, 1H, Ar); 8.73(d, J=9.2Hz, 1H, Ar). |
| 8-NH₂-9-Br | 7.21(s, 1H, Ar); 7.40(d, J=8.9Hz, 1H, Ar); 7.95(br s, 2H, NH₂); 8.01(d, J=9.4Hz, 1H, Ar); 9.63(s, 1H, Ar). |
| 8-NH₂-9-Br-5,6-dihydro | 2.42–2.68(m, 4H, CH₂CH₂); 5.11(s, 2H, NH₂); 6.50(s, 2H, NH₂); 6.57(s, 1H, Ar); 8.46(s, 1H, Ar); 10.91(br s, 1H, NH). |

All compounds gave elemental analyses consistent with the indicated structures.

EXAMPLE 12

3,9-Diaminobenzo[f]quinazolin-1(2H)-one

A. 3-Amino-8-bromo-5,6-dihydrobenzo[f]quinazolin-1(2H)-one

Ethyl 6-bromo-3,4-dihydro-2-hydroxy-1-naphthoate (6.0 g, 20.2 mmoles) was reacted with guanidine (6.9 g of hydrochloride salt, 72.2 mmoles) in the same manner as in example 1. The product was precipitated from aqueous sodium hydroxide with acetic acid, filtered, washed with water and dried to give 3-amino-8-bromo-5,6-dihydrobenzo[f]quinazolin-1(2H)-one as an off-white solid. (2.75 g, 46%) ¹H NMR (DMSO-d₆, 300 MHz) δ: 2.55 (t, J=7.5 Hz, 2H, CH₂); 2.79 (t, J=7.4 Hz, 2H, CH₂); 6.75 (br s, 2H, NH₂); 7.32 (dd, J=8.4, 2.3 Hz, 1H, Ar); 7.34 (s, 1H, Ar); 8.40 (d, J=8.4 Hz, 1H, Ar); 11.00 (br s, 1H, NH).

B. N-(8-Bromo-1,2,5,6-tetrahydro-9-nitro-1-oxobenzo[f]quinazolin-3-yl)pivalamide To a stirred solution of 3-amino-8-bromo-5,6-dihydrobenzo[f]quinazolin-1(2H)-one (2.56 g, 8.76 mmoles) in 98% sulphuric acid (180 ml) at 0° C. was added a solution of potassium nitrate (0.89 g, 8.80 mmoles) in sulphuric acid (20 ml) dropwise over a 40 minute period. The reaction mixture was poured onto 1000 ml of crushed ice and allowed to stand until all the ice melted. A light yellow precipitate was filtered, washed with water, and resuspended in 1 N NaOH with stirring at 50° C. for 2 hours. After this time, the suspension was neutralized with glacial acetic acid, refiltered and dried to obtain a light yellow solid.

The crude product was reacted with pivalic anhydride in the same manner as in example 2, and purified by two crystallizations from chloroform to give N-(8-bromo-1,2,5,6-tetrahydro-9-nitro-1-oxo-benzo[f]quinazolin-3-yl)pivalamide as a light yellow solid. (0.68 g, 17%) ¹H NMR (DMSO-d₆, 200 MHz) δ: 1.23 (s, 9H, t-butyl); 2.78 (m, 2H, CH₂); 2.99 (m, 2H, CH₂); 7.80 (s, 1H, Ar); 8.30 (s, <1H, CHCl₃); 9.11 (s, 1H, Ar); 11.45 (br s, 1H, NH); 12.20 (br s, 1H, NH).

C. N-(8-Bromo-1,2-dihydro-9-nitro-1-oxobenzo[f]quinazolin-3-yl)pivalamide

N-(8-Bromo-1,2,5,6-tetrahydro-9-nitro-1-oxobenzo[f]quinazolin-3-yl)pivalamide (0.23 g, 0.5 mmole) was reacted with N-bromosuccinimide (0.12 g, 0.7 mmole) and pyridine (0.06 ml, 0.8 mmole) in dry benzene (150 ml) in the same manner as in example 2. The crude product was purified by trituration with methanol:water (1:9), followed by filtration and washing (water and methanol) to give, after drying, N-(8-bromo-1,2-dihydro-9-nitro-1-oxobenzo[f]quinazolin-3-yl)pivalamide as a pale yellow solid. (0.20 g, 94%) ¹H NMR (DMSO-d₆, 200 MHz) δ: 1.27 (s, 9H, t-Butyl); 7.76 (d, J=9.0 Hz, 1H, Ar); 8.32 (d, J=9.0 Hz, 1H, Ar); 8.65 (s, 1H, Ar); 10.21 (s, 1H, Ar); 11.40 (s, 1H, NH); 12.45 (br s, 1H, NH).

D. N-(9-Amino-1,2-dihydro-1-oxobenzo[f]quinazolin-3-yl)pivalamide

N-(8-Bromo-1,2-dihydro-9-nitro-1-oxobenzo[f]quinazolin-3-yl)pivalamide (0.18 g, 0.43 mmole) was dissolved into ethanol (200 ml) with heating in a 500 ml Parr hydrogenation flask. A slurry of 10% palladium on carbon (0.13 g) in a small volume of ethanol was added, and the reaction was begun with 42.5 psi hydrogen pressure. When uptake of hydrogen had ceased (3.5 hours.), the reaction mixture was filtered through celite, and the solvent was removed under reduced pressure to leave a yellow solid. The product was purified on a silica gel column eluting with methanol:chloroform (1:99) to give N-9-amino-1,2-dihydro-1-oxobenzo[f]quinazolin-3-yl)pivalamide as a tan solid. (0.09 g, 63%) ¹H NMR (DMSO-d₆, 200 MHz) δ: 1.25 (s, 9H, t-butyl); 5.75 (br s, 2H, NH₂); 6.92 (dd, J=8.7, 2.2 Hz, 1H, Ar); 7.10 (d, J=8.5 Hz, 1H, Ar); 7.64 (d, J=8.6 Hz, 1H, Ar); 7.91 (d, J=8.8 Hz, 1H, Ar); 8.77 (d, J=1.4 Hz, 1H, Ar); 11.10 (br s, 1H, NH);. 12.10 (br s, 1H, NH).

E. 3,9-Diaminobenzo[f]quinazolin-1(2H)-one

N-(9-Amino-1,2-dihydro-1-oxobenzo[f]quinazolin-3-yl)pivalamide (0.065 g, 0.2 mmole) was reacted with aqueous sodium hydroxide in the same manner as in example 2. The product was precipitated from the basic reaction mixture with acetic acid, filtered and washed with water to give 3,9-diaminobenzo[f]quinazolin-1(2H)-one as a tan solid. (0.04 g, 84%) ¹H NMR (DMSO-d₆, 300 MHz) δ: 5.54 (br s, 2H, NH₂); 6.35 (br s, 2H, NH₂); 6.80 (dd, J=8.5, 2.3 Hz, 1H, Ar); 6.87 (d, J=8.6 Hz, 1H, Ar); 7.52 (d, J=8.6 Hz, 1H, Ar); 7.73 (d, J=8.6 Hz, 1H, Ar); 8.73 (s, 1H, Ar); 10.91 (br s, 1H, NH).

The following compounds were prepared by catalytic reduction of the N-pivalamide derivatives of the corresponding nitro-substituted compounds as described in the above example:

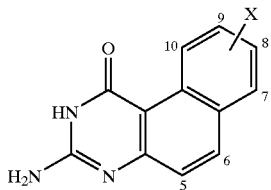

| X | $^1$H NMR (200 MHz)$^a$ in DMSO-d$_6$ (δ) |
|---|---|
| 7-NH$_2$ | 6.59(br s, 4H, 2NH$_2$); 6.65(d, J=7.6Hz, 1H, Ar); 7.12(d, J=9.2Hz, 1H, Ar); 7.25(t, J=8.0Hz, 1H, Ar); 8.23(d, J=9.2Hz, 1H, Ar); 8.86(d, J=8.4Hz, 1H, Ar). |
| 8-NH$_2$ | 5.26(br s, 2H, NH$_2$); 6.25(s, 2H, NH$_2$); 6.85(d, J=2.3Hz, 1H, Ar); 6.96(dd, J=9.0, 2.3Hz, 1H, Ar); 7.13(d, J=8.8Hz, 1H, Ar); 7.69(d, J=8.8Hz, 1H, Ar); 9.31(d, J=9.0Hz, 1H, Ar); 10.9(br s, 1H, NH). |
| 9-NH$_2$-5,6-dihydro$^a$ | 2.40–2.64(m, 4H, CH$_2$CH$_2$); 4.71(br s, 2H, NH$_2$); 6.25 (dd, J=7.8, 2.2Hz, 1H, Ar); 6.53(br s, 2H, NH$_2$); 6.75(d, J=7.8Hz, 1H, Ar); 7.75(d, J=2.4Hz, 1H, Ar); 10.84(br s, 1H, NH). |
| 10-NH$_2$ | 6.25(br s, 2H, NH$_2$); 6.55(s, 2H, NH$_2$); 6.88(dd, J=7.4, 1.4Hz, 1H, Ar); 7.07–7.25(m, 3H, Ar); 7.86(d, J=8.9Hz, 1H, Ar); 11.28(br s, 1H, NH). |
| 7-NH$_2$-8-F$^b$ | 5.63(br s, 2H, NH$_2$); 6.47(br s, 2H, NH$_2$); 7.18(d, J=9.3Hz, 1H, Ar); 7.29(t, J=10.3Hz, 1H, Ar); 8.28(d, J=9.3Hz, 1H, Ar); 8.92(dd, J=9.3, 5.4Hz, 1H, Ar); 11.06(br s, 1H, NH). |
| 8-F-10-NH$_2$$^b$ | 7.18(dd, J=11.4, 3.0Hz, 1H, Ar); 7.38(dd, J=8.8, 2.3Hz, 1H Ar); 7.52(d, J=8.8Hz, 1H, Ar); 8.14(br s, 2H, NH$_2$); 8.19(d, J=8.7Hz, 1H, Ar). |
| 8,10-(NH$_2$)2$^b$ | 7.15(d, J=2.1Hz, 1H, Ar); 7.18(d, J=2.6Hz, 1H, Ar); 7.44(d, J=9.2Hz, 1H, Ar); 7.98(br s, 2H, NH$_2$); 8.10(d, J=9.2Hz, 1H, Ar). |

$^a$The starting material was N-(8-bromo-1,2,5,6-tetrahydro-9-nitro-1-oxobenzo[f]quinazolin-3-yl)pivalamide.
$^b$The product was isolated as the hydrochloride salt by treating a solution of the compound in methanol with an excess of concentrated hydrochloric acid followed by evaporation of the solvent.

All compounds gave elemental analyses consistent with the indicated structures.

EXAMPLE 13

3,8-Diamino-5,6-dihydrobenzo[f]quinazolin-1(2H)-one

A suspension of 3-amino-5,6-dihydro-8-nitrobenzo[f]quinazolin-1(2H)-one sulfate monohydrate (2.0 g, 5.3 mmoles) and 5% palladium on carbon (10 mg) in 1 N HCl (20 ml) was reacted with hydrogen using a Parr hydrogenation apparatus. When uptake of hydrogen ceased, the mixture was filtered and the filtrate was evaporated, leaving a white residue which was resuspended in water (20 ml) with stirring, and filtered. The crude product was recrystallized from 2 M H$_2$SO$_4$ to give, after drying, 3,8-diamino-5,6-dihydrobenzo[f]quinazolin-1(2H)-one as a white solid. (1.1 g, 61%) $^1$H NMR (DMSO-d$_6$, 80 MHz) δ: 2.60–2.65 (m, 4H, CH$_2$CH$_2$); 4.99–5.69 (br s, 2H, NH$_2$); 6.75–6.79 (m, 4H, NH$_2$+Ar); 8.24–8.35 (d, J=9 Hz, 1H, Ar). Anal. Calculated for C$_{12}$H$_{12}$N$_4$O.H$_2$SO$_4$.1/2H$_2$O: C, 42.98; H, 4.51; N, 16.71; S, 9.56. Found: C, 42.95; H, 4.54; N, 16.66; S, 9.57.

EXAMPLE 14

3-Amino-8-bromobenzo[f]quinazolin-1(2H)-one

To a stirred suspension of 3-aminobenzo[f]quinazolin-1(2H)-one (0.56 g, 2.65 mmoles) in glacial acetic acid at 60° C. was added dropwise a solution of bromine (0.85 g, 5.3 mmoles) in glacial acetic acid (1.1 ml) over a 20 minute period. When the addition was completed, the mixture was heated to reflux for 4 hours, and then allowed to cool before filtering. The solid was dissolved into 1 N NaOH and reprecipitated with acetic acid, filtered, washed with water and methanol, and dried.

The crude product was derivatized by reaction with pivalic anhydride in the same manner as in example 2. The resulting N-pivalamide was purified by recrystallization from ether, and then reacted with base as described previously. The product was precipitated from aqueous base with acetic acid, filtered, washed with water and dried to give 3-amino-8-bromobenzo[f]quinazolin-1(2H)-one as a tan solid. (0.25 g, 32%) $^1$H NMR (DMSO-d$_6$, 200 MHz) δ: 6.60 (s, 2H, NH$_2$); 7.33 (d, J=9.0 Hz, 1H, Ar); 7.70 (dd, J=9.2, 2.2 Hz, 1H, Ar); 8.00 (d, J=9.0 Hz, 1H, Ar); 8.13 (d, J=2.2 Hz, 1H, Ar); 9.55 (d, J=9.2 Hz, 1H, Ar); 11.22 (s, 1H, NH). Anal. Calculated for C$_{12}$H$_8$BrN$_3$O.1/2H$_2$O: C, 48.18; H, 3.03; N, 14.05. Found: C, 48.22; H, 3.04; N, 14.07.

EXAMPLE 15

3,8-Diamino-7,9-dibromobenzo[f]quinazolin-1(2H)-one

To a stirred mixture of 3,8-diamino-5,6-dihydrobenzo[f]quinazolin-1(2H)-one sulfate hemihydrate (0.5 g, 1.5 mmoles) in acetic acid (15 ml) at 60° C. under a nitrogen atmosphere was added bromine (1 ml) in one portion. The temperature was raised to 90° C. for 1 hour and then cooled before pouring onto ice (40 g). After the mixture had stood for 10 minutes the precipitate was filtered, washed with water and recrystallized from 2 M H$_2$SO to give 3,8-diamino-7,9-dibromobenzo[f]quinazolin-1(2H)-one as an off-white solid. (0.2 g, 27%) $^1$H NMR (DMSO-d$_6$, 80 MHz) δ: 5.0–6.5 (br s, 2H, NH$_2$); 7.53–7.65 (d, J=9 Hz, 1H, Ar); 8.23–8.27 (br s, 3H, NH$_3$$^+$); 8.30–8.42 (d, J=9 Hz, 1H, Ar); 9.78 (s, 1H, Ar).

EXAMPLE 16

3-(Benzylamino)-7-bromobenzo[f]quinazolin-1(2H)-one

A. N-(7-Bromo-1,2-dihydro-1-oxobenzo[f]quinazolin-3-yl)pivalamide

The title compound was prepared in three steps from 5-bromo-3,4-dihydro-2-hydroxy-1-naphthoate using the same route described for the analogous 9-bromo compound, without significant modification. The final product was purified by trituration with water, followed by filtration and drying to give N-(7-bromo-1,2-dihydro-1-oxobenzo[f]quinazolin-3-yl)pivalamide as a pale yellow solid. (Overall yield was 49%). $^1$H NMR (DMSO-d$_6$, 200 MHz) δ: 1.27 (s, 9H, t-butyl); 7.62 (t, J=8.1 Hz, 1H, Ar); 7.71 (d, J=9.2 Hz, 1H, Ar); 7.95 (dd, J=7.6, 1.0 Hz, 1H, Ar); 8.48 (d, J=9.3 Hz, 1H, Ar); 9.81 (d, J=8.6 Hz, 1H, Ar); 11.29 (br s, 1H, NH); 12.3 (br s, 1H, NH).

B. 3-(Benzylamino)-7-bromobenzo[f]quinazolin-1(2H)-one

A mixture of N-(7-bromo-1,2-dihydro-1-oxobenzo[f]quinazolin-3-yl)pivalamide (0.3 g, 0.8 mmole) and benzylamine (10 ml) was stirred and heated at reflux under a nitrogen atmosphere for 18 hours. The cooled reaction mixture was then mixed with 4 volumes of ether to cause precipitation of the product. The precipitate was filtered and recrystallized from methanol to give 3-(benzylamino)-7-bromobenzo-[f]quinazolin-1(2H)-one as an off-white solid. (0.11 g, 37%) $^1$H NMR (DMSO-d$_6$, 200 MHz) δ: 4.62 (d, J=5.7 Hz, 2H, CH$_2$); 7.02 (m, 1H, benzyl-NH); 7.20–7.55 (m, 7H, Ar); 7.79 (dd, J=7.5, 1.1 Hz, 1H, Ar); 8.30 (d, J=9.2 Hz, 1H, Ar); 9.74 (d, J=8.6 Hz, 1H, Ar); 11.2 (br s, 1H, pyr-NH).

In a similar manner, the following compounds were prepared from the indicated precursors

| X | $^1$H NMR (200 MHz) in DMSO-$d_6$ ($\delta$) Elemental Analysis |
|---|---|
| 7-F[a] | 4.61(d, J = 6 Hz, 2H, CH$^2$); 6.96(br t, J = 6 Hz, 1H, pyr-NH-benzyl); 7.20–7.48(m, 7H, Ar); 7.58(ddd, J = 8, 8, 6 Hz, 1H, Ar); 8.17(d, J = 9 Hz, 1H, Ar); 9.43(d, J = 10 Hz, 1H, Ar); 11.20(br s, 1H, NH). |
| 9-Cl[b] | 4.61(d, J = 6 Hz, 2H, CH$_2$); 6.95(br t, J = 6 Hz, 1H, pyr-NH-benzyl); 7.18–7.43(m, 6H, Ar); 7.46(dd, J = 9, 2 Hz, 1H, Ar); 7.92(d, J = 9 Hz, 1H, Ar); 8.05(d, J = 9 Hz, 1H, Ar); 9.68(d, J = 2 Hz, 1H, Ar); 11.24(br s, 1H, NH). |

[a]Prepared from the corresponding N-pivalamide.
[b]Prepared from the corresponding 3-amino compound.

The following additional examples of compounds bearing modifications of the 3-amino group were prepared as described.

N-(9-Bromo-1,2-dihydro-1-oxobenzo[f]quinazolin-3-yl)formamide

To a solution of mixed anhydride prepared by adding 96% formic acid (10 ml) to acetic anhydride (20 ml) and stirring 45 minutes, was added 2-amino-9-bromobenzo-[f]quinazolin-1(2H)-one (0.20 g, 0.69 mmol). The suspension was heated until homogeneous, and the solution stirred 45 minutes without additional heat and then 15 minutes with warming until TLC (methanol:methylene chloride (1:9)) indicated complete reaction. The solution was chilled briefly in an ice bath and then allowed to stand at room temperature for 45 minutes. The resulting crystals were filtered, washed with water, and dried at 95° C. under reduced pressure to give N-(9-bromo-1,2-dihydro-1-oxobenzo[f]quinazolin-3-yl)formamide (0.135 g) as a white solid. $^1$H NMR (DMSO-$d_6$, 200 MHz) $\delta$: 7.55 (d, J=9 Hz, 1H, Ar), 7.73 (dd, J=9 Hz, 1H, Ar), 7.97 (d, J=9 Hz, 1H, Ar); 8.22 (d, J=9 Hz, 1H, Ar); 8.97 (br s, 1H, CHO); 9.89 (s, 1H, Ar), 10.75 (br s, 1H, CONH), 11.89 (brs, 1H, NH).

5,6-Dihydro-3-(methylamino)benzo[f]quinazolin-1(2H)-one

Methyl 3,4-dihydro-2-hydroxy-1-naphthoate was reacted with methylguanidine in the same manner as for the analogous reaction using guanidine (example 1) to obtain 5,6-dihydro-3-(methylamino)benzo[f]quinazolin-1(2H)-one. $^1$H NMR (DMSO-$d_6$, 200 MHz) $\delta$: 2.52–2.64 (m, 2H, CH$_2$), 2.68–2.82 (m, 2H, CH$_2$), 2.81 (d, J=5 Hz, 3H, NCH$_3$), 6.54 (br s, 1H, C$^3$NH), 7.02 (ddd, J=8, 8, 2 Hz, 1H, Ar), 7.07–7.18 (m, 2H, Ar), 8.42 (dd, J=8, 2 Hz, 1H, Ar), 10.98 (br s, 1H, N$^2$H).

All compounds gave elemental analyses consistent with the indicated structures.

EXAMPLE 17

3-Amino-9-ethynylbenzo[f]quinazolin-1(2H)-one
A. N-(1,2-Dihydro-1-oxo-9-(2(trimethylsilyl)ethynyl)benzo[f]quinazolin-3-yl)pivalamide A suspension of 3-amino-9-bromobenzo[f]quinazolin-1(2H)-one (0.99 g, 3.4 mmol) in pivalic anhydride (10 ml) was heated to reflux. The resulting solution was stirred at this temperature for 10 minutes and then concentrated in vacuo. The solid was resuspended in triethylamine:acetonitrile (1:3, 80 ml) and triphenyl phosphine (0.53 g, 2.0 mmol), trimethylsilylacetylene (3.0 ml, 21 mmol) (Aldrich), and Pd (OAc)$_2$ (0.23 g, 1.0 mmol) were added and the reaction mixture was stirred for 25 hours at 65° C. After cooling, the resulting solid was filtered and washed with diethyl ether to give crude product (0.84 g). This was combined with material (0.83 g) from a similar reaction and purified by chromatography on silica gel eluting with ethyl acetate-methylene chloride (1:99) to give N-(1,2-dihydro-1-oxo-9-(trimethylsilylethynyl)benzo[f]quinazolin-3-yl)pivalamide (0.25 g). $^1$H NMR (DMSO-$d_6$, 200 MHz) $\delta$: 0.28 (s, 9H, Si(CH$_3$)$_3$), 1.27 (s, 9H, t-butyl), 7.56 (d, J=9 Hz, 1H, Ar), 7.60 (dd, J=8, 1 Hz, 1H, Ar), 8.00 (d, J=8 Hz, 1H, Ar), 8.22 (d, J=9 Hz, 1H, Ar), 9.81 (s, 1H, Ar), 11.27 (br s, 1H, N$^2$H), 12.44 (br s, 1H, C$^3$—NH). Anal. Calculated for C$_{22}$H$_{25}$N$_3$O$_2$Si: C, 67.49; H, 6.44; N, 10.73. Found: C, 67.35; H, 6.48; N, 10.65.

B. 3-Amino-9-ethynylbenzo[f]quinazolin-1(2H)-one

A solution of N-(1,2-dihydro-1-oxo-9-(trimethylsilylethynyl)benzo[f]quinazolin-3-yl)pivalamide (0.24 g, 0.61 mmol) and K$_2$CO$_3$ (0.50 g, 3.6 mmol) in methanol (~50 ml) was stirred at reflux for 2.5 hours. The solution was then diluted with water (~20 ml) acidified with acetic acid, and the resulting solid filtered and dried at 90° C. under reduced pressure. The solid was resuspended in ethanol (~20 ml), filtered, and dried to give 3-amino-9-ethynyl benzo[f]quinazolin-1(2H)-one (0.084 g) as a tan solid. $^1$H NMR (DMSO-d, 200 MHz) $\delta$: 4.26 (s, 1H, ethynylCH), 6.63 (br s, 2H, NH$_2$), 7.32 (d, J=9 Hz, 1H, Ar), 7.47 (dd, J=8, 2 Hz, 1H, Ar), 7.87 (d, J=8 Hz, 1H, Ar), 8.02 (d, J=9 Hz, 1H, Ar), 9.78 (s, 1H, Ar), 11.34 (br s, 1H, NH). Mass spectrum (CI-CH$_4$): 236 (M+1, 100%). Anal. Calculated for C$_{14}$H$_9$N$_3$O: C, 71.48; H, 3.86; N, 17.86. Found: C, 71.30; H, 3.92; N, 17.68.

EXAMPLE 18

3-Amino-9-vinylbenzo[f]quinazolin-1(2H)-one

A solution of 3-amino-9-ethynyl benzo[f]quinazolin-1(2H)-one (0.19 g, 0.18 mmol) in pivalic anhydride (4 ml) was stirred at reflux for 10 minutes and then concentrated in vacuo. A solution of the residual solid and Lindlar catalyst (50 mg) in ethanol (50 ml) was shaken under hydrogen (~10 psi) for 30 minutes and then filtered through celite and concentrated in vacuo. The residue was purified by chromatography on silica gel eluting with ethyl acetate:hexane (1:4) to give N-(1,2-dihydro-1-oxo-9-vinylbenzo[f]quinazolin-3-yl)pivalamide. A solution of this solid in methanol (9 ml) and 1 N NaOH (1 ml) was stirred at reflux for 1.5 hours and, after cooling, was neutralized with acetic acid. The resulting precipitate was filtered and dried at 85° C. under reduced pressure to give 3-amino-9-vinyl benzo[f]quinazolin-1(2H)-one (0.067 g) as a white solid. $^1$H NMR (DMSO-$d_6$, 200 MHz) $\delta$: 5.36 (d, J=12 Hz, 1H, vinylCH), 5.94 (d, J=18 Hz, 1H, vinylCH), 6.54 (br s, 2H, NH$_2$), 6.89 (dd, J=18, 12 Hz, 1H, vinylCH), 7.26 (d, J=9 Hz, 1H, Ar), 7.64 (dd, J=8, 2 Hz, 1H, Ar), 7.83 (d, J=8 Hz, 1H, Ar), 7.98 (d, J=9 Hz, 1H, Ar), 9.63 (s, 1H, Ar), 11.13 (br s, 1H, NH). Mass spectrum (CI-CH$_4$): 238 (M+1, 100%). Anal. Calculated for C$_{14}$H$_{11}$N$_3$O: C, 70.87; H, 4.67; N, 17.71. Found: C, 70.77, H, 4.73; N, 17.66.

EXAMPLE 19

3-Amino-9-ethylbenzo[f]quinazolin-1(2H)-one

A solution of 3-amino-9-vinylbenzo[f]quinazolin-1(2H)-one (0.060 g, 0.25 mmol) and 10% palladium on carbon (0.10 g) (Aldrich) in ethanol (200 ml) was shaken under hydrogen (40 psi) for 1 hour and then filtered through celite and concentrated in vacuo. The residue was suspended in ethanol, filtered, and dried at 85° C. under reduced pressure to give 3-amino-9-ethylbenzo[f]-quinazolin-1(2H)-one (0.039 g) as a white solid. $^1$N NMR (DMSO-d$_6$, 200 MHz) δ: 1.26 (t, J=7 Hz, 3H, CH$_3$), 2.76 (q, J=7 Hz, 2H, CH$_2$), 6.49 (br s, 2H, NH$_2$), 7.21 (d, J=9 Hz, 1H, Ar), 7.31 (dd, J=8, 2 Hz, 1H, Ar), 7.77 (d, J=8 Hz, 1H, Ar), 7.96 (d, J=9 Hz, 1H, Ar), 9.47 (s, 1H, Ar), 11.08 (br s, 1H, NH). Mass spectrum (CI-CH$_4$): 240 (M+1, 100%). Anal. Calculated for C$_{14}$H$_{13}$N$_3$O.0.1H$_2$O: C, 69.75; H, 5.52; N, 17.43. Found: C, 69.79; H, 5.53; N, 17.37.

EXAMPLE 20

3-Amino-1,2,5,6-tetrahydro-1-oxobenzo[f]quinazoline-8-sulfonamide

A. 3-Amino-1,2,5,6-tetrahydro-1-oxobenzo[f]quinazolin-8-sulfonylchloride

Chlorosulfonic acid (25 ml, Aldrich), cooled to 5° C. in ice, was stirred during its addition to 3-amino-1,2,5,6-tetrahydro-1-oxo-benzo[f]quinazoline (5 g, 0.025 mole) contained in a beaker immersed in an ice bath. The solution was removed from the ice bath, stirred for a further 20 min, then poured onto ice (1000 g). The solid product was removed by filtration, washed with water, and dried under high vacuum at room temperature. The sulfonyl chloride was used without further purification.

D. 3-Amino-1,2,5,6-tetrahydro-1-oxobenzo[f]quinazoline-8-sulfonamide

3-Amino-1,2,5,6-tetrahydro-1-oxobenzo[f]quinazolin-8-sulfonyl chloride (1 g) was heated at reflux with concentrated (s.g.=0.9) aqueous ammonia (10 ml) for 10 min. The solution was allowed to cool to room temperature, water (10 ml) was added, the gold solid was removed by filtration, washed well with water, a little ethanol, then dried at 60° C. in vacuo to yield the sulfonamide, (0.703 g, 76%) $^1$H NMR (DMSO-d$_6$, 200 MHz) δ: 2.55–2.62 (m, 2H, ArCH$_2$); 2.80–2.87 (m, 2H, ArCH$_2$); 6.80 (br s, 2H, NH$_2$); 7.16 (s, 2H, NH$_2$); 7.54–7.59 (m, 2H, Ar); 8.56 (d, J=9 Hz, 1H, Ar); 11.02 (br s, 1H, NH). Mass spectrum (CI) 293: (M+1, 100%).

The following compounds were similarly prepared.

3-Amino-N,N-diethyl-1,2,5,6-tetrahydro-1-oxobenzo[f]quinazoline-8-sulfonamide (0.118 g, 70.7%), by heating the acid chloride (0.15 g) with a 25% aqueous solution of diethylamine (3 ml). $^1$H NMR (DMSO-d$_6$, 200 MHz) δ: 1.04 (t, J=7.1 Hz, 6H, CH$_2$CH$_3$); 2.53–2.62 (m, 2H, ArCH$_2$); 2.80–2.90 (m, 2H, ArCH$_2$); 3.12 (q, J=7.1 Hz, 4H, CH$_2$CH$_3$); 6.85 (br s, 2H, NH$_2$); 7.49–7.55 (m, 2H, Ar); 8.59 (d, J=9 Hz, 1H, Ar); 10.8–11.3 (v br s, 1H, NH). Mass spectrum (CI): 349 (M+1, 4.29%).

3-Amino-1,2,5,6-tetrahydro-1-oxo-N-(prop-2-vnyl)benzo[f]quinazoline-8-sulfonamide (0.105 g, 23.3%), by heating the acid chloride (0.4 g) with propargylamine (5 ml), evaporating the mixture in vacuo, triturating the residue with water (3 ml), and crystallizing the solid product from ethanol. $^1$H NMR (DMSO-d$_6$, 200 MHz) δ: 2.50–2.62 (m, 2H, ArCH$_2$); 2.80–2.88 (m, 2H, ArCH$_2$); 3.07 (t, J=2.51 Hz, 1H, propargylCH); 3.62–3.66 (m, 2H, propargylCH$_2$); 6.79–6.85 (br s, 2H, NH$_2$); 7.52–7.57 (m, 2H, Ar); 7.93 (t, J=5.86 Hz, 1H, SO$_2$NH); 8.59 (d, J=8.94 Hz, 1H, Ar); 11.02–11.04 (br s, 1H, NH). Mass spectrum (CI): 331 (M+1, 100%).

3-Amino-1,2,5,6-tetrahydro-1-oxo-N,N-bis(prop-2-vnyl)benzo[f]quinazoline-8-sulfonamide (0.089, 15.5%) from the acid chloride (0.4 g) and dipropargylamine (5 ml) as above. $^1$H NMR (DMSO-d$_6$, 200 MHz) δ: 2.59–2.66 (m, 2H, ArCH$_2$); 2.83–2.91 (m, 2H, ArCH$_2$); 3.24 (t, J=2.3 Hz, 2H, propargylCH); 4.06 (d, J=2.3 Hz, 4H, propargylCH$_2$); 7.09–7.14 (br s, 2H, NH$_2$); 7.56–7.60 (m, 2H, Ar); 8.60 (d, J=9.14 Hz, 1H, Ar). Mass spectrum (CI): 369 (M+1, 72%).

All compounds gave elemental analyses consistent with the indicated structures.

EXAMPLE 21

1,2,5,6-Tetrahydro-3-methyl-1-oxobenzo[f]quinazoline-9-sulfonamide

A. 1,2,5,6-Tetrahydro-3-methyl-1-oxobenzo[f]quinazolin-9-sulfonylchloride 1,2,5,6-tetrahydro-3-methyl-1-oxobenzo[f]quinazoline (5 g, 0.024 mole) was added to chlorosulfonic acid (50 ml, Aldrich) and stirred for 12 hours at room temperature. The reaction mixture was poured over ice (750 g), and the dark brown solid collected by filtration. The solid was washed with water, suspended in water (500 ml), and the pH of the suspension adjusted to 5.00 by addition of sodium bicarbonate. The suspension was filtered, the product washed with H$_2$O and dried under high vacuum at room temperature to give 1,2,5,6-tetrahydro-3-methyloxobenzo[f]quinazolin-9-sulfonyl chloride as a light brown solid (3.054 g, 41%). $^1$H NMR (DMSO-d$_6$, 300 MHz) δ: 2.60 (s, 3H, CH$_3$); 2.90 (s, 4H, ArCH$_2$); 7.22 (d, J=9 Hz, 1H, Ar); 7.53 (d, J=9 Hz, 1H, Ar); 8.75 (s, 1H, Ar).

B. 1,2,5,6-Tetrahydro-3-methyl-1-oxobenzo[f]quinazoline-9-sulfonamide (0.48 g, 51%), was prepared by the action of concentrated aqueous ammonia on the foregoing acid choride (1.0 g) essentially as described for the corresponding 3-amino compound. Mp>240° C. $^1$H NMR (DMSO-d$_6$, 300 MHz) δ: 2.33 (s, 3H, CH$_3$), 2.74 (t, J=8 Hz, ArCH$_2$), 2.92 (t, J=8 Hz, ArCH$_2$), 7.29 (s, 2H, NH$_2$), 7.41 (d, J=8 Hz, 1H, Ar), 7.64 (dd, J=8, 2 Hz, 1H, Ar), 9.10 (d, J=2 Hz, 1H, Ar), 12.71 (br s, 1H, NH). Anal Calculated for C$_{13}$H$_{13}$N$_3$O$_3$S.3/20H$_2$O: C, 53.11; H, 4.56; N, 14.29; S, 10.90. Found: C, 53.04; H, 4.53; N, 14.28; S, 10.90.

The following compounds were also prepared from 1,2,5,6-tetrahydro-3-methyl-1-oxobenzo[f]quinazolin-9-sulfonyl chloride by procedures essentially similar to those described above for the corresponding 3-amino compounds.

N,N-Diethyl-1,2,5,6-tetrahydro-3-methyl-1-oxobenzo[f]quinazoline-9-sulfonamide (50%), M.P.=249–251° C. $^1$H NMR (DMSO-d$_6$, 200 MHz) δ: 1.05 (t, J=7 Hz, 6H, amideCH$_3$ s), 2.32 (s, 3H, C$^3$—CH$_3$), 2.69–2.77 (m, 2H, ArCH$_2$), 2.88–2.96 (m, 2H, ArCH$_2$), 3.15 (q, J=7 Hz, 2H, amideCH$_2$'s), 7.40 (d, J=8 Hz, 1H, Ar)), 7.57 (dd, J=8, 2 Hz, 1H, Ar), 9.05 (d, J=2 Hz, 1H, Ar), 12.61 (br s, 1H, NH). Mass spectrum (CI-CH$_4$): 348 (M+1, 100%). Anal. Calculated for C$_{17}$H$_{21}$N$_3$O$_3$S: C, 58.77; H, 6.09; N, 12.09; S, 9.23. Found: C, 58.59; H, 6.15; N, 12.03; S, 9.16.

1,2,5,6-Tetrahydro-N,N, 3-trimethylbenzo[f]quinazoline-9-sulfonamide (45%) $^1$H NMR (DMSO-d$_6$, 200 MHz) δ: 2.30 (s, 3H, C$^3$—CH$_3$), 2.60 (s, 6H, N(CH$_3$)$_2$), 2.70–2.79 (m, 2H, ArCH$_2$), 2.90–2.98 (m, 2H, ArCH$_2$), 7.46 (d, J=8 Hz, 1H, Ar), 7.53 (dd, J=8, 1.5 Hz, 1H, Ar), 9.00 (d, J=1.5 Hz, 1H, Ar), 12.62 (br s, 1H, NH). Mass spectrum (CI-CH$_4$) 320 (M+1, 100%). Anal. Calculated for C$_{15}$H$_{17}$N$_3$O$_3$S: C, 56.41; H, 5.36; N, 13.16; S, 10.04. Found C, 56.35; H, 5.38; N, 13.09; S, 10.03.

EXAMPLE 22

3-Amino-N,N-diethyl-1,2-dihydro-1-oxobenzo[f]quinazoline-9-sulfonamide

A. 3-Amino-8-bromo-5,6-dihydrobenzo[f]quinazolin-1(2H)one-9-sulfonylchloride

Chlorosulfonic acid (100 g) was added to 3-amino-8-bromo-5,6-dihydro-benzo[f]quinazolin-1(2H)-one (5.20 g, 17.8 mmole) and the solution stirred overnight at room temperature. The reaction mixture was poured over ice, the collected solid washed with water, and dried under high vacuum to give 3-amino-8-bromo-5,6-dihydrobenzo[f]quinazolin-1(2H)-one-9-sulfonyl chloride (7.25 g, 90%). $^1$H NMR (DMSO-d$_6$, 200 MHz) δ: 2.67–2.75 (m, 2H, ArCH$_2$), 2.81–2.88 (m, 2H, ArCH$_2$), 7.43 (s, 1H, Ar), 8.23 (br s, 2H, NH$_2$), 8.91 (s, 1H, Ar), 9.90–10.50 (v br s, 1H, NH). Anal Calculated for C$_{12}$H$_9$BrClN$_3$O$_3$S1/2H$_2$O.9/20H$_2$SO$_4$: C, 32.48; H, 2.48; N, 9.47; S, 10.46. Found: C, 32.68; H, 2.37; N, 9.20; S, 10.40.

B. 3-Amino-8-bromo-N,N-diethyl-5,6-dihydrobenzo[f]quinazolin-1(2H)-one-9-sulfonamide 3-Amino-8-bromo-5,6-dihydrobenzo[f]quinazolin-1(2H)-one-9-sulfonylchloride (1.10 g, 2.8 mmole) and diethylamine (5 ml) were dissolved in water (15 ml) and heated to reflux for 30 minutes. The reaction mixture was cooled to room temperature and neutralized with dilute acetic acid. The collected precipitate was suspended in boiling methanol, the suspension allowed to cool, and the solid filtered off and dried under high vacuum to give 3-amino-8-bromo-N,N-diethyl-5,6-dihydrobenzo[f]quinazolin-1(2H)-one-9-sulfonamide (0.708 g, 59%). $^1$H NMR (DMSO-d$_6$, 200 MHz) δ: 1.07 (t, J=7 Hz, 6H, ethylCH$_3$), 2.54–2.62 (m, 2H, ArCH$_2$), 2.81–2.88 (m, 2H, ArCH$_2$), 3.26 (q, J=7 Hz, 4H, ethylCH$_2$), 6.83 (br s, 2H, NH$_2$), 7.60 (s, 1H, Ar), 9.13 (s, 1H, Ar), 10.95 (br s, 1H, NH). Anal Calculated for C$_{16}$H$_{19}$BrN$_4$O$_3$S: C, 44.97; H, 4.48; Br, 18.70; N, 13.11; S, 7.50. Found: C, 44.90; H, 4.49; Br, 18.65; N, 13.03; S, 7.57.

C. 3-Amino-8-bromo-N,N-diethyl-1,2-dihydro-1-oxobenzo[f]quinazoline-9-sulfonamide 3-Amino-8-bromo-N,N,-diethyl-5,6-dihydrobenzo[f]quinazolin-1(2H)-one-9-sulfonamide (0.165 g, 0.39 mmole) was suspended in pivalic anhydride (5 ml) (Aldrich) and heated under nitrogen until dissolved. The solution was heated under reflux for 10 minutes, cooled, and the pivalic anhydride removed in vacuo. The dried solid was dissolved in benzene (20 ml), pyridine (0.05 ml) added, and the solution heated to boiling under nitrogen. N-Bromosuccinimide (0.07 g, 0.47 mmole) was added, and the mixture refluxed for an additional 6 hours. The reaction mixture was cooled to room temperature, solvent removed in vacuo, and the solid residue crystallized from methanol. The pivalamide (0.105 g) was dissolved in methanol (2 ml), 1N NaOH (4 ml) added, and the solution heated to reflux under nitrogen for 1 hour. The cooled reaction mixture was neutralized with dilute acetic acid, the crystals collected by filtration and suspended in methanol. The collected crystals were dried in vacuo to give 3-amino-8-bromo-N,N-diethyl-1,2-dihydro-1-oxobenzo[f]quinazolin-9-sulfonamide (0.055 g, 33%). Mp>250° C. $^1$H NMR (DMSO-d$_6$, 200 MHz) δ: 1.10 (t, J=7 Hz, 6H, ethylCH$_3$), 3.38 (q, J=7 Hz, 4H, ethylCH$_2$), 6.78 (br s, 2H, NH$_2$), 7.47 (d, J=9 Hz, 1H, Ar), 8.09 (d, J=9 Hz, 1H, Ar), 8.40 (s, 1H, Ar), 10.30 (s, 1H, Ar), 11.32 (br s 1H, NH). Anal Calculated for C$_{16}$H$_{17}$BrN$_4$O$_3$S: C, 45.19; H, 4.03; Br, 18.79; N, 13.17; S, 7.54. Found: C, 45.10; H, 4.03; Br, 18.74; N, 13.07; S, 7.56.

EXAMPLE 23

3-Amino-N,N,-diethyl-1,2-dihydro-1-oxobenzo[f]quinazoline-9-sulfonamide

A. N-(9-((Diethylamino)sulfonyl)-1,2-dihydro-1-oxobenzo[f]quinazolin-3-yl)pivalamide and N-(9-((Diethylaminosulfonyl)-1,2,5,6-tetrahydro-1-oxobenzo[f]quinazolin-3-yl)pivalamide 3-Amino-8-bromo-N,N-diethyl-5,6-dihydrobenzo[f]quinazolin-1(2H)-one-9-sulfonamide (0.43 g, 1 mmole) was suspended in methanol (200 ml). 10% Palladium on carbon (0.60 g) was added to the suspension and the mixture was shaken under a hydrogen atmosphere at 23 psi for 3 hours. Methanol (750 ml) was added, and the mixture refluxed until the solid dissolved. The hot solution was filtered through celite. The celite and catalyst were washed by heating under reflux in methanol (500 ml) and the suspension filtered through fresh celite. Methanol was removed from the combined filtrates and the solid heated under reflux with pivalic anhydride (8 ml, Aldrich) under nitrogen for 30 minutes. The reaction mixture was evaporated to dryness, the residue applied to a silica column, and eluted with methanol/methylene chloride (1:199). The main fractions represented the title compounds;

N-(9-((diethylamino)sulfonyl-1,2-dihydro-1-oxobenzo[f]quinazolin-3-yl)pivalamide (0.073 g, 17%) $^1$H NMR (DMSO-d$_6$, 200 MHz) δ: 1.06 (t, J=7 Hz, 6H, ethylCH$_3$), 1.27 (s, 9H, t-butyl) 3.23 (q, J=7 Hz, 4H, ethylCH$_2$), 7.70 (d, J=9 Hz, 1H, Ar), 7.91 (dd, J=8, 2 Hz, 1H, Ar), 8.22 (d, J=8 Hz, 1H, Ar), 8.35 (d, J=9 Hz, 1H, Ar), 10.22 (d, J=2 Hz, 1H, Ar), 11.31 (br s, 1H, NH), 12.41 (br s, 1H, NH) and N-(9-((diethylamino)sulfonyl]-1,2,5,6-tetrahydro-1-oxobenzo[f]quinazolin-3-yl)-pivalamide (0.074 g, 17%) $^1$H NMR (DMSO-d$_6$, 200 MHz) δ: 1.05 (t, J=7 Hz, 6H, ethylCH$_3$), 1.24 (s, 9H, t-butyl), 2.73–2.80 (m, 2H, ArCH$_2$), 2.91–2.99 (m, 2H, ArCH$_2$), 3.14 (q, J=7 Hz, 4H, ethylCH$_2$) 7.41 (d, J=8 Hz, 1H, Ar), 7.56 (dd, J=8, 2 Hz, 1H, Ar), 8.98 (d, J=2 Hz, 1H, Ar), 11.32 (br s, 1H, NH), 12.19 (br s, 1H, NH).

B. 3-Amino-N,N-diethyl-5,6-dihydrobenzo[f]quinazolin-1(2H)-one-9-sulfonamide

N-(9-((diethylamino)sulfonyl)-1,2,5,6-tetrahydro-1-oxobenzo[f]quinazolin-3-yl)pivalamide (0.074 g, 0.17 mmole) was dissolved in a mixture of methanol (2 ml) and 1N NaOH (4 ml) and heated to reflux under nitrogen for 30 minutes. The cooled reaction mixture was neutralized with dilute acetic acid, the precipitate collected by filtration, washed with methanol and dried in vacuo at 95° C. to give the free amine, (0.031 g, 52%). Mp>250° C. $^1$H NMR (DMSO-d$_6$, 200 MHz) δ: 1.05 (t, J=7 Hz, 6H, ethylCH$_3$), 2.53–2.62 (m, 2H, ArCH$_2$), 2.79–2.89 (m, 2H, ArCH$_2$), 3.13 (q, J=7 Hz, 4H, ethylCH$_2$), 6.79 (br s, 2H, NH$_2$), 7.32 (d, J=8 Hz, 1H, Ar), 7.41 (dd, J=2,8 Hz, 1H, Ar), 8.93 (s, 1H, Ar), 10.93 (br s, 1H, NH). Anal. Calculated for C$_{16}$H$_{20}$N$_4$O$_3$S: C, 55.16; H, 5.79; N, 16.08. Found: C, 55.10; H, 5.83; N, 16.00.

C. Similarly prepared from the corresponding pivalamide was

3-Amino-N,N,-diethyl-1,2-dihydro-1-oxobenzo[f]quinazoline-9-sulfonamide (0.045 g, 76%). Mp>250° C. $^1$H NMR (DMSO-d$_6$, 200 MHz) δ: 1.05 (t, J=7 Hz, 6H, ethylCH$_3$), 3.21 (q, J=7 Hz, 4H, ethylCH$_2$), 6.69 (br s, 2H, NH$_2$), 7.44 (d, J=9 Hz, 1H, Ar), 7.74 (dd, J=8, 2 Hz, 1H, Ar), 8.07 (d, J=8 Hz, 1H, Ar), 8.13 (d, J=9 Hz, 1H, Ar), 10.14 (s, 1H, Ar), 11.24 (br s, 1H, NH). Anal. Calculated for C$_{16}$R$_{18}$N$_4$O$_3$S.1/4H$_2$O: C, 54.77; H, 5.31; N, 15.97. Found: C, 54.75; H, 5.16; N, 15.93.

EXAMPLE 24

N-(4-((3-Amino-1,2,5,6-tetrahydro-1-oxobenzo[f]quinazolin-8-yl)sulfonamido)benzoyl)-L-glutamic acid A. Diethyl-N-(4-((3-amino-1,2,5,6-tetrahydro-1-oxobenzo[f]quinazolin-8-yl)sulfonamido)benzoyl)-L-glutamate N-(4-Aminobenzoyl)-L-glutamic acid diethyl ester (3.2 g, 0.01 mole) (Aldrich) and 3-amino-1,2,5,6-tetrahydro-1-oxobenzo[f]-quinazolin-8-sulfonyl chloride (0.62 g, 0.002 mole) were fused at 150° C. until a clear melt was obtained (10 min). A solution of the crude product in methylene chloride was subjected to chromatography on silica, eluting with methanol:methylene chloride (1:4). Fractions containing the product were evaporated, the residue recrystallized from ethanol and dried under high vacuum to yield the diethyl ester (0.48 g, 40.2% based on sulfonyl chloride). $^1$H NMR (DMSO-d$_6$, 200 MHz) δ: 1.00–1.2 (overlapping t, 6H, CH$_2$CH$_3$); 1.88–2.15 (m, 2H, gluCH$_2$); 2.32–2.45 (m , 2H, gluCH$_2$); 2.45–2.60 (m, 2H, ArCH$_2$); 2.72–2.86 (m, 2H, ArCH$_2$); 3.92–4.12 (overlapping q, 4H, CH$_2$CH$_3$); 4.26–4.11 (m, 1H, gluCH); 6.66–7.00 (br s, 2H, NH$_2$); 7.16 (d, J=8.6 Hz, 2H, Ar); 7.52–7.63 (m, 2H, Ar); 7.71 (d, J=8.6 Hz, 1H, Ar); 8.54 (d, J=7.2 Hz, 1H, gluNH); 8.54 (d, J=9 Hz, 1H, Ar); 10.55 (br s, 1H, SO$_2$NH); 11.03 (br s, 1H, N$^2$H). Anal Calculated for C$_{28}$H$_{31}$N$_5$O$_8$S: C, 56.27; H, 5.23; N, 11,72; S, 5.36. Found: C, 56.19; H, 5.24; N, 11.63; S, 5,41.

B. N-(4-((3-Amino-1,2,5,6-tetrahydro-1-oxobenzo[f]quinazolin-8-yl)sulfonamido)benzoyl)-L-glutamic acid Diethyl-N-(4-((3-amino-1,2,5,6-tetrahydro-1-oxobenzo[f]quinazolin-8-yl)sulfonamido)benzoyl)-L-glutamate (0.15 g, 7.6 mmole) was dissolved in a mixture of 2N-NaOH (3 ml) and ethanol (6 ml) and the solution stored at room temperature for 14 hours. The ethanol was evaporated and the pH of the solution was adjusted to 2 with 1 N HCl. The solid was collected by filtration, washed with water and dried at 60° C. under vacuum. The product was crystallized once from ethanol to yield a white solid (0.12 g, 85%). $^1$H NMR (DMSO-d$_6$, 200 MHz) δ: 1.75–2.18 (m, 2H, gluCH$_2$); 2.20–2.40 (m, 2H, gluCH$_2$); 2.54–2.64 (m, 2H, ArCH$_2$); 2.70–2.89 (m, 2H, ArCH$_2$); 4.23–4.40 (m, 1H, gluCH); 6.70–7.08 (br s, 2H, NH$_2$); 7.16 (d, J=8.64 Hz, 2H, Ar); 7.56–7.61 (m, 2H, Ar); 7.72 (d, J=8.63 Hz, 2H, Ar); 8.42 (d, J=7.81 Hz, 1H, gluNH); 8.54 (d, J=8.99 Hz, 1H, Ar); 10.55 (s, 1H, SO$_2$NH); 10.91–11.24 (br s, 1H, N$^2$H); 11.98–12.63 (v br s, 2H, CO$_2$H); shows presence of water and EtOH. Anal Calculated for C$_{24}$H$_{23}$N$_5$O$_8$S.3/5H$_2$O.1/5EtOH: C, 52.19; H, 4.56; N, 12.47; S, 5.71. Found: C, 52.24; H, 4.61; N, 12.51; S, 5.76.

Similar reaction of diethyl N-(4-(prop-2-ynylaminobenzoyl)-L-glutamate (T. R. Jones et al., U.S. Pat. No. 4,564,616, 1986) with 3-amino-1,2,5,6-tetrahydro-1-oxobenzo[f]quinazolin-8-sulfonyl chloride and subsequent hydrolysis of the diester intermediate gave N-(4-(((3-amino-1,2,5,6-tetrahydro-1-oxobenzo[f]quinazolin-8-yl)sulfonyl(prop-2-ynyl)-amino)benzoyl)-L-glutamic acid (8.3% from sulfonyl chloride) $^1$H NMR (DMSO-d$_6$, 200 MHz) δ: 1.82–2.20 (m, 2H, gluCH$_2$); 2.30–2.38 (m, 2H, gluCH$_2$); 2.56–2.65 (m, 2H, ArCH$_2$); 2.83–2.87 (m, 2H, ArCH$_2$); 3.23 (t, J=2 Hz, 1H, propynylCH); 4.34–4.40 (m, 1H, gluCH); 4.53 (d, J=2 Hz, 2H, propynylCH$_2$); 7.03 (br s, 2H, NH$_2$); 7.29 (d, J=8.6 Hz, 2H, Ar); 7.37 (dd, J=2.5, 8.6 Hz, 1H, Ar); 7.45 (d, J=2.5 Hz, 1H, Ar); 7.83 (d, J=8.6 Hz, 2H, Ar); 8.56 (d, J=8.6 Hz, 1H, Ar); 8.64 (d, J=7.8 Hz, 1H, gluNH); 10.94–11.56 (v br s, 1H, N$^2$H); 11.80–12.90 (v br s, 1H, CO$_2$H); shows presence of H$_2$O. Anal Calculated for C$_{27}$H$_{25}$N$_5$O$_8$S.23/10H$_2$O: C, 52.22; H, 4.80; N, 11.28. Found: C, 52.30; H, 4.61; N, 11.14.

EXAMPLE 25

N-(4-((3-amino-9-bromo-1,2-dihydro-1-oxobenzo[f]quinazolin-8-yl)sulfonamido)benzoyl)-L-glutamic acid was prepared from 3-amino-9-bromo-1,2-dihydro-1-oxobenzoquinazoline (6 g) essentially as described above; yields and analytical data on the product and intermediates are given below.

A. 3-Amino-9-bromo-1,2-dihydro-1-oxobenzo[f]quinazoline-8-sulfonylchloride (3 g, 36%). $^1$H NMR (DMSO-d$_6$, 200 MHz) δ: 7.59 (d, J=9 Hz, 1H, Ar), 8.44 (d, J=8 Hz, 1H, Ar), 8.54 (s, 1H, Ar), 9.75 (s, 1H, Ar), 11.30 (v br s, H$_2$O+exchangeable H's).

B. Diethyl N-(4-((amino-9-bromo-1,2-dihydro-1-oxobenzo[f]quinazolin-8-yl)sulfonamidobenzoyl)-L-glutamate (0.91 g, 17%). Mp>240° C. $^1$H NMR (DMSO-d$_6$, 200 MHz) δ: 1.08 (t, J=7 Hz, 3H, esterCH$_3$), 1.11 (t, J=7 Hz, 3H, esterCH$_3$), 1.72–2.12 (m, 2H, glu-CH$_2$), 2.34 (t, J=7 Hz, glu-CH$_2$), 3.97 (q, J=7 Hz, 2H, esterCH$_2$), 4.02 (q, J=7 Hz, 2H, esterCH$_2$), 4.24–4.36 (m, 1H, glu-CH), 6.84 (br s, 2H, NH$_2$), 7.17 (d, J=9 Hz, 2H, Ar), 7.39 (d, J=9 Hz, 1H, Ar), 7.66 (d, J=8 Hz, 2H, Ar), 8.26 (d, J=9 Hz, 1H, Ar), 8.47 (d, J=7 Hz, 1H, NH), 8.76 (s, 1H, Ar), 9.95 (s, 1H, Ar), 11.01 (s, 1H, NH), 11.39 (s, 1H, NH). Anal Calculated for C$_{28}$H$_{28}$BrN$_5$O$_8$S:1/2H$_2$O C, 49.20; H, 4.28; Br, 11.69; N, 10.25; S, 4.69. Found: C, 49.19; H, 4.23; Br, 11.66; N, 10.30; S, 4.71.

C. N-(4-((3-Amino-9-bromo-1,2-dihydro-1-oxobenzo[f]quinazolin-8-yl)sulfonamido)benzoyl)-L-glutamic acid (0.68 g, 79%). Mp=238–242° C. $^1$H NMR (DMSO-d$_6$, 200 MHz) δ: 1.72–2.07 (m, 2H, glu-CH$_2$), 2.25 (t, J=7 Hz, glu-CH$_2$), 4.24–4.29 (m, 1H, glu-CH), 6.65 (br s, 2H, NH$_2$), 7.17 (d, J=9 Hz, 2H, Ar), 7.39 (d, J=9 Hz, 1H, Ar), 7.67 (d, J=9 Hz, 2H, Ar), 8.26 (d, J=9 Hz, 1H, Ar), 8.36 (d, J=8 Hz, 1H, NH), 8.78 (s, 1H, Ar), 9.95 (s, 1H, Ar), 11.00 (s, 1H, NH), 11.41 (v br s, 1H, NH), 12.30 (v br s, 2H, OH). Anal Calculated for C$_{24}$H$_{20}$BrN$_5$O$_8$S.7/5H$_2$O: C, 44.79; H, 3.57; N, 10.88. Found: C, 44.88; H, 3.54; N, 10.75.

EXAMPLE 26

N-(4-((3-Amino-1,2,5,6-tetrahydro-1-oxobenzo[f]quinazolin-9-yl)sulfonamido)benzoyl)-L-glutamic acid A. Diethyl N-(4-(((3-amino-8-bromo-1,2,5,6-tetrahydro-1-oxobenzo[f]quinazolin-9-yl)sulfonyl)amino)benzoyl)-L-glutamate 3-Amino-8-bromo-5,6-dihydrobenzo[f]quinazolin-1(2H)-one-9-sulfonyl chloride (2.00 g, 4.50 mmole) and N-(4-aminobenzoyl)-L-glutamic acid diethyl ester (7.26 g, 22.5 mmole) (Aldrich) were placed together in a test tube and melted at 175° C. The mixture was heated for 1 hour, 20 minutes, the cooled residue suspended in methylene chloride and filtered to remove undissolved solid. The filtrate was evaporated to dryness and the residue subjected to chromatography on a Waters Prep 500 instrument (silica column, elution with methanol/methylene chloride (1:24)). The combined fractions containing product were evaporated and the residue dried under high vacuum. The solid was suspended in boiling ethanol (900 ml), the suspension cooled to room temperature and filtered to give diethyl N-(4-(((3-amino-8-bromo-1,2,5,6-tetrahydro-1-oxobenzo[f]quinazolin-9-yl)sulfonyl)amino)benzoyl)-L-glutamate (0.794 g, 260). Mp>250° C. $^1$H NMR (DMSO-d$_6$, 200 MHz) δ: 1.12 (t, J=7 Hz, 3H, ester-CH$_3$), 1.14 (t, J=7 Hz, 3H, ester-CH$_3$), 1.89–2.09 (m, 2H, glu-CH$_2$), 2.37 (t, J=7 Hz, 2H, glu-CH$_2$), 2.48–2.59 (m, 2H, ArCH$_2$), 2.77–2.85 (m, 2H, ArCH$_2$), 3.99 (q, J=7 Hz, 2H, esterCH$_2$), 4.05 (q, J=7 Hz, 2H, esterCH$_2$), 4.29–4.40 (m, 1H, glu-CH), 6.84 (br s, 2H, NH$_2$), 7.14 (d, J=9 Hz, 2H, Ar), 7.54 (s, 1H, Ar), 7.69 (d, J=9 Hz, 2H, Ar), 8.48 (d, J=8 Hz, 1H, NH), 9.37 (s, 1H, Ar), 10.87 (br s, 1H, NH), 11.04 (br s, 1H, NH). Anal. Calculated for C$_{28}$H$_{30}$BrN$_5$O$_8$S:1/4H$_2$O C, 49.38; H, 4.51; Br, 11.73; N, 10.20; S, 4.71. Found: C, 49.33; H, 4.40; Br, 11.79; N, 10.20; S, 4.74.

B. Diethyl N-(4-(((3-amino-1,2,5,6-tetrahydro-1-oxobenzo[f]quinazolin-9-yl)sulfonyl)amino)benzoyl)-L-glutamate Diethyl N-(4-(((3-amino-8-bromo-1,2,5,6-tetrahydro-1-oxobenzo[f]-quinazolin-9-yl)sulfonyl)amino)benzoyl)-L-glutamate (0.3 g, 0.44 mmole) was dissolved in boiling ethanol (250 ml), the solution cooled to room temperature, and 10% palladium on carbon (0.20 g) added. The mixture was shaken under a hydrogen atmosphere for 35 hours. Additional 10% palladium on carbon (0.20 g) was added to the reaction mixture which was then shaken under a hydrogen atmosphere for a further 15 hours. Ethanol (750 ml) was added, the reaction mixture heated to reflux, and filtered while hot through celite. Water (33 ml) was added, and the solution neutralized with ammonium hydroxide. The solvent was removed in vacuo, the solid suspended in water and the mixture neutralized with dilute ammonium hydroxide and dilute acetic acid. The resulting solid was collected by filtration and air dried. The crude product was passed through silica gel, eluting with methanol:methylene chloride. Combined fractions containing product—were evaporated, and the solid residue suspended in a small amount of methanol, filtered, and dried under high vacuum to give the diester (0.095 g). $^1$H NMR (DMSO-d$_6$, 200 MHz) δ: 1.12 (t, J=7 Hz, 3H, CH$_3$), 1.14 (t, J=7 Hz, 3H, CH$_3$), 1.85–2.15 (m, 2H, glu-CH$_2$), 2.38 (t, J=7 Hz, 2H, glu-CH$_2$), 2.48–2.61 (m, 2H, ArCH$_2$), 2.75–2.87 (m, 2H, Ar CH$_2$), 4.00 (q, J=7 Hz, 2H, esterCH$_2$), 4.06 (q, J=7 Hz, 2H, esterCH$_2$), 4.28–4.42 (m, 1H, glu-CH), 6.78 (br s, 2H, NH$_2$), 7.16 (d, J=9 Hz, 2H, Ar), 7.27 (d, J=8 Hz, 1H, Ar), 7.46 (dd, J=8, 2 Hz, 1H, Ar), 7.70 (d, J=9 Hz, 2H, Ar), 8.52 (d, J=7 Hz, 1H, glu-NH), 9.06 (d, J=2 Hz, 1H, Ar), 10.66 (br s, 1H, SO$_2$NH), 11.03 (br s, 1H, N$^2$H). Anal. Calculated for C$_{28}$H$_{31}$N$_5$O$_8$S: C, 56.27; H, 5.23; N, 11.72. Found: C, 56.35; H, 5.27; N, 11.62.

C. N-(4-((3-Amino-1,2,5,6-tetrahydro-1-oxobenzo[f]quinazolin-9-yl)sulfonamido)benzoyl)-L-glutamic acid (0.043 g, 52%) was obtained by hydrolysis of the foregoing diester (0.088 g, 0.15 mmol) in sodium hydroxide as described above. $^1$H NMR (DMSO-d$_6$, 200 MHz) δ: 1.74–2.16 (m, 2H, gluCH$_2$), 2.29 (t, J=7 Hz, 2H, gluCH$_2$), 2.48–2.60 (m, 2H, ArCH$_2$), 2.72–2.86 (m, 2H, ArCH$_2$), 4.23–4.38 (m, 1H, gluCH), 6.78 (br s, 2H, NH$_2$), 7.16 (d, J=9 Hz, 2H, Ar), 7.26 (d, J=8 Hz, 1H, Ar), 7.45 (dd, J=8, 2 Hz, 1H, Ar), 7.70 (d, J=9 Hz, 2H, Ar), 8.42 (br d, J=8 Hz, 1H, gluNH), 9.06 (d, J=2 Hz, 1H, Ar), 10.65 (br s, 1H, SO$_2$NH), 11.05 (br s, 1H, N$^2$H), 12.33 (br s, 2H, CO$_2$H). Anal. Calculated for C$_{24}$H$_{23}$N$_5$O$_8$S$^1$H$_2$O: C, 51.52; H, 4.50; N, 12.52. Found: C, 51.47; H, 4.51; N, 12.52.

EXAMPLE 27

N-(4-(((3-Amino-1,2-dihydro-1-oxobenzo[f]quinazolin-9-yl)amino)sulfonyl)benzoyl)-L-glutamic acid A. Methyl 4-(((3-Amino-1,2-dihydro-1-oxobenzo[f]quinazolin-9-yl)amino)sulfonyl)benzoate To a solution of N-(9-Amino-1,2-dihydro-1-oxobenzo[f]quinazolin-3-yl)pivalamide (1.38 g, 4.5 mmoles) in dry pyridine (10 ml) was added 4-(chlorosulfonyl)benzoic acid (5.0 g, 22.6 mmoles) at room temperature under a nitrogen atmosphere. After stirring for 3 days, the pyridine was removed under reduced pressure to leave a gummy brown residue which was suspended in water (30 ml), filtered, washed with water and dried to give 4-((N-(1,2-dihydro-1-oxobenzo[f]quinazolin-3-yl)pivalamide)-9-yl)amino)sulfonyl)benzoic acid (1.65 g).

The foregoing material was dissolved in anhydrous 5% HCl/methanol (30 ml) and heated to 50° C. with stirring under a nitrogen atmosphere for 27 hrs. Upon cooling, a fine precipitate formed which was then filtered, washed with methanol and dried to give methyl 4-(((3-Amino-1,2-dihydro-1-oxobenzo[f]quinazolin-9-yl)amino)sulfonyl)benzoate as an off-white solid. (0.41 g, 27%) $^1$H NMR (DMSO-d$_6$, 200 MHz) δ: 3.82 (s, 3H, OCH$_3$); 7.36 (dd, J=8.8, 2Hz, 1H, Ar); 7.39 (d, J=8.8 Hz, 1H, Ar); 7.90 (d, J=8.8 Hz, 1H, Ar); 7.98–8.11 (m, 6H, Ar); 8.17 (d, J=9.1 Hz, 1H, Ar); 9.33 (d, J=2 Hz, 1H, Ar); 11.00 (br s, 1H, NH). Anal. Calculated for C$_{20}$H$_{16}$N$_4$O$_5$S.3/5CH$_3$OH: C, 51.53; H, 4.07; Cl, 7.38; N, 11.67; S, 6.68. Found: C, 51.28; H, 3.80; Cl, 7.65; N, 11.90; S, 6.75.

B. 4-(((3-Amino-1,2-dihydro-1-oxobenzo[f]quinazolin-9-yl)amino)sulfonyl)benzoic acid A solution of methyl 4-(((3-Amino-1,2-dihydro-1-oxobenzo[f]quinazolin-9-yl)amino)sulfonyl)benzoate (0.54 g, 1.2 mmoles) in 0.1 N NaOH (30 ml) was stirred at room temperature under a nitrogen atmosphere for 19 hrs. After this time, the solution was acidified (pH 4) with 1 N HCl to cause precipitation of the product which was filtered and dried to give 4-(((3-amino-1,2-dihydro-1-oxobenzo[f]quinazolin-9-yl)amino)sulfonyl)benzoic acid as a light brown solid. (0.46 g, 86%) $^1$H NMR (DMSO-d$_6$, 200 MHz) δ: 7.28 (d, J=8.9 Hz, 1H, Ar); 7.30 (dd, J=8.3, 2 Hz, 1H, Ar); 7.37 (br s, 2H, NH$_2$); 7.82 (d, J=8.6 Hz, 1H, Ar); 7.95–8.06 (m, 5H, Ar); 9.38 (d, J=2 Hz, 1H, Ar); 10.85 (s, 1H, NH). Anal. Calculated for C$_{19}$H$_{14}$N$_4$O$_5$.4/5HCl.11/10H$_2$O: C, 49.68; H, 3.73; N, 12.20. Found: C, 49.61; H, 3.78; N, 12.30.

C. Diethyl N-(4-(((3-amino-1,2-dihydro-1-oxobenzo[f]quinazolin-9-yl)amino)sulfonyl)benzoyl)-L-glutamate To a solution of L-glutamic acid diethyl ester (0.81 g, 4.0 mmoles) and 4-(((3-amino-1,2-dihydro-1-oxobenzo[f]quinazolin-9-yl)amino)sulfonyl)benzoic acid (0.43 g, 0.9 mmoles) in dry dimethylformamide (20 ml) was added 1-hydroxybenzotriazole monohydrate (0.43 g, 3.2 mmoles) and dicyclohexylcarbodiimide (0.66 g, 3.2 mmoles). The solution was stirred at room temperature under a nitrogen atmosphere for 20 hrs, after which time the solvent was removed under reduced pressure. The residue was recrystallized successively from methylene chloride:methanol/9:1 and methanol to give diethyl N-(4-(((3-amino-1,2-dihydro-1-oxobenzo[f]quinazolin-9-yl)amino)sulfonyl)benzoyl)-L-glutamate as a white solid. (0.215 g, 36%). $^1$H NMR (DMSO-d$_6$, 300 MHz) δ: 1.12 (t, J=7 Hz, 3H, ester-CH$_3$); 1.15 (t, J=7 Hz, 3H, ester-CH$_3$); 1.89–2.13 (m, 2H, glu-CH$_2$); 2.40 (t, J=7.6 Hz, 2H, glu-CH$_2$); 4.00 (q, J=7 Hz, 2H, ester-CH$_2$); 4.08 (q, J=7 Hz, 2H, ester-CH$_2$); 6.55 (br s, 2H, NH$_2$); 7.16 (d, J=8.9 Hz, 1H, Ar); 7.23 (dd, J=8.7, 2 Hz, 1H, Ar); 7.73 (d, J=8.7 Hz, 1H, Ar); 7.89 (d, J=8.9 Hz, 1H, Ar);

7.96 (m, 4H, Ar); 8.89 (d, J=7.4 Hz, 1H, glu-NH); 9.48 (d, J=2 Hz, 1H, Ar); 10.67 (s, 1H, NH); 11.08 (s, 1H, NH). Anal. Calculated for $C_{28}H_{29}N_5O_8S$: C, 56.46; H, 4.91; N, 11.76; S, 5.38. Found: C, 56.45; H, 4.94; N, 11.75; S, 5.43.

D. N-(4-(((3-Amino-1,2-dihydro-1-oxobenzo[f]quinazolin-9-yl)amino)sulfonyl)benzoyl)-L-glutamic acid A solution of diethyl N-(4-(((3-amino-1,2-dihydro-1-oxobenzo[f]quinazolin-9-yl)amino)sulfonyl)benzoyl)-L-glutamate (0.175 g, 0.3 mmoles) in 1 N NaOH (12 ml) was stirred and heated to 50° C. under a nitrogen atmosphere for 24 hrs. After cooling, the solution was acidified (pH 3) with concentrated HCl to cause precipitation of the product which was filtered, washed with water and dried to give N-(4-(((3-amino-1,2-dihydro-1-oxobenzo[f]quinazolin-9-yl)-amino)sulfonyl)benzoyl)-L-glutamic acid as an off-white solid. (0.18 g, 99%) $^1$H NMR (DMSO-$d_6$, 300 MHz) δ: 1.81–2.13 (m, 2H, glu-$CH_2$); 2.32 (t, J=7.6 Hz, 2H, glu-$CH_2$); 4.34 (m, 1H, glu-CH); 6.58 (br s, 2H, $NH_2$); 7.16 (d, J=8.9 Hz, 1H, Ar); 7.22 (dd, J=8.6, 2 Hz, 1H, Ar); 7.74 (d, J=8.7 Hz, 1H, Ar); 7.89 (d, J=9.0 Hz, 1H, Ar); 7.96 (m, 4H, Ar); 8.78 (d, J=7.6 Hz, 1H, glu-NH); 9.49 (d, J=2 Hz, 1H, Ar); 10.68 (s, 1H, NH); 11.1 (br s, 1H, NH); 12.3 (br s, 2H, $(CO_2H)_2$). Anal. Calculated for $C_{24}H_{21}N_5O_8S.3H_2O$: C, 48.56; H, 4.58; N, 11.80; S, 5.40. Found: C, 48.38; H, 4.30; N, 11.69; S, 5.34.

EXAMPLE 28

N-(4-((1,2,5,6-tetrahydro-3-methyl-1-oxobenzo[f]quinazolin-9-yl)sulfonamido)benzoyl)-L-glutamic acid A. Diethyl-N-(4-((1,2,5,6-tetrahydro-3-methyl-1-oxobenzo[f]quinazolin-9-yl)sulfonamido)benzoyl)-L-glutamate N-(4-Aminobenzoyl)-L-glutamic acid diethyl ester (6.06 g, 0.0188 mole) (Aldrich) and 1,2,5,6-tetrahydro-3-methyl-1-oxobenzo[f]-quinazolin-9-sulfonyl chloride (5.84 g, 0.0188 mole) were dissolved in pyridine (55 ml) and the reaction mixture stirred at room temperature for 3.5 hours. The pyridine was removed in vacuo, the residue washed with water, and the pink solid collected by filtration. The crude product was dried under high vacuum, then subjected to chromatography on a Waters Prep 500 instrument (silica cartridge, elution with methanol:methylene chloride (1:4). The product was recrystallized from ethanol and dried under high vacuum to yield the diethyl ester (5.68 g, 51%). $^1$H NMR (DMSO-$d_6$, 300 MHz) δ: 1.14 (t, J=7 Hz, 3H, $CH_2\underline{CH_3}$); 1.16 (t, J=7 Hz, 3H, $CH_2\underline{CH_3}$); 1.88–2.13 (m, 2H, glu$CH_2$); 2.32 (s, 3H, $CH_3$); 2.40 (t, J=8 Hz, 2H, glu$CH_2$); 2.71 (m, 2H, Ar$CH_2$); 2.89 (m, 2H, Ar-$\underline{CH_2}$); 4.02 (q, J=7 Hz, 2H, $\underline{CH_2}CH_3$); 4.08 (q, J=7 Hz, 2H, $\underline{CH_2}CH_3$); 4.33–4.41 (m, 1H, CH); 7.20 (d, J=9 Hz, 2H, Ar); 7.39 (d, 1H, J=8 Hz, Ar); 7.62 (dd, J=8, 2 Hz, Ar); 7.73 (d, J=9 Hz, 2H, Ar); 8.55 (d, J=8 Hz, 1H, gluNH); 9.21 (d, 2 Hz, 1H, Ar); 10.74 (s, 1H, NH); 12.72 (s, 1H, NH). Anal. Calculated for $C_{29}H_{32}N_4O_8S.1/10EtOH:3/4H_2O$ C, 57.05; H, 5.59; N, 9.11; S, 5.22. Found: C, 57.08; H, 5.58; N, 9.15; S, 5.17.

B. N-(4-((1,2,5,6-Tetrahydro-3-methyl-1-oxobenzo[f]quinazolin-9-yl)sulfonamido)benzoyl)-L-glutamic acid Diethyl-N-(4-((1,2,5,6-tetrahydro-3-methyl-1-oxobenzo[f]quinazolin-9-yl)sulfonamido)benzoyl)-L-glutamate (4.53 g, 7.6 mmole) was dissolved in N-NaOH (64 ml) and the solution stirred at room temperature for 4 hours. The pH of the solution was adjusted to 3.00 with 1 N HCl, the solid collected by filtration, washed with water and dried under high vacuum to yield the product as an off-white solid (3.94 g, 96%). $^1$H NMR (DMSO-$d_6$, 300 MHz) δ: 1.84–1.96 (m, 1H, gluCH); 2.00–2.10 (m, 1H, gluCH); 2.32 (s, 3H, $CH_3$, superimposed over t, 2H, glu$CH_2$); 2.71 (m, 2H, Ar$CH_2$); 2.89 (m, 2H, Ar$CH_2$); 4.28–4.36 (m, 1H, gluCH); 7.20 (d, J=9 Hz, 2H, Ar); 7.39 (d, J=8 Hz, 1H, Ar); 7.62 (dd, J=8, 2 Hz, 1H, Ar); 7.74 (d, J=9 Hz, 2H, Ar); 8.44 (d, J=8 Hz, 1H, gluNH); 9.21 (d, J=2 Hz, 1H, Ar); 10.73 (s, 1H, $SO_2NH$); 12.36 (br s, 2H, $CO_2H$); 12.72 (br s, 1H, NH). Anal Calculated for $C_{25}H_{24}N_4O_8S.3/2H_2O$: C, 52.91; H, 4.79; N, 9.87; S, 5.65. Found: C, 52.98; H, 4.78; N, 9.87; S, 5.58.

An essentially similar sequence of reactions using diethyl 4-(methylamino)benzoylglutamate (T. R. Jones et al, UK Patent Application GB 2175 903A, 1986) (2.0 g, 6.0 mmol) with the sulfonyl chloride (2.0 g, 6.4 mmol) gave the corresponding product bearing a methyl substituent on the sulfonamido-nitrogen atom; data on the product and intermediate are given below.

Diethyl N-(4-(methyl((1,2,5,6-tetrahydro-3-methyl-1-oxobenzo[f]quinazolin-9-yl)sulfonyl)amino)benzoyl)-L-glutamate (1.47 g, 40%) M.P.=168–170.50° C. $^1$H NMR (DMSO-$d_6$, 200 MHz) δ: 1.14 (t, J=7 Hz, 3H, ester$CH_3$), 1.16 (t, J=7 Hz, 3H, ester$CH_3$), 1.85–2.20 (m, 2H, glu$CH_2$), 2.30 (s, 3H, $C^3$—$CH_3$), 2.42 (t, J=7 Hz, 2H, glu$CH_2$), 2.67–2.80 (m, 2H, Ar$CH_2$), 2.85–2.99 (m, 2H, Ar$CH_2$), 3.17 (s, 3H, $NCH_3$), 4.02 (q, J=7 Hz, 2H, ester$CH_2$), 4.08 (q, J=7 Hz, 2H, ester$CH_2$), 4.32–4.48 (m, 1H, gluCH), 7.22 (dd, J=8, 2 Hz, 1H, Ar), 7.28 (d, J=9 Hz, 2H, Ar), 7.38 (d, J=8 Hz, 1H, Ar), 7.82 (d, J=9 Hz, 2H, Ar), 8.73 (d, J=7 Hz, 1H, gluNH), 9.00 (d, J=2 Hz, 1H, Ar), 12.68 (br s, 1H, $N^2H$). Anal. Calculated for $C_{30}H_{34}N_4O_8S.1/3H_2O$: C, 58.44; H, 5.67; N, 9.09; S, 5.20. Found: C, 58.46; H, 5.65; H, 9.09; S, 5.19.

N-(4-(Methyl((1,2,5,6-tetrahydro-3-methyl-1-oxobenzo[f]quinazolin-9-yl)sulfonyl)amino)benzoyl)-L-glutamic acid (0.89 g, 99% from diester (1.0 g, 1.6 mmol); $^1$H NMR (DMSO-$d_6$, 200 MHz) δ: 1.80–2.20 (m, 2H, glu$CH_2$), 2.31 (s, 3H, $C^3$—$CH_3$), 2.34 (t, J=7 Hz, 2H, glu$CH_2$), 2.67–2.80 (m, 2H, Ar$CH_2$), 2.85–2.98 (m, 2H, Ar$CH_2$), 3.17 (s, 3H, $NCH_3$), 4.30–4.43 (m, 1H, gluCH), 7.22 (dd, J=8, 2 Hz, 1H, Ar), 7.28 (d, J=9 Hz, 2H, Ar), 7.38 (d, J=8 Hz, 1H, Ar), 7.83 (d, J=9 Hz, 2H, Ar), 8.62 (d, J=8 Hz, 1H, gluNH), 9.00 (d, J=2 Hz, 1H, Ar), 12.39 (br s, 2H, $CO_2H$'s), 12.69 (br s, 1H, $N^2H$). Anal. Calculated for $C_{26}H_{26}N_4O_8S.3/20H_2O$: C, 56.04; H, 4.76; N, 10.05; S, 5.75. Found: C, 56.04; H, 4.66; N, 10.03; S, 5.68.

EXAMPLE 29

1,2,5,6-Tetrahydro-3-methyl-4'-nitro-1-oxobenzo[f]quinazoline-9-sulfonanilide 1,2,5,6-Tetrahydro-3-methyl-1-oxobenzo[f]quinazolin-9-sulfonyl chloride (0.53 g, 1.7 mmole) and p-nitroaniline (0.25 g, 1.8 mmole) (Eastman) were dissolved in pyridine (5 ml) and the reaction mixture stirred at room temperature for 48 hours. The pyridine was removed in vacuo, and the residue washed with water. The dried solid was subjected to chromatography on silica (80 g), eluting with methanolmethylene chloride (1:19). Fractions containing product were evaporated to dryness, the residue sonicated with ether (75 ml) and filtered. The beige solid was washed with ether and dried under high vacuum to yield 1,2,5,6-tetrahydro-3-methyl-4'-nitro-1-oxobenzo[f]quinazoline-9-sulfonanilide. (0.18 g, 26%). Mp>240° C. $^1$H NMR (DMSO-$d_6$, 300 MHz) δ: 2.32 (s, 3H, $CH_3$); 2.72 (m, 2H, ArCH); 2.91 (m, 2H, Ar$CH_2$); 7.33 (d, J=9 Hz, 2H, Ar); 7.43 (d, J=8 Hz, 1H, Ar); 7.69 (dd, J=2,8 Hz, Ar); 8.13 (d, J=9 Hz, 2H, Ar); 9.23 (d, J=2 Hz, 1H, Ar); 11.13 (s, 1H, NH); 12.73 (s, 1H, NH). Anal Calculated for $C_{19}H_{16}N_4O_5S.13/25H_2O$: C, 54.10; H, 4.07; N, 13.28; S, 7.60. Found: C, 54.07; H, 3.98; N, 13.19; S, 7.66.

Similarly the following compounds were prepared by reaction of the appropriate aromatic amine with the foregoing benzoquinazoline-9-sulfonyl chloride;

4'-Acetyl-1,2,5,6-tetrahydro-3-methyl-1-oxobenzo[f]quinazoline-9-sulfonanilide (0.172 g, 25%). Mp>240° C. $^1$H NMR (DMSO-$d_6$, 300 MHz) δ: 2.32 (s, 3H, $CH_3$); 2.46 (s, 3H, $CH_3$); 2.71 (t, J=8 Hz, 2H, $ArCH_2$); 2.90 (t, J=8 Hz, 2H, $ArCH_2$); 7.24 (d, J=9 Hz, 2H, Ar); 7.41 (d, J=8 Hz, 1H, Ar); 7.65 (dd, J=8, 2 Hz, Ar); 7.83 (d, J=9 Hz, 2H, Ar); 9.21 (d, J=2 Hz, 1H, Ar); 10.93 (s, 1H, NH); 12.73 (s, 1H, NH). Anal Calculated for $C_{21}H_{19}N_3O_4S.8/25$:EtOH3/20$H_2O$ C, 60.88; H, 5.01; N, 9.84; S, 7.51. Found: C, 60.96; H, 4.85; N, 9.69; S, 7.45.

4'-Fluoro-1,2,5,6-tetrahydro-3-methyl-1-oxobenzo[f]quinazoline-9-sulfonanilide (0.07 g, 11%). Mp>260° C. $^1$H NMR (DMSO-$d_6$, 200 MHz) δ: 2.30 (s, 3H, $CH_3$); 2.65–2.73 (m, 2H, $ArCH_2$); 2.83–2.92 (m, 2H, $ArCH_2$); 7.00–7.15 (m, 4H, Ar); 7.34 (d, J=8 Hz, 1H, Ar); 7.49 (dd, J=2,8 Hz, 1H, Ar); 9.08 (d, J=2 Hz, 1H, Ar); 10.25 (s, 1H, NH); 12.68 (br s, 1H, NH). Anal Calculated for $C_{19}H_6FN_3O_3S.H_2O$ C, 56.57; H, 4.50; N, 10.42; F, 4.71; S, 7.95. Found: C, 56.17; H, 4.12; N, 10.26; F, 5.00; S, 8.13.

4-((1,2,5,6-tetrahydro-3-methyl-1-oxobenzo[f]quinazolin-9-yl)sulfonamido)benzamide (0.084 g, 6%). Mp=190° C. sintered. $^1$H NMR (DMSO-$d_6$, 300 MHz) δ: 2.32 (s, 3H, $CH_3$); 2.71 (t, J=8 Hz, $ArCH_2$); 2.89 (t, J=8 Hz, 2H, $ArCH_2$); 7.16 (d, J=9 Hz, 2H, Ar); 7.22 (br s, 1H, NH); 7.39 (d, J=8 Hz, 1H, Ar); 7.62 (dd, J=8, 2 Hz, 1H, Ar); 7.72 (d, J=8 Hz, 1H, Ar); 7.80 (br s, 1H, NH); 9.19 (d, J=2H, 1H, Ar); 10.70 (s, 1H, NH); 12.72 (br s, 1H, NH). Anal Calculated for $C_{20}H_{18}N_4O_4S.H_2O$: C, 56.07; H, 4.70; N, 13.08; S, 7.48. Found: C, 56.11; H, 4.75; N, 12.99; S, 7.43.

EXAMPLE 30

N-(4-((1,2-Dihydro-3-methyl-1-oxobenzo[f]quinazolin-9-yl)sulfonamido)benzoyl)-L-glutamic acid A. Diethyl N-(4-((1,2-dihydro-3-methyl-1-oxobenzo[f]quinazolin-9-yl)sulfonamido)benzoyl)-L-glutamate A solution of diethyl N-(4-((1,2,5,6-tetrahydro-3-methyl-1-oxo-benzo[f]quinazolin-9-yl)sulfonamido)benzoyl)-L-glutamate (0.50 g, 0.84 mmol) in diglyme (10 ml) was stirred with 10% palladium on carbon (0.25 g) (Aldrich) under nitrogen at reflux for 3 hours. The solution was diluted with diglyme (20 ml), filtered hot through celite, and concentrated under high vacuum. The resulting solid was suspended in hot methanol (50 ml), stirred overnight at room temperature, filtered, and dried under high vacuum to give diethyl N-(4-((1,2-dihydro-3-methyl-1-oxobenzo[f]quinazolin-9-yl)sulfonamido)benzoyl)-L-glutamate as a white solid (0.25 g). $^1$H NMR (DMSO-$d_6$, 200 MHz) δ: 1.10 (t, J=7 Hz, 3H, ester$CH_3$), 1.12 (t, J=7 Hz, 3H, ester$CH_3$), 1.78–2.15 (m, 2H, glu$CH_2$), 2.35 (t, J=7 Hz, 2H, glu$CH_2$), 2.43 (s, 3H, $C^3$—$CH_3$), 3.98 (q, J=7 Hz, 2H, ester$CH_2$), 4.04 (q, J=7 Hz, 2H, ester$CH_2$), 2.35–4.39 (m, 1H, gluCH), 7.21 (d, J=9 Hz, 2H, Ar), 7.69 (d, J=9 Hz, 2H, Ar), 7.76 (d, J=9 Hz, 1H, Ar), 7.91 (dd, J=9, 2 Hz, 1H, Ar), 8.19 (d, J=9 Hz, 1H, Ar), 8.29 (d, J=9 Hz, 1H, Ar), 8.51 (d, J=7 Hz, 1H, gluNH), 10.44 (d, J=2 Hz, 1H, Ar), 10.88 (br s, 1H, $SO_2NH$), 12.75 (br s, 1H, N H). Mass spectrum (CI-$CH_4$): 595 (M+1, 24.1%). Anal. Calculated for $C_{29}H_{30}N_4O_8S$: C, 58.58; H, 5.08; N, 9.42; S. 5.39. Found: C, 58.46; H, 5.10; N, 9.34; S. 5.41.

B. N-(4-((1,2-Dihydro-3-methyl-1-oxobenzo[f]quinazolin-9-yl)sulfonamido)benzoyl)-L-glutamic acid A solution of diethyl N-(4-((1,2-dihydro-3-methyl-1-oxobenzo[f]quinazolin-9-yl)sulfonamido)benzoyl)-L-glutamate (0.22 g, 0.37 mmol) in ethanol (3 ml) and 0.25 N NaOH (12 ml) was stirred at room temperature for 3 hours. The solution was slowly acidified to pH 3 with 1N HCl and the resulting precipitate filtered, washed with water, and dried under high vacuum to give N-(4-((1,2-dihydro-3-methyl-1-oxobenzo[f]quinazolin-9-yl)sulfonamido)benzoyl)-L-glutamic acid as a white solid (0.20 g). $^1$H NMR (DMSO-$d_6$, 200 MHz) δ: 1.73–2.15 (m, 2H, glu$CH_2$), 2.27 (t, J=7 Hz, 2H, glu$CH_2$), 2.43 (s, 3H, $CH_3$), 4.22–4.36 (m, 1H, gluCH), 7.20 (d, J=9 Hz, 2H, Ar), 7.69 (d, J=9 Hz, 2H, Ar), 7.76 (d, J=9 Hz, 1H, Ar), 7.90 (dd, J=9, 2 Hz, 1H, Ar), 8.18 (d, J=9 Hz, 1H, Ar), 8.28 (d, J=9 Hz, 1H, Ar), 8.39 (d, J=8 Hz, 1H, gluNH), 10.44 (d, J=2 Hz, 1H, Ar), 10.86 (br s, 1H, $SO_2NH$), 12.32 (br s, 2H, $CO_2H$'s), 12.75 (br s, 1H, $N^2H$). Anal. Calculated for $C_{25}H_{22}N_4O_8S.4/5H_2O$): C, 54.30; H, 4.30; N, 10.13; S. 5.80. Found: C, 54.29; H, 4.25; N, 10.13; S. 5.72.

EXAMPLE 31

N-(4-((1,2-dihydro-3-methyl-1-oxobenzo[f]quinazolin-7-yl)sulfonamido)benzoyl)-L-glutamic acid A. Diethyl N-(4-((1,2-dihydro-3-methyl-1-oxobenzo[f]quinazolin-7-yl)sulfonamido)benzoyl)-L-glutamate Chlorosulfonic acid (15 ml) was reacted with 3-methylbenzo[f]quinazolin-1(2H)-one (2.6 g, 12.4 mmoles) in the same manner as described for the analogous 3-amino-5,6-dihydro compound (example 20) to obtain a mixture of 1,2-dihydro-3-methyl-1-oxobenzo[f]quinazolin-7-, 8-, and 9-sulfonyl chlorides (2.91 g).

The foregoing mixture of sulfonyl chlorides was added to a solution of N-(4-aminobenzoyl)-L-glutamic acid diethyl ester (3.85 g, 11.9 mmoles) in dry pyridine (30 ml) and stirred under a nitrogen atmosphere at room temperature for 19 hrs. After this time the solvent was evaporated under reduced pressure to leave a gummy residue which was suspended in water (100 ml) with vigorous stirring and sonication, filtered and dried. The crude mixture of products was subjected to six successive silica gel column chromatography separations using methanol:methylene chloride (1:24 to 3:47) to obtain diethyl N-(4-((1,2-dihydro-3-methyl-1-oxobenzo-[f]quinazolin-7-yl)sulfonamido)benzoyl)-L-glutamate as an off-white solid. (0.22 g, 3%) $^1$H NMR (DMSO-$d_6$, 200 MHz) δ: 1.10 (t, J=7 Hz, 3H, ester-$CH_3$); 1.12 (t, J=7 Hz, 3H, ester-$CH_3$); 1.80–2.15 (m, 2H, glu-$CH_2$); 2.35 (t, J=7.6 Hz, 2H, glu-$CH_2$); 2.43 (s, 3H, pyr-$CH_3$); 3.98 (q, J=7 Hz, 2H, ester-$CH_2$); 4.03 (q, J=7 Hz, 2H, ester-$CH_2$); 4.32 (m, 1H, glu-CH); 7.08 (d, J=8.6 Hz, 2H, Ar); 7.64 (d, J=8.4 Hz, 2H, Ar); 7.83 (t, J=8.2 Hz, 1H, Ar); 7.86 (d, J=8.6 Hz, 1H, Ar); 8.33 (d, J=7.5 Hz, 1H, glu-NH); 8.48 (d, J=7.3 Hz, 1H, Ar); 9.06 (d, J=9.3 Hz, 1H, Ar); 10.18 (d, J=8.6 Hz, 1H, Ar); 11.15 (br s, 1H, NH); 12.73 (br s, 1H, NH). Anal. Calculated for $C_{29}H_{30}N_4O_8S.1/4H_2O$: C, 58.14; H, 5.13; N, 9.35; S, 5.35. Found: C, 58.12; H, 5.16; N, 9.27; S, 5.42.

B. N-(4-((1,2-Dihydro-3-methyl-1-oxobenzo[f]quinazolin-7-yl)sulfonamido)benzoyl)-L-glutamic acid A solution of diethyl N-(4-((1,2-dihydro-3-methyl-1-oxobenzo[f]quinazolin-7-yl)sulfonamido)benzoyl)-L-glutamate (0.16 g, 0.3 mmoles) in 0.1 $\underline{N}$ NaOH (10 ml) was stirred at room temperature under a nitrogen atmosphere for 48 hrs, after which time the solution was acidified (pH 3.5) with acetic acid. The precipitate was collected, washed with water and dried to give N-(4-((1,2-dihydro-3-methyl-1-oxobenzo[f]quinazolin-7-yl)sulfonamido)benzoyl)-L-glutamic acid as an off-white solid. (0.12 g, 86%) $^1$H NMR (DMSO-$d_6$, 200 MHz) δ: 1.72–2.08 (m, 2H, glu-CH$_2$); 2.26 (t, J=Hz, 2H, glu-CH$_2$); 2.43 (s, 3H, CH$_3$); 4.18–4.35 (m, 1H, glu-CH); 7.07 (d, J=8.4 Hz, 2H, Ar); 7.63 (d, J=8.3 Hz, 2H, Ar); 7.82 (t, J=7.3 Hz, 1H, Ar); 7.84 (d, J=8.9 Hz, 1H, Ar); 8.32 (m, 2H, glu-NH+Ar); 9.07 (d, J=9.3 Hz, 1H, Ar); 10.16 (d, J=8.8 Hz, 1H, Ar); 12.71 (br s, 1H, NH). Anal. Calculated for $C_{25}H_{22}N_4O_8S \cdot 7/4H_2O$: C, 52.67; H, 4.51; N, 9.83. Found: C, 52.52; H, 4.36; N, 9.70.

EXAMPLE 32

N-(4-(((1,2-Dihydro-3-methyl-1-oxobenzo[f]quinazolin-9-yl)methyl)amino)-2-fluorobenzoyl)-L-glutamic acid A. Diethyl N-(4-(((1,2-dihydro-3-methyl-1-oxobenzo[f]quinazolin-9-yl)methyl)amino)-2-fluorobenzoyl)-L-glutamate To a hot solution of 3,9-dimethylbenzo[f]quinazolin-1(2H)-one (2.0 g, 8.9 mmol) in benzene (1000 ml) under nitrogen was added N-bromosuccinimide (NBS) (2.0 g, 11 mmol). The solution was stirred at reflux for 1 hour and then concentrated in vacuo to give crude 9-bromomethyl-3-methylbenzo[f]quinazolin-1(2H)-one. The solid was suspended with diethyl N-(4-amino-2-fluorobenzoyl)-L-glutamate (T. R. Jones et al., UK Patent GB 2175 903A, 1986) (6.0 g, 18 mmol) in DMF (20 ml) and stirred under nitrogen at 100° C. for 30 minutes. The reaction mixture was allowed to cool, N-methylmorpholine (1.0 ml, 9.1 mmol) (Aldrich) was added, and the solution concentrated under high vacuum. The residue was purified with silica gel chromatography eluting with methylene chloride:THF (5:1). Fractions containing product were concentrated in vacuo to a thick paste, the solid suspended in a small volume of diethyl ether, filtered under nitrogen, and dried under high vacuum to give diethyl N-(4-(((1,2-dihydro-3-methyl-1-oxobenzo[f]quinazolin-9-yl)methyl)amino)-2-fluorobenzoyl)-L-glutamate as a white solid (2.3 g). $^1$H NMR (DMSO-$d_6$, 300 MHz) δ: 1.15 (t, J=7 Hz, 3H, esterCH$_3$), 1.18 (t, J=7 Hz, 3H, esterCH$_3$), 1.87–2.13 (m, 2H, gluCH$_2$), 2.38 (t, J=7 Hz, 2H, esterCH$_2$), 2.43 (s, 3H, C$^3$—CH$_3$), 4.02 (q, J=7 Hz, 2H, esterCH$_2$), 4.09 (q, J=7 Hz, 2H, esterCH$_2$), 4.34–4.44 (m, 1H, gluCH), 4.57 (d, J=6 Hz, 2H, C$^9$—CH$_2$), 6.39 (dd, J=15,2 Hz, 1H, Ar), 6.53 (dd, J=9, 2 Hz, 1H, Ar), 7.30 (t, J=6 Hz, 1H, ArNH), 7.44 (dd, J=9, 9 Hz, 1H, Ar), 7.60 (d, J=9 Hz, 1H, Ar), 7.61 (dd, J=8, 2Hz, 1H, Ar), 7.88 (dd, J=7,5 Hz, 1H, gluNH), 8.01 (d, J=8 Hz, 1H, Ar), 8.22 (d, J=9 Hz, 1H, Ar), 9.85 (s, 1H, Ar), 12.53 (s, 1H, N$^2$H). Mass spectrum (CI-CH$_4$): 563 (M+1, 100%). Anal. Calculated for $C_{30}H_{31}FN_4O_6$: C, 64.05; H, 5.55; N, 9.96. Found: C, 64.14; H, 5.59; N, 9.94.

N-(4-(((1,2-Dihydro-3-methyl-1-oxobenzo[f]quinazolin-9-yl)methyl)amino)-2-fluorobenzoyl)-L-glutamic acid A solution of diethyl N-(4-(((1,2-dihydro-3-methyl-1-oxobenzo[f]quinazolin-9-yl)methyl)amino)-2-fluorobenzoyl)-L-glutamate (2.3 g, 4.1 mmol) in ethanol (25 ml) and 0.2 N NaOH (100 ml) was stirred under nitrogen at room temperature for 3 hours. The solution was adjusted to pH 7 with 1N HCl and reduced in volume under vacuum to remove the ethanol. The product was precipitated by acidifying the solution with 1N HCl to pH 3 with stirring under nitrogen. The suspension was stirred 15 minutes, filtered under nitrogen, washed with water, pressed with a sheet of latex to remove excess water, and dried under high vacuum to give N-(4-(((1,2-dihydro-3-methyl-1-oxobenzo[f]quinazolin-9-yl)methyl)amino)-2-fluorobenzo-yl)-L-glutamic acid as a white solid (2.1 g). $^1$H NMR (DMSO-$d_6$, 300 MHz) δ: 1.82–2.12 (m, 2H, gluCH$_2$), 2.29 (t, J=7 Hz, 2H, gluCH$_2$), 2.43 (s, 3H, C$^3$—CH$_3$), 4.32–4.42 (m, 1H, gluCH), 4.57 (d, J=6 Hz, 2H, C$^3$—CH$_2$), 6.39 (dd, J=15,2 Hz, 1H, Ar), 6.53 (dd, J=9, 2 Hz, 1H, Ar), 7.30 (t, J=6 Hz, 1H, ArNH), 7.47 (dd, J=9, 9 Hz, 1H, Ar), 7.59 (d, J=9 Hz, 1H, Ar), 7.61 (dd, J=8, 2 Hz, 1H, Ar), 7.73 (t, J=7 Hz, 1H, gluNH), 8.01 (d, J=8 Hz, 1H, Ar), 8.22 (d, J=9 Hz, 1H, Ar), 9.85 (s, 1H, Ar), 12.42 (br s, 2H, CO$_2$H's), 12.53 (s, 1H, N$^2$H). Anal. Calculated for $C_{26}H_{23}FN_4O_6 \cdot 3/2H_2O \cdot 1/3NaCl$: C, 56.49; H, 4.74; N, 10.14; Cl, 2.12; Na, 1.37. Found: C, 56.48; H, 4.64; N, 10.20; Cl, 2.01; Na, 1.30.

An essentially similar sequence of reactions with diethyl 4-aminobenzoyl-L-glutamate (2.8 g, 8.7 mmol) and diethyl 4-methylamino(benzoyl)-L-glutamate (1.4 g, 4.2 mol) gave, upon coupling of each with 3,9-dimethylbenzo[f]quinazolin-1(2H)-one (0.5 g, 2.2 mmol) via the bromomethyl derivative;

i) N-(4(((1,2-Dihydro-3-methyl-1-oxobenzo[f]quinazolin-9-yl)methyl)amino)benzoyl)-L-glumatic acid, and ii) N-(4-(((1,2-Dihydro-3-methyl-1-oxobenzo[f]quinazolin-9-yl)-methyl)methylamino)benzoyl-L-glutamic acid:

data on these compounds and their diester intermediates are given below.

i) A. Diethyl N-(4-(((1,2-Dihydro-3-methyl-1-oxobenzo[f]quinazolin-9-yl)methyl)amino)benzoyl)-L-glutamate (0.57 g, 47%); $^1$H NMR (DMSO-$d_6$, 300 MHz) δ: 1.15 (t, J=7 Hz, 3H, esterCH$_3$), 1.17 (t, J=7 Hz, 3H, esterCH$_3$), 1.87–2.13 (m, 2H, gluCH$_2$), 2.39 (t, J=7 Hz, 2H, gluCH$_2$), 2.43 (s, 3H, C$^3$—CH$_3$), 4.03 (q, J=7 Hz, 2H, esterCH$_2$), 4.07 (q, J=7 Hz, 2H, esterCH$_2$), 4.31–4.41 (m, 1H, gluCH), 4.57 (d, J=6 Hz, 2H, C$^3$—CH$_2$), 6.64 (d, J=9 Hz, 2H, Ar), 7.02 (t, J=6 Hz, 1H, ArNH), 7.57–7.67 (m, 4H, Ar), 8.00 (d, J=8 Hz, 1H, Ar), 8.21 (overlapping d, J=8 Hz, 2H, Ar, gluNH), 9.85 (s, 1H, Ar), 12.53 (s, 1H, N$^2$H). Mass spectrum (CI-CH$_4$): 545 (M+1, 94.8%), 342 (100%). Anal. Calculated for $C_{30}H_{32}N_4O_6 \cdot 1/10H_2O$: C, 65.95; H, 5.94; N, 10.25. Found: C, 65.99; H, 5.94; N, 10.21.

i) B. N-(4(((1,2-Dihydro-3-methyl-1-oxobenzo[f]quinazolin-9-yl)methyl)amino)benzoyl)-L-glumatic acid (0.48 g, 93% from diester (0.56 g, 1.02 mmol). $^1$H NMR (DMSO-$d_6$, 300 MHz) δ: 1.82–2.12 (m, 2H, gluCH$_2$), 2.31 (t, J=7 Hz, 2H, gluCH$_2$), 2.43 (s, 3H, CH$_3$), 4.28–4.38 (m, 1H, gluCH), 4.57 (d, J=6 Hz, 2H, C$^9$—CH$_2$), 6.64 (d, J=9 Hz, 2H, Ar), 7.00 (t, J=6 Hz, 1H, ArNH), 7.59 (d, J=9 Hz, 1H, Ar), 7.63 (dd, J=8, 2 Hz, 1H, Ar), 7.63 (d, J=9 Hz, 2H, Ar), 8.00 (d, J=8 Hz, 1H, Ar), 8.09 (d, J=8 Hz, 1H, gluNH), 8.21 (d, J=9 Hz, 1H, Ar), 9.85 (s, 1H, Ar), 12.33 (br s, 2H, CO$_2$H's), 12.53 (s, 1H, N$^2$H). Anal. Calculated for $C_{26}H_{24}N_4O_6 \cdot H_2O$: C, 61.65; H, 5.17; N, 11.06. Found: C, 61.51; H, 5.01; N, 11.05.

ii) A. Diethyl N(4-(((1,2-Dihydro-3-methyl-1-oxobenzo[f]quinazolin-9-yl)methyl)methylamino)benzoyl)-L-glutamate (0.66 g, 53%. $^1$H NMR (DMSO-$d_6$, 300 MHz) δ: 1.15 (t, J=7 Hz, 3H, esterCH$_3$); 1.17 (t, J=7 Hz, 3H, esterCH$_3$), 1.88–2.13 (m, 2H, gluCH$_2$), 2.40 (t, J=8 Hz, 2H, gluCH$_2$), 2.42 (s, 3H, C$^3$—CH$_3$), 3.19 (s, 3H, NCH$_3$), 4.03 (q, J=7 Hz, 2H, esterCH$_2$), 4.08 (q, J=7 Hz, 2H, esterCH$_2$), 4.33–4.43 (m, 1H, gluCH), 4.91 (s, 2H, C$^9$—CH$_2$), 6.81 (d, J=9 Hz, 2H, Ar), 7.44 (dd, J=8, 2 Hz, 1H, Ar), 7.58 (d, J=9 Hz, 1H, Ar), 7.72 (d, J=9 Hz, 2H, Ar), 7.98 (d, J=8 Hz, 1H, Ar), 8.20 (d, J=9 Hz, 1H, Ar), 8.29 (d, J=7 Hz, 1H, gluNH), 9.76 (s, 1H, Ar), 12.48 (s, 1H, N$^2$H). Mass spectrum (CI-CH$_4$): 559 (M+1, 100%). Anal. Calculated for C$_{31}$H$_{34}$N$_4$O$_6$: C, 66.65; H, 6.13; N, 10.03. Found: C, 66.46; H, 6.18; N, 9.98.

ii) B. N-(4-(((1,2-Di-3-methyl-1-oxobenzo[f]quinazolin-9-yl)methylamino)benzoyl-L-glutamic acid (0.58 g, 94% from diester (0.65 g, 1.2 mmol)). $^1$H NMR (DMSO-d$_6$, 300 MHz) δ: 1.83–2.14 (m, 2H, gluCH$_2$), 2.32 (t, J=7 Hz, 2H, gluCH$_2$), 2.42 (s, 3H, C$^3$—CH$_3$), 3.18 (s, 3H, NCH$_3$), 4.30–4.42 (m, 1H, gluCH), 4.91 (s, 2H, C$^9$—CH$_2$), 6.81 (d, J=9 Hz, 2H, Ar), 7.44 (dd, J=8, 2 Hz, 1H, Ar), 7.58 (d, J=9 Hz, 1H, Ar), 7.73 (d, J=9 Hz, 2H, Ar), 7.98 (d, J=8 Hz, 1H, Ar), 8.18 (d, J=8 Hz, 1H, gluNH), 8.19 (d, J=9 Hz, 1H, Ar), 9.76 (s, 1H, Ar), 12.32 (br s, 2H, CO$_2$H's), 12.50 (br s, 2H, N$^2$H). Anal. Calculated for C$_{27}$H$_{26}$N$_4$O$_6$·7/5H$_2$O: C, 61.45; H, 5.50; N, 10.62. Found: C, 61.46; H, 5.45; N, 10.59.

EXAMPLE 33

(S)-2-(5-(((1,2-Dihydro-3-methyl-1-oxobenzo[f]quinazolin-9-yl)methyl)amino)-1-oxo-2-isoindolinyl)glutaric acid A. Diethyl (S)-2-(4-nitrophthalimido)glutarate Diisopropylethylamine (24 ml, 0.138 mole) (Aldrich) was added to a suspension of 4-nitrophthalic anhydride (25 g, 0.13 mole) (Tokyo Kasei) and L-glutamic acid diethyl ester hydrochloride (35 g, 0.146 mole) (Aldrich) in toluene (130 ml). The reaction mixture was stirred at reflux utilizing a Dean-Stark trap for 2.5 hours. After cooling, the solution was diluted with diethyl ether (300 ml), washed with water (75 ml), saturated NaHCO$_3$ solution (50 ml), dried (MgSO$_4$), and concentrated in vacuo at 70° C. to give diethyl (S)-2-(4-nitrophthalimido) glutarate as an oil that solidified to a white solid on standing (35.8 g). M.P.=65.5–66.5° C. $^1$H NMR (DMSO-d$_6$, 300 MHz) δ: 1.12 (t, J=7 Hz, 3H, esterCH$_3$), 1.14 (t, J=7 Hz, 3H, esterCH$_3$), 2.2–2.5 (m, 4H, gluCH$_2$CH$_2$), 3.96 (q, J=7 Hz, 2H, esterCH$_2$), 4.08–4.19 (m, 2H, esterCH$_2$), 4.97–5.04 (m, 1H, gluCH), 8.19 (dd, J=8,0.5 Hz, 1H, Ar), 8.56 (dd, J=2,0.5 Hz, 1H, Ar), 8.68 (dd, J=8, 2 Hz, 1H, Ar). Mass spectrum (CI-CH$_4$); 379 (M+1, 28.8%), 333 (71.6%), 305 (100%). Anal. Calculated for C$_{17}$H$_{18}$N$_2$O$_8$: C, 53.97; H, 4.80; N, 7.40. Found: C, 53.89; H, 4.82; N, 7.42.

B. Diethyl (S)-2-(4-aminophthalimido)glutarate

A suspension of diethyl (S)-2-(4-nitrophthalimido) glutarate (35.6 g, 94.1 mmol) and 10% palladium on carbon (0.5 g) (Aldrich) in ethanol (200 ml) was shaken under a hydrogen atmosphere (40–50 psi) for 26 hours. The solution was filtered through celite and concentrated in vacuo. The residue was purified by chromatography on silica gel (250 g) eluting with diethyl ether:hexane (4:1) to give diethyl (S)-2-(4-aminophthalimido)glutarate as a viscous yellow oil (29.1 g). $^1$H NMR (DMSO-d$_6$, 300 MHz) δ: 1.10 (t, J=7 Hz, 3H, esterCH$_3$), 1.12 (t, J=7 Hz, 3H, esterCH$_3$), 2.17–2.39 (m, 4H, gluCH$_2$CH$_2$), 3.87–3.98 (m, 2H, esterCH$_2$), 4.05–4.18 (m, 2H, esterCH$_2$), 4.75–4.82 (m, 1H, gluCH), 6.57 (br s, 2H, NH$_2$), 6.82 (dd, J=8, 2 Hz, 1H, Ar), 6.93 (d, J=2 Hz, 1H, Ar), 7.51 (d, J=8 Hz, 1H, Ar). Mass spectrum (CI-CH$_4$) 349 (M+1, 40.8%), 303 (60.1%), 275 (100%). Anal. Calculated for C$_{17}$H$_{20}$N$_2$O$_6$: C, 58.62; H, 5.79; N, 8.04. Found: C, 58.62; H, 5.80; N, 8.00.

C. Diethyl (S)-2-(5-amino-1-oxo-2-isoindolinyl)glutarate

A solution of diethyl (S)-2-(4-aminophthalimido) glutarate (10.5 g, 30.2 mmol) in ethanol (150 ml) was cooled in an acetonitrile/CO$_2$ bath. Concentrated HCl (25 ml) was added followed by 30 mesh granular Zn (10.5 g, 0.161 mole) (Fisher) when the internal temperature had reached −40° C. The reaction mixture was stirred 1.5 hours at this temperature and a further 1 hour at −10° C. The excess of Zn was filtered from the solution, 10% palladium on carbon (1.0 g) was added, and the solution shaken under hydrogen at (30–50 psi) overnight. The catalyst was removed by filtration through celite and the filtrate concentrated in vacuo. The residue was made basic by the addition of saturated NaHCO$_3$ solution (~300 ml), extracted with diethyl ether (3×100 ml), and the ether extracts were dried (K$_2$CO$_3$) and concentrated in vacuo. The residue was absorbed onto silica gel (15 g) and purified by chromatography on silica gel (400 g) eluting with ethyl acetate:methylene chloride (1:4) to give diethyl (S)-2-(5-amino-1-oxo-2-isoindolinyl)glutarate as a viscous oil (4.14 g). $^1$H NMR (DMSO-d$_6$, 300 MHz) δ: 1.12 (t, J=7 Hz, 3H, 3H, esterCH$_3$), 1.17 (t, J=7 Hz, 3H, esterCH$_3$), 1.98–2.33 (m, 4H, gluCH$_2$CH$_2$), 3.92–4.03 (m, 2H, esterCH$_2$), 4.11 (q, J=7 Hz, 2H, esterCH$_2$), 4.26 (very strongly coupled AB pair, 2H, ArCH$_2$N), 4.77–4.84 (m, 1H, gluCH), 5.83 (br s, 2H, NH$_2$), 6.58–6.65 (m, 2H, Ar), 7.32 (d, J=8 Hz, 1H, Ar). Mass spectrum (CI-CH$_4$): 335 (M+1, 100%). Anal. Calculated for C$_{17}$H$_{22}$N$_2$O$_5$: C, 61.07; H, 6.63; N, 8.38. Found: C, 60.93; H, 6.71; H, 8.30.

D. 9-Bromomethyl-3-methylbenzo[f]quinazolin-1(2H)-one

To a hot solution of 3,9-dimethylbenzo[f]quinazolin-1 (2H)-one (4.00 g, 17.9 mmol) in benzene (2000 ml) under nitrogen was added N-bromo-succinimide (4.00 g, 22.5 mmol). The reaction mixture was stirred just below reflux for 30 minutes, then at a gentle reflux for 30 minutes. The resulting suspension was allowed to cool for 2 hours, the solid filtered and dried at 70° C. under reduced pressure to give 9-bromomethyl-3-methylbenzo[f]quinazolin-1(2H)-one (4.32 g, 83% purity by NMR). $^1$H NMR (DMSO-d$_6$, 300 MHz) δ: 2.45 (s, 3H, CH$_3$), 4.96 (s, 2H, CH$_2$), 7.65 (d, J=9 Hz, 1H, Ar), 7.70 (dd, J=8, 2 Hz, 1H, Ar), 8.05 (d, J=8 Hz, 1H, Ar), 8.16 (d, J=9 Hz, 1H, Ar), 9.89 (s, 1H, Ar), 12.7 (br s, 1H, NH).

E. Diethyl (S)-2-(5-(((1,2-dihydro-3-methyl-1-oxobenzo [f]quinazolin-9-yl)methyl)amino)-1-oxo-2-isoindolinyl) glutarate A solution of crude 9-bromomethyl-3-methylbenzo[f] quinazolin-1(2H)-one (4.32 g), (S)-diethyl 2-(5-amino-1-oxo-2-isoindolinyl) glutarate (4.0 g, 12 mmol), and NaHCO$_3$ (2.0 g, 24 mmol) in DMF (30 ml) was stirred under nitrogen at 105° C. for 1.5 hours. After cooling, acetic acid (1 ml, 17 mmol) was added, the reaction mixture transferred to a larger round bottom flask with ethanol, and then concentrated in vacuo onto silica gel (30 g). The absorbed material was purified by chromatography on silica gel eluting with methanol:methylene chloride (1:24) and then precipitation of the solid from methylene chloride (~20 ml) with ethyl acetate (~45 ml) and methanol (~5 ml). The white solid was filtered under nitrogen and dried under high vacuum to give diethyl (S)-2-(5-(((1,2-dihydro-3-methyl-1-oxobenzo[f]-quinazolin-9-yl)methyl)amino)-1-oxo-2-isoindolinyl)glutarate (3.27 g). $^1$H NMR (DMSO-d$_6$, 300 MHz), δ: 1.10 (t, J=7 Hz, 3H, esterCH$_3$), 1.15 (t, J=7 Hz, 3H, esterCH$_3$), 1.93–2.33 (m, 4H, gluCH$_2$CH$_2$), 2.43 (s, 3H, C$^3$—CH$_3$), 3.87–4.03 (m, 2H, esterCH$_2$), 4.09 (q, J=7 Hz, 2H, esterCH$_2$), 4.25 (very strongly coupled AB pair, 2H, gluNCH$_2$Ar), 4.58 (d, J=6 Hz, 2H, C$^9$—CH$_2$N), 4.74–4.83 (m, 1H, gluCH), 6.71 (br d, J=2 Hz, 1H, Ar), 6.74 (dd, J=8, 2 Hz, 1H, Ar), 7.20 (t, J=6 Hz, 1H, ArNH), 7.37 (d, J=8 Hz, 1H Ar), 7.59 (d, J=9 Hz, 1H, Ar), 7.63 (dd, J=8, 2 Hz, 1H, Ar), 8.00 (d, J=8 Hz, 1H, Ar), 8.21 (d, J=9 Hz, 1H, Ar), 9.87 (s, 1H, Ar), 12.54 (s, 1H, $N^2H$). Mass spectrum (CI-$CH_4$) 557 (M+1, 100%). Anal. Calculated for $C_{31}H_{32}N_4O_6$: C, 66.89; H, 5.79; N, 10.07. Found: C, 66.80; H, 5.82; N, 10.10.

F. (S)-2-(5-(((1,2-Dihydro-3-methyl-1-oxobenzo[f]quinazolin-9-yl)methyl)amino)-1-oxo-2-isoindolinyl)glutaric acid A solution of diethyl (S)-2-(5-(((1,2-dihydro-3-methyl-1-oxo-benzo[f]quinazolin-9-yl)methyl)amino)-1-oxo-2-isoindolinyl)glutarate (3.20 g, 5.75 mmol) in 0.2 N NaOH (140 ml) was stirred under nitrogen for 3 hours at room temperature. The solution was then slowly adjusted to pH 3 with 1 N HCl and the resulting suspension allowed to stir briefly. The white solid was filtered under nitrogen, washed with water, and dried under high vacuum to give (S)-2-(5-(((1,2-dihydro-3-methyl-1-oxobenzo[f]quinazolin-9-yl)methyl)amino)-1-oxo-2-isoindolinyl)glutaric acid (2.85 g). $^1$H NMR (DMSO-$d_6$/$D_2O$, 300 MHz) δ: 1.86–2.34 (m, 4H, gluCH$_2$CH$_2$), 2.44 (s, 3H, CH$_3$), 4.25 (very strongly coupled AB pair, 2H, gluNCH$_2$Ar), 4.58 (s, 2H, $C^9$—CH$_2$), 4.67–4.75 (m, 1H, gluCH), 6.69–6.77 (m, 2H, Ar), 7.37 (d, J=8 Hz, 1H, Ar), 7.59 (d, J=9 Hz, 1H, Ar), 7.64 (dd, J=8, 2 Hz, 1H, Ar), 8.01 (d, J=8 Hz, 1H, Ar), 8.22 (d, J=9 Hz, 1H, Ar), 9.85 (s, 1H, Ar). Anal. Calculated for $C_{27}H_{24}N_4O_6$.1.6$H_2O$: C, 61.27; H, 5.18; N, 10.58. Found: C, 61.29; H, 5.18; N, 10.57.

By a similar sequence of reactions, the N-methyl derivative of the foregoing compound was prepared by condensation of the bromomethyl benzoquinazoline with diethyl (S)-2-(5-(methylamino)-1-oxo-2-isoindolinyl)glutarate. The preparation of the latter, and physical data on the final benzoquinazoline product and diester intermediate are given below.

Diethyl (S)-2-(5-(methylamino)-1-oxo-2-isoindolinyl)glutarate

To a solution of diethyl (S)-2-(5-amino-1-oxo-2-isoindolinyl)glutarate (3.1 g, 9.3 mmol), 37% aqueous formaldehyde (0.81 g, 10 mmol), and acetic acid (0.5 ml) in ethanol (30 ml) was added sodium cyanoborohydride (0.63 g, 10 mmol). After stirring the reaction mixture for 45 minutes additional acetic acid (0.5 ml) and sodium borohydride (0.32 g, 5 mmol) were added and after a further 15 minutes additional 37% aqueous formaldehyde (0.30 g, 3.7 mmol) was added. The reaction mixture was stirred for 1 hour, water (1 ml) was added, then the mixture concentrated in vacuo.

Purification by chromatography on silica gel eluting with ethyl acetate:methylene chloride (1:6) gave diethyl (S)-2-(5-(methylamino)-1-oxo-2-isoindolinyl)glutarate (1.8 g). $^1$H NMR (DMSO-$d_6$, 300 MHz) δ: 1.12 (t, J=7 Hz, 3H esterCH$_3$), 1.17 (t, J=7 Hz, 3H, esterCH$_3$), 1.95–2.35 (m, 4H, gluCH$_2$'s), 2.74 (d, J=5 Hz, 3H, NCH$_3$), 3.90–4.03 (m, 2H, esterCH$_2$), 4.11 (q, J=7 Hz, 2H, esterCH$_2$), 4.30 (very strongly coupled AB pair, 2H, ArCH$_2$), 4.77–4.84 (m, 1H, gluCH), 6.43 (br q, J=5 Hz, 1H, NH), 6.58–6.64 (m, 2H, Ar), 7.38 (d, J=9 Hz, 1H, Ar). Anal. Calculated or $C_{18}H_{24}N_2O_3$/10$H_2O$: C, 61.11; H, 7.01; N, 7.92. Found: C, 61.09; H, 7.03; N, 7.94.

Diethyl (S)-2-(5-(((1,2-dihydro-3-methyl-1-oxobenzo[f]quinazolin-9-yl)methyl)methylamino)-1-oxo-2-isoindolinyl)glutarate $^1$H NMR (DMSO-$d_6$, 300 MHz) δ: 1.10 (t, J=7 Hz, 3H, esterCH$_3$), 1.15 (t, J=7 Hz, 3H, esterCH$_3$), 1.97–2.35 (m, 4H, gluCH$_2$'s), 2.42 (s, 3H, $C^3$—CH$_3$), 3.23 (s, 3H, NCH$_3$), 3.89–4.02 (m, 2H, esterCH$_2$), 4.10 (q, J=7 Hz, 2H, esterCH$_2$), 4.30 (very strongly coupled AB pair, 2H, gluNCH$_2$Ar), 4.77–4.84 (m, 1H, gluCH), 4.94 (s, 2H, $C^9$—CH$_2$), 6.84–6.12 (m, 2H, Ar), 7.45 (d, J=8.5 Hz, 2H, Ar), 7.58 (d, J=9 Hz, 1H, Ar), 7.99 (d, J=8.5 Hz, 1H, Ar), 8.20 (d, J=9 Hz, 1H, Ar), 9.77 (s, 1H, Ar), 12.49 (s, 1H, $N^2H$). Anal. Calculated for $C_{32}H_{34}N_4O_6$.1/4$H_2O$: C, 66.83; H, 6.05; N, 9.74. Found: C, 66.81; H, 5.97; N, 9.74.

(S)-2-(5-(((1,2-Dihydro-3-methyl-1-oxobenzo[f]quinazolin-9-yl)methyl)methylamino)-1-oxo-2-isoindolinyl)glutaric acid $^1$H NMR (DMSO-$d_6$, 300 MHz) δ: 1.88–2.35 (m, 4H, gluCH$_2$'s), 2.43 (s, 3H, $C^3$—CH$_3$), 3.22 (s, 3H, NCH$_3$), 4.31 (s, 2H, gluNCH$_2$Ar), 4.67–4.76 (m, 1H, gluCH), 4.93 (s, 2H, $C^9$—CH$_2$), 6.87 (dd, J=8.5, 2 Hz, 1H, Ar), 6.91 (s, 1H, Ar), 7.44 (d, J=8.5 Hz, 1H, Ar), 7.46 (dd, J=8.5, 1.5 Hz, 1H, Ar), 7.58 (d, J=9 Hz, 1H, Ar), 7.99 (d, J=8.5 Hz, 1H, Ar), 8.20 (d, J=9 Hz, 1H, Ar), 9.76 (s, 1H, Ar), 11.8–13.0 (br s, 2H, CO$_2$H's), 12.52 (br s, 1H, $N^2H$). Anal. Calculated for $C_{28}H_{26}N_4O_6$.2$H_2O$: C, 61.08; H, 5.49; N, 10.18. Found: C, 61.14; H, 5.22; N, 10.18.

EXAMPLE 34

(S)-2-(2.3-Dihydro-6-(((1,2-dihydro-3-methyl-1-oxobenzo[f]quinazolin-9-yl)methyl)amino)-3-oxo-1,2-benxisothiazol-2-yl)glutaric acid A. 2,2'-Dithiobis(4-nitrobenzoic acid) (Adapted from Organic Syntheses Coll. Vol. 2, p. 580).

A suspension of 4-nitroanthranilic acid (32.7 g, 180 mmol) (Aldrich) in water (100 ml) and concentrated HCl (35 ml) was stirred 30 minutes at room temperature and then chilled in an ice bath. A solution of sodium nitrite (12.4 g, 180 mmol) in water (25 ml) was added in small aliquots below the surface of the suspension via pipette. Crushed ice was added during the addition to maintain an internal temperature below 50° C. The reaction mixture was then stirred 1 hour at 0° C.

In a 1 liter flask, sulphur (6.4 g, 0.20 mole) and Na$_2$S.9H$_2$O (48 g, 0.20 mole) were dissolved in hot water (100 ml). A solution of NaOH (7.2 g, 0.18 mole) in water (40 ml) was added and the resulting solution cooled in an ice bath. The solution of diazonium salt was then added in aliquots (15–25 ml) along with crushed ice to maintain an internal temperature below 5° C. The reaction mixture was stirred 2 hours at room temperature, filtered, and the filtrate adjusted to neutral pH with acetic acid. The solution was treated with activated charcoal (5 g), filtered, adjusted to pH 2.5–3.0 with concentrated HCl and the resulting precipitate was filtered and washed with water. The solid was nearly dissolved in hot ethanol (200 ml), treated with activated charcoal (5 g), filtered, concentrated in vacua, then resuspended in methanol (~80 ml), filtered and dried under reduced pressure at 110° C. to give crude 2,2'-dithiobis(4-nitrobenzoic acid) (9.9 g). An analytical sample was prepared by recrystallization from methanol and was dried under reduced pressure at 120° C. $^1$H NMR (DMSO-$d_6$, 300 MHz) δ: 8.15 (dd, J=9, 2 Hz 1H, Ar), 8.27 (d, J=9 Hz, 1H, Ar), 8.39 (d, J=2 Hz, 1H, Ar). Anal. Calculated for $C_{14}H_8N_2O_8S_2$: C, 42.43; H, 2.03; N, 7.07; S, 16.18. Found: C, 42.48; H, 2.04; N, 7.12; S, 16.25.

B. Diethyl (S)-2-(2,3-dihydro-6-nitro-3-oxo-1,2-benzisothiazol-2-yl)glutarate

A solution of crude 2,2'-dithiobis (4-nitrobenzoic acid) (8.35 g, ~21 mmol) in $SOCl_2$ (50 ml) was stirred at reflux for 1.5 hours and then concentrated in vacuo. The residual solid was suspended in methylene chloride (50 ml) and $Cl_2$ (3.3 g, 47 mmol) gas was bubbled in and the solution stirred 1.5 hours at room temperature. Nitrogen gas was then bubbled into the solution until moistened starch-iodine paper indicated the absence of $Cl_2$. L-Glutamic acid diethyl ester hydrochloride (6.5 g, 27 mmol) (Aldrich) was then added, followed by the dropwise addition of diisopropylethylamine (~10 ml, ~57 mmol) (Aldrich) and the reaction mixture was stirred under nitrogen for 45 minutes. Additional diisopropylethylamine was added dropwise until formation of white amine hydrochloride fumes above the solution ceased. After a further 30 minutes of stirring, the reaction mixture was concentrated in vacuo onto silica gel (40 g); chromatography on silica gel (200 g), eluting with ethyl acetate:hexane (1:2) gave diethyl (S)-2-(2,3-dihydro-6-nitro-3-oxo-1,2-benzoisothiazol-2-yl)glutarate (4.0 g) as an oil. $^1H$ NMR (DMSO-$d_6$, 300 MHz) δ: 1.14 (t, J=7 Hz, 3H, esterCH$_3$), 1.18 (t, J=7 Hz, 3H, esterCH$_3$), 2.12–2.46 (m, 4H, gluCH$_2$CH$_2$), 4.01 (q, J=7 Hz, 2H, esterCH$_2$), 4.17 (q, J=7 Hz, 2H, esterCH$_2$), 5.22–5.29 (m, 1H, gluCH), 8.11 (d, J=9 Hz, 1H, Ar), 8.21 (dd, J=9, 2 Hz, 1H, Ar), 9.03 (d, J=2 Hz, 1H, Ar). Anal. Calculated for $C_{16}H_8N_2O_7S$: C, 50.26; H, 4.74; N, 7.33; S, 8.38. Found: C, 50.35; H, 4.76; N, 7.33; S, 8.28.

C. Diethyl (S)-2-(6-amino-2.3-dihydro-3-oxo-1,2-benzisothiazol-2-yl)glutarate

A solution of diethyl (S)-2-(2,3-dihydro-6-nitro-3-oxo-1,2-benzisothiazol-2-yl)glutarate (4.0 g, 10 mmol) and suspended iron (1.0 g, 18 mmol) in acetic acid (100 ml) was stirred under nitrogen for 1 hour at 550° C. Additional iron (3×0.25 g, 13 mmol) was added at intervals of 1, 1.25, and 1.75 hours. The reaction mixture was stirred 30 minutes after the last addition, filtered, concentrated in vacuo, and the residue absorbed onto silica gel (20 g) from a methylene chloride solution. Purification by chromatography on silica gel (150 g) eluting with ethyl acetate:hexane (1:1→2:1) gave diethyl (S)-2-(6-amino-2,3-dihydro-3-oxo-1,2-benzisothiazol-2-yl)glutarate (3.3 g) as an oil. $^1H$ NMR (DMSO-$d_6$, 300 MHz) δ: 1.15 (t, J=7 Hz, 3H, esterCH$_3$), 1.17 (t, J=7 Hz, 3H, esterCH$_3$), 1.95–2.38 (m, 4H, gluCH$_2$CH$_2$), 4.02 (q, J=7 Hz, 2H, esterCH$_2$), 4.13 (q, J=7 Hz, 2H, esterCH$_2$), 5.08–5.15 (m, 1H, gluCH), 6.09 (br s, 2H, NH$_2$), 6.62 (dd, J=9, 2 Hz, 1H, Ar), 6.84 (d, J=2 Hz, 1H, Ar), 7.50 (d, J=9 Hz, 1H, Ar). Mass spectrum (CI-CH$_4$): 353 (M+1, 100%). Anal. Calculated for $C_{16}H_{20}N_2O_5S$: C, 54.53; H, 5.72; N, 7.95; S, 9.10. Found: C, 54.34; H, 5.73; N, 7.87; S, 9.00.

D. Diethyl (S)-2-(2,3-Dihydro-6-(((1,2-dihydro-3-methyl-1-oxo-benzo[f]quinazolin-9-yl)methyl)amino)-3-oxo-1,2-benzisothiazol-2-yl)glutarate (0.34 g) was prepared by condensation of the foregoing ester (3.2 g, 9.1 mmol) with 9-bromomethyl-3-methylbenzo[f]quinazolin-1(2H)-one (2.3 g) essentially as described in the previous example. $^1H$ NMR (DMSO-$d_6$, 300 MHz) δ: 1.12 (t, J=7 Hz, 3H, esterCH$_3$), 1.14 (t, J=7 Hz, 3H, esterCH$_3$), 1.93–2.34 (m, 4H, gluCH$_2$CH$_2$), 2.42 (s, 3H, C$^3$—CH$_3$), 4.00 (q, J=7 Hz, 2H, esterCH$_2$), 4.11 (q, J=7 Hz, 2H, esterCH$_2$), 4.59 (d, J=6 Hz, 2H, C$^9$—CH$_2$), 5.06–5.14 (m, 1H, gluCH), 6.79 (dd, J=9, 2 Hz, 1H, Ar), 6.92 (d, J=2 Hz, 1H, Ar), 7.44 (t, J=6 Hz, 1H, ArNH), 7.53 (d, J=9 Hz, 1H, Ar), 7.59 (d, J=9 Hz, 1N, Ar), 7.63 (dd, J=8, 2 Hz, 1H, Ar), 8.01 (d, J=8 Hz, 1H, Ar), 8.21 (d, J=9 Hz, 1H, Ar), 9.86 (s, 1H, Ar), 2.54 (s, 1H, N$^2$H). Mass spectrum (CI-CH$_4$) 575 (M+1, 36.5%). Anal. Calculated for $C_{30}H_{30}N_4O_6S$: C, 62.70; H, 5.26; N, 9.75; S, 5.58. Found: C, 62.62; H, 5.28; H, 9.73; S, 5.48.

E. (S)-2-(2.3-Dihydro-6-(((1,2-dihydro-3-methyl-1-oxobenzo[f]quinazolin-9-yl)methyl)amino)-3-oxo-1,2-benzisothiazol-2-yl)glutaric acid was obtained by hydrolysis of the foregoing diester essentially as described in the previous example.

$^1H$ NMR (DMSO-$d_6$, 300 MHz) δ: 1.88–2.38 (m, 4H, gluCH$_2$CH$_2$), 2.43 (s, 3H, CH$_3$), 4.60 (br d, J=5 Hz, 2H, C$^9$—CH$_2$), 4.98–5.08 (m, 1H, gluCH), 6.78 (dd, J=9, 2 Hz, 1H, Ar), 6.92 (d, J=2 Hz, 1H, Ar), 7.41 (br t, J=6 Hz, 1H, ArNH), 7.53 (d, J=9 Hz, 1H, Ar), 7.59 (d, J=9 Hz, 1H, Ar), 7.63 (dd, J=8, 2 Hz, 1H, Ar), 8.02 (d, J=8 Hz, 1H, Ar), 8.22 (d, J=9 Hz, 1H, Ar), 9.86 (s, 1H, Ar), 11.8–13.3 (3H, CO$_2$H's and N$^2$H). Anal. Calculated for $C_{26}H_{22}N_4O_6S \cdot 2H_2O$: C, 56–31; H, 4.73; N, 10.10. Found: C, 56.28; H, 4.65; N, 10.13.

Analogs of N-(4(((1,2-dihydro-3-methyl-1-oxobenzo[f]quinazolin-9-yl)-methyl)amino)benzoyl)-L-glutamic acid (Example 32) were often prepared by coupling of an appropriately protected p-aminobenzoylglutamate analog with 9-bromomethyl-3-methylbenzo[f]quinazolin-1(2H)-one followed by hydrolysis of the glutamate diesters.

The analog of the above compounds where the benzene ring of the p-aminobenzoic acid moiety had been replaced by a thiophene ring was prepared by condensation of diethyl 5-amino-2-thenoyl-L-glutamate (L. R. Hughes, U.K. Patent GB 2188319A) with the requisite 9-bromomethylbenzoquinazoline essentially as described above.

Diethyl N-((5-(((1,2-Dihydro-3-methyl-1-oxobenzo [f]quinazolin-9-yl)methyl)amino)-2-thienyl) carbonyl)-L-glutamate $^1H$ NMR (DMSO-$d_6$, 300 MHz) δ: 1.15 (t, J=7 Hz, 3H, esterCH$_3$), 1.17 (t, J=7 Hz, 3H esterCH$_3$), 1.82–2.10 (m, 2H, gluCH$_2$), 2.38 (t, J=7.5 Hz, 2H, gluCH$_2$), 2.43 (s, 3H, C$^3$—CH$_3$), 4.03 (q, J=7 Hz, 2H, esterCH$_2$), 4.08 (q, J=7 Hz, 2H, esterCH$_2$), 4.26–4.36 (m, 1H, gluCH), 4.51 (d, J=5.5 Hz, 2H, C$^9$—CH$_2$), 5.90 (d, J=4 Hz, 1H, Ar), 7.46 (d, J=4 Hz, 1H, Ar), 7.60 (d, J=9 Hz, 1H, Ar), 7.63 (dd, J=8, 1.5 Hz, 1H, Ar), 7.70 (t, J=5.5 Hz, 1H, ArNH), 8.01 (d, J=8.5 Hz, 1H, Ar), 8.14 (d, J=7.5 Hz, 1H, gluNH), 8.22 (d, J=9 Hz, 1H, Ar), 9.84 (s, 1H, Ar), 2.55 (s, 1H, N$^2$H). Mass spectrum (CI-CH$_4$): 551 (M+1, 90.3%), 329 (100%). Anal. Calculated for $C_{28}H_{30}N_4O_6S \cdot 4/3H_2O$: C, 58.53; H, 5.73; N, 9.75; S, 5.58. Found C, 58.48; H, 5.61; N, 9.71; S, 5.65.

N-((5-(((1,2-Dihydro-3-methyl-1-oxobenzo[f] quinazolin-9-yl)methyl)amino-2-thienyl)carbonyl)-L-glutamic acid $^1H$ NMR (DMSO-$d_6$, 300 MHz) δ: 1.77–2.08 (m, 2H, gluCH$_2$), 2.30 (t, J=5 Hz, gluCH$_2$), 2.43 (s, 3H, CH$_3$), 4.22–4.32 (m, 1H, gluCH), 4.51 (d, J=5.5 Hz, 2H, C$^9$—CH$_2$), 5.89 (d, J=4 Hz, 1H, Ar), 7.46 (d, J=4 Hz, 1H, Ar), 7.58–7.70 (m, 3H, 2 Ar & ArNH), 8.01 (d, J=8 Hz, 1H, Ar), 8.03 (d, J=7.5 Hz, 1H, gluNH), 8.22 (d, J=9 Hz, 1H, Ar), 9.84 (s, 1H, Ar), 12.34 (br s, 2H, CO$_2$H's), 12.55 (s, 1H, N$^2$H). Anal. Calculated for $C_{24}H_{22}N_4O_6S \cdot 4/3H_2O$: C, 55.60; H, 4.79; N, 10.81; S, 6.18. Found: C, 55.60; H, 4.69; N, 10.73; S, 6.16.

An analog in which the NH of the glutamate moiety was replaced by a methylene group was also prepared by a similar sequence of reactions. The preparation of the requisite side chain moiety and analytical data on the final products are given below.

(RS)-2-(2-(4-(((1,2-Dihydro-3-methyl-1-oxobenzo[f] quinazolin-9-yl)methyl)amino)phenyl)-2-oxoethyl) glutaric acid A. Diethyl 2-ethoxycarbonyl-2-(2-(4-nitrophenyl)-2-oxoethyl)glutarate To a solution of diethyl 2-ethoxycarbonyl glutarate (11 g, 42 mmol) in diethyl ether:dimethylformamide (1:1, 90 ml) at 0° C. was added NaOMe (2.16 g, 40 mmol). After stirring the mixture for 15 minutes a solution of 2-tiromo-4'-nitoacetophenone in diethyl ether:dimethylformamide (1:1, 30 ml) was added dropwise over 5 minutes. The reaction mixture was removed from the ice bath, stirred for 30 minutes, diluted with water (200 ml) and extracted with diethyl ether (2×75 ml). The organic solution was washed with 10% LiCl solution (40 ml), dried (MgSO$_4$), and concentrated in vacuo. Purification by repeated chromatography on silica gel eluting with ethylacetate:hexane (1:4) and ethylacetate:methylene chloride:hexane (1:1:8) gave diethyl 2-ethoxycarbonyl-2-(2-(4-nitrophenyl)-2-oxoethyl)glutarate (2.8 g) as an oil $^1$H NMR (DMSO-d$_6$, 200 MHz) δ: 1.12 (t, J=7 Hz, 6H, CH$_3$, s), 1.13 (t, J=7 Hz, 3H, CH$_3$), 2.18–2.42 (m, 4H, CH$_2$CH$_2$), 3.75 (s, 2H, COCH$_2$), 3.99 (q, J=7 Hz, 2H, esterCH$_2$), 4.11 (q, J=7 Hz, 4H, esterCH$_2$'s), 8.20 (d, J=9 Hz, 2H, Ar), 8.33 (d, J=9 Hz, 2H, Ar). Anal. Calculated for C$_{20}$H$_{25}$NO$_9$: C, 56.73; H, 5.95; N, 31. Found: C, 56.66; H, 5.83; N, 3.36.

B. Diethyl (RS)-2-(2-(4-nitrophenyl)-2-oxoethyl)glutarate

A solution of diethyl 2-ethoxycarbonyl-2-(2-(4-nitrophenyl)-2-oxoethyl)glutarate (2.5 g, 5.9 mmol) in ethanol:1N NaOH (2:1, 105 ml) was stirred 20 hours at room temperature and then acidified to pH 1.5 with concentrated HCl and concentrated in vacuo. The residue was dissolved in diglyme (50 ml) and the solution stirred at reflux for 20 minutes and then concentrated in vacuo. The residue was then dissolved in ethanol (50 ml). HCl gas was bubbled into the solution for 30 seconds, and the solution was stirred at room temperature over the weekend and then concentrated in vacuo. The product was taken up in diethyl ether (100 ml), washed with saturated sodium bicarbonate solution (35 ml), dried (MgSO$_4$), and concentrated in vacuo. Purification by chromatography on silica gel eluting with ethyl acetate:hexane (1:4) gave diethyl (RS)-2-(2-(4-nitrophenyl)-2-oxoethyl)glutarate (1.49 g) as an oil $^1$H NMR (DMSO-d$_6$, 200 MHz) δ: 1.13 (t, J=7 Hz, 3H, CH$_3$), 1.19 (t, J=7 Hz, 3H, CH$_3$), 1.74–1.93 (m, 2H, CH$_2$), 2.35–2.45 (m, 2H, CH$_2$CO$_2$), 2.82–3.00 (m, 1H, CH), 3.24–3.67 (m, 2H, COCH$_2$), 4.03 (q, J=7 Hz, 2H, esterCH$_2$), 4.04 (q, J=7 Hz, 2H, esterCH$_2$), 8.20 (d, J=9 Hz, 2H, Ar), 8.33 (d, J=9 Hz, 2H, Ar). Anal. Calculated for C$_{17}$H$_{21}$NO$_7$.1/4H$_2$O: C, 57.38; H, 6.09; N, 3.94. Found: C, 57.35; H, 6.11; N, 3.89.

C. Diethyl (RS)-2-(2-(4-aminophenyl)-2-oxoethyl)glutarate

A solution of diethyl (RS)-2-(2-(4-nitrophenyl)-2-oxoethyl)glutarate (1.48 g, 4.2 mmol) and 10% palladium on carbon (0.23 g) in ethanol (100 ml) was shaken under hydrogen (30–35 psi)for 40 minutes. The catalyst was filtered off and the filtrate concentrated in vacuo. Purification by chromatography on silica gel eluting with ethyl acetate: hexane (1:1) gave diethyl (RS)2-(2-(4-aminophenyl)-2-oxoethyl)glutarate (1.07 g) as an oil that solidified on standing. M.P. 58–61° C. $^1$H NMR (DMSO-d$_6$, 200 MHz) δ: 1.13 (t, J=7 Hz, 3H, CH$_3$), 1.16 (t, J=7 Hz, 3H, CH$_3$), 1.67–1.87 (m, 2H, CH$_2$), 2.28–2.40 (m, 2H, CH$_2$CO$_2$), 2.72–2.88 (m, 1H, CH), 2.99 (ABX, apparent J$_{AB}$=17.5 Hz, J$_{AX}$=4.5 Hz, 1H, COCH—H), 3.19 (ABX, apparent J$_{AB}$=17.5 Hz, J$_{BX}$=9.5 Hz, 1H, COCH—H), 4.00 (q, J=7 Hz, 2H, esterCH$_2$), 4.03 (q, J=7 Hz, 2H, esterCH$_2$), 6.04 (br s, 2H, NH$_2$), 6.53 (d, J=9 Hz, 2H, Ar), 7.66 (d, J=9 Hz, 2H Ar). Mass spectrum (CI-CH$_4$): 322 (M+1, 94.4%), 276 (100%). Anal. Calculated for C$_{17}$H$_{23}$NO$_5$.0.15H$_2$O: C, 63.01; H, 7.25; N, 4.32. Found: C, 62.98; H, 7.24; N, 4.28.

D. Diethyl (RS)-2-(2-(4-(((1,2-dihydro-3-methyl-1-oxobenzo[f]quinazolin-9-yl)methyl)amino)phenyl)-2-oxoethyl)glutarate M.P.=189–190° C. $^1$H NMR (DMSO-d$_6$, 300 MHz) δ: 1.13 (t, J=7 Hz, 3H, esterCH$_3$), 1.17 (t, J=7 Hz, 3H, esterCH), 1.67–1.88 (m, 2H, CH$_2$), 2.30–2.40 (m, 2H, CH$_2$CO$_2$), 2.43 (s, 3H, C$^3$—CH$_3$), 2.73–2.89 (m, 1H, CH), 3.00 (ABX, apparent J$_{AB}$=17.5 Hz, J$_{AX}$=4.5 Hz, 1H, COCH—H), 3.22 (ABX, apparent J$_{AB}$=17.5 Hz, ABX=9.5 Hz, 1H, COCH—H), 4.01 (q, J=7 Hz, 2H, esterCH$_2$), 4.04 (q, J=7 Hz, 2H, esterCH$_2$), 4.60 (br d, J=5.5 Hz, 2H, C$^9$—CH$_2$), 6.66 (d, J=9 Hz, 2H, Ar), 7.39 (br, t, J=5.5 Hz, 1H, ArNH), 7.60 (d, J=9 Hz, 1H, Ar), 7.62 (dd, J=8, 1.5 Hz, 1H, Ar), 7.71 (d, J=Hz, 2H, Ar), 8.01 (d, J=8.5 Hz, 1H, Ar), 8.22 (d, J=9 Hz, 1H, Ar), 9.85 (s, 1H, Ar), 12.53 (s, 1H, N$^2$—H). Mass spectrum (CI-CH$_4$): 544 (M+1, 100%). Anal. Calculated for C$_{31}$H$_{33}$N$_3$O$_6$: C, 68.49; H, 6.12; N, 7.73. Found: C, 68.43; H, 6.15; N, 7.72.

E. (RS)-2-(2-(4-(((1,2-Dihydro-3-methyl-1-oxobenzo[f]quinazolin-9-yl)methyl)amino)phenyl)-2-oxoethyl)glutaric acid $^1$H NMR (DMSO-d$_6$/D$_2$O, 300 MHz, δ: 1.63–1.85 (m, 2H, CH$_2$), 2.17–2.37 (m, 2H, CH$_2$CO$_2$), 2.43 (s, 3H, C$^3$—CH$_3$), 2.70–2.82 (m, 1H, CH), 2.91 (ABX, apparent J$_{AB}$=17.5 Hz, J$_{AX}$=4 Hz, 1H, COCH—H), 3.17 (ABX, apparent J$_{AB}$=17.5 Hz, J$_{BX}$=9.5 Hz, 1H, COCH—H), 4.59 (s, 2H, C$^9$—CH$_2$), 6.65 (d, J=9 Hz, 2H, Ar), 7.59 (d, J=9 Hz, 1H, Ar), 7.61 (dd, J=8.5, 1.5 Hz, 1H, Ar), 7.70 (d, J=9 Hz, 2H, Ar), 8.00 (d, J=8.5 Hz, 1H, Ar), 8.21 (d, J=9H, 1H, Ar), 9.83 (s, 1H, Ar). Anal. Calculated for C$_{27}$H$_{25}$N$_3$O$_6$.7/4 H$_2$O: C, 62.48; H, 5.53; N, 8.10. Found: C, 62.46; H, 91.42; N, 8.06.

Analogs in which the aminomethylene moiety of the bridge was replaced by two-carbon moieties were also prepared;

(E)-N-(4-(2-(1,2-dihydro-3-methyl-1-oxobenzo[f] quinazolin-9-yl)vinyl)benzoyl-L-glutamic acid A. Diethyl (E)-N-(4-(2-(1,2-dihydro-3-methyl-1-oxobenzo [f]quinazolin-9-yl)vinyl)benzoyl-L-glutamate A solution of 9-bromo-3-methylbenzo[f]quinazolin-1 (2H)-one (0.87 g, 3.0 mmol), 4-vinylbenzoic acid (0.87 g, 5.9 mmol), palladium acetate (0.45 g, 2.0 mmol), and tri(2-tolyl)phosphine (1.2 g, 3.9 mmol) in N-methylmorpholine (90 ml) was stirred under nitrogen at reflux for 1 hour. Additional palladium acetate (0.45 g, 2.0 mmol) and tri(2-tolyl)phosphine (1.2 g, 3.9 mmol) were added and the reaction mixture was refluxed for a further 4 hours. The resulting suspension was allowed to cool, the solid filtered and washed with diethyl ether. The solid was resuspended in a small volume of boiling ethanol, filtered hot, washed with diethyl ether and dried under vacuum at 80° C. to give 4-(2-(1,2-dihydro-3-methyl-1-oxobenzo[f]quinazolin-9-yl)vinyl)benzoic acid $^1$H NMR (DMSO-d$_6$, 300 MHz) δ: 2.44 (s, 3H, CH$_3$), 7.50 (d, J=16.5 Hz, 1H, vinylCH), 7.61 (d, J=8 Hz, 1H, Ar), 7.65 (d, J=16 Hz, 1H, vinylCH), 7.83 (d, J=8 Hz, 2H, Ar), 7.96 (d, J=8 Hz, 2H, Ar), 8.05 (s, 2H, Ar), 8.23 (d, J=9 Hz, 1H, Ar), 9.96 (s, 1H, Ar), 12–13.2 (v br s, 1H, CO$_2$H), 12.6 (br s, 1H, N$^2$H) containing 6.7% by NMR of 9-bromo-3-methylbenzo[f]quinazolin-1-(2H)-one (0.80 g). To a suspension of the acid in a solution of L-glutamic acid diethyl ester hydrochloride (0.72 g, 3.0 mmol) and triethylamine (0.42 ml, 3.0 mmol) in dimethylformamide (50 ml) was added 1-(3-dimethylaminopropyl) 3-ethylcarbodiimide hydrochloride (0.48 g, 2.5 mmol). After stirring the mixture for 4 hours, more dimethylformamide (50 ml) was added and the suspension stirred overnight. The reaction mixture was heated to 65° C., 1-(3-dimethylaminopropyl)3-ethylcarbodiimide hydrochloride (0.32 g, 1.7 mmol) was added and the suspension was stirred for 6 hours to give a homogeneous solution. The solution was stirred for 60 hours at room temperature, then concentrated in vacuo onto silica gel (log). Purification by chromatography on silica gel (450 g) eluting with methanol:methylene chloride (1:39 to 1:24), evaporation, filtration of the resulting solid from a small volume of methanol and drying under high vacuum gave diethyl(E)-N-(4-(2-(1,2-dihydro-3-methyl-1-oxobenzo[f]quinazolin-9-yl)vinyl)benzoyl)-L-glutamate (0.22 g). $^1$H NMR (DMSO-d$_6$, 300 MHz) δ: 1.17 (t, J=7 Hz, 3H, esterCH$_3$), 1.20 (t, J=7 Hz, 3H, esterCH$_3$), 1.95–2.20 (m, 2H, gluCH$_2$), 2.44 (s, 3H, C$^3$—CH$_3$), 2.47 (t, J=7 Hz, 2H, gluCH$_2$), 4.06 (q, J=7 Hz, 2H, esterCH$_2$), 4.12 (q, J=7 Hz, 2H, esterCH$_2$), 4.41–4.51 (m, 1H, gluCH), 7.50 (d, J=16.5 Hz, 1H, vinylCH), 7.61 (d, J=9 Hz, 1H, Ar), 7.64 (d, J=16.5 Hz, 1H, vinylCH), 7.83 (d, J=8.5 Hz, 2H, Ar), 7.93 (d, J=8.5 Hz, 2H, Ar), 8.05 (s, 2H, Ar), 8.24 (d, J=9 Hz, 1H, Ar), 8.76 (d, J=7.5 Hz, 1H, gluNH), 9.96 (s, 1H, Ar), 12.58 (br, s, 1H, N$^2$H). Mass spectrum (CI-CH$_4$): 542 (M+1, 100%). Anal. Calculated for C$_{31}$H$_3$N$_3$O$_6$.0.55H$_2$O: C, 67.51; H, 5.87; N, 7.62. Found: C, 67.40; H, 5.72; N, 7.67.

B. (E)-N-(4-(2-(1,2-Dihydro-3-methyl-1-oxobenzo[f]quinazolin-9-yl)vinyl)benzoyl)-L-glutamic acid was obtained by base hydrolysis of the foregoing glutamate diester by the method described above.

$^1$H NMR (DMSO-d$_6$, 300 MHz) δ: 1.91–2.20 (m, 2H, gluCH$_2$), 2.39 (t, J=7.5 Hz, 2H, gluCH$_2$), 2.45 (s, 3H, C$^3$—CH$_3$), 4.38–4.48 (m, 1H, gluCH), 7.51 (d, J=16.5 Hz, 1H, vinylCH), 7.62 (d, J=8.5 Hz, 1H, Ar), 7.65 (d, J=16.5 Hz, 1H, vinylCH), 7.84 (d, J=8.5 Hz, 2H, Ar), 7.94 (d, J=8.5 Hz, 2H, Ar), 8.06 (s, 2H, Ar), 8.25 (d, J=9 Hz, 1H, Ar), 8.66 (d, J=6 Hz, 1H, gluNH), 9.96 (s, 1H, Ar), 12.0–12.8 (br s, 2H, CO$_2$H's), 12.61 (br s, N$^2$H). Anal. Calculated for C$_{27}$H$_{23}$N$_3$O$_6$.H$_2$O: C, 64.41; H, 5.00; N, 8.35. Found: C, 64.60; H, 4.90; N, 8.29.

N-(4-(2-(1,2-Dihydro-3-methyl-1-oxobenzo[f]quinazolin-9-yl)ethyl)benzoyl)-L-glutamic acid A. Diethyl N-(4-(2-(1,2-dihydro-3-methyl-1-oxobenzo[f]quinazolin-9-yl)ethyl)benzoyl)-L-glutamate A suspension of diethyl N-(4-(2-(1,2-dihydro-3-methyl-1-oxobenzo[f]quinazolin-9-yl)vinyl)benzoyl)-L-glutamate (0.16 g, 0.29 mmol) and 10% palladium on carbon (0.10 g) in ethanol (100 ml) was shaken under hydrogen (40 psi) overnight. Ethanol (80 ml) and acetic acid (20 ml) were added and the mixture was hydrogenated (40 psi) for 1 day. The solution was filtered, concentrated in vacuo, and the residue and catalyst were recombined in acetic acid (40 ml) and hydrogenated over the weekend. The solution was filtered, concentrated in vacuo and the product twice filtered from a small volume of methanol to give diethyl N-(4-(2-(1,2-dihydro-3-methyl-1-oxobenzo[f]quinazolin-9-yl)ethyl)benzoyl)-L-glutamate (0.10 g). $^1$H NMR (DMSO-d$_6$, 300 MHz) δ: 1.16 (t, J=7 Hz, 3H, esterCH$_3$), 1.19 (t, J=7 Hz, 3H, esterCH$_3$), 1.90–2.18 (m, 2H, gluCH$_2$), 2.43 (s, 3H, C$^3$—CH$_3$), 2.44 (t, J=7.5 Hz, 2H, gluCH$_2$), 3.03–3.22 (m, 4H, ArCH$_2$'s), 4.04 (q, J=7 Hz, 2H, esterCH$_2$), 4.10 (q, J=7 Hz, 2H, esterCH$_2$), 4.37–4.47 (m, 1H, gluCH), 7.40 (d, J=8 Hz, 2H, Ar), 7.54 (dd, J=8, 1.5 Hz, 1H, Ar), 7.57 (d, J=8.5 Hz, 1H, Ar), 7.80 (d, J=8 Hz, 2H, Ar), 7.95 (d, J=8 Hz, 1H, Ar), 8.20 (d, J=9 Hz, 1H, Ar), 8.65 (d, J=7.5 Hz, 1H, gluNH), 9.72 (s, 1H, Ar), 12.51 (br s, 1H, N$^2$H). Mass spectrum (CI-CH$_4$): 544 (M+1, 4.2%). Anal. Calculated for C$_{31}$H$_{33}$N$_3$O$_6$.1/10H$_2$O: C, 68.27; H, 6.14; N, 7.70. Found: C, 68.34; H, 6.10; N, 7.68.

B. N-(4-(2-(1,2-Dihydro-3-methyl-1-oxobenzo[f]quinazolin-9-yl)ethyl)benzoyl)-L-glutamic acid $^1$H NMR (DMSO-d$_6$, 300 MHz) δ: 1.86–2.16 (m, 2H, gluCH$_2$), 2.35 (t, J=7.5 Hz, 2H, gluCH$_2$), 2.43 (s, 3H, C$_3$—CH$_3$), 3.03–3.22 (m. 4H, ArCH$_2$'s), 4.34–4.44 (m, 1H, gluCH), 7.40 (d, J=8 Hz, 2H, Ar), 7.54 (dd, J=8, 1.5 Hz, 1H, Ar), 7.57 (d, J=8.5 Hz, 1H, Ar), 7.81 (d, J=8 Hz, 2H, Ar), 7.95 (d, J=8, 5 Hz, 1H, Ar), 8.20 (d, J=9 Hz, 1H, Ar), 8.53 (d, J=7.5 Hz, 1H, gluNH), 9.72 (s, 1H, Ar), 12.15–12.6 (br s, 2H, CO$_2$H's), 12.51 (s, 1H, N$^2$H). Anal. Calculated for C$_{27}$H$_{25}$N$_3$O$_6$.1/3H$_2$O: C, 65.72; H, 5.24; N, 8.52. Found: C, 65.74; H, 5.22; N, 8.51.

An analog in which the linking aminomethylene moiety of the side chain was replaced with a carbonamido-group was prepared as described below;

N-(4-(((1,2-Dihydro-3-methyl-1-oxobenzo[f]quinazolin-9-yl)carbonyl)amino)benzoyl)-L-glutamic acid A. Diethyl N-(4-(((1,2-dihydro-3-methyl-1-oxobenzo[f]quinazolin-9-yl)carbonyl)amino)benzoyl)-L-glutamate A solution of 9-bromo-3-methylbenzo[f]quinazolin-1(2H)-one (0.50 g, 1.7 mmol) and cuprous cyanide (0.46 g, 5.1 mmol) in dimethylacetamide (10 ml) under nitrogen was heated under reflux for 2 hours, cuprous cyanide (0.16 g, 1.8 mmol) added and refluxing continued for 18 hours. The solvent was removed under high vacuum to give crude 9-cyano-3-methylbenzo[f]quinazolin-1(2H)-one. The solid was suspended in sulphuric acid (2M, 300 ml), the suspension stirred at reflux under nitrogen for 40 hours, cooled and adjusted to pH 8.5 with sodium hydroxide (21 g) and saturated sodium bicarbonate solution. The resulting suspension was filtered to give the partially purified nitrile which was subjected to refluxing 2N hydrochloric acid in 95% ethanol for 24 hours. The solution was made basic with NaOH, filtered, the filtrate adjusted to neutral and filtered. The resulting filtrate was adjusted to pH 1.5 and the precipitate filtered and dried under high vacuum to give a 2:1 mixture of carboxylic acid to nitrile (225 mg). A solution of the mixture (0.22 g), N-(4-aminobenzoyl)-L-glutamic acid diethyl ester (0.32 g, 1.0 mmol), and 1-(3-dimethylaminopropyl)-3-ethyl carbodiimide hydrochloride (0.19 g, 1.0 mmol) in dimethylformamide (25 ml) was stirred overnight, more 1-(3-dimethyl-aminopropyl)-3-ethylcarbodiimide hydrochloride (0.19 g, 1.0 mmol) added, the reaction mixture stirred for another 4 hours, then concentrated in vacuo onto silica gel (2 g). Purification by chromatography on silica gel (150 g) eluting with methanol:methylene chloride (3:97 to 1:19) and filtration of the resulting solid from methanol gave, after drying under high vacuum, diethyl (N-(4-(((1,2-dihydro-3-methyl-1-oxobenzo[f]quinazolin-9-yl)carbonyl)amino)benzoyl-L-glutamate (0.027 g). $^1$H NMR (DMSO-d$_6$, 300 MHz) δ: 1.18 (t, J=7 Hz, esterCH$_3$), 1.20 (t, J=7 Hz, esterCH$_3$), 1.95–2.20 (m, 2H, gluCH$_2$), 2.46 (s, 3H, 3-CH$_3$ and t, J=7 Hz, 2H, gluCH$_2$), 4.06 (q, J=7 Hz, 2H, esterCH$_2$), 4.12 (q, J=6.5 Hz, 2H, esterCH$_2$), 4.39–4.49 (m, 1H, gluCH), 7.75 (d, J=9 Hz, 1H, Ar), 7.93 (s, 4H, Ar), 8.12 (dd, J=8.5, 1.5 Hz, 1H, Ar), 8.19 (d, J=8.5 Hz, 1H, Ar), 8.35 (d, J=9 Hz, 1H, Ar), 8.67 (d, J=7.5 Hz, 1H, gluNH), 10.37 (s, 1H, Ar), 10.76 (s, 1H, CONHAr), 12.72 (s, 1H, N$^2$H). Exact mass spectrum calculated for (C$_{30}$H$_{30}$N$_4$O$_7$)$^+$: 559.2193. Found: 559.2191.

B. N-(4-(((1,2-Dihydro-3-methyl-1-oxobenzo[f]quinazolin-9-yl)carbonyl)amino)benzoyl)-L-glutamic acid $^1$H NMR (DMSO-d$_6$, 300 MHz) δ: 1.90–2.18 (m, 2H, gluCH$_2$, 2.39 (t, J=7.5 Hz, 2H, gluCH$_2$), 2.47 (s, 3H, 3-CH₃), 4.37–4.47 (m, 1H, gluCH), 7.76 (d, J=7 Hz, 1H, Ar), 7.94 (s, 4H, Ar), 8.13 (dd, J=8.5, 1.5 Hz, 1H, Ar), 8.20 (d, J=8.5 Hz, 1H, Ar), 8.35 (d, J=9 Hz, 1H, Ar), 8.56 (d, J=8 Hz, 1H, gluNH), 10.38 (d, J=1 Hz, 1H, Ar), 10.76 (s, 1H, CONHAr), 12.1–12.7 (v br s, 2H, CO₂H's), 12.72 (s, 1H, N²H). Anal. Calculated for C₂₆H₂₂N₄O₇.3/4H₂O: C, 60.52; H, 4.59; N, 10.86. Found: C, 60.55; H, 4.54; N, 10.88.

Further variations in the side chain structure were effected by condensation of the requisite p-aminobenzoate analog with 3-methyl-9-bromomethylbenzo[f]quinazolin-1(2H) one; preparations of the side chain amines and data on the final products are given below.

4-(4-(((1,2-Dihydro-3-methyl-1-oxobenzo[f]quinazolin-9-yl)methyl)amino)phenyl)-4-oxobutyric acid A. Ethyl-2-ethoxycarbonyl-4-(4-nitrophenyl)-4-oxobutyrate To a solution of diethylmalonate (25 ml, 0.16 mole) in dimethylformamide (300 ml) was added sodium methoxide (8.6 g, 0.16 mole) and the solution chilled in an ice bath. When temperature of the solution reach 10° C., 2-bromo-4'-nitroacetophenone (41 g, 0.16 mole) was added; after a few minutes the reaction mixture was removed from the ice bath and stirred for 2 hours. The solution was concentrated in vacuo, water (500 ml) added, and the mixture extracted with diethyl ether (250 and 150 ml). The combined ether extracts were washed with saturated sodium chloride solution (100 ml), dried (MgSO₄), and concentrated in vacuo. Purification by chromatography on silica gel eluting with ethyl acetate:hexane (1:4) gave ethyl 2-ethoxycarbonyl-4-(4-nitrophenyl)-4-oxobutyrate (21.1 g) as an oil. ¹H NMR (DMSO-d₆, 300 MHz) δ: 1.20 (t, J=7 Hz, 6H, CH₃'s), 3.70 (d, J=7 Hz, 2H, COCH₂), 3.96 (t, J=7 Hz, 1H, CH), 4.08–4.23 (m, 4H, esterCH₂'s), 8.24 (d, J=9 Hz, 2H, Ar), 8.36 (d, J=9 Hz, 2H, Ar). Anal. Calculated for C₁₅H₁₇N₇.1/10H₂O: C, 55.42; H, 5.33; N, 4.31. Found: C, 55.44; H, 5.23; N, 4.27.

B. Ethyl 4-(4-nitrophenyl)-4-oxobutyrate

A solution of ethyl 2-ethyl 2-ethoxycarbonyl-4-(4-nitrophenyl)-4-oxobutyrate (7.0 g, 22 mmol) and sulphuric acid (1.5 g) in acetic acid:water (20:1, 42 ml), was stirred at reflux for 4 hours and then allowed to stand for 60 hours at room temperature. The suspension was diluted with water (5 ml) and the solid filtered, washed with water, and air dried. A solution of the solid in ethanol (50 ml) containing a few drops of sulphuric acid was stirred overnight, then concentrated in vacuo. The residue was taken up in diethyl ether (75 ml), washed with saturated sodium bicarbonate solution (40 ml), dried (MgSO₄, and silica gel); concentration of the solution in vacuo gave ethyl 4-(4-nitrophenyl)-4-oxobutyrate (1.4 g) as an oil. ¹h NMR (DMSO-d₆, 300 MHz), δ: 1.18 (t, J=7 Hz, 3H, CH₃), 2.68 (t, J=6 Hz, 2H, CH₂), 3.39 (t, J=6 Hz, 2H, CH₂), 4.07 (q, J=7 Hz, 2H, esterCH₂), 8.22 (d, J=9 Hz, 2H, Ar), 8.36 (d, J=9 Hz, 2H, Ar). Anal. Calculated for C₁₂H₁₃NO₅: C, 57.37; H, 5.22; N, 5.58. Found: C, 57.44; H, 5.24; N, 5.53.

C. Ethyl 4-(4-aminophenyl)-4-oxobutyrate

A solution of ethyl 4-(4-nitrophenyl)-4-oxobutyrate (1.4 g, 5.6 mmol) and 10% palladium on carbon (0.18 g) in ethanol (50 ml) was shaken under hydrogen (50 psi) for 2 hours then filtered and concentrated in vacuo. The residue was absorbed onto silica gel (5 g) from an ethyl acetate solution and purified by chromatography on silica gel (100 g) eluting with ethyl acetate:hexane (1:2) to give ethyl 4-(4-aminophenyl)-4-oxobutyrate (0.38 g) as a white solid. ¹H NMR (DMSO-d₆, 300 MHz) δ: 1.17 (t, J=7 Hz, 3H, CH₃), 2.56 (t, J=6.5 Hz, 2H, CH₂), 3.10 (t, J=6.5 Hz, 2H, CH₂), 4.04 (q, J=7 Hz, 2H, esterCH₂), 6.04 (br s, 2H, NH₂), 6.57 (d, J=9 Hz, 2H, Ar), 7.69 (d, J=9 Hz, 2H, Ar). Anal. Calculated for C₁₂H₁₅NO₃: C, 65.14; H, 6.83; N, 6.33. Found: C, 65.23; H, 6.85; N, 6.32.

D. Ethyl-4-(4-(((1,2-dihydro-3-methyl-1-oxobenzo[f]quinazolin-9-yl)methyl)amino)phenyl-4-oxobutyrate ¹H NMR (DMSO-d₆, 300 MHz) δ 1.17 (t, J=7 Hz, 3H, esterCH₃), 2.43 (s, 3H, C³—CH₃), 2.55 (t, J=6.5 Hz, 2H, CH₂), 3.09 (t, J=6.5 Hz, 2H, CH₂), 4.02 (q, J=7 Hz, 2H, esterCH₂), 4.60 (d, J=5.5 Hz, 2H, C⁹—CH₂), 6.66 (d, J=9 Hz, 2H, Ar), 7.34 (t, J=5.5 Hz, 1H, ArNH), 7.59 (d, J=8.5 Hz, 1H, Ar), 7.61 (dd, J=8, 1.5 Hz, 1H), 7.71 (d, J=9 Hz, 2H, Ar), 8.00 (d, J=8,5 Hz, 1H, Ar), 8.21 (d, J=8.5 Hz, 1H, Ar), 9.85 (s, 1H, Ar), 12.53 (s, 1H, N²H). Mass spectrum (CI-CH₄): 444 (M+1, 82.1%), 225 (100%), Anal. Calculated for C₂₆H₂₅N₃O₄.3/10H₂O: C, 69.57; H, 5.75; N, 9.36. Found: C, 69.61; H, 5.75; N, 9.28.

E. 4-(4-(((1,2-Dihydro-3-methyl-1-oxobenzo[f]quinazolin-9-yl)methyl)amino)phenyl)-4-oxobutyric acid ¹H NMR (DMSO-d₆, 300 MHz) δ: 2.43 (s, 3H, C³—CH₃), 2.50 (t, J=6.5 Hz, 2H, CH₂), 3.04 (t, J=6.5 Hz, 2H, CH₂), 4.60 (d, J=6 Hz, 2H, C₉—CH₂), 6.66 (d, J=9 Hz, 2H, Ar), 7.37 (t, J=6 Hz, 1H, ArNH), 7.59 (d, J=8.5 Hz, 1H, Ar), 7.61 (dd, J=8.5, 1.5 Hz, 1H, Ar), 7.71 (d, J=9 Hz, 2H, Ar), 8.00 (d, J=8.5 Hz, 1H, Ar), 8.21 (d, J=9 Hz, 1H, Ar), 9.85 (s, 1H, Ar), 12.02 (s, 1H, CO₂H), 12.53 (s, 1H, N²H). Anal. Calculated for C₂₄H₂₁N₃O₄.3/4H₂O: C, 67.20; H, 5.29; N, 9.80. Found: C, 67.19; H, 5.24; N, 9.82.

Dodecyl 4-(4-(((1,2-dihydro-3-methyl-1-oxobenzo[f]quinazolin-9-yl)methyl)amino)phenyl)-4-oxobutyrate A. 4-(4-nitrophenyl)-4-oxobutyric acid A solution of ethyl 2-ethoxycarbonyl-4-(4-nitrophenyl)-4-oxobutyrate (6.2 g, 19 mmol) and sulphuric acid (1.0 g) in acetic acid:water (4:1, 50 ml) was stirred at reflux for 4 hours, then concentracted in vacuo to small volume. Dilution with water (100 ml) gave a precipitate which was filtered and dried at 50° C. under vacuum. Purification by chromatography on silica gel eluting with methanol:methylene chloride (3:97) and filtration of the resulting solid from diethyl ether containing a small percentage of methanol gave, after drying under high vacuum, 4-(4-nitrophenyl)-4-oxobutyric acid (2.1 g). ¹H NMR (DMSO-d₆, 300 MHz) δ: 2.62 (t, J=6 Hz, 2H, CH₂), 3.33 (t, J=6 Hz, 2H, CH₂), 8.22 (d, J=8.5 Hz, 2H, Ar), 8.36 (d, J=8.5 Hz, 2H, Ar), 12.22 (s. 1H, CO₂H). Anal. Calculated for C₁₀H₉NO₅: C, 53.82; H, 4.06; N, 6.28. Found: C, 53.65; H, 4.02; N, 6.21.

B. Dodecyl 4-(4-nitrophenyl)-4-oxobutyrate

A solution of 4-(4-nitrophenyl)-4-oxobutyric acid (0.50 g, 2.2 mmol), 1-dodecanol (5.0 ml, 22 mmol), and p-toluenesulfonic acid (50 mg) in tetrahydrofuran (2.5 ml) was stirred 60 hours at room temperature then heated under reflux for 1.5 hours. Concentration of the reaction mixture in vacuo and purification by chromatography or silica gel (200 g) eluting with methylene chloride:hexane (1.1 to 2:1) followed by filtration of the solid product from a small volume of hexane gave, after drying under high vacuum, dodecyl 4-(4-nitrophenyl)-4-oxobytyrate (0.43 g) as a white solid. ¹H NMR (DMSO-₆, 300 MHz) δ: 0.86 (t, J=6.5 Hz, 3H, esterCH₃), 1.07–1.35 (m, 18H, esterCH₂'s), 1.47–1.60 (m, 2H, esterCH₂), 2.69 (t, J=6 Hz, 2H, CH₂), 3.39 (t, J=6 Hz, 2H, CH₂), 4.00 (t, J=6.5 Hz, 2H, esterCH₂), 8.22 (d, J=9 Hz, 2H, Ar), 8.36 (d, J=9 Hz, 2H, Ar). Anal. Calculated for C₂₂H₃₃NO₅: C, 67.49; H, 8.50; N, 3.58. Found: C, 67.36; H, 8.54; N, 3.55.

C. Dodecyl 4-(4-aminophenyl)-4-oxobutyrate

A solution of dodecyl 4-(4-nitrophenyl)-4-oxobutyrate (0.42 g, 1.1 mmol), in ethyl acetate (50 ml) and 10% palladium on carbon (0.10 g) were shaken under hydrogen (30–40 psi) for 10 minutes. The mixture was filtered and the filtrate concentrated in vacuo to give dodecyl 4-(4-aminophenyl)-4-oxobutyrate (0.38 g) as a white solid. $^1$H NMR (DMSO-$d_6$, 300 MHz) δ: 0.86 (t, J=6.5 Hz, 3H, esterCH$_3$), 1.10–1.37 (m, 18H, esterCH$_2$'s), 1.47–1.60 (m, 2H, esterCH), 2.57 (t, J=6.5 Hz, 2H, CH$_2$), 3.10 (t, J=6.5 Hz, 2H, CH$_2$), 3.98 (t, J=6.5 Hz, 2H, esterCH$_2$), 6.04 (br s, 2H, NH$_2$), 6.56 (d, J=8.5 Hz, 2H, Ar), 7.68 (d, J=8.5 Hz, 2H, Ar). Anal. Calculated for $C_{22}H_{35}NO_3 \cdot 1/20 H_2O$: C, 72.91; H, 9.76; N, 3.86. Found: C, 72.86; H, 9.83; N, 3.82.

D. Dodecyl 4-(4-(((1,2-dihydro-3-methyl-1-oxobenzo[f]quinazolin-9-yl)methyl)amino)phenyl)-4-oxobutyrate M.P.=213–214° C. $^1$H NMR (DMSO-$d_6$, 300 MHz) δ 0.84 (t, J=6.5 Hz, 3H, esterCH$_3$), 1.07–1.33 (m, 18H, esterCH$_2$'s), 1.46–1.58 (m, 2H, esterCH$_2$), 2.43 (s, 3H, C$^3$—CH$_3$), 2.55 (t, J=6 Hz, 2H, CH$_2$), 3.09 (t, J=6 Hz, 2H, CH$_2$), 3.96 (t, J=6.5 Hz, 2H, esterCH$_2$), 4.60 (d, J=6 Hz, 2H, C$_9$—CH$_2$), 6.66 (d, J=9 Hz, 2H, Ar), 7.38 (t, J=6 Hz, 1H, ArNH), 7.59 (d, J=8.5 Hz, 1H, Ar), 7.61 (dd, J=8, 1.5 Hz, 1H, Ar), 7.71 (d, J=8.5 Hz, 2H, Ar), 8.00 (d, J=8.5 Hz, 1H, Ar), 8.21 (d, J=9 Hz, 1H, Ar), 9.85 (s, 1H, Ar), 12.53 (s, 1H, N$^2$H). Mass spectrum (CI-CH$_4$): 584 (M+1, 1.2%). Anal. Calculated for $C_{36}H_{45}N_3O_4$: C, 74.07; H, 7.77; N, 7.20. Found: C, 74.11; H, 7.76; N, 7.25.

Ethyl N-(4-(((1,2-dihydro-3-methyl-1-oxobenzo[f]quinazolin-9-yl)methyl)amino)-2-fluorobenzoyl)glycinate A. Ethyl N-(2-fluoro-4-nitrobenzoyl)glycinate Triethylamine (0.85 ml, 6.1 mmol) was added to a solution of 2-fluoro-4-nitrobenzoic acid (T. R. Jones et al., UK Patent GB 2175 903A, 1986) (1.0 g, 5.4 mmol), glycine ethyl ester hydrochloride (0.85 g, 6.1 mmol), and 1-(3-dimethylaminopropyl)-3-ethylcarbodiimide hydrochloride (1.1 g, 5.7 mmol) in methylene chloride (30 ml). After stirring 1 hour at room temperature the solution was passed through a short pad of silica gel eluting with ethyl acetate-:methylene chloride (1:3) and the resulting white solid was filtered from hexane and dried under high vacuum to give ethyl N-(2-fluoro-4-nitrobenzoyl)glycinate (1.04 g). $^1$H NMR (DMSO-$d_6$, 300 MHz) δ: 1.22 (t, J=7 Hz, 3H, CH$_3$), 4.05 (d, J=6 Hz, 2H, glyCH$_2$), 4.15 (q, J=7 Hz, 2H, esterCH$_2$), 7.88 (t, J=8 Hz, 1H, Ar), 8.17 (dd, J=8.5, 1.5 Hz, 1H, Ar), 8.25 (dd, J=10, 2 Hz, 1H), 9.09 (br t, J=5.5 Hz, 1H, CONH). Anal. Calculated for $C_{11}H_{11}FN_2O_5$: C, 48.89; H, 4.10; N, 10.37. Found: C, 49.00; H, 4.11; N, 10.43.

B. Ethyl N-(4-amino-2-fluorobenzoyl)glycinate

A solution of ethyl N-(2-fluoro-4-nitrobenzoyl)glycinate (0.40 g, 1.5 mmol) and 10% palladium on carbon (0.10 g) in ethanol (25 ml) was shaken under hydrogen (30–40 psi) for 1.5 hours. The solution was filtered and concentrated in vacuo to give N-(4-amino-2-fluorobenzoyl)glycinate as a solid (0.34 g). $^1$H NMR (DMSO-$d_6$, 300 MHz) δ: 1.20 (t, J=7.1 Hz, 3H, CH$_3$), 3.95 (d, J=5.7 Hz, 2H, glyCH$_2$), 4.11 (q, J=7.1 Hz, 2H, esterCH$_2$), 6.03 (br s, 2H, NH$_2$), 6.32 (dd, J=14.6, 2.0 Hz, 1H, Ar), 6.41 (dd, J=8.6, 2.0 Hz, 1H, Ar), 7.50 (t, J=8.8 Hz, 1H, Ar), 7.92 (dd, J=6.5, 5.9H$_2$, 1H, CONH). Anal. Calculated for $C_{11}H_{13}FN_2O_3$: C, 55.00; H, 5.45; H, 11.66. Found: C, 55.08; H, 5.45; N, 11.63.

C. Ethyl N-(4-(((1,2-dihydro-3-methyl-1-oxobenzo[f]quinazolin-9-yl)methyl)amino)-2-fluorobenzoyl)glycinate $^1$H NMR (DMSO-$d_6$, 300 MHz) δ: 1.19 (t, J=7.1 Hz, 3H, esterCH$_3$), 2.43 (s, 3H, C$^3$—CH$_3$), 3.93 (d, J=5.6 Hz, 2H, glyCH$_2$), 4.09 (q, J=7.1 Hz, 2H, esterCH$_2$), 4.57 (d, J=5.6 Hz, 2H, C$^9$—CH$_2$), 6.40 (dd, J=14.9, 1.6 Hz, 1H, Ar), 6.54 (dd, J=8.7, 1.9 Hz, 1H, Ar), 7.34 (t, J=5.7 Hz, 1H, ArNH), 7.52 (t, J=8.9 Hz, 1H, Ar), 7.60 (d, J=8.8 Hz, 1H, Ar), 7.62 (t, J=8.9 Hz, 1H, Ar), 7.95 (dt, J=6.5, 5.8 Hz, 1H, CONH), 8.02 (d, J=8.3 Hz, 1H, Ar), 8.22 (d, J=8.9 Hz, 1H, Ar), 9.85 (s, 1H, Ar), 12.55 (s, 1H, N$^2$H). Mass spectrum (CI-CH$_4$): 463 (M+1, 100%). Anal. Calculated for $C_{25}H_{23}FN_4O_4 \cdot 2/5 H_2O$: C, 63.93; H, 5.11; J, 11.93. Found: C, 63.89: H, 5.08; N, 11.93.

N-((1,2-Dihydro-3-methyl-1-oxobenzo[f]quinazolin-9-yl)methyl)amino)-N-(2-hydroxyethyl)benzamide A. 4-Amino-N-(2-hydroxyethyl)benzamide A solution of 4-aminobenzoic acid (2.7 g, 20 mmol), ethanolamine (1.4 g, 23 mmol), and 1-(3-dimethylaminopropyl)-3-ethyl carbodiimide hydrochloride (4.1 g, 21 mmol) in dimethylformamide (60 ml) was stirred overnight at room temperature. More carbodiimide (0.3 g, 2 mmol) was added and after stirring for one hour the reaction mixture was concentrated in vacuo onto silica gel (15 g). Purification by chromatography on silica gel (125 g) eluting with methanol:methylene chloride (3:97 to 1:19) and recrystallization from methanol:ethyl acetate gave, after drying under high vacuum, 4-amino-N-(2-hydroxyethyl)benzamide (1.65 g) as a white solid. $^1$H NMR (DMSO-$d_6$, 300 MHz) δ: 3.26 (q, J=6 Hz, 2H, NCH$_2$), 3.46 (q, J=6 Hz, 2H, OCH$_2$), 4.68 (t, J=5.5, 1H, OH), 5.58 (br s, 2H, NH$_2$), 6.51 (d, J=8.5 Hz, 2H, Ar), 7.56 (d, J=8.5 Hz, 2H, Ar), 7.94 (br t, J=5.4 Hz, 1H, CONH). Mass spectrum (CI-CH$_4$): 181 (M+1, 100%). Anal. Calculated for $C_9H_{12}N_2O_2$: C, 59.99; H, 6.71; N, 15.55. Found: C, 60.05; H, 6.72; N, 15.55.

B. N-(((1,2-Dihydro-3-methyl-1-oxobenzo[f]quinazolin-9-yl)methyl)amino)-N-(2-hydroxyethyl)benzamide $^1$H NMR (DMSO-$d_6$, 300 MHz) δ: 2.43 (s, 3H, C$^3$—CH$_3$), 3.21–3.30 (m, 2H, NCH$_2$), 3.41–3.49 (m, 2H, OCH$_2$), 4.55 (d, J=6 Hz, 2H, C$^9$—CH$_2$), 4.68 (t, J=5.5 Hz, 1H, OH), 6.62 (d, J=8.5 Hz, 2H, Ar), 6.94 (t, J=6 Hz, 1H, ArNH), 7.55–7.64 (m, 4H, Ar), 7.96 (t, J=5.5 Hz, 1H, CONH), 7.99 (d, J=8.5 Hz, 1H, Ar), 8.21 (d, J=9 Hz, 1H, Ar), 9.84 (s, 1H, Ar), 12.53 (s, 1H, N$^2$H). Mass spectrum (CI-CH$_4$): 403 (M+1, 71.6%), 342 (100%). Anal. Calculated for $C_{23}H_{22}N_4O_3 \cdot 4/3 H_2O$: C, 64.79; H, 5.83; N, 13.14. Found: C, 64.82; H, 5.71; N, 13.12.

N-(4-(((1,2-Dihydro-3-methyl-1-oxobenzo[f]quinazolin-8-yl)methyl)amino)benzoyl)-L-glutamic acid an analog in which the sidechain is attached to the 8-position of the benzoquinazoline nucleus, was prepared by a sequence of reactions essentially similar to those described above.

A. 5,6-Dihydro-3.8-dimethylbenzo[f]quinazolin-1(2H)-one was prepared from 4'-methylphenylacetic acid as described in Example A(Method B).

$^1$H NMR (DMSO-$d_6$, 200 MHz) δ: 2.26 (s, 3H, CH$_3$), 2.27 (s, 3N, CH$_3$), 2.60–2.84 (m, 4H, ArCH$_2$'s), 6.95–7.05 (m, 2H, Ar), 8.43 (d, J=8.4 Hz, 1H, Ar), 12.49 (br s, 1H, N$^2$H). Anal. Calculated for $C_{14}H_{14}H_2O$: C, 74.31; H, 6.24; N, 12.38. Found: C, 74.25; H, 6.27; N, 12.31.

B. 3.8-Dimethylbenzo[f]quinazolin-1(2H)-one was prepared from the foregoing dihydro-derivative as described in Example 5.

$^1$H NMR (DMSO-$d_6$, 200 MHz) δ: 2.40 (s, 3H, CH$_3$), 2.49 (s, 3H, CH$_3$), 7.54 (dd, J=8.7, 1.8 Hz, 1H, Ar), 7.57 (d, J=8.8 Hz, 1H, Ar), 7.79 (s, 1H, Ar), 8.13 (d, J=8.7 Hz, 1H, Ar), 9.68 (d, J=8.8 Hz, 1H, Ar), 12.49 (br s, 1H, 2-NH). Anal. Calculated for $C_{14}H_{12}N_2O$: C, 74.98; H, 5.39; N, 12.49. Found: C, 74.85; H, 5.44; N, 12.41.

C. N-(4-(((1,2-Dihydro-3-methyl-1-oxobenzo[f]quinazolin-8-yl)methyl)amino)benzoyl)-L-glutamic acid was made from the foregoing dimethyl benzoquinazoline essentially as described for the 9-isomer above. Physical and analytical data on the product and the glutamate diester intermediate are given below.

Diethyl N-(4-(((1,2-dihydro-3-methyl-1-oxobenzo[f] quinazolin-8-yl)methyl)amino)benzoyl-L-glutamate $^1$H NMR (DMSO-d$_6$, 300 MHz) δ: 1.15 (t, J=7 Hz, 3H, esterCH$_3$), 1.17 (t, J=7 Hz, 3H, esterCH$_3$), 1.86–2.14 (m, 2H, gluCH$_2$), 2.39 (t, J=7 Hz, 2H, gluCH$_2$), 2.43 (s, 3H, C$^3$—CH$_3$), 4.03 (q, J=7 Hz, 2H, esterCH$_2$), 4.07 (m, 2H, gluCH$_2$), 4.31–4.40 (m, 1H, gluCH), 4.55 (d, J=6 Hz, 1H, C$^8$CH$_2$), 6.64 (d, J=9 Hz, 2H, Ar), 6.99 (t, J=6 Hz, 1H, ArNH), 7.60 (d, J=8.7 Hz, 1H, Ar), 7.63 (d, J=8.5 Hz, 2H, Ar), 7.73 (dd, J=8.8, 2 Hz, 1H, Ar), 7.97 (s, 1H, Ar), 8.19 (d, J=8 Hz, 1H, Ar), 8.21 (d, J=7.5 Hz, 1H, gluNH), 9.77 (d, J=8.8 Hz, 1H, Ar), 12.53 (br s, 1H, N$^2$H). Anal. Calculated for C$_{30}$H$_{32}$N$_4$O$_6$.17/20H$_2$O: C, 64.35; H, 6.07; N, 10.01. Found: C, 64.38; H, 6.08; N, 10.04.

N-(4-(((1,2-Dihydro-3-methyl-1-oxobenzo[f] quinazolin-8-yl)methyl)amino)benzoyl)-L-glutamic acid $^1$H NMR (DMSO-d$_6$, 300 MHz) δ: 1.82–2.10 (m, 2H, gluCH$_2$), 2.31 (t, J=7.3 Hz, 2H, gluCl$_2$), 2.44 (m, 3H, C$^3$—CH$_3$), 4.28–4.38 (m, 1H, gluCH), 4.55 (br s, 2H, C$^8$—CH$_2$), 6.65 (d, J=8.7 Hz, 2H, Ar), 6.98 (br s, 1H, ArNH), 7.61 (d, J=9 Hz, 1H, Ar), 7.64 (d, J=9 Hz, 2H, Ar), 7.74 (dd, J=8.8, 2 Hz, 1H, Ar), 7.97 (d, J=1 Hz, 1H, Ar), 8.10 (d, J=7.6 Hz, 1H, gluNH), 8.21 (d, J=8.9 Hz, 1H, Ar), 9.77 (d, J=8.8 Hz, 1H, Ar), 12.30 (br s, 2H, CO$_2$H's), 12.55 (br s, 1H, N$^2$H). Anal. Calculated for C$_{26}$H$_{24}$N$_4$O$_6$.H$_2$O: C, 61.65; H, 5.17; N, 11.06. Found: C, 61.65; H, 5.19; N, 11.00.

EXAMPLE 35

9-((4-Acetylanilino)methyl)-3-methylbenzo[f] quinazolin-1(2H)-one

9-Bromomethyl-3-methylbenzo[f]quinazolin-1(2H)-one (1 g, 3.3 mmole) and 4-aminoacetophenone (0.89 g, 6.6 mmole) (Aldrich) were dissolved in dimethylformamide (15 ml). The solution was stirred under nitrogen at 100° C. for 30 min. Sodium bicarbonate (0.55 g, 6.6 mmole) was added and stirring was continued for a further 30 min. Dimethylformamide was removed in vacuo, the residue triturated with water and the solid collected by filtration. The dried solid was subjected to chromatography on silica (methanol/methylene chloride (1:19)). Fractions containing product were concentrated until solid began to precipitate. The solution was chilled at 50° C. for 12 hours, then the solid filtered off and dried under high vacuum to yield the title compound (0.48 g, 41%). Mp>235° C. $^1$H NMR (DMSO-d$_6$, 300 MHz) δ: 2.37 (s, 3H, CH$_3$); 2.43 (s, 3H, CH$_3$); 4.59 (d, J=6 Hz, 2H, CH$_2$); 6.65 (d, J=9 Hz, 2H, Ar); 7.37 (t, J=6 Hz, 1H, ArNH); 7.59 (d, J=9 Hz, 1H, Ar); 7.61 (dd, J=8, 2 Hz, 1H, Ar); 7.69 (d, J=9 Hz, 2H, Ar); 8.00 (d, J=8 Hz, 1H, Ar); 8.21 (d, J=9 Hz, 1H, Ar); 9.85 (s, 1H, Ar); 12.52 (s, 1H, NH). Anal Calculated for C$_{22}$H$_{19}$N$_3$O$_2$.1/2H$_2$O: C, 72.11; H, 5.50; N, 11.47. Found: C, 72.26; H, 5.46; N, 11.35.

3-Methyl-9-((4-(trifluoromethyl)anilino)methyl)benzo[f] quinazolin-1(2H)-one was similarly prepared from 4-trifluoromethylaniline $^1$H NMR (DMSO-d$_6$, 300 MHz) δ: 2.43 (s, 3H, CH$_3$), 4.56 (d, J=6 Hz, 2H, ArCH$_2$), 6.72 (d, J=9 Hz, 2H, Ar), 7.17 (t, J=6 Hz, 1H, ArNH), 7.35 (d, J=9 Hz, 2H, Ar), 7.59 (d, J=9 Hz, 1H, Ar), 7.62 (dd, J=8, 2 Hz, 1H, Ar), 8.00 (d, J=8 Hz, 1H, Ar), 8.21 (d, J=9 Hz, 1H, Ar), 9.85 (s, 1H, Ar), 12.54 (br s, 1H, N$^2$H). Mass spectrum (CI-CH$_4$): 384 (M+1, 13.9%), 383 (M, 23.9%), 364 (100%). Anal. Calculated for C$_{21}$H$_6$F$_3$N$_3$O: C, 65.79; H, 4.21; N, 10.96. Found: C, 65.71; H, 4.22; N, 10.90.

3-Methyl-9-((4-nitroanilino)methyl)benzo(f)quinazolin-1(2H)-one was similarly prepared from 4-nitroaniline. $^1$H NMR (DMSO-d$_6$, 300 MHz) δ: 2.43 (s, 3H, CH$_3$); 4.66 (d, J=6 Hz, 2H, ArCH$_2$); 6.72 (d, J=9 Hz, 2H, Ar); 7.58–7.61 (m, 1H, Ar); 7.97–8.03 (m, 1H, Ar); 7.98 (d, J=9 Hz, 2H, Ar); 8.22 (d, J=9 Hz, 1H, Ar); 9.84 (s, 1H, Ar); 12.53 (s, 1H, NH). Mass Spectrum (CI-CH$_4$): 361 (M+1, 100%). Anal. Calculated for C$_{20}$H$_{16}$N$_4$O$_3$.1/4H$_2$O: C, 66.21; H, 4.74; N, 15.07. Found: C, 66.24; H, 4.63; N, 14.95.

4-(((1,2-Dihydro-3-methyl-1-oxobenzo(f)quinazolin-9-yl)methyl)amino)benzonitrile was similarly prepared from 4-aminobenzonitrile. $^1$H NMR (DMSO-d$_6$, 300 MHz) δ: 2.43 (s, 3H, CH$_3$); 4.57 (d, J=6 Hz, 2H, ArCH$_2$); 6.70 (d, J=9 Hz, 2H, Ar); 7.43 (d, J=9 Hz, 1H, Ar); 7.42–7.46 (m, 1H, Ar); 7.59 (m, 1H, Ar); 8.00 (d, J=8 Hz, 1H, Ar); 8.21 (d, J=9 Hz, 1H, A ; 9.84 (s, 1H, Ar); 12.53 (s, 1H, NH). Mass Spectrum (CI-CH$_4$): 341 (M+1,29.84%), 74 (100%). Anal. Calculated for C$_{21}$H$_{16}$N$_4$O: C, 74.10; H, 4.74; N, 16.46. Found: C, 74.03; H, 4.77; N, 16.40.

3-Methyl-9-(anilinomethyl)benzo(f)quinazoline-1(2)-one was similarly prepared from aniline. $^1$H NMR (DMSO-$_6$, 300 MHz) δ: 2.43 (s, 3H, CH$_3$); 4.49 (d, J=5.9 Hz, 2H, ArCH$_2$); 6.39 (t, J=5.9 Hz, 1H, NH); 6.50 (t, J=7.3 Hz, 1H, Ar); 6.61 (dd, J$_1$=1 Hz, J$_2$=8.6 Hz, 2H, Ar); 7.03 (dd, J$_1$=8.5 Hz, J$_2$=7.3 Hz, 2H, Ar); 7.58 (d, J=8.7 Hz, 1H, Ar); 7.64 (dd, J$_1$=1.6 Hz, J$_2$=8.3 Hz, 1H, Ar); 7.99 (d, J=8.2 Hz, 1H, Ae); 8.20 (d, J=8.7 Hz, 1H, Ar); 9.85 (s, 1H, Ar); 12.52 (br s, J=8.2 Hz, 1H, NH). Mass Spectrum (CI-CH$_4$): 316 (M+1, 52.80%), 223 (100%). Anal. Calculated for C$_{20}$H$_{17}$N$_3$O: C, 76.17; H, 5.43; N, 13.22. Found C, 76.15; H, 5.48; N, 13.24.

9-((4-Methoxyanilino)methyl)-3-methylbenzo(f) quinazolin-1(2H)-one was similarly prepared from p-anisidine. $^1$H NMR (DMSO-d$_6$, 300 MHz) δ: 2.43 (s, 3H, CH$_3$); 3.60 (s, 3H, CH$_3$): 4.43 (d, J=6 Hz, 2H, ArCH$_2$); 5.97 (t, J=6 Hz, 1H, NH); 6.57 (d, J=9 Hz, 2H, Ar); 6.68 (d, J=9 Hz, 2H, Ar); 7.58 (d, J=9 Hz, 1H, Ar); 7.64 (dd, J$_1$=1 Hz, J$_2$=8 Hz, 1H, Ar); 7.99 (d, J=9 Hz, 1H, Ar); 8.20 (d, J=9 Hz, 1H, Ar); 9.84 (s, 1H, Ar); 12.52 (br s, J=8.2 Hz, 1H, NH). Mass Spectrum (CI-CH$_4$): 346 (M+1, 100%). Anal. Calculated for C$_{21}$H$_{19}$N$_3$O$_2$.3/10H$_2$O: C, 71.90; H, 5.63; N, 11.98. Found: C, 71.92; H, 5.55; N, 11.97.

9-((3-Chloroanilino)methyl)-3-methylbenzo(f) quinazolin-1(2H)-one was similarly prepared from 3-chloroaniline. $^1$H NMR (DMSO-d$_6$, 200 MHz) δ: 2.40 (s, 3H, CH$_3$); 4.47 (d, J=5.7 Hz, 2H, ArCH$_2$); 6.46–6.60 (m, 3H, Ar), 6.74 (t, J=5.7 Hz, 1H, NH); 7.01 (t, J=8 Hz, 1H, Ar); 7.54–5.62 (m, 2H, Ar); 7.98 (d, J=8.4 Hz, 1H, Ar); 8.19 (d, J=8.9 Hz, 1H, Ar); 9.82 (s, 1H, Ar); 13.40 (s, 1H, NH). Mass Spectrum (CI-CH$_4$): 350 (M+1, 17.93%), 223 (100%). Anal. Calculated for C$_{20}$H$_{16}$ClN$_3$O: C, 68.67; H, 4.61; N, 12.01; Cl, 10.13. Found: C, 68.51; H, 4.65; N, 11.93; Cl, 10.01.

9-((2-Fluoroanilino)methyl)-3-methylbenzo(f) quinazolin-1(2H)-one was similarly prepared from 2-fluoroaniline. $^1$H NMR (DMSO-d$_6$, 200 MHz) δ: 2.40 (s, 3H, CH$_3$); 4.54 (t, 5.9 Hz, 2H, ArCH$_2$); 6.31 (t, J=4.2 Hz, 1H, NH); 6.41–6.59 (m, 2H, Ar); 6.80 (t, J=7.8 Hz, 1H, Ar); 6.99 (ddd, J$_1$=12.2 Hz, J$_2$=7.8 Hz, J$_3$=1.3 Hz, 1H, Ar); 7.56 (d, J=8.8 Hz, 1H, Ar); 7.60 (dd, J$_1$=8.2 Hz, J$_2$=1.3 Hz, 1H, Ar); 7.94 (d, J=8.4 Hz, 1H, Ar); 8.15 (d, J=8.8 Hz, 1H, Ar); 9.82 (s, 1H, Ar); 12.48 (br s, 1H, NH). Mass Spectrum (CI-CH$_4$): 334. (M+1, 54.42%), 223 (100%). Anal. Calculated for C$_{20}$H$_{16}$FN$_3$O.C$_2$H$_4$O$_2$: C, 67.17; H, 5.12; N, 10.68. Found: C, 67.17; H, 5.31; N, 10.64.

9-((3,4-Difluoroanilino)methyl)-3-methylbenzo(f) quinazolin-1(2H)-one was similarly prepared from 3,4-difluoroaniline. $^1$H NMR (DMSO-d$_6$, 200 MHz) δ: 2.40 (s, 3H, CH$_3$); 4.44 (d, J=6 Hz, 2H, ArCH$_2$); 6.32–6.40 (m, 1H, NH); 6.48–6.61 (m, 2H, Ar); 7.05 (ddd, J$_1$=19.2 Hz, J$_2$=9.9 Hz, J$_3$=1.4 Hz, 1H, Ar); 7.58 (d, J=8.7 Hz, 1H, Ar); 7.59 (dd, J$_1$=8.3 Hz, J$_2$=1.6 Hz, 1H, Ar); 7.98 (d, J=8.3 Hz, 1H, Ar); 8.18 (d, J=8.6 Hz, 1H, Ar); 9.81 (s, 1H, Ar); 12.48 (br s, 1H, NH). Mass Spectrum (CI-CH$_4$): 352 (M+1, 28.42%). 223 (100%). Anal. Calculated for C$_{20}$H$_{15}$F$_2$N$_3$O C$_2$H$_4$O$_2$: C, 68.37; H, 4.30; N, 11.96. Found: C, 68.26; H, 4.35; N, 11.90.

3-Methyl-9-(((1oxo-5-indahyl)amino)methyl)benzo[f] quinazolin-1(2H)-one was similarly prepared from 5-amino-1-indanone (J. Org. Chem., 1962, 27, 70). $^1$H NMR (DMSO-d$_6$, 300 MHz) δ: 2.37–2.48 (m, 2H, CH$_2$), 2.43 (s, 3H, CH$_3$), 2.82–2.92 (m, 2H, CH$_2$), 4.61 (d, J=5.5 Hz, 2H, ArCH$_2$N), 6.60 (s, 1H, Ar), 6.69 (dd, J=8.5, 1.5 Hz, 1H, Ar); 7.33 (d, J=8.5 Hz, 1H, Ar), 7.51 (t, J=6 Hz, 1H, ArNH), 7.60 (d, J=9 Hz, 1H, Ar), 7.62 (dd, J=8.5, 1.5 Hz, 1H, Ar), 8.01 (d, J=8.5 Hz, 1H, Ar), 8.22 (d, J=9 Hz, 1H, Ar), 9.86 (s, 1H, Ar), 12.54 (s, 1H, N$^2$H). Mass Spectrum (CI-CH$_4$): 370 (M+1, 100%). Anal. Calculated for C$_{23}$H$_{19}$N$_3$O$_2$.3/10H$_2$O: C, 73.70; H, 5.27; N, 11.21. Found: C, 73.78; H, 5.28; N, 11.21.

Ethyl 4-(((1,2-dihydro-3-methyl-1-oxobenzo[f] quinazolin-9-yl)methyl)amino)benzoate was similarly prepared from ethyl 4-aminobenzoate.

$^1$H NMR (DMSO-d$_6$, 300 MHz) δ: 1.25 (t, J=7 Hz, 3H, esterCH$_3$), 2.43 (s, 3H, C$^3$—CH 3), 4.19 (q, J=7 Hz, 2H, esterCH$_2$), 4.58 (br d, J=6 Hz, 2H, C$_9$—CH$_2$), 6.66 (d, J=9 Hz, 2H, Ar), 7.28 (br t, J=6 H, 1H, ArNH), 7.59 (d, J=8.5 Hz, 1H, Ar), 7.61 (dd, J=8, 1.5 Hz, 1H, Ar), 7.66 (d, J=9 Hz, 2H, Ar, 8.00 (d, J=8.5 Hz, 1H, Ar), 8.21 (d, J=9 Hz, 1H, Ar), 9.84 (s, 1H, Ar), 12.53 (s, 1H, N$^2$H). Mass Spectrum (CI-CH$_4$): 388 (M+1, 44.2%), 387 (M, 24.2%), 342 (100%). Anal. Calculated for C$_{23}$H$_{21}$N$_3$O$_3$.1/5H$_2$O: C, 70.65; H, 5.52; N, 10.75. Found: C, 70.65; H, 5.49; N, 10.77.

4-(((1,2-Dihydro-3-methyl-1-oxobenzo[f]quinazolin-9-yl)methyl)amino)benzoic acid was prepared by hydrolysis of the foregoing ester under conditions essentially similar to those described for the p-aminobenzoylglutamate esters.

$^1$H NMR (DMSO-d$_6$/D$_2$O, 300 MHz) δ: 2.43 (s, 3H, C$^3$—CH$_3$), 4.56 (s, 2H, C$^9$—CH$_2$), 6.64 (d, J=9 Hz, 2H, Ar), 7.55–7.67 (m, 4H, Ar), 8.00 (d, J=Hz, 1H, Ar), 8.22 (d, J=9 Hz, 1H, Ar), 9.83 (s, 1H, Ar). Mass Spectrum (CI-CH$_4$): 359 (M, 25.9%). Anal. Calculated for C$_{21}$H$_{17}$N$_3$O$_3$.7/6H$_2$O: C, 66.31; H, 5.12; N, 11.05. Found: C, 66.24; H, 5.13; N, 11.06.

4-((1,2-Dihydro-3-methyl-1-oxobenzo[f]quinazolin-9-yl)oxy)benzonitrile

A. Ethyl-3-(4-cyanophenyloxy)phenylacetate

A solution of ethyl 3-hydroxyphenylacetate (28 g, 0.15 mole) and 4-fluorobenzonitrile (25 g, 0.21 mole) in dimethylsulfoxide (150 ml) was stirred with 87% potassium hydroxide (10 g, 0.15 mole) at 75–80° C. for 80 minutes under nitrogen. The resulting mixture was allowed to cool, diluted with water (1000 ml), and extracted with diethyl ether (2×50 ml). The organic solution was washed with water (100 ml), dried (MgSO$_4$), concentrated in vacuo and the residue eluted on silica gel (500 g) with ethyl acetate::hexane (0 to 1:6). A solution of the product in diethyl ether (125 ml) was washed with 1N NaOH (15 ml) to remove some residual phenol, dried (K$_2$CO$_3$ and MgSO$_4$), and concentrated in vacuo to give ethyl 3-(4-cyanophenyloxy)phenylacetate (20.8 g). $^1$H NMR (DMSO-d$_6$, 300 MHz) δ: 1.18 (t, J=7 Hz, 3H, CH$_3$), 3.71 (s, 2H, Ar CH$_2$), 4.08 (q, J=7 Hz, 2H, esterCH$_2$), 7.02–7.13 (m, 4H, Ar), 7.18 (d, J=8 Hz, 1H, Ar), 7.42 (t, J=8 Hz, 1H, Ar), 7.85 (d, J=9 Hz, 2H, Ar). Anal. Calculated for C$_{17}$H$_{15}$NO$_3$: C, 72.58: H, 5.37; N, 4.98. Found: C, 72.67; H, 5.43; N, 4.94.

B. 3-(4-Cyanophenyloxy)phenylacetic acid

A solution of ethyl 3-4(4-cyanophenyloxy)phenylacetate (20.8 g, 74 mmol) in methanol:1N sodium hydroxide (1:1, 160 ml) was stirred at reflux for 1.5 hours, IN sodium hydroxide (5 ml) added and refluxing continued for one hour. The solution was cooled and acidified with 2N hydrochloric acid (45 ml), the resulting suspension chilled in an ice bath, and the product filtered, washed with water and dried at 70° C. under vacuum to give 3-(4-cyanophenyloxy) phenylacetic acid (17.1 g). $^1$H NMR (DMSO-d$_6$, 300 MHz) δ: 3.62 (s, 2H, CH$_2$), 7.00–7.14 (m, 4H, Ar), 7.17 (d, J=8 Hz, 1H, Ar), 7.41 (t, J=8 Hz, 1H, Ar), 7.85 (d, J=9 Hz, 2H, Ar), 12.39 (br s, 1H, CO$_2$H). Anal. Calculated for C$_{15}$H$_{11}$NO$_3$.1/25H$_2$O: C, 70.94; H, 4.40; N, 5.51. Found: C, 71.01; H, 4.40; N, 5.45.

C. 4-((1,2-Dihydro-3-methyl-1-oxobenzo[f]quinazolin-9-yl)oxy)benzonitrile was prepared from 3-(4-cyanophenyloxy)phenylacetic acid by the sequence essentially described in Examples A, 3 and 5.

$^1$H NMR (DMSO-d$_6$, 300 MHz) δ: 2.44 (s, 3H, CH$_3$), 7.21 (AA'BB', 2H, Ar), 7.48 (dd, J=9.3 Hz, 1H, Ar), 7,63 (d, J=9 Hz, 1H, Ar), 7.88 (AA'BB', 2H, Ar), 8.17 (d, J=9 Hz, 1H, Ar), 8.31 (d, J=9 Hz, 1H, Ar), 9.55 (d, J=3 Hz, 1H, Ar), 12.58 (br s, 1H, N$^2$H). Anal. Calculated for C$_{20}$H$_{13}$N$_3$O$_2$: C, 73.39, H, 4.00; N, 12.84. Found: C, 73.27; H, 4.05; N, 12.75.

EXAMPLE 36

N-(4-((1,2-Dihydro-3-methyl-1-oxobenzo[f] quinazolin-9-yl)methoxy)benzoyl)-L-glutamic acid A. 3,9-Dimethyl-2-methoxymethylbenzo[f]quinazolin-1 (2H)-one To a suspension of 3,9-dimethylbenzo[f]quinazolin-1 (2H)-one (1.0 g, 4.5 mmol) in DMF (25 ml) was added 80% NaH (0.15 g, 5.0 mmol) (Aldrich) portion wise and the mixture was stirred 35 minutes. Bromomethyl methyl ether (0.39 ml, 4.8 mmol) (Aldrich) was added in one portion and the solution was stirred at room temperature overnight. The solution was then diluted with water (100 ml) and extracted twice with methylene chloride (100, 40 ml). The combined methylene chloride extracts were washed with a small volume of water, dried (K$_2$CO$_3$), and concentrated in vacuo. The residue was purified by silica gel (40 g) chromatography eluting with ethyl acetate:methylene chloride (0 to 1:19) to give 3,9-dimethyl-2-methoxymethylbenzo[f]quinazolin-1 (2H)-one and the corresponding O-alkylated material in a 4:1 ratio as determined by NMR (0.79 g). $^1$H NMR (DMSO-d$_6$, 300 MHz) for major isomer δ: 2.57 (s, 3H, C$^9$—CH$_3$), 2.68 (s, 3H, C$^3$—CH$_3$), 3.38 (s, 3H, OCH$_3$), 5.62 (s, 2H, NCH$_2$O), 7.51 (dd, J=8, 2 Hz, 1H, Ar), 7.56 (d, J=9 Hz, 1H, Ar), 7.96 (d, J=8 Hz, 1H, Ar), 8.24 (d, J=9 Hz, 1H, Ar), 9.63 (s, 1H, Ar). Anal. Calculated for C$_{16}$H$_6$N$_2$O$_2$: C, 71.62; H, 6.01; H, 10.44. Found: C, 71.55; H, 6.03; H, 10.43.

B. Ethyl 4-((1,2-dihydro-2-methoxymethyl-3-methyl-1-oxobenzo[f]quinazolin-9-yl)methoxy)benzoate N-bromosuccinimide (0.50 g, 2.8 mmol) (Kodak) was added to a hot solution of the protected 3,9-dimethylbenzo [f]quinazoline (0.75 g, 2.8 mmol) in benzene (100 ml) under nitrogen. The solution was stirred at reflux for 45 minutes and then concentrated in vacuo to give 9-bromomethyl-2-methoxymethyl-3-methylbenzo[f]quinazolin-1(2H)-one as the major product. NaH (80%, 0.25 g, 8.3 mmol) was added portion wise to a solution of ethyl p-hydroxybenzoate (1.4 g, 8.4 mmol) (Eastman) in DMF (10 ml) and stirred 30 minutes. The crude 9-bromomethyl-2-methoxymethyl-3-methylbenzo[f]quinazolin-1(2H)-one was added with more DMF (10 ml) and the reaction mixture stirred 2.5 hours at 35° C. and briefly heated to 90° C. After cooling, the solution was diluted with water (100 ml) and extracted with methylene chloride:ethyl acetate (2:1, 2×150 ml). The extracts were washed with water (100 ml), dried ($K_2CO_3$), and concentrated in vacuo. The residue was purified by chromatography on silica gel (100 g) eluting with ethyl acetate:methylene chloride (0 to 3:17). The solid was recrystallized from a small volume of ethanol and dried under high vacuum to give ethyl 4-((1,2-dihydro-2-methoxymethyl-3-methyl-1-oxobenzo[f]quinazolin-9-yl)methoxybenzoate (0.235 g). $^1$H NMR (DMSO-$d_6$, 300 MHz) δ: 1.31 (t, J=7 Hz, 3H, esterCH$_3$), 2.70 (s, 3H, $C^3$—CH$_3$), 3.39 (s, 3H, OCH$_3$), 4.28 (q, J=7 Hz, 2H, esterCH$_2$), 5.45 (s, 2H, $C^9$—CH$_2$O), 5.63 (s, 2H, NCH$_2$O), 7.20 (d, J=9 Hz, 2H, Ar), 7.66 (d, J=9 Hz, 1H, Ar), 7.76 (dd, J=8, 2 Hz, 1H, Ar), 7.94 (d, J=9 Hz, 2H, Ar), 8.11 (d, J=8 Hz, 1H, Ar), 8.32 (d, J=9 Hz, 1H, Ar), 9.92 (s, 1H, Ar). Anal. Calculated for $C_{25}H_{24}N_2O$: C, 69.43; H, 5.59; N, 6.48. Found: C, 69.32; H, 5.61; N, 6.41.

C. 4-((1,2-Dihydro-3-methyl-1-oxobenzo[f]quinazolin-9-yl)methoxy)benzoic acid

A solution of ethyl 4-((1,2-dihydro-2-methoxymethyl-3-methyl-1-oxobenzo[f]quinazolin-9-yl)methoxy)benzoate in THF:1N HCl: concentrated HCl (15:10:1, 26 ml) was stirred at 60° C. overnight. The resulting suspension was diluted with water, concentrated in vacuo to remove the THF, and chilled in an ice bath. The solid was filtered, washed with water, and dried in vacuo at 100° C. The resulting ester was dissolved in 1N NaOH (10 ml) and ethanol (~3 ml) and stirred at 60° C. for 4 hours. The solution was acidified with concentrated HCl to pH 1.5 and the resulting precipitate filtered and dried in vacuo at 110° C. to give 4-((1,2-dihydro-3-methyl-1-oxobenzo[f]quinazolin-9-yl)methoxy) benzoic acid (0.195 g). $^1$H NMR (DMSO-$d_6$, 300 MHz) δ: 2.59 (s, 3H, CH$_3$), 5.46 (s, 2H, CH$_2$O), 7.17 (d, J=9 Hz, 2H, Ar), 7.80 (overlapping d, J=9 Hz, 2H, Ar), 7.91 (d, J=9 Hz, 2H, Ar), 8.16 (d, J=8 Hz, 1H, Ar), 9.85 (s, 1H, Ar).

D. Diethyl N-(4-((1,2-dihydro-3-methyl-1-oxobenzo[f] quinazolin-9-yl)methoxy)benzoyl)-L-glutamate To a stirred suspension of 4-((1,2-dihydro-3-methyl-1-oxobenzo[f]quinazolin-9-yl)methoxy)benzoic acid (0.19 g, 0.53 mmol) and L-glutamic acid diethyl ester hydrochloride (0.14 g, 0.58 mmol) (Aldrich) in DMF (3 ml) were added diethyl cyanophosphonate (0.09 ml, 0.6 mmol) (Aldrich) and triethylamine (0.15 ml, 1.1 mmol). Additional DMF (7 ml) was added but homogeneous solution was not obtained. The reaction mixture was stirred 45 minutes at room temperature and TLC analysis indicated remaining benzoic acid. Diethyl cyanophosphonate (2 drops) was added, the mixture stirred 45 minutes, and was then concentrated in vacuo. The residue was purified by chromatography on silica gel (50 g) eluting with ethanol:methylene chloride (1:9). The solid was filtered from a small volume of ethanol and dried under reduced pressure to give diethyl N-(4-((1,2-dihydro-3-methyl-1-oxobenzo[f]quinazolin-9-yl)methoxy)benzoyl)-L-glutamate (0.187 g). $^1$H NMR (DMSO-$d_6$, 300 MHz) δ: 1.16 (t, J=7 Hz, 3H, esterCH$_3$), 1.18 (t, J=7 Hz, 3H, esterCH$_3$), 1.90–2.18 (m, 2H, gluCH$_2$), 2.43 (t, J=7 Hz, 2H, gluCH$_2$), 2.44 (s, 3H, $C^3$—CH$_3$), 4.05 (q, J=7 Hz, 2H, esterCH$_2$), 4.10 (q, J=6 Hz, 2H, esterCH$_2$), 4.36–4.46 (m, 1H, gluCH), 5.43 (s, 2H, CH$_2$O), 7.17 (d, J=9 Hz, 2H, Ar), 7.65 (d, J=9 Hz, 1H, Ar), 7.74 (dd, J=8, 2 Hz, 1H, Ar), 7.88 (d, J=9 Hz, 2H, Ar), 8.08 (d, J=8 Hz, 1H, Ar), 8.26 (d, J=9 Hz, 1H, Ar), 8.58 (d, J=7 Hz, 1H, gluNH), 9.94 (s, 1H, Ar), 12.59 (s, 1H, $N^2$H). Anal. Calculated for $C_{30}H_{31}N_3O_7 \cdot 1/4H_2O$: C, 65.50; H, 5.77; N, 7.64. Found: C, 65.54; H, 5.77; N, 7.61.

E. N-(4-((1,2-Dihydro-3-methyl-1-oxobenzo[f]quinazolin-9-yl)methoxy)benzoyl)-L-glutamic acid Diethyl N-(4-((1,2-dihydro-3-methyl-1-oxobenzo[f] quinazolin-9-yl)methoxy)benzoyl)-L-glutamate (0.18 g, 0.33 mmol) was suspended in ethanol (2 ml) and 0.25 N NaOH (8 ml) and stirred 1.5 hours at room temperature with intermittent periods of sonication. Additional ethanol (4 ml) and warming were required to obtain a homogeneous solution. The solution was stirred 3 hours at room temperature and then adjusted to pH 3 with 1 N HCl. The resulting suspension was filtered, and the white solid washed with water and dried under high vacuum to give N-(4-((1,2-dihydro-3-methyl-1-oxobenzo[f]quinazolin-9-yl)methoxy) benzoyl)-L-glutamic acid (0.158 g). $^1$H NMR (DMSO-$d_6$, 300 MHz) δ: 1.87–2.16 (m, 2H, gluCH$_2$), 2.35 (t, J=7 Hz, 2H, gluCH$_2$), 2.44 (s, 3H, CH$_3$), 4.33–4.43 (m, 1H, gluCH), 5.43 (s, 2H, CH$_2$O), 7.16 (d, J=9 Hz, 2H, Ar), 7.64 (d, J=9 Hz, 1H, Ar), 7.74 (dd, J=8, 2 Hz, 1H, Ar), 7.88 (d, J=9 Hz, 2H, Ar), 8.08 (d, J=8 Hz, 1H, Ar), 8.26 (d, J=9 Hz, 1H, Ar), 8.47 (d, J=8 Hz, 1H, gluNH), 9.94 (s, 1H, Ar), 12.36 (br s, 2H, CO$_2$H's), 12.59 (s, 1H, $N^2$H). Anal. Calculated for $C_{26}H_{23}N_3O_7 \cdot 1/4H_2O$: C, 63.22; H, 4.79; N, 8.51. Found: C, 63.23; H, 4.80; N, 8.48.

EXAMPLE 37

N-(4-(((3-Amino-1,2-dihydro-1-oxobenzo[f] quinazolin-9-yl)methyl)amino)benzoyl)-L-glutamic acid A. Diethyl N-(4-(((1,2-dihydro-1-oxo-3-pivalamidobenzo[f] quinazolin-9-yl)methyl)amino)benzoyl)-L-glutamate To a hot solution of N-(1,2-dihydro-9-methyl-1-oxobenzo [f]quinazolin-3-yl)pivalamide (0.94 g, 3.0 mmol) in benzene (250 ml) under nitrogen were added N-bromosuccinimide (0.57 g, 3.2 mmol) (Kodak) and 2,2'-azobisisobutyronitrile (AIBN) (35 mg, 0.21 mmol) (Kodak). The solution was stirred at reflux for 1.5 hours and then concentrated in vacuo to give crude N-(9-bromomethyl-1,2-dihydro-1-oxobenzo [f]quinazolin-3-yl)pivalamide. The pivalamide and N-(4-aminobenzoyl)-L-glutamic acid diethyl ester (2.5 g, 7.8 mmol) (Aldrich) in DMF (10 ml) were stirred under nitrogen at 105–110° C. for 5 minutes and then allowed to cool. Triethylamine (0.5 ml, 3.6 mmol) was added and the solution was concentrated under high vacuum. The residue was purified by chromatography on silica gel (130 g) eluting with ethyl acetate:methylene chloride (1:19→2:3), followed by recrystallization of the solid from ethanol/diethyl ether. This was filtered and dried under high vacuum to give diethyl N-(4-(((1,2-dihydro-1-oxo-3-pivalamido-benzo[f] quinazolin-9-yl)methyl)amino)benzoyl)-L-glutamate (0.32 g) as a white solid. The filtrate was concentrated and the residue purified by chromatography and crystallization to give an additional 0.243 g. $^1$H NMR (DMSO-$d_6$, 300 MHz) δ: 1.15 (t, J=7 Hz, 3H, esterCH$_3$), 1.16 (t, J=7 Hz, 3H, esterCH$_3$), 1.28 (s, 9H, t-butyl), 1.87–2.13 (m, 2H, gluCH$_2$), 2.39 (t, J=7 Hz, 2H, gluCH$_2$), 4.03 (q, J=7 Hz, 2H, esterCH$_2$), 4.07 (q, J=7 Hz, 2H, esterCH$_2$), 4.30–4.40 (m, 1H, gluCH), 4.57 (d, J=6 Hz, 2H, $C^9$—CH$_2$), 6.63 (d, J=9 Hz, 2H, Ar), 7.04 (t, J=6 Hz, 1H, ArNH), 7.53 (d, J=9 Hz, 1H, Ar), 7.61 (dd, J=8, 2 Hz, 1H, Ar), 7.62 (d, J=9 Hz, 2H, Ar), 7.99 (d, J=8 Hz, 1H, Ar), 8.21 (d, J=8 Hz, 1H, gluNH), 8.22 (d, J=9 Hz, 1H, Ar), 9.75 (s, 1H, Ar), 11.25 (s, 1H, $N^2$H), 12.30 (br s, 1H, NH). Mass spectrum (CI-CH$_4$) 630 (M+1, 6.5%), 243 (100%). Anal. Calculated for $C_{34}H_{39}N_5O_7$: C, 64.85; H, 6.24; N, 11.12. Found: C, 64.74; H, 6.25; N, 11.10.

B. N-(4-(((3-Amino-1,2-dihydro-1-oxobenzo[f]quinazolin-9-yl)methyl)amino)benzoyl)-L-glutamic acid A solution of diethyl N-(4-(((1,2-dihydro-1-oxo-3-pivalamidobenzo[f]quinazolin-9-yl)methyl)amino)benzoyl)-L-glutamate (0.31 g, 0.49 mmol) in methanol (15 ml) and 1 N NaOH (5 ml) was stirred under nitrogen at reflux for 1.5 hours and then allowed to cool. The solution was adjusted to pH 3 with 1 N-HCl under nitrogen and the resulting precipitate was filtered under nitrogen, washed with water, and dried under high vacuum to give N-(4-(((3-amino-1,2-dihydro-1-oxobenzo[f]quinazolin-9-yl)methyl)amino)benzoyl)-L-glutamic acid (0.22 g) as a white solid. $^1$H NMR (DMSO-$d_6$, 300 MHz δ: 1.82–2.12 (m, 2H, gluCH$_2$), 2.31 (t, J=7 Hz, 2H, gluCH$_2$), 4.27–4.38 (m, 1H, gluCH), 4.50 (d, J=6 Hz, 2H, C$^9$—CH 2), 6.55 (br s, 2H, NH$_2$), 6.62 (d, J=9 Hz, 2H, Ar), 6.96 (t, J=6 Hz, 1H, ArNH), 7.26 (d, J=9 Hz, 1H, Ar), 7.44 (dd, J=8, 2 Hz, 1H, Ar), 7.63 (d, J=9 Hz, 2H, Ar), 7.84 (d, J=8 Hz, 1H, Ar), 7.99 (d, J=9 Hz, 1H, Ar), 8.09 (d, J=8 Hz, 1H, gluNH), 9.67 (s, 1H, Ar), 11.14 (br s, 1H, N$^2$H), 12.32 (br s, 2H, CO$_2$H's). Anal. Calculated for $C_{25}H_{23}N_5O_6H_2O$: C, 59.17; H, 4.97; N, 13.80. Found: C, 59.31; H, 4.90; N, 13.72.

EXAMPLE 38

3-Amino-9-((4-fluoroanilino)methyl)benzo[f]quinazolin-1(2H)-one

A. N-(9-Bromomethyl-1,2-dihydro-1-oxobenzo[f]quinazolin-3-yl)pivalamide N-(9-Methyl-1,2-dihydro-1-oxobenzo[f]quinazolin-3-yl)pivalamide (6.58 g, 0.02 mole) was dissolved in refluxing benzene (1650 ml). The reaction was removed from heat and N-bromosuccinimide (4.54 g, 0.026 mmole, Kodak) added. The solution was heated under reflux for 1.5 hours. Benzene was removed in vacuo and the residue dried under high vacuum to give the bromomethyl derivative. $^1$H NMR (DMSO-$d_6$, 200 MHz) δ: 1.29 (s, 9H, t-butyl); 4.94 (s, 2H, CH$_2$Br); 7.58 (d, J=9 Hz, 1H, Ar); 7.67 (dd, J=8, 2 Hz, Ar); 8.03 (d, J=8 Hz, 1H, Ar); 8.24 (d, J=9 Hz, 1H, Ar); 9.80 (s, 1H, Ar).

B. N-(9-((4-Fluoroanilino)methyl-1,2-dihydro-1-oxobenzo[f]quinazolin-3-yl)pivalamide N-(9-Bromomethyl-1,2-dihydro-1-oxobenzo[f]quinazolin-3-yl)pivalamide (0.97 g, 2.5 mmole) and 4-fluoroaniline (0.56 g, 5 mmole) (Aldrich) were dissolved in dimethylformamide (15 ml). The reaction was stirred for 30 minutes at 100° C., sodium bicarbonate (0.42 g, 5 mmole) added and the suspension stirred for a further 30 minutes. The dimethylformamide was removed in vacuo, the residue washed with methylene chloride and filtered. The filtrate was evaporated, and the residue was subjected to chromatography on a Waters Prep 500 instrument (silica cartridge, elution with ethyl acetate/methylene chloride (1:19)). Fractions containing product were concentrated in vacuo, the residue dissolved in a minimum amount of ethyl acetate, and the solution diluted with hexane until precipitate formed. The solid was collected by filtration and dried under high vacuum to give the title compound as a beige solid (0.305 g, 29%). $^1$H NMR (DMSO-$d_6$, 200 MHz) δ: 1.25 (s, 9H, t-butyl); 4.42 (d, J=6 Hz, 2H, CH$_2$); 6.33 (t, J=6 Hz, 1H, NH); 6.53–6.60 (m, 2H, Ar); 6.85 (t, J=8 Hz, 2H, Ar); 7.50 (d, J=10 Hz, 1H, Ar); 7.60 (dd, J=8, 2 Hz, 1H, Ar); 7.96 (d, J=8 Hz, 1H, Ar); 8.19 (d, J=8 Hz, 1H, Ar); 9.72 (s, 1H, Ar); 11.23 (s, 1H, NH); 12.28 (s, 1H, NH).

C. 3-Amino-9-((4-fluoroanilino)methyl)benzo[f]quinazolin-1(2H)-one

A mixture of methanol (8.75 ml) and 0.5 N-sodium hydroxide (5.8 ml) was heated under reflux under nitrogen for 15 minutes. N-(9-((4-Fluoroanilino)methyl-1,2-dihydro-1-oxobenzo[f]quinazolin-3-yl)pivalamide (0.305 g, 0.73 mole) was added and the solution heated under reflux for 2 hours. The reaction mixture was cooled to room temperature and adjusted to pH 7 with N-hydrochloric acid. The white solid was collected and washed with water, then suspended in 100 ml of boiling ethanol. The cooled solution was filtered and the collected solid dried under high vacuum to give 3-amino-9-((4-fluoroanilino)methyl)benzo[f]quinazolin-1(2H)-one. (0.161 g, 66%). Mp>230° C. $^1$H NMR (DMSO-$d_6$, 200 MHz) δ: 4.38 (s, 2H, CH$_2$); 6.25 (br s, 1H, NH); 6.52–6.59 (m, 2H, Ar); 6.68 (br s, 2H, NH$_2$); 6.85 (t, J=9 Hz, 2H, Ar); 7.25 (d, J=9 Hz, 1H, Ar); 7.45 (d, J=9 Hz, 1H, Ar); 7.83 (d, J=8 Hz, 1H, Ar); 8.00 (d, J=9 Hz, 1H, Ar); 9.62 (s, 1H, Ar); 11.35 (br s, 1H, NH). Anal Calculated for $C_{19}H_{15}FN_4O.17/50H_2O$: C, 67.03; H, 4.64; N, 16.46. Found: C, 66.94; H, 4.51; N, 16.44.

Similarly the following compounds were prepared by reaction of the appropriate aromatic amine with the foregoing (benzoquinazoline-3-yl)pivalamide.

3-Amino-9-((4-nitroanilino)methyl)benzo[f]quinazolin-1(2H)-one (0.095 g, 95%). Mp>230° C. $^1$H NMR (DMSO-$d_6$, 200 MHz) δ: 4.58 (d, J=6 Hz, 2H, CH$_2$); 6.54 (s, 2H, NH$_2$); 6.69 (d, J=9 Hz, 2H, Ar); 7.26 (d, J=9 Hz, 1H, Ar); 7.41 (d, J=8 Hz, 1H, Ar); 7.84 (d, J=8 Hz, 1H, Ar); 7.94–8.01 (m, 4H, Ar & NH); 9.63 (s, 1H, Ar) 11.12 (s, 1H, NH). Anal Calculated for $C_{19}H_{15}N_5O_3.1/4H_2O$: C, 62.38; H, 4.27; N;19.14. Found: C, 62.44; H, 4.28; N, 19.06.

3-Amino-9-((4-acetylanilino)methyl)benzo[f]quinazolin-1(2H)-one (0.245 g, 98%). $^1$H NMR (DMSO-$d_6$, 300 MHz) δ: 2.37 (s, 3H, CH$_3$); 4.53 (d, J=6 Hz, CH$_2$); 6.56 (br s, 2H, NH$_2$); 6.64 (d, J=9 Hz, 2H, Ar); 7.27 (d, J=9 Hz, 2H, Ar); 7.34 (t, J=6 Hz, 1H, NH); 7.43 (dd, J=8, 2 Hz, 1H, Ar); 7.68 (d, J=9 Hz, 2H, Ar); 7.84 (d, J=8 Hz, 1H, Ar); 8.00 (d, J=9 Hz, 1H, Ar); 9.66 (s, 1H, Ar); 11.14 (br s, 1H, NH). Anal Calculated for $C_{21}H_{17}N_4O_2.H_2O$: C, 67.19; H, 5.10; N, 14.92. Found: C, 67.16; H, 5.18; N, 14.90.

3-Amino-9-((3-fluoroanilino)methyl)benzo[f]quinazolin-1(2H)-one (0.19 g, 95%). Mp>235° C. $^1$H NMR (DMSO-$d_6$, 200 MHz) δ: 4.41 (d, J=6 Hz, 2H, CH$_2$); 6.24–6.44 (m, 3H, Ar); 6.55 (s, 2H, NH$_2$); 6.68 (t, J=5 Hz, 1H, NH); 7.01 (q, J=8 Hz, 1H, Ar); 7.25 (d, J=9 Hz, 1H, Ar); 7.43 (d, J=8 Hz, 1H, Ar); 7.82 (d, J=8 Hz, 1H, Ar); 7.98 (d, J=9 Hz, 1H, Ar); 9.64(s, 1H, Ar); 11.15 (br s, 1H, NH). Anal Calculated for $C_{19}H_{15}FN_4O.3/4H_2O$: C, 65.60; H, 4.78; N, 16.11. Found: C, 65.52; H, 4.76; N, 16.08.

EXAMPLE 39

N-(4-((3-Amino-1,2,5,6-tetrahydro-1-oxobenzo[f]quinazolin-7-yl)amino)benzoyl)-L-glutamic acid and N-(4-((3-Amino-1,2-dihydro-1-oxobenzo[f]quinazolin-7-yl)amino)benzoyl)-L-glutamic acid A. N-(5,6,7,8-Tetrahydro-1-naphthyl)acetamide Acetic anhydride (100 ml, 1.06 mole) was added rapidly to neat 1-amino-5,6,7,8-tetrahydronaphthalene (25 g, 0.17 mole) (Aldrich) with stirring. The mixture quickly solidified and was allowed to stand overnight. The broken mass was suspended in hexane (200 ml), filtered, then resuspended in methylene chloride (150 ml). After stirring 10 minutes, the suspension was diluted with an equal volume of hexane, filtered, and the solid dried at 95° C. under reduced pressure to give N-(5,6,7,8-tetrahydro-1-naphthyl)acetamide (23 g). $^1$H NMR (CDCl$_3$, 200 MHz) δ: 1.68–1.90 (m, 4H, CH$_2$'s), 2.20 (s, 3H, CH$_3$), 2.52–2.68 (m, 2H, ArCH$_2$), 2.70–2.84 (m, 2H, ArCH$_2$), 3.94 (br s, 1H, NH), 6.92 (d, J=8 Hz, 1H, Ar), 7.10 (t, J=8 Hz, 1H, Ar), 7.53 (d, J=8 Hz, 1H, Ar). Anal. Calculated for C$_{12}$H$_{15}$NO: C, 76.16; H, 7.99; N, 7.40. Found: C, 76.13; H, 8.04; N, 7.40.

B. N-(4-Cyanophenyl)-N-(5,6,7,8-tetrahydro-1-naphthyl) acetamide

To a solution of N-(5,6,7,8-tetrahydro-1-naphthyl) acetamide (23 g, 0.12 mole) in DMF (120 ml) was added 80% NaH (3.9 g, 0.13 mole) portion wise over a 45 minute period and the mixture was stirred until hydrogen evolution had ceased as monitored by bubbler. 4-Fluorobenzonitrile (18 g, 0.15 mole) (Aldrich) was added, and the solution stirred at 90° C. under nitrogen for 3 hours. The reaction mixture was acidified with acetic acid, diluted with water (500 ml), and extracted with methylene chloride (2×500 ml). The combined extracts were washed with water (100 ml), dried (MgSO$_4$), and concentrated in vacuo. The residue in a small volume of methylene chloride was applied to a silica gel column and eluted with ethyl acetate:hexane (1:3) to give N-(4-cyanophenyl)-N-(5,6,7,8-tetrahydro-1-naphthyl) acetamide (13.4 g). $^1$H NMR (CDCl$_3$, 200 MHz) δ: 1.55–1.85 (m, 4H, CH$_2$'s), 1.96 (s, 3H, CH$_3$), 2.10–2.32 (m, 1H, ArCH$_2$), 2.47–2.66 (m, 1H, ArCH$_2$), 2.76–2.88 (m, 2H, ArCH$_2$), 7.06 (dd, J=7, 2 Hz, 1H, Ar), 7.13–7.29 (m, 2H, Ar), 7.40 (d, J=9 Hz, 2H, Ar), 7.55 (d, J=9 Hz, 2H, Ar). Anal. Calculated for C$_{19}$H$_{18}$N$_2$O: C, 77.16; H, 6.34; N, 9.47. Found: C, 77.08; H, 6.12; N, 9.51.

C. N-(4-Cyanophenyl)-N-(5,6,7,8-tetrahydro-1-naphthyl)-2,2,2-trifluoroacetamide

A solution of N-(4-cyanophenyl)-N-(5,6,7,8-tetrahydro-1-naphthyl)acetamide (13.4 g, 45.3 mmol) in ethanol (100 ml) and 5N NaOH (11 ml) was stirred at reflux for 25 minutes, then acidified with acetic acid and concentrated in vacuo. The residue was taken up in diethyl ether (200 ml), washed with water (30 ml), and dried (K$_2$CO$_3$). Trifluoroacetic anhydride (25 ml, 0.18 mole) (Aldrich) was added cautiously and the solution stirred overnight at room temperature. The reaction mixture was concentrated in vacuo to a volume of 100 ml, additional trifluoroacetic anhydride (20 ml, 0.14 mole) added, stirred for 2 hours, then concentrated in vacuo. The residue was purified by chromatography on silica gel eluting with diethyl ether:hexane (1:2); the product crystallized upon concentration of the solution. The solid was filtered, washed with hexane, and dried at 95° C. under reduced pressure to give N-(4-cyanophenyl)-N-(5,6,7,8-tetrahydro-1-naphthyl)-2,2,2-trifluoro acetamide (10.7 g). $^1$H NMR (CDCl$_3$, 200 MHz) δ: 1.60–1.85 (m, 4H, CH$_2$'s), 2.01–2.21 (m, 1H, ArCH$_2$), 2.55–2.73 (m, 1H, ArCH$_2$), 2.73–2.86 (m, 2H, ArCH$_2$), 7.10–7.29 (m, 3H, Ar), 7.39 (d, J=9 Hz, 2H, Ar), 7.64 (d, J=9 Hz, 2H, Ar). Anal. Calculated for C$_{19}$H$_5$F$_3$N$_2$O: C, 66.27; H, 4.39; N, 8.14. Found: C, 66.35; H, 4.40; N, 8.07.

D. N-(4-Cyanophenyl)-N-(7,8-dihydro-1-naphthyl)-2,2,2-trifluoroacetamide

A solution of N-(4-cyanophenyl)-N-(5,6,7,8-tetrahydro-1-naphthyl)-2,2,2-trifluoro acetamide (10.7 g, 31.1 mmol), N-bromosuccinimide (6.6 g, 37 mmol), and AIBN (200 mg, 1.2 mmol) in CCl$_4$ (300 ml) was stirred at reflux under nitrogen for 1 hour. After coupling the solution was filtered, concentrated in vacuo to a volume of 25 ml, and applied to a column of silica gel. Elution with ethyl acetate:hexane (1:10) gave a mixture of benzylic bromides (10.7 g). A solution of the bromides and Li$_2$CO$_3$ (5.0 g, 68 mmol) in DMF (50 ml) was stirred at 110–120° C. under nitrogen for 3 hours and then overnight at room temperature. The solution was concentrated in vacuo and the residue taken up in methylene chloride (150 ml) and washed with water (50 ml). The aqueous phase was separated, extracted with more methylene chloride (100 ml), and the combined organic solutions were then washed with a small volume of water, dried (K$_2$CO$_3$) and concentrated in vacuo. The residue was purified by chromatography on silica gel eluting with ethyl acetate:hexane (1:13) to give N-(4-cyanophenyl)-N-(7,8-dihydro-1-naphthyl)-2,2,2-trifluoroacetamide and the corresponding 5,6-dihydro isomer in a 3:1 ratio as determined by NMR (4.3 g). $^1$H NMR (DMSO-d$_6$, 200 MHz) δ: 2.10–2.46 (m, 3H, CH$_2$), 2.63–2.89 (m, 1H, CH$_2$), 6.03–6.22 (m, 1H, CH), 6.41 (dt, J=10,2 Hz, 0.25H, CH), 6.48 (dt, J=10,2 Hz, 0.75H, CH), 7.08–7.33 (m, 3H, Ar), 7.41 (d, J=9 Hz, 2H, Ar), 7.64 (d, J=9 Hz, 2H, Ar). Anal. Calculated for C$_{19}$H$_{13}$F$_3$N$_2$O: C, 66.67; H, 3.83; N, 8.18. Found: C, 66.55; H, 3.86; N, 8.10.

E. N-(4-Cyanophenyl)-2,2,2-trifluoro-N-(1b,2,3,7a-tetrahydronaphth[1,2-b]oxiren-4-yl)acetamide A solution of a 3:1 mixture of N-(4-cyanophenyl)-N-(7,8-dihydro-1-naphthyl)-2,2,2-trifluoro acetamide and the corresponding 5,6-dihydro isomer (4.3 g, 13 mmol) and m-chloroperoxybenzoic acid (80–85%, 4.0 g, 19 mmol) (Aldrich) in methylene chloride (60 ml) was stirred for 50 minutes at room temperature. The solution was diluted with methylene chloride (100 ml), washed with saturated NaHCO$_3$ solution (2×30 ml), dried (K$_2$CO$_3$), and concentrated in vacuo. The epoxide isomers were separated by chromatography on silica gel eluting with diethyl ether:hexane (7:13 to 9:11) and recrystallization of the enriched isomer from diethyl ether:hexane. The mother liqour was combined with some mixed fractions from the chromatography and purified by repeating the procedure. The combined solid was dried under high vacuum to give N-(4-cyanophenyl)-2,2,2-trifluoro-N-(1a,2,3,7b-tetrahydronaphth[1,2-b]oxiren-4-yl)acetamide (2.8 g). $^1$H NMR (CDCl$_3$, 200 MHz) δ: 1.69 (dt, J=14,5 Hz, 1H, CH$_2$), 2.03–2.25 (m, 1H, CH$_2$), 2.31–2.69 (m, 2H, CH$_2$), 3.70–3.78 (m, 1H, OCH), 3.90 (d, J=4 Hz, 1H, OCH), 7.29–7.42 (m, 4H, Ar), 7.50–7.60 (m, 1H, Ar), 7.63 (d, J=9 Hz, 2H, Ar). Anal. Calculated for C$_{19}$H$_{13}$F$_3$N$_2$O$_2$: C, 63.69; H, 3.66; N, 7.82. Found: C, 63.70; H, 3.66; N, 7.76.

F. N-(4-Cyanophenyl)-2,2,2-trifluoro-N-(5,6,7,8-tetrahydro-6-oxo-1-naphthyl)acetamide A solution of N-(4-cyanophenyl)-2,2,2-trifluoro-N-(1a,2,3,7b-tetrahydronaphth[1,2-b]oxiren-4-yl)acetamide (2.8 g, 7.8 mmol) in diethyl ether (80 ml) was treated with BF$_3$.Et$_2$O (2.0 ml, 16 mmol) and the resulting suspension was stirred at room temperature. The suspension was diluted with methylene chloride after 1 and 3 hours (80 and 40 ml) and additional BF$_3$.Et$_2$O (2×1.0 ml, 16 mmol) was added at 2 and 4 hour intervals. The reaction mixture was stirred overnight, then saturated NaHCO$_3$ solution (70 ml) slowly added. The aqueous phase was separated and extracted with methylene chloride (40 ml). The organic solutions were dried (K$_2$CO$_3$), concentrated in vacuo, and the residue purified by chromatography on silica gel with diethyl ether:hexane (2:3 to 1:1) to give N-(4-cyanophenyl)-2,2,2-trifluoro-N-(5,6,7,8-tetrahydro-6-oxo-1-naphthyl)acetamide (1.17 g). $^1$H NMR (CDCl$_3$, 200 MHz) δ: 2.44 (t, J=7 Hz, 2H, CH$_2$), 2.69 (dt, J=16, 7 Hz, 1H, CH$_2$), 3.03 (dt, J=16, 6 Hz, 1H, CH$_2$), 3.63 (strongly coupled AB pair, 2H, C$^5$H$_2$), 7.25–7.45 (m, 5H, Ar), 7.67 (d, J=9 Hz, 2H, Ar). Anal. Calculated for C$_{19}$H$_3$F$_3$N$_2$O$_2$: C, 63.69; H, 3.66; N, 7.82. Found: C, 63.75; H, 3.72; H, 7.74.

G. Methyl 5-(N-(4-cyanophenyl)-2 2.2-trifluoroacetamido)-3,4-dihydro-2-hydroxy-1-naphthalene carboxylate A solution of N-(4-cyanophenyl)-2,2,2-trifluoro-N-(5,6,7,8-tetrahydro-6-oxo-1-naphthyl)acetamide (1.17 g, 3.27 mmol) in THF (15 ml) was added dropwise over a 15 minute period to a stirred suspension of 80% NaH (0.30 g, 10 mmol) (Aldrich) in methyl cyanoformate (1.5 ml, 19 mmol) (Aldrich) and THF (15 ml) under nitrogen. The reaction mixture was stirred 30 minutes at room temperature then quenched with acetic acid (0.7 ml, 12 mmol). The solution was concentrated in vacuo onto silica gel (3 g) and the absorbed material purified by chromatography on silica gel (30 g) eluting with ether:hexane (1:4 to 1:3) to give methyl 5-(N-(4-cyanophenyl)-2,2,2-trifluoroacetamido)-3,4-dihydro-2-hydroxy-naphthalene carboxylate (0.64 g). $^1$H NMR (CDCl$_3$, 200 MHz) δ: 2.5–2.9 (m, 4H, CH$_2$CH$_2$), 3.93 (s, 3H, CH$_3$), 7.10 (d, J=8 Hz, 1H, Ar), 7.32 (t, J=8 Hz, 1H, Ar), 7.39 (d, J=9 Hz, 2H, Ar), 7.64 (d, J=9 Hz, 2H, Ar), 7.82 (d, J=8 Hz, 1H, Ar), 13.35 (s, 1H, OH). Anal. Calculated for C$_{21}$H$_{15}$F$_3$N$_2$O$_4$: C, 60.58; H, 3.63; N, 6.73. Found: C, 60.66; H, 3.66; N, 6.68.

H. N-(7-(4-Cyanoanilino)-1,2-dihydro-1-oxobenzo[f]quinazolin-3-yl)pivalamide To a solution of sodium ethoxide, prepared by reacting sodium (0.28 g, 12 mmol) with ethanol (6 ml), was added guanidine hydrochloride (1.2 g, 12 mmol) and the mixture was briefly stirred at reflux. A solution of methyl 5-(N-(4-cyanophenyl)-2,2,2-trifluoroacetamido)-3,4-dihydro-2-hydroxy-1-naphthalene carboxylate (0.63 g, 1.5 mmol) in ethanol (6 ml) was added and the reaction mixture was stirred at reflux under nitrogen for 18 hours. The solution was diluted with water (50 ml), neutralized with acetic acid, and the resulting precipitate filtered and dried at 110° C. under reduced pressure. A solution of the solid in pivalic anhydride (10 ml) was refluxed for ~5 minutes and then concentrated under high vacuum. The residue was eluted on silica gel (30 g) with ethyl acetate:methylene chloride (1:9) and the resulting solid recrystallized from diethyl ether, the slurry diluted with hexane, filtered, and the solid dried at 100° C. under reduced pressure to give N-(7-(4-cyanoanilino)-1,2,5,6-tetrahydro-1-oxobenzo[f]quinazolin-3-yl)pivalamide (0.48 g). $^1$H NMR (DMSO-d$_6$, 200 MHz) δ: 1.23 (s, 9H, t-butyl), 2.67 (s, 4H, ArCH$_2$'s), 6.68 (d, J=9 Hz, 2H, Ar), 7.10 (d, J=8 Hz, 1H, Ar), 7.26 (t, J=8 Hz, 1H, Ar), 7.50 (d, J=9 Hz, 2H, Ar), 8.38 (d, J=8 Hz, 1H, Ar), 8.53 (s, 1H, C$^7$—NH), 11.28 (br s, 1H, N$^2$H), 12.16 (br s, 1H, C$^3$—NH). A solution of the pivalamide (0.15 g) and 10% palladium on carbon (70 mg) in diglyme (5 ml) was stirred at reflux under nitrogen for 10 hours. Pivalic anhydride (2×0.5 ml, 4.9 mmol) was added at 5 and 9 hours. The solution was diluted with diglyme (15 ml), filtered hot through celite, and concentrated under high vacuum. The residue was purified by chromatography on silica gel (15 g) eluting with ethyl acetate:methylene chloride (1:9) and then recrystallization from methanol. The solid was filtered and dried at 90° C. under reduced pressure to give N-(7-(4-cyanoanilino)-1,2-dihydro-1-oxobenzo[f]quinazolin-3-yl)pivalamide (86 mg). $^1$H NMR (DMSO-d$_6$, 200 MHz) δ: 1.26 (s, 9H, t-butyl), 6.85 (d, J=9 Hz, 2H, Ar), 7.49–7.60 (m, 4H, Ar), 7.72 (t, J=8 Hz, 1H, Ar); 8.29 (d, J=9 Hz, 1H, Ar); 9.07 (s, 1H, C$^7$—NH), 9.61 (d, J=9 Hz, 1H, Ar), 11.25 (br s, 1H, N H), 12.32 (br s, 1H, C$^3$—NH). Mass spectrum (CI-CH$_4$) 412 (M+1, 100%). Anal. Calculated for C$_{24}$H$_{21}$N$_5$O$_2$.17/100H$_2$O: C, 69.54; H, 5.19; N, 16.89. Found: C, 69.56; H, 5.23; N, 16.88.

I. Diethyl N-(4-((3-amino-1,2-dihydro-1-oxobenzo[f]quinazolin-7-yl)amino)benzoyl)-L-glutamate A suspension of N-(7-(4-cyanoanilino)-1,2-dihydro-1-oxobenzo[f]-quinazolin-3-yl)pivalamide (82 mg, 0.20 mmol) in ethanol (1 ml) and 1N NaOH (4 ml) was stirred under nitrogen at reflux overnight. The solution was allowed to cool, acidified to pH 3 with concentrated HCl, the resulting suspension stirred for 30 minutes, then filtered. The solid was washed with water and dried at 120° C. under reduced pressure to give 4-((3-amino-1,2-dihydro-1-oxobenzo[f]quinazolin-7-yl)amino)benzoic acid. $^1$H NMR (DMSO-d$_6$, 200 MHz) δ: 6.85 (d, J=9 Hz, 2H, Ar), 7.30 (br s, 2H, NH$_2$), 7.39 (d, J=9 Hz, 1H Ar), 7.43 (d, J=8 Hz, 1H, Ar), 7.64 (t, J=8 Hz, 1H, Ar), 7.73 (d, J=9 Hz, 2H, Ar), 8.28 (d, J=9 Hz, 1H, Ar), 8.85 (s, 1H, C$^7$—NH), 9.44 (d, J=9 Hz, 1H, Ar), 11.5–12.9 (2H, CO$_2$H and N$^2$H). A solution of the foregoing benzoic acid, L-glutamic acid diethyl ester hydrochloride (80 mg, 0.33 mmol) (Aldrich), benzotriazol-1-yloxytris(dimethylamino)-phosphonium hexafluorophosphate (90 mg, 0.20 mmol) (Richelieu Biotechnologies), and triethylamine (90 l, 0.64 mmol) in DMF (6 ml) was stirred at room temperature for 1 hour, then concentrated under high vacuum. The residue was purified by chromatography on silica gel (10–15 g) three times eluting with methanol/methylene chloride. Water (~5 ml) was added to a solution of the solid in ethanol, the ethanol removed under vacuum, and the solid filtered, washed with water, and dried under high vacuum to give diethyl N-(4-((3-amino-1,2-dihydro-1-oxobenzo[f]quinazolin-7-yl)amino)benzoyl)-L-glutamate (35 mg). $^1$H NMR (DMSO-d$_6$, 200 MHz) δ: 1.14 (t, J=7 Hz, 3H, CH$_3$), 1.16 (t, J=7 Hz, 3H, CH$_3$), 1.85–2.15 (m, 2H, gluCH$_2$), 2.40 (t, J=7 Hz, 2H, gluCH$_2$), 4.03 (q, J=7 Hz, 2H, esterCH$_2$), 4.08 (q, J=7 Hz, 2H, esterCH$_2$), 4.30–4.45 (m, 1H, gluCH), 6.63 (br s, 2H, NH$_2$), 6.85 (d, J=9 Hz, 2H, Ar), 7.29 (d, J=9 Hz, 1H, Ar), 7.35 (d, J=8 Hz, 1H, Ar), 7.56 (t, J=8 Hz, 1H, Ar), 7.71 (d, J=9 Hz, 2H, Ar), 8.18 (d, J=9 Hz, 1H, Ar), 8.36 (d, J=7 Hz, 1H, gluNH), 8.64 (s, 1H, C$^7$—NH), 9.45 (d, J=9 Hz, 1H, Ar), 11.22 (br s, 1H, N$^2$H). Mass spectrum (CI-CH$_4$): 532 (M+1, 62.5%), Anal. Calculated for C$_{28}$H$_{29}$N$_5$O$_6$.H$_2$O: C, 61.19; H, 5.69; N, 12.74. Found: C, 61.20; H, 5.44; N, 12.68.

J. Diethyl N-(4-((3-amino-1,2,5,6-tetrahydro-1-oxobenzo[f]quinazolin-7-yl)amino)benzoyl)-L-glutamate (0.061 g, 46%) was similarly prepared from N-(7-(4-cyanoanilino)-1,2,5,6-tetrahydro-1-oxobenzo[f]quinazolin-3-yl)pivalamide (0.10 g, 0.24 mmol). $^1$H NMR (DMSO-d$_6$, 300 MHz) δ: 1.17 (t, J=7 Hz, 3H, CH$_3$), 1.19 (t, J=7 Hz, 3H, CH$_3$), 1.90–2.16 (m, 2H, gluCH$_2$), 2.42 (t, J=7 Hz, 2H, gluCH$_2$), 2.45–2.55 (m, 2H, ArCH$_2$), 2.58–2.67 (m, 2H, ArCH$_2$), 4.05 (q, J=7 Hz, 2H, esterCH$_2$), 4.09 (q, J=7 Hz, 2H, esterCH$_2$), 4.34–4.44 (m, 1H, gluCH), 6.67 (d, J=9 Hz, 2H, Ar), 6.7 (br s, 2H, NH$_2$), 6.99 (d, J=8 Hz, 1H, Ar), 7.16 (t, J=8 Hz, 1H, Ar), 7.70 (d, J=9 Hz, 2H, Ar), 8.10 (S, 1H, ArNH), 8.30 (d, J=8 Hz, 1H, Ar), 8.33 (d, J=8 Hz, 1H, gluNH), 10.92 (S, 1H, N$^2$H). Mass spectrum (CI-CH$_4$): 534 (M+1, 100%). Anal. Calculated for C$_{28}$H$_{31}$N$_5$O$_6$.17/20H$_2$O: C, 61.27; H, 6.00; N, 12.76. Found: C, 61.21; H, 5.94; N, 12.70.

K. N-(4-((3-Amino-1,2-dihydro-1-oxobenzo[f]quinazolin-7-yl)amino)benzoyl)-L-glutamic acid A solution of diethyl N-(4-((3-amino-1,2-dihydro-1-oxobenzo[f]-quinazolin-7-yl)amino)benzoyl)-L-gluamate (31 mg, 0.056 mmol) in ethanol (1 ml) and 0.25 N NaOH (4 ml) was stirred under nitrogen at room temperature for 3 hours. The solution was then acidified to pH 3 with 1N hydrochloric acid and the resulting suspension allowed to stir for 15 minutes. The solid was filtered, washed with water, and dried under high vacuum to give N-(4-((3-amino-1,2-dihydro-1-oxobenzo[f]quinazolin-7-yl)amino)benzoyl)-L-glutamic acid (27 mg). $^1$H NMR (DMSO-d$_6$, 200 MHz) δ: 1.79–2.16 (m, 2H, gluCH$_2$), 2.32 (t, J=7 Hz, 2H, gluCH$_2$), 4.27–4.41 (m, 1H, gluCH), 6.55 (br s, 2H, NH$_2$), 6.85 (d, J=9 Hz, 2H, Ar), 7.27 (d, J=9 Hz, 1H, Ar), 7.34 (d, J=7 Hz, 1H, Ar), 7.55 (t, J=8 Hz, 1H, Ar), 7.72 (d, J=9 Hz, 2H, Ar), 8.16 (d, J=9 Hz, 1H, Ar), 8.24 (d, J=8 Hz, 1H, gluNH), 8.62 (s, 1H, C$^7$—NH), 9.45 (d, J=9 Hz, 1H, Ar), 11.13 (br s, 1H, N$^2$H), 12.31 (br s, 2H, CO$_2$H's). Anal. Calculated for C$_{24}$H$_{21}$N$_5$O$_6$.5/4H$_2$O: C, 57.89; H, 4.76; N, 14.06. Found: C, 57.93; H, 4.73; N, 13.99.

L. N-(4-((3-Amino-1,2,5,6-tetrahydro-1-oxobenzo[f]quinazolin-7-yl)amino)benzoyl)-L-glutamic acid (27 mg, 52%) was similarly prepared from diethyl N-(4-((3-amino-1,2,5,6-tetrahydro-1-oxobenzo[f]quinazolin-7-yl)amino)benzoyl)-L-glutamate (56 mg, 0.10 mmol). $^1$H NMR (DMSO-d$_6$, 200 MHz) δ: 1.78–2.16 (m, 2H, gluCH$_2$), 2.32 (t, J=7 Hz, 2H, gluCH$_2$), 2.40–2.54 (m, 2H, ArCH$_2$), 2.54–2.67 (m, 2H, ArCH$_2$), 4.27–4.43 (m, 1H, gluCH), 6.65 (overlapping br s, 2H, NH$_2$ and d, J=9 Hz, 2H, Ar), 6.97 (dd, J=8, 1 Hz, 1H, Ar), 7.14 (t, J=8 Hz, 1H, Ar), 7.68 (d, J=9 Hz, 2H, Ar), 3.07 (s, 1H, ArNH), 8.19 (d, J=8 Hz, 1H, gluNH), 8.27 (dd, J=8, 1 Hz, 1H, Ar), 10.90 (br s, 1H, N$^2$H), 12.30 (br s, 2H, CO$_2$H's). Anal. Calculated for C$_{24}$H$_{23}$N$_5$O$_6$.8/5H$_2$O: C, 56.94; H, 5.22; N, 13.83. Found: C, 56.96; H, 5.21; N, 13.86.

EXAMPLE 40

3-Amino-9-chloro-5,6-dihydrobenzo[f]quinazolin-1(2H)-one hydrochloride 1,3-Diamino-9-chloro-5,6-dihydroquinazoline (4.0 g) (A. Rosowsky et al., J. Heterocyclic Chem., 9, 263, (1972)) was heated under reflux with 6-M HCl (400 ml) for 2.5 hr. The solution was filtered to remove the 1-amino-3-oxo-isomer of the title compound (0.6 g), and the filtrate heated for a further 1.5 hr. The product was collected by filtration from the cooled reaction mixture, washed with water and dried under vacuum (0.508 g) $^1$H NMR (DMSO-d$_6$, 250 MHz) δ: 2.82 (m, 4H, CH$_2$), 4.0 (v br s, 1H), 7.26 (m, 2H, Ar), 8.27, br s, 2H, NH$_2$), 8.38 (s, 1H, Ar). Anal. Calculated for C$_{12}$H$_{10}$ClN$_3$O.HCl: C, 50.72; H, 3.90; N, 14.59. Found: C, 50.56; H, 4.04; N, 14.51.

Also prepared from the corresponding diamines (A. Rosowsky et al., J. Heterocyclic Chem., 9, 263, (1972)) by an essentially similar procedure were 3-Amino-5,6-dihydro-8-methoxybenzo[f]quinazolin-1(2H)-one hydrochloride, (9.5% from diamine), $^1$H NMR (DMSO-d$_6$, 250 MHz) δ: 2.77 (m, 4H, CH$_2$), 3.76 (s, 3H, OCH$_3$), 6.81 (m, 1H), 8.27 (m, 2H), 8.10 (br s, 1H). Mass spectrum (EI): 243, (M$^+$), 100%. Anal. Calculated for C$_{13}$H$_{13}$N$_3$O$_2$.HCl.11/25H$_2$O: C, 54.27; H, 5.21; N, 14.61. Found: C, 54.55; H, 5.53; N, 14.46.

3-Amino-5,6-dihydro-7-methoxybenzo[f]quinazolin-1(2H)-one hydrochloride, (24.7% from diamine), $^1$H NMR (DMSO-d$_6$, 80 MHz) δ: 2.75 (m, 4H, CH$_2$), 3.80 (s, 3H, OCH$_3$), 7.08 (m, 2H, Ar), 8.00 (m, 1H, Ar), 8.21 (br s, 1H, NH). Anal. Calculated for C$_{13}$H$_{13}$N$_3$O$_2$.HCl.4/5H$_2$O: C, 53.08; H, 5.35; N, 14.29. Found: C, 52.99; H, 5.36; N, 14.32; and 3-Amino-5,6-dihydro-9-methoxybenzo[f]quinazolin-1(2H)-one hydrochloride, (15.6% from diamine), $^1$H NMR (DMSO-d$_6$, 80 MHz) δ: 2.76 (m, 4H, CH$_2$), 3.73 (s, 3H, OCH$_3$), 6.76 (dd, J=8, 2.5 Hz, 1H, Ar), 7.14(d, J=8 Hz, 1H, Ar), 8.00 (d, J=2.5 Hz, 1H, Ar), 8.19 (br s, 1H, NH). Anal. Calculated for C$_{13}$H$_{13}$N$_3$O2.HCl: C, 55–82; H, 5.04; N, 15.02. Found: C, 55.67; H, 5.09; N, 15.03.

EXAMPLE 41

2,4-Diaminodibenzo[f,h]quinazoline

A solution of 9-aminophenanthrene (1.0 g, 5.2 mmol) (Aldrich) and sodium dicyanamide (0.90 g, 10 mmol) in warm acetic acid (50 ml) was allowed to cool to room temperature and stirred for 1 hour. The solution was diluted with water (200 ml), adjusted to pH 6 with NH$_4$OH, and extracted with methylene chloride (200 ml). The organic phase was dried (K$_2$CO$_3$), concentrated in vacuo, and the residue purified by chromatography on silica gel eluting with ethyl acetate:methylene chloride (1:1) to give an uncyclized adduct (0.82 g). A solution of this solid in diglyme (20 ml) was stirred at reflux under nitrogen for 1 hour and then concentrated in vacuo. The solid was suspended in methylene chloride, filtered, and then eluted on silica gel (15 g) with methanol:methylene chloride (1:9). Solid precipitated upon concentration in vacuo of eluent and was filtered and dried at 85° C. under reduced pressure to give 2,4-diaminodibenzo[f,h]quinazoline (0.26 g). $^1$H NMR (DMSO-d$_6$, 200 MHz) δ: 6.24 (brs, 2H, NH$_2$), 6.92 (brs, 2H, NH$_2$), 7.42–7.80 (m, 4H, Ar), 8.57 (dd, J=8, 2 Hz, 1H, Ar), 8.67 (d, J=8 Hz, 2H, Ar), 8.94 (dd, J=8, 2 Hz, 1H, Ar). Anal. Calculated for C$_{16}$H$_{12}$N$_4$.O.25H$_2$O: C, 72.57; H, 4.76; N, 21.16. Found: C, 72.63; H, 4.69; N, 21.14.

2-Aminodibenzo[f,h]quinazolin-4(3H)-one

A suspension of 2,4-diaminodibenzo[f,h]quinazoline (0.20 g, 0.76 mmol) in 1 N HCl (150 ml) was stirred at reflux for 24 h, then neutralized with NH$_4$OH. The resulting solid was filtered, washed with water and methanol, then suspended in warm methanol (50 ml) for 20 minutes, filtered and dried at 90° C. under reduced pressure. The solid was nearly dissolved in ethanol (100 ml) and 1 N NaOH (˜1.5 ml), filtered, and the filtrate neutralized with acetic acid to give a precipitate which was filtered, washed with ethanol, and dried at 90° C. under reduced pressure. The solid was briefly heated to reflux in pivalic anhydride (4 ml), the solution concentrated in vacuo, and the residue subjected to chromatography on silica gel, eluting with methylene chloride containing a small precentage of ethyl acetate. The pivalamide (not characterized) was hydrolyzed in a solution of methanol (9 ml) and 1 N NaOH (1 ml) at reflux for 1.5 hours. The solution was neutralized with acetic acid, and the precipitate filtered, washed with methanol and dried at 90° C. under reduced pressure to give 2-aminodibenzo[f,h]quinazolin-4-(3H)-one as a beige solid (0.10 g). $^1$H NMR (DMSO-d$_6$, 200 MHz) δ: 6.69 (br s, 2H, NH$_2$), 7.47–7.84 (m, 4H, Ar), 8.66–8.80 (m, 2H, Ar), 8.96 (dd, J=8, 1 Hz, 1H, Ar), 9.75–9.83 (m, 1H, Ar), 11.26 (br s, 1H, NH). Mass spectrum (CI-CH$_4$) 262 (M+1, 100%). Anal. Calculated for C$_{16}$H$_{11}$N$_3$O: C, 73.55; H, 4.24; N, 16.08. Found: C, 73.52; H, 4.27; N, 16.03.

Biological Test Data

The procedures used for evaluation of compounds of the invention as antitumour agents are detailed below.

Thymidylate Synthase Inhibition

Human thymidylate synthase (TS) from a SV40-transformed human fibroblast cell was cloned in *Escherichia coli* (I. Dev and W. Dallas, personal communication) and the protein purified to homogeneity by affinity chromatography (Rode, W., Scanlon, K. J., Hynes, J. B., Bertino, J. R., *J. Biol. Chem.*, 254, 1979, 11538).

The enzymes were assayed, and extent of inhibition of the enzyme by the various compounds was determined by the tritium release assay of Roberts (*Biochemistry*, 5, 1966, 3546.) as modified by Dev et al. (*J. Biol. Chem.*, 264, 1989, 19132).

Inhibition of the Growth of tumor cells was determined as described previously (Patil, S. D., Jones, C., Nair, M. G., Galivan, J., Maley, F., Kisliuk, R. L., Gaumont, Y., Duch, D., and Ferone, R., *J. Med. Chem.*, 32, 1989, 1284) and modified as indicated below.

Cells and Medium

SW480 and WiDr colon adenocarcinomas, MCF-7 breast adenocarcinoma, A427 lung carcinoma and MOLT-4 T-cell leukemia were used for the primary screening of compounds. WiDr and MOLT-4 cells were grown in RPMI 1640 medium supplemented with 10 nM calcium leucovorin instead of folic acid as the folate source, 10% dialyzed fetal calf serum, penicillin and streptomycin. MCF-7, A427 and SW480 were grown in the above medium further supplemented with sodium pyruvate. (110 g/ml).

Cytotoxicity Assay

Cells are seeded into 96-well plates using a Perkin-Elmer Pro/pette. SW480 and A427 were seeded at 8,000 cells per well, MCF-7 at 10,000, Widr at 7500, and MOLT-4 at 12,500 cells per well, all in 150 l of medium. Prior to the addition of drugs, cultures were incubated for 24 hrs at 37°. Compounds were added at 2×concentration in 150 l of medium and each concentration was assayed in triplicate. If DMSO or ethanol were used to solubilize compounds, appropriate controls were run if the concentration exceeded 0.01%. Cultures were incubated for 72 hours (96 hours for SW480 and MCF-7) in a 37° humidified incubator at 5% $CO_2$. Inhibition of cell growth was measured using the MTT dye reduction assay.

MTT Dye Reduction Assay

Cell dilutions for a standard curve were prepared from a 72 hour log-phase culture. Serial dilutions were seeded in triplicate in 96-well plates and incubated at 37 degrees for one hour. MTT (3-(4,5-dimethylthiazol-2-yl)-2,5-diphenyltetrazolium bromide) was dissolved in PBS at 5 mg/ml and sonicated for 30 seconds. Using the Perkin Elmer Pro/pette, 200 µl of medium was removed and 100 µl of MTT added to the wells of the standard curve and test plates. Suspension cultures were spun for 5 min at 1000 rpm before removing medium from the wells. Plates were incubated for 1 hour at 370 on a platform shaker. Following this incubation 100 ml of medium was removed from the wells and 100 µl of DMSO added to each well. The plates were sonicated for approximately 10 seconds to solubilize the precipitated formazan dye. The absorbance of each well was measured using a Titertek Multiscan MC microtiter plate reader at 570 nm with a reference wavelength of 750 nm. Data was collected using a Mariachi Seed-2 and stored and analyzed using an IBM-AT and Lotus 1-2-3 software.

Table A.

Mammalian Thymidylate Synthase Enzyme Inhibition Data for Compounds of the present invention.

The following compounds had an $I_{50}$ of between 1 and 300 µM vs. mammalian enzymes.

3-Amino-9-chloro-5,6-dihydrobenzo(f)quinazolin-1(2H)-one *
3,9-Diamino-5,6-dihydrobenzo(f)quinazolin-1(2H)-one
3-Amino-9-ethoxy-5,6-dihydrobenzo(f)quinazolin-1(2H)-one *
3-Amino-N,N-diethyl-1,2,5,6-tetrahydro-1-oxobenzo(f)quinazoline-9-sulfonamide *
3-Amino-7-fluoro-5,6-dihydrobenzo(f)quinazolin-1(2H)-one *
3-Amino-5,6-dihydro-7-iodobenzo(f)quinazolin-1(2H)-one *
3,8-Diamino-5,6-dihydrobenzo(f)quinazolin-1(2H)-one *
3-Amino-8-chloro-5,6-dihydrobenzo(f)quinazolin-1(2H)-one *
3-Amino-1,2,5,6-tetrahydro-1-oxobenzo(f)quinazoline-8-sulfonamide
3-Amino-5,6-dihydro-6,6-dimethylbenzo(f)quinazolin-1(2H)-one *
3-Amino-8-chloro-5,6-dihydro-6-methylbenzo(f)quinazolin-1(2H)-one *
3-Amino-9-bromo-5,6-dihydrobenzo(f)quinazolin-1(2H)-one
3-Amino-5,6-dihydro-9-hydroxybenzo(f)quinazolin-1(2H)-one *
3-Amino-5,6-dihydro-9-(methylthio)benzo(f)quinazolin-1(2H)-one *
3-Amino-5,6-dihydro-7-methylbenzo(f)quinazolin-1(2H)-one
3-Amino-5,6-dihydro-8-nitro(f)quinazolin-1(2H)-one
3-Amino-8-bromo-5,6-dihydrobenzo(f)quinazolin-1(2H)-one
3-Amino-8,9-dichloro-5,6-dihydrobenzo(f)quinazolin-1(2H)-one
3-Amino-9-bromo-5,6-dihydro-8-nitrobenzo(f)quinazolin-1(2H)-one *
3-Amino-9-fluoro-5,6-dihydrobenzo(f)quinazolin-1(2H)-one *
3-Amino-9-ethynyl-5,6-dihydrobenzo(f)quinazolin-1(2H)-one *
3-Amino-9-(ethylthio)-5,6-dihydrobenzo(f)quinazolin-1(2H)-one *
3-Amino-5,6-dihydro-6-methylbenzo(f)quinazolin-1(2H)-one
3-Amino-7-bromo-5,6-dihydrobenzo(f)quinazolin-1(2H)-one
3-Amino-8-fluoro-5,6-dihydrobenzo(f)quinazolin-1(2H)-one *
3-Amino-5,6-dihydro-7,9-dimethylbenzo(f)quinazolin-1(2H)-one
3,8-Diamino-9-bromo-5,6-dihydrobenzo(f)quinazolin-1(2H)-one *
3-Amino-8-bromo-N,N-diethyl-1,2,5,6-tetrahydro-1-oxobenzo(f)quinazoline-9-sulfonamide *
3-Amino-6-methylbenzo(f)quinazolin-1(2H)-one
3-Amino-7-bromobenzo(f)quinazolin-1(2H)-one *
3-Amino-9-methoxybenzo(f)quinazolin-1(2H)-one
3,8-Diaminobenzo(f)quinazolin-1(2H)-one *
3,10-diaminobenzo(f)quinazolin-1(2H)-one *
3-Amino-7,9-dimethylbenzo(f)quinazolin-1(2H)-one
3-Amino-8-bromo-9-nitrobenzo(f)quinazolin-1(2H)-one
3-Amino-8-fluoro-10-nitrobenzo(f)quinazolin-1(2H)-one *
3-Amino-8-bromo-7-nitrobenzo(f)quinazolin-1(2H)-one
3,10-Diamino-8-fluorobenzo(f)quinazolin-1(2H)-one
3-Amino-9-bromo-8-nitrobenzo(f)quinazolin-1(2H)-one
3,7-Diaminobenzo(f)quinazolin-1(2H)-one
3-Amino-8-fluorobenzo(f)quinazolin-1(2H)-one *
3-Amino-7-methylbenzo(f)quinazolin-1(2H)-one *
3-Amino-7-iodobenzo(f)quinazolin-1(2H)-one *
3-Amino-6-(methoxymethyl)benzo(f)quinazolin-1(2H)-one *
3,7-Diamino-8-bromobenzo(f)quinazolin-1(2H)-one
3-Amino-8-fluoro-7-nitrobenzo(f)quinazolin-1(2H)-one *
3-Amino-8-chloro-6-methylbenzo(f)quinazolin-1(2H)-one *
3,8,10-Triaminobenzo(f)quinazolin-1(2H)-one 3-Amino-8-bromo-N,N-diethyl-1,2-dihydro-1-oxobenzo (f)quinazoline-9-sulfonamide *
3-Amino-6-(hydroxymethyl)benzo(f)quinazolin-1(2H)-one
3-Amino-7-fluorobenzo(f)quinazolin-1(2H)-one *
3-Amino-8-chlorobenzo(f)quinazolin-1(2H)-one *
3-Amino-9-ethoxybenzo(f)quinazolin-1(2H)-one *
3-Amino-10-nitrobenzo(f)quinazolin-1(2H)-one *
2-Aminodibenzo(f,h)quinazolin-4(3H)-one *
3-Amino-8,10-dinitrobenzo(f)quinazolin-1(2H)-one *
3,8-Diamino-7,9-dibromobenzo(f)quinazolin-1(2H)-one
3-Amino-7-chlorobenzo(f)quinazolin-1(2H)-one
3-Amino-9-(ethylthio)benzo(f)quinazolin-1(2H)-one
3-Amino-N,N-dimethyl-1,2-dihydro-1-oxobenzo(f) quinazoline-9-sulfonamide
9-Chloro-5,6-dihydro-3-methylbenzo(f)quinazolin-1 (2H)-one *
1,2,5,6-Tetrahydro-3-methyl-1-oxobenzo(f)quinazoline-9-sulfonylchloride *
1,2,5,6-Tetrahydro-3-methyl-1-oxobenzo(f)quinazoline-9-sulfonamide *
9-Bromo-5,6-dihydro-3-methylbenzo(f)quinazolin-1 (2H)-one *
N,N-Diethyl-1,2,5,6-tetrahydro-3-methyl-1-oxobenzo(f) quinazoline-9-sulfonamide
5,6-Dihydro-7-iodo-3-methylbenzo(f)quinazolin-1(2H)-one *
9-Fluoro-5,6-dihydro-3-methylbenzo(f)quinazolin-1 (2H)-one *
5,6-Dihydro-9-iodo-3-methylbenzo(f)quinazolin-1(2H)-one *
1,2,5,6-Tetrahydro-N,N, 3-trimethylbenzo(f)quinazoline-9-sulfonamide *
7-Chloro-5,6-dihydro-3-methylbenzo(f)quinazolin-1 (2H)-one *
7-Chloro-3-methylbenzo(f)quinazolin-1(2H)-one *
9-Fluoro-3-methylbenzo(f)quinazolin-1(2H)-one *
7-Iodo-3-methylbenzo(f)quinazolin-1(2H)-one *
N-(4-(Methyl((1,2,5,6-tetrahydro-3-methyl-1-oxobenzo (f)quinazolin-9-yl)sulfonyl)amino)benzoyl)-L-glutamic acid *
N-(4-((3-Amino-1,2,5,6-tetrahydrobenzo(f)quinazolin-7-yl)amino)benzoyl)-L-glutamic acid *
N-(4-(((3-Amino-1,2,5,6-tetrahydro-1-oxobenzo(f) quinazolin-8-yl)sulfonyl)(2-propynyl)amino)benzoyl)-L-glutamic acid*
N-(4-((3-Amino-9-bromo-1,2-dihydro-1-oxobenzo(f) quinazolin-8-yl)sulfonamido)benzoyl)-L-glutamic acid *
N-(4-((1,2,-Dihydro-3-methyl-1-oxobenzo(f)quinazolin-7-yl)sulfonamido)benzoyl)-L-glutamic acid *
3-Methyl-9-((4-nitroanilino)methyl)benzo)(f)quinazolin-1(2H)-one *
4-(((1,2-Dihydro-3-methyl-1-oxobenzo(f)quinazolin-9-yl)methyl)amino)benzonitrile *
9-((2-Fluoroanilino)methyl)-3-methylbenzo(f) quinazolin-1(2H)-one *
9-((3,4-Difluoroanilino)methyl)-3-methylbenzo(f) quinazolin-1(2H)-one *
4-((1,2-Dihydro-3-methyl-1-oxobenzo[f]quinazolin-9-yl)oxy)benzonitrile *
N-(4-(((1,2-Dihydro-3-methyl-1-oxobenzo[f]quinazolin-9-yl)carbonyl)amino)benzoyl)-1-glutamic acid *

N-(4-(((1,2-Dihydro-3-methyl-1-oxobenzo[f]quinazolin-8-yl)methyl)amino)benzoyl)-L-glutamic acid *

The following compounds have $I_{50}$ values of less than 1 μM

3-Amino-5,6-dihydro-9-methylbenzo(f)quinazolin-1 (2H)-one *
3-Amino-9-chloro-5,6-dihydro-6-methylbenzo(f) quinazolin-1(2H)-one *
3-Amino-5,6-dihydro-9-iodobenzo(f)quinazolin-1(2H)-one *
3-Amino-9-chlorobenzo(f)quinazolin-1(2H)-one *
3-Amino-9-ethylbenzo(f)quinazolin-1(2H)-one *
3,10-Diamino-9-bromobenzo(f)quinazolin-1(2H)-one *
3-Amino-9-hydroxybenzo(f)quinazolin-1(2H)-one
3-Amino-9-((4-acetylanilino)methyl)benzo(f)quinazolin-1(2H)-one *
3-Amino-9-bromobenzo(f)quinazolin-1(2H)-one *
3-Amino-9-methylbenzo(f)quinazolin-1(2H)-one *
3,8-Diamino-9-bromobenzo(f)quinazolin-1(2H)-one
3-Amino-9-(methylthio)benzo(f)quinazolin-1(2H)-one
3,9-Diaminobenzo(f)quinazolin-1(2H)-one
3-Amino-9-fluorobenzo(f)quinazolin-1(2H)-one *
3-Amino-9-iodobenzo(f)quinazolin-1(2H)-one *
3-Amino-9-ethynylbenzo(f)quinazolin-1(2H)-one *
3-Amino-9-chloro-6-methylbenzo(f)quinazolin-1(2H)-one *
3-Amino-8,9-dichlorobenzo(f)quinazolin-1(2H)-one *
3-Amino-9-bromo-10-nitrobenzo(f)quinazolin-1(2H)-one *
4-(((3-Amino-1,2-dihydro-1-oxobenzo(f)quinazolin-9-yl)amino)sulfonyl)benzoic acid *
4'-Fluoro-1,2,5,6-tetrahydro-3-methyl-1-oxobenzo(f) quinazoline-9-sulfonanilide *
1,2,5,6-Tetrahydro-3-methyl-4'-nitro-1-oxobenzo(f) quinazoline-9-sulfonanilide *
4-((1,2,5,6-Tetrahydro-3-methyl-1-oxobenzo(f) quinazolin-9-yl)sulfonamido)benzamide *
4'-Acetyl-1,2,5,6-tetrahydro-3-methyl-1-oxobenzo(f) quinazoline-9-sulfonanilide *
9-Chloro-3-methylbenzo(f)quinazolin-1(2H)-one *
9-Bromo-3-methylbenzo(f)quinazolin-1(2H)-one *
9-Iodo-3-methylbenzo(f)quinazolin-1(2H)-one *
N-(4-((3-Amino-1,2,5,6-tetrahydro-1-oxobenzo(f) quinazolin-9-yl)-sulfonamido)benzoyl)-L-glutamic acid *
N-(4-(((3-Amino-8-bromo-1,2,5,6-tetrahydro-1-oxobenzo(f)quinazolin-9-yl) *
sulfonyl)amino)benzoyl)-L-glutamic acid *
N-(4-(((3-Amino-1,2,5,6-tetrahydro-1-oxobenzo(f) quinazolin-8-yl)sulfonyl)amino)benzoyl)-L-glutamic acid *
N-(4-((1,2,5,6-Tetrahydro-3-methyl-1-oxobenzo(f) quinazolin-9-yl)sulfonamido)benzoyl)-L-glutamic acid *
N-(4-(((3-Amino-1,2-dihydro-1-oxobenzo(f)quinazolin-9-yl)methyl)amino)benzoyl)-L-glutamic acid *
N-(4-(((1,2-Dihydro-3-methyl-1-oxobenzo(f)quinazolin-9-yl)methyl)amino)benzoyl)-L-glutamic acid *
(S)-2-(5-(((1,2-Dihydro-3-methyl-1-oxobenzo(f) quinazolin-9-yl)methyl)amino)-1-oxo-2-isoindolinyl) glutaric acid *
N-(4-((3-Amino-1,2-dihydro-1-oxobenzo(f)quinazolin-7-yl)amino)benzoyl)-L-glutamic acid *

N-(4-((1,2-Dihydro-3-methyl-1-oxobenzo(f)quinazolin-9-yl)methyl)methylamino)benzoyl)-L-glutamic acid *

N-(4-((1,2-Dihydro-3-methyl-1-oxobenzo(f)quinazolin-9-yl)methoxy)benzoyl)-L-glutamic acid *

N-(4-(((3-Amino-1,2-dihydro-1-oxobenzo(f)quinazolin-9-yl)amino)sulfonyl)benzoyl)-L-glutamic acid *

N-(4-((1,2-Dihydro-3-methyl-1-oxabenzo(f)quinazolin-9-yl)sulfonamido)benzoyl)-L-glutamic acid *

N-(4-(((1,2-Dihydro-3-methyl-1-oxobenzo(f)quinazolin-9-yl)methyl)amino)-2-fluorobenzoyl)-L-glutamic acid *

3-Methyl-9-(((1-oxo-5-indanyl)amino)methyl)benzo)[f]quinazolin-1(2H)-one *

4-(((1,2-Dihydro-3-methyl-1-oxobenzo[f]quinazolin-9-yl)methyl)amino)benzoic acid *

3-Methyl-9-(anilinomethyl)benzo(f)quinazolin-1(2H)-one *

9-((3-Chloroanilino)methyl)-3-methylbenzo(f)quinazolin-1(2H)-one *

(S)-2-(5-(((1,2-Dihydro-3-methyl-1-oxobenzo[f]quinazolin-9-yl)methyl)methylamino)-1-oxo-2-isoindolinyl)glutaric acid *

(RS)-2-(2-(4-(((1,2-Dihydro-3-methyl-1-oxobenzo[f]quinazolin-9-yl)methyl)amino)phenyl)-2-oxoethyl)glutaric acid *

(E)-N-(4-(2(1,2-Dihydro-3-methyl-1-oxobenzo[f]quinazolin-9-yl)vinyl)benzoyl)-L-glutamic acid *

N-(4-(2-(1,2-Dihydro-3-methyl-1-oxobenzo[f]quinazolin-9-yl)ethyl)benzoyl)-L-glutamic acid *

4-(4-(((1,2-Dihydro-3-methyl-1-oxobenzo[f]quinazolin-9-yl)methyl)amino)phenyl)-4-oxobutyric acid *

Dodecyl 4-(4-(((1,2-dihydro-3-methyl-1-oxobenzo[f]quinazolin-9-yl)methyl)amino)phenyl)-4-oxobutyrate *

N-((1,2-Dihydro-3-methyl-1-oxobenzo[f]quinazolin-9-yl)methyl)amino)-N-(2-hydroxyethyl)benzamide *

TABLE B

Tumor Cell Culture Cytotoxicity Data for Fully Aromatic Benzoquinazolines (3-Amino Derivatives)

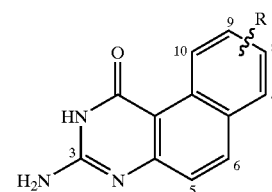

| Structure R | Tumor Cell Culture Cytotoxicity $IC_{50}$ ($\mu$M) | |
|---|---|---|
| | SW480[a] | Other[b] |
| 8-Fluoro | 50 | 100 (D98) |
| 7-Fluoro | 30 | |
| 7-Methyl | 35 | 53 (D98); 32 (L) |
| 7-Bromo | 10 | 56 (D98); 28 (L) |
| 7-Iodo | 10 | |
| 9-Fluoro | 10 | 10 (MCF-7); 7 (A-427) |
| 9-Chloro | 3 | |
| 9-Bromo | 10 | 30 (D98); 2.5 (L) |
| 9-Iodo | 5 | |
| 9-Methoxy | 20 | |
| 9-Methyl | 30 | 8 (L) |
| 9-Ethoxy | 20 | |
| 9-Ethyl | 20 | |

TABLE B-continued

Tumor Cell Culture Cytotoxicity Data for Fully Aromatic Benzoquinazolines (3-Amino Derivatives)

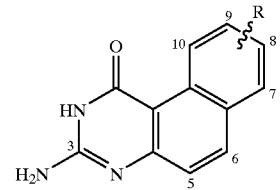

| Structure R | Tumor Cell Culture Cytotoxicity $IC_{50}$ ($\mu$M) | |
|---|---|---|
| | SW480[a] | Other[b] |
| 9-Ethenyl | 6 | |
| 9-Ethynyl | 20 | 60 (D98); 18 (L) |
| 8-Amino | 100 | 53 (D98); 40 (L) |
| 6-Methoxymethyl | 60 | 74 (D98); 56 (L) |
| 7-$NH_2$-8-Br | 20 | |
| 7-$NH_2$-8-F | 30 | |
| 7-$NO_2$-8-F | 30 | 20 (D98); 14 (L) |
| 5,6-Benzo | 4 | |
| 8-F-10-$NO_2$ | 50 | |
| 6-Methyl-9-chloro | 2 | |
| 7-$NO_2$-8-Br | 25 | |
| 8,9-Dichloro | 20 | 50 (D98); 45 (L) |
| 8-F-10-$NH_2$ | 70 | |
| 8-$NH_2$-9-Br | 15 | |
| 8-$NO_2$-9-Br | 2.5 | |
| 8-Br-9-$SO_2NEt_2$ | 2.5 | |
| 9-Br-10-$NO_2$ | 20 | |
| 9-Br-10-$NH_2$ | 30 | |
| 7-Chloro | 25 | 60 (D98); 46 (L) |
| 9-OH | 40 | |
| 9-$NH_2$ | 80 | |
| 9-$SO_2NEt_2$ | 15 | |
| 9-$CH_2NH$-4'-$C_6H_4COCH_3$ | 0.045 | 0.03 (MCF-7) |

[a]SW480 is a human colon adenocarcinoma;
[b]MCF-7 is a human breast adenocarinoma; A-427 is a lung carcinoma; D98 is a human bone marrow cell line; L is a mouse fibroblast cell line

TABLE C

Tumor Cell Culture Cytotoxicity Data for 5,6-Dihydrobenzoquinazolines (3-Amino Derivatives)

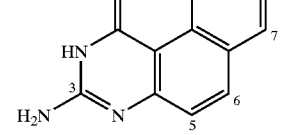

| Structure R | Tumor Cell Culture Cytotoxicity $IC_{50}$ ($\mu$M) | |
|---|---|---|
| | SW480[a] | Other[b] |
| 9-Fluoro | 80 | 90 (D98); 30 (L) |
| 9-Chloro | 25 | 25 (L) |
| 9-Bromo | 25 | 12.5 (L) |
| 9-Iodo | 15 | 20 (MCF-7); 10 (A-427); |
| 9-Ethynyl | 35 | |
| 9-Methoxy | 25 | 70 (D98); 3.3 (L) |
| 9-Ethoxy | 70 | 58 (D98); 40 (L) |
| 9-Methylthio | 60 | 46 (L) |
| 9-Ethylthio | 40 | 54 (D98); 33 (L) |
| 9-$SO_2NEt_2$ | 30 | |

TABLE C-continued

Tumor Cell Culture Cytotoxicity Data for 5,6-Dihydrobenzoquinazolines (3-Amino Derivatives)

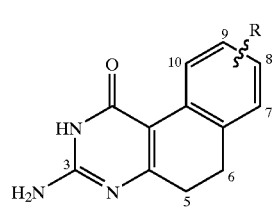

Tumor Cell Culture Cytotoxicity IC$_{50}$ ($\mu$M)

| Structure R | SW480[a] | Other[b] |
|---|---|---|
| 8-SO$_2$N-(Propargyl)$_2$ | 60 | |
| 8-Fluoro | 80 | |
| 8,9-Dichloro | 24 | 10 (MCF-7); 43 (D98); 19 (L) |
| 7,8-Benzo | 30 | 50 (D98); 14 (L) |
| 8-NO$_2$-9-Br | 12 | |
| 8-NH$_2$-9-Br | 15 | |
| 8-Bromo-9-N,N-diethyl-sulfonamido | 7.5 | |

[a]SW480 is a human colon adenocarcinoma
[b]MCF-7 is a human breast adenocarcinoma; D98 is a human bone marrow cell line; L is a mouse fibroblast cell line; A-427 is a lung carcinoma.

TABLE D

Tumor Cell Culture Cytotoxicity Data for 5,6-Dihydrobenzoquinazolines (3-Methyl Derivatives)

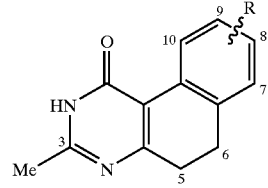

Tumor Cell Culture Cytotoxicity IC$_{50}$ ($\mu$M)

| Structure R | SW480[a] | Other[b] |
|---|---|---|
| 9-Br | 65 | |
| 9-I | 25 | 70 (D98); 80 (L) |
| 9-SO$_2$NH-4'-C$_6$H$_4$NO$_2$ | 30 | |
| 9-SO$_2$NH-4'-C$_6$H$_4$COCH$_3$ | 8 | |
| 9-SO$_2$NH-4'-C$_6$H$_4$F | 25 | |
| 9-SO$_2$NH-4'-C$_6$H$_4$CONH$_2$ | 80 | |
| 7-Br | 50 | |
| 7-I | 80 | 45 (D98); 50 (L) |
| 8-NO$_2$ | 100 | 52 (D98); 52 (L) |
| 8-Br | 65 | |

[a]SW480 is a human colon adenocarcinoma
[b]D98 is a human bone marrow cell line; L is a mouse fibroblast cell line

TABLE E

Tumor Cell Culture Cytotoxicity Data for Fully Aromatic Benzoquinazolines (3-Methyl Derivatives)

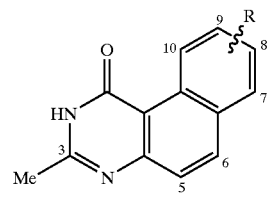

Tumor Cell Culture Cytotoxicity IC$_{50}$ ($\mu$M)

| Structure R | SW480[a] | Other[b] |
|---|---|---|
| 9-F | 100 | 72 (D98); 50 (L) |
| 9-Cl | 10 | 82 (D98); 80 (L) |
| 9-Br | 6 | 68 (L) |
| 7-Cl | 50 | 50 (D98); 84 (L) |
| 7-Br | 50 | |
| 7-I | 50 | |
| 8-F | 15 | 68 (D98) |
| 8-Br | 30 | |
| 9-CH$_2$NH-4'-C$_6$H$_4$NO$_2$ | 0.4 | |
| 9-CH$_2$NH-4'-C$_6$H$_4$CN | 0.03 | |
| 9-CH$_2$NH-C$_6$H$_5$ | 7.0 | |
| 9-CH$_2$NH-4'-C$_6$H$_4$OMe | n.a. | |
| 9-CH$_2$NH-3'-C$_6$H$_4$Cl | n.a. | |
| 9-CH$_2$NH-2'C$_6$H$_4$F | n.a. | |
| 9-CH$_2$NH-3',4'-C$_6$H$_3$F$_2$ | n.a. | |
| 9-CH$_2$NH-5-(1-oxoindanyl) | 0.015 | 0.25 (D98); 0.058 (L) |
| 9-CH$_2$NH-4'-C$_6$H$_4$CO$_2$H | 2.2 | |
| 9-O-4'-C$_6$H$_4$CN | >10 | |
| 9-CH$_2$NH-4'-C$_6$H$_4$CO(CH$_2$)$_2$CO$_2$H | 0.7 | 13.5 (D98); 8.8 (L) |
| 9-CH$_2$NH-4'-C$_6$H$_4$COCH$_2$CH(CO$_2$H)(CH$_2$)$_2$CO$_2$H | 0.03 | |
| 9-CH$_2$NH-4'-C$_6$H$_4$CO$_2$-n-C$_{12}$H$_{25}$ | 0.4 | |
| 9-CH$_2$NH-4'-C$_6$H$_4$CONH(CH$_2$)$_2$OH | n.a. | |
| 9-CH$_2$NH-2',5'-thienyl-CONHCH(CO$_2$H)(CH$_2$)$_2$CO$_2$H | 0.1 | |

[a]SW480 is a human colon adenocarcinoma
[b]MCF-7 is a human breast adenocarcinoma; D98 is a human bone marrow cell line; L is a mouse fibroblast cell line

TABLE F

Cell Culture Cytotoxicity (CCCT) Data for Fully Aromatic Benzoquinazoline p-Aminobenzoylglutamates.

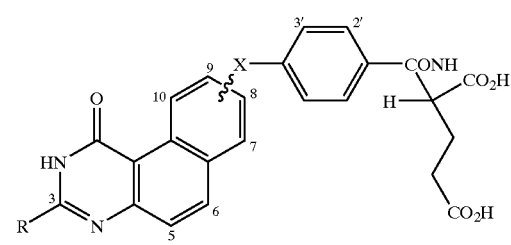

| R | X | Other | CCCT ($\mu$M) SW-480 | MCF-7 |
|---|---|---|---|---|
| NH$_2$ | 0-CH$_2$NH | | 0.60 | 0.025 |
| NH$_2$ | 7-pABAglu[a] | | n.a.[b] | 8 |

TABLE F-continued

Cell Culture Cytotoxicity (CCCT) Data for Fully Aromatic Benzoquinazoline p-Aminobenzoylglutamates.

| R | X | Other | CCCT ($\mu$M) SW-480 | MCF-7 |
|---|---|---|---|---|
| $NH_2$ | 9-$NHSO_2$ | | >100 | n.a. |
| $NH_2$ | 8-$SO_2NH$ | 9-Br | >50 | >50 |
| $CH_3$ | 7-$SO_2NH$ | | .100 | 50 |
| $CH_3$ | 9-$SO_2NH$ | | 2.4 | 0.07 |
| $CH_3$ | 9-$CH_2NH$ | | 0.35 | 0.0075 |
| $CH_3$ | 9-$CH_2NMe$ | | 1.5 | 0.018 |
| $CH_3$ | 9-$CH_2NH$ | 2'-F | 0.02 | 0.0007 |
| $CH_3$ | 9-$CH_2NH$ | 2'-$CH_2$Nglu[c] | 0.0008 | 0.0002 |
| $CH_3$ | 9-$CH_2NH$ | 2'-SNglu[d] | 2.0 | n.a. |
| $CH_3$ | 9-$CH_2O$ | | 70 | 7 |
| $CH_3$ | 9-$CH_2NMe$ | 2'-$CH_2$Nglu[c] | 0.5 | n.a. |
| $CH_3$ | 8-$CH_2NH$ | | >100 | |
| $CH_3$ | 9-CH=CH | | >100 | |
| $CH_3$ | 9-$CH_2CH_2$ | | 9.0 | |
| $CH_3$ | 9-CONH | | n.a. | |

[a]pABAglu = p-aminobenzoylglutamate residue attached to indicated position.
[b]Not assayed.
[c]Methylene bridge between 2'-position of aromatic ring and aminoacid nitrogen.
[d]Sulfide bridge between 2'-position of aromatic ring and aminoacid nitrogen.

TABLE G

Cell Culture Cytotoxicity (CCCT) Data for Dihydrobenzoquinazoline p-Aminobenzoylglutamates.

| R | X | Other | CCCT ($\mu$M) SW-480 | MCF-7 |
|---|---|---|---|---|
| $NH_2$ | 9-$SO_2NH$ | | 7.9 | 0.650 |
| $NH_2$ | 8-$SO_2NH$ | | 25 | n.a.[a] |
| $NH_2$ | 8-$SO_2$N-propargyl | | >50 | n.a. |
| $NH_2$ | 9-$SO_2NH$ | 8-Br | >50 | n.a. |
| $NH_2$ | 7-pABAglu[b] | | >50 | n.a. |
| $CH_3$ | 9-$SO_2NH$ | | 4.0 | 0.650 |
| $CH_3$ | 9-$SO_2NMe$ | | >50 | n.a. |

[a]Not assayed.
[b]pABAglu = p-aminobenzoylglutamate residue attached directly to indicated position.

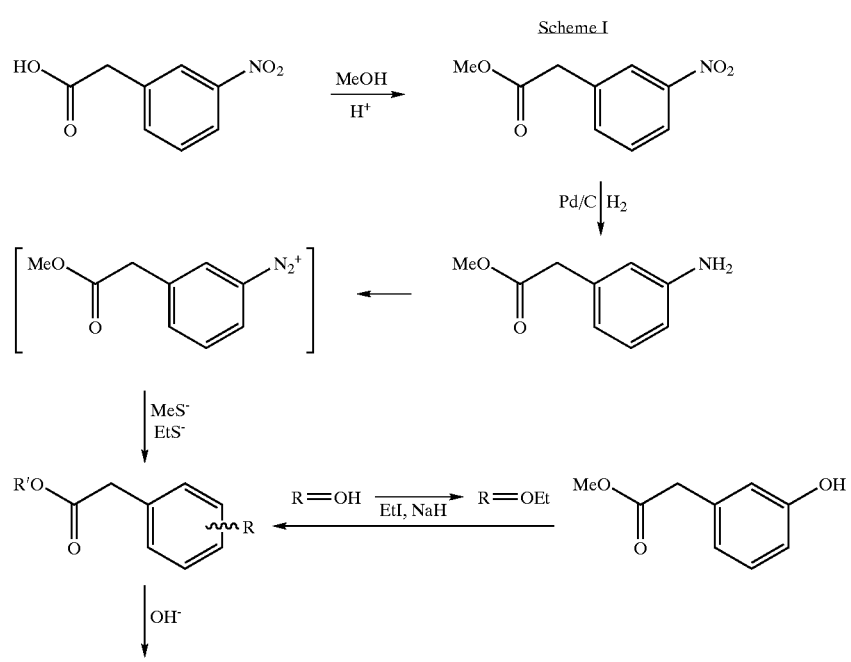

Scheme I

-continued

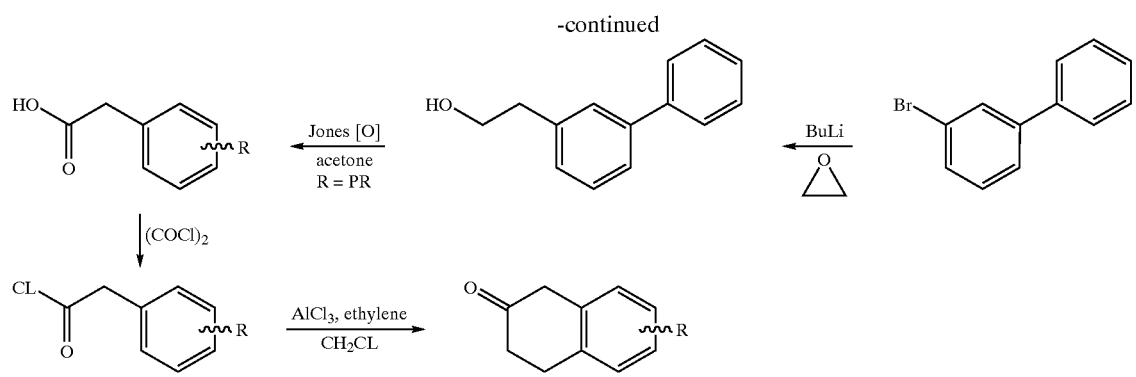

Scheme 2

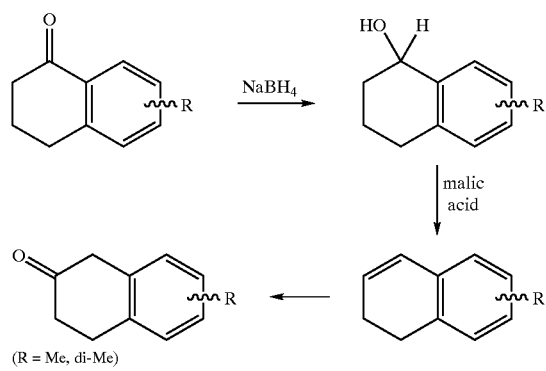

(R = Me, di-Me)

Scheme 3

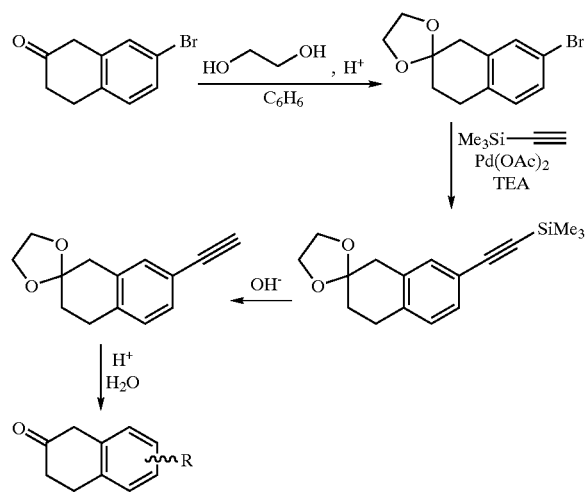

The following examples illustrate pharmaceutical formulations according to the present invention:

| Injectable solution |
| --- |
| A solution for intramuscular injection may be prepared by mixing:- |

| Compound of formula (I) | 9.5 parts by weight |
| --- | --- |
| Dimethyl sulphoxide | 19.0 parts by weight |

| Injectable solution |
| --- |
| A solution for intramuscular injection may be prepared by mixing:- |

| Sorbitan monooleate | 4.5 parts by weight |
| --- | --- |
| Corn oil | 67.0 parts by weight |
| | 100.0 |

| Injectable solution |
| --- |

| Compound of formula (I) | 5 parts by weight |
| --- | --- |
| N-methyl-pyrollidone | 48.3 parts by weight |
| Tween 80 | 2 parts by weight |
| Span 80 | 4.7 parts by weight |
| Miglyol 812 | 40 parts by weight |
| | 100.0 |

| Tablet | |
| --- | --- |
| Compound of formula (I) | 25.0 mg |
| Lactose BP | 48.5 mg |
| Microcrystalline Cellulose BP ("Avicel pH 101") | 10.0 mg |
| Low-substituted Hydroxypropyl; Cellulose BP ("LHPC LH-11") | 10.0 mg |
| Sodium Starch Glycollate BP ("Explotab") | 3.0 mg |
| Povidone BP ("K30") | 3.0 mg |
| Magnesium Stearate BP | 0.5 mg |
| | 100.0 mg |

| Oral suspension | |
| --- | --- |
| Compound of formula (I) | 50 mg |
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |
| Water | to 5 ml |

| Injectable suspension | |
|---|---|
| Compound of formula (I) | 100 mg |
| Polyvinyl pyrrolidone (PVP) | 170 mg |
| Tween 80 | 0.2% v/v |
| Methylhydroxybenzoate | 0.1% w/v |
| Water for Injection | to 3 ml |

| Capsule | |
|---|---|
| Compound of formula (I) | 100 mg |
| Starch 1500 | 150 mg |
| Magnesium stearate | 2.5 mg |
| filled into a hard gelatin capsule | |

| Suspension for Nebulisation | |
|---|---|
| Compound of formula (I), sterile | 1.0 mg |
| Water for Injections | to 10.0 ml |

Disperse the compound of formula (I) in the Water for Injections previously sterilised in a sterile container. Fill in to sterile glass ampoules, 10 ml/ampoule under aseptic conditions, and seal each ampoule by fusion of the glass.

| Aerosol Formulation | |
|---|---|
| Compound of formula (I), micronised | 1.0 mg |
| Aerosol propellant | to 5.0 ml |

Suspend the micronised compound of Formula (I) in the aerosol propellant. Fill this suspension into preformed aerosol cannisters, 5 ml/cannister under pressure, through the valve orifice.

| Powder Inhalation | |
|---|---|
| Compound of formula (I), micronised | 1.0 mg |
| Lactose | 29.0 mg |

Triturate and blend the micronised compound of formula (I) with the lactose. Fill the resulting powder blend into hard gelatin capsule shells, 30 mg per capsule.

| Nasal Drops | |
|---|---|
| Compound of formula (I) | 100.0 mg |
| Methylhydroxybenzoate | 10.0 mg |
| Water for Injections | to 10.0 ml |

Disperse the compound of formula (I) and the methylhydroxybenzoate in the Water for Injections. Fill this suspension into suitable dropper bottles, 10 ml/bottle, and close by securing the dropper nozzle and bottle cap.

We claim:

1. A method for the treatment of a carcinoma in a mammal, wherein the carcinoma is a colon, breast or lung carcinoma, comprising: administering to said mammal a pharmaceutically effective amount of a compound of formula (I),

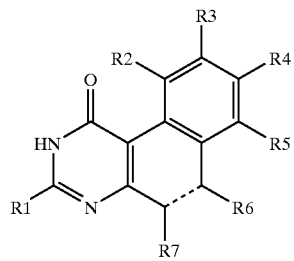

(I)

or a salt thereof, wherein the dotted line represents a single or double bond, $R^1$ is $C_{1-4}$ alkyl or amino optionally substituted by a $C_{1-4}$ alkyl, $C_{1-5}$ alkanoyl or benzyl group;

$R^2$, $R^3$, $R^4$ and $R^5$ are the same or different and each is selected from hydrogen, phenyl, halo, nitro, or a group $S(O)_n R^8$ wherein n is the integer 0, 1 or 2 and $R^8$ is halo, $C_{1-4}$ alkyl, a group $NR^9 R^{10}$ wherein $R^9$ and $R^{10}$ are both hydrogen, a group $NR^{11}R^{12}$ wherein $R^{11}$ and $R^{12}$ are the same or different and each is hydrogen or $C_{1-4}$ alkyl, or a group $OR^{13}$ wherein $R^{13}$ is hydrogen or $C_{1-4}$ alkyl optionally substituted by halo, or a $C_{1-4}$ aliphatic group optionally substituted by a group $OR^{14}$ or $NR^{14}R^{15}$ wherein $R^{14}$ and $R^{15}$ are the same or different and each is hydrogen or $C_{1-4}$ alkyl; or two of $R^2$ to $R^5$ are linked together to form a benzo group, or one of $R^2$ to $R^5$ is a group —X—Y—$R^{16}$, wherein
X is $CH_2$, $NR^{17}$, CO or $S(O)_m$,
m is 0, 1 or 2,
$R^{17}$ is hydrogen or a $C_{1-4}$ aliphatic group,
Y is $CH_2$, $NR^{17'}$, O, or $S(O)_{m'}$,
m' is 0, 1 or 2,
$R^{17'}$ is hydrogen or a $C_{1-4}$ aliphatic group
provided that X and Y are only the same when each is $CH_2$, or —X—Y— is a group —O—, —$NR^{17}$—, —CH=CH— or —N=N— wherein $R^{17}$ is as hereinbefore defined, $R^{16}$ is
a $C_{1-4}$ aliphatic group or
a 5- or 6-membered aromatic ring optionally substituted by a group $R^{18}$ at a position at least one carbon atom removed from that linked to Y, the 5- or 6-membered ring being optionally further substituted by a halo atom;

$R^{18}$ is halo, $C_{1-4}$ alkoxy, nitro, nitrile, $C_{1-4}$ alkyl optionally substituted by halo, halo or a group $COR^{19}$, $R^{19}$ is
hydroxy, $C_{1-4}$ alkoxy or $C_{1-6}$ alkyl optionally substituted by one or two carboxyl groups or $C_{1-12}$ esters thereof or a group $NR^{20}R^{21}$ wherein $R^{20}$ and $R^{21}$ are the same or different and each is hydrogen or $C_{1-4}$ alkyl optionally substituted by hydroxy or a $C_{2-3}$ alkylene group linked to the 5- or 6-membered aromatic ring to form a further 5- or 6-membered ring, or when $R^{18}$ is a $C_{1-4}$ alkyl group substituted by $COR^{19}$, $R^{19}$ is an amino acid or an ester thereof in which the first nitrogen atom of the amino acid together with the carbons of the $C_{1-4}$ alkyl and the carbonyl carbon of $COR^{19}$ may be linked to the 5- or 6-membered aromatic ring to form a further 5- or 6-membered heterocyclic ring;

$R^6$ and $R^7$ are the same or different and each is hydrogen, $C_{1-4}$ alkyl optionally substituted by hydroxy or $C_{1-4}$ alkoxy, or methyl substituted by bromo or together form a benzo group;

provided that at least one of $R^2$ to $R^7$ is other than hydrogen or methyl and that $R^4$ is not methoxy or ethoxy when $R^1$ is hydroxy or methyl.

2. A method as claimed in claim 1, wherein $R^1$ is —X—Y—$R^{16}$.

3. A method as claimed in claim 1, wherein $R^3$ is —X—Y—$R^{16}$, wherein X is $CH_2$, and Y is $NR^{17'}$.

4. A method as claimed in claim 1, wherein $R^3$ is —X—Y—$R^{16}$, wherein X is $CH_2$, Y is $NR^{17'}$ and $R^{16}$ is a 5- or 6-membered aromatic ring optionally substituted by a group $R^{18}$ at a position at least one carbon atom removed from that linked to Y, the 5- or 6-membered ring being optionally further substituted by a halo atom.

5. A method as claimed in claim 1, wherein $R^3$ is —X—Y—$R^{16}$, wherein X is $CH_2$, Y is $NR^{17'}$, $R^{16}$ is a 5- or 6-membered aromatic ring optionally substituted by a group $R^{16}$ at a position at least one carbon atom removed from that linked to Y, the 5- or 6-membered ring being optionally further substituted by a halo atom wherein $R^{18}$ is a $C_{1-4}$ alkyl group substituted by $COR^{19}$, and $R^{19}$ is an amino acid or an ester thereof in which the first nitrogen atom of the amino acid together with the carbons of the $C_{1-4}$ alkyl and the carbonyl carbon of $COR^{19}$ may be linked to the 5- or 6-membered aromatic ring to form a further 5- or 6-membered heterocyclic ring.

6. A method as claimed in claim 5, wherein the amino acid is selected from the group glycine, glutamic acid or polyglutamic acid.

7. A method as claimed in claim 5, wherein $R^{16}$ is

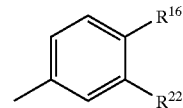

wherein $R^{22}$ is hydrogen or fluoro.

8. A method as claimed in claim 5, wherein $R^{16}$ is

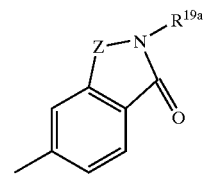

wherein $H_2NR^{19a}$ is glutamic or polyglutamic acid and Z is $CH_2$, S or O.

9. A method as claimed in claim 5, wherein $R^{16}$ is

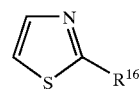

10. A method as claimed in claim 1, wherein the carcinoma is a colon carcinoma.

11. A method as claimed in claim 1, wherein the carcinoma is a lung carcinoma.

12. A method as claimed in claim 1, wherein the carcinoma is a breast carcinoma.

13. A method as claimed in claim 1, wherein the carcinoma is a colon adenocarcinoma.

14. A method as claimed in claim 1, wherein the carcinoma is a breast adenocarcinoma.

* * * * *